(12) United States Patent
Salom et al.

(10) Patent No.: US 8,106,069 B2
(45) Date of Patent: Jan. 31, 2012

(54) PYRROLO[2,3-B]PYRIDINE DERIVATIVES ACTIVE AS KINASE INHIBITORS AND PHARMACEUTICAL COMPOSITIONS COMPRISING THEM

(75) Inventors: Barbara Salom, Milan (IT); Matteo D'Anello, Milan (IT); Maria Gabriella Brasca, Milan (IT); Patrizia Giordano, Cuneo (IT); Katia Martina, Novara (IT); Francesco Angelucci, Milan (IT); Frederick Arthur Brookfield, Oxon (GB); William John Trigg, Oxon (GB); Edward Andrew Boyd, Berkshire (GB); Jonathan Anthony Larard, York (GB)

(73) Assignee: Pfizer Italia S.r.l., Rome (IT)

( * ) Notice: Subject to any disclaimer, the term of this patent is extended or adjusted under 35 U.S.C. 154(b) by 0 days.

(21) Appl. No.: 12/766,230

(22) Filed: Apr. 23, 2010

(65) Prior Publication Data
US 2010/0210476 A1 Aug. 19, 2010

Related U.S. Application Data

(62) Division of application No. 11/020,793, filed on Dec. 23, 2004, now Pat. No. 7,728,140.

(51) Int. Cl.
*A61K 31/44* (2006.01)
*A61K 31/50* (2006.01)
*A61K 31/497* (2006.01)
*A61K 31/445* (2006.01)

(52) U.S. Cl. .................. 514/300; 514/319; 514/252.13; 514/253.04; 514/231.5; 514/233.8; 514/234.5; 514/235.5

(58) Field of Classification Search .................. 514/300, 514/319, 252.13, 253.04, 231.5, 233.8, 234.5, 514/235.5
See application file for complete search history.

(56) References Cited

U.S. PATENT DOCUMENTS

| | | | |
|---|---|---|---|
| 3,320,268 A | 5/1967 | Tsung-Ying Shen et al. | |
| 5,468,757 A | 11/1995 | Jakubowski et al. | |
| 6,476,034 B2 | 11/2002 | Wang et al. | |
| 6,632,819 B1 | 10/2003 | Wang et al. | |

FOREIGN PATENT DOCUMENTS

| | | |
|---|---|---|
| WO | WO 95/28400 | 10/1995 |
| WO | WO 96/11929 | 4/1996 |
| WO | WO 97/03069 | 1/1997 |
| WO | WO 98/50364 | 11/1998 |
| WO | WO 99/32111 | 7/1999 |
| WO | WO 99/37637 | 7/1999 |
| WO | WO 99/58496 | 11/1999 |
| WO | WO 00/21950 | 4/2000 |
| WO | WO 00/21951 | 4/2000 |
| WO | WO 00/24717 | 5/2000 |
| WO | WO 00/71537 | 11/2000 |
| WO | WO 01/01986 | 1/2001 |
| WO | WO 01/58869 | 8/2001 |
| WO | WO 01/98299 | 12/2001 |
| WO | WO 03/082868 | 10/2003 |

OTHER PUBLICATIONS

Cohen P., "The Development and Therapeutic Potential of Protein Kinase Inhibitors", *Current Opinion in Chemical Biology* 3:459-465 (1999).
Hosoi T. et al., "Evidence for CdkS as a Major Activity Phosphorylating Tau Protein in Porcine Brain Extract", *J. Biochem.* 117(4):741-749 (1995).
Schneller S.W. et al., "Synthesis of 4-Amino-1H-Pyrrolo[2,3-b]Pyridine (1,7-Dideazaadenine) and 1H-Pyrrolo[2,3-b]Pyridin-4-ol (1,7-Dideazahypoxanthine)", *Journal of Organic Chemistry* 45(20):4045-4048 (1980), Chemical Abstracts C.A. 93:168162.
Huang X. et al., "Expanding Pd-Catalyzed C-N Bond-Forming Processes: The First Amidation of Aryl Sulfonates, Aqueous Amination, and Complementarity with Cu-Catalyzed Reactions", *J. Am. Chem. Soc.* 125(22):6653-6655 (2003).
Ali M.H. et al., "An Improved Method for the Palladium-Catalyzed Amination of Aryl Iodides", *J. Org. Chem.* 66(8):2560-2565 (2001).
Kuwano R. et al., "Aqueous Hydroxide as a Base for Palladium-Catalyzed Amination of Aryl Chlorides and Bromides", *J. Org. Chem.* 67(18):6479-6486 (2002).
Mouaddib A. et al., "Synthesis of Benzo[5',6']Cyclohepta[4,5]pyrrolo[2,3-*b*]Pyridine-12-One", *Tetrahedron Letters* 40:5853-5854 (1999).
Fivush A.M. et al., "AMEBA: An Acid Sensitive Aldehyde Resin for Solid Phase Synthesis", *Tetrahedron Letters* 38(44):7151-7154 (1997).
Jensen K.J. et al., "Backbone Amide Linker (BAL) Strategy for Solid-Phase Synthesis of C-Terminal-Modified and Cyclic Peptides",*J. Am. Chem. Soc.* 120(22):5441-5452 (1998).
Alsina J. et al al., "Solid-Phase Synthesis with Tris(alkoxy)benzyl Backbone Amide Linkage (BAL)", *Chem. Eur. J.* 5(10):2787-2795 (1999).
Palmer B.D. et al., "Structure-Activity Relationships for 5-Substituted 1-Phenylbenzimidazoles as Selective Inhibitors of the Platelet-Derived Growth Factor Receptor",*J. Med. Chem.* 42(13):2373-2382 (1999).
Lackey K. et al., "The Discovery of Potent cRaf1 Kinase Inhibitors", *Bioorganic & Medicinal Chemistry Letters* 10:223-226 (2000).
McGraw-Hill Dictionary of Chemical Terms, p. 282 (1990).
Concise Encyclopedia Chemistry, p. 490 (1993).
Hawlev's Condensed Chemical Dictionary, p. 594 (1993).
Wolff, Manfred E., "Burger's Medicinal Chemistry, 5ed Part 1", John Wiley & Sons, pp. 975-977 (1995).
Banker, G.S. et al., "Modern Pharmaceutics, 3ed.", Marcel Dekker, New York, pp. 451 and 596 (1996).

*Primary Examiner* — Andrew D Kosar
*Assistant Examiner* — Raymond Covington
(74) *Attorney, Agent, or Firm* — Scully, Scott, Murphy & Presser, P.C.

(57) ABSTRACT

Compounds which are pyrrolo[2,3-b]pyridine derivatives or pharmaceutically acceptable salts thereof, their preparation process and pharmaceutical compositions comprising them are disclosed; these compounds are useful in the treatment of diseases caused by and/or associated with an altered protein kinase activity such as cancer, cell proliferative disorders, Alzheimer's disease, viral infections, auto-immune diseases and neurodegenerative disorders; also disclosed is a process under SPS conditions for preparing the compounds of the invention and chemical libraries comprising a plurality of them.

4 Claims, No Drawings

PYRROLO[2,3-B]PYRIDINE DERIVATIVES ACTIVE AS KINASE INHIBITORS AND PHARMACEUTICAL COMPOSITIONS COMPRISING THEM

CROSS REFERENCE TO RELATED APPLICATIONS

The present application is a divisional of copending application Ser. No. 11/020,793 filed on Dec. 23, 2004 which claims benefit of British Patent Application No. 0330043.1 filed Dec. 24, 2003.

BACKGROUND OF THE INVENTION

1. Field of the Invention

The present invention relates to pyrrolo[2,3-b]pyridine derivatives active as kinase inhibitors and, more in particular, it relates to pyrrolo[2,3-b]pyridine derivatives further substituted in position 5, to a process for their preparation, to combinatorial libraries thereof, to pharmaceutical compositions comprising them and to their use as therapeutic agents, particularly in the treatment of diseases linked to disregulated protein kinases.

2. Discussion of the Background

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs are believed to also play a major role in the pathogenesis and development of neurodegenerative disorders.

For a general reference to PKs malfunctioning or disregulation see, for instance, Current Opinion in Chemical Biology 1999, 3, 459-465.

SUMMARY OF THE INVENTION

It is an object of the invention to provide compounds that are useful in therapy as agents against a host of diseases caused by and/or associated to a disregulated protein kinase activity.

It is another object to provide compounds that are endowed with protein kinase inhibiting activity.

The present inventors have now discovered that some pyrrolo[2,3-b]pyridine derivatives are endowed with protein kinase inhibiting activity and are thus useful in therapy in the treatment of diseases associated with disregulated protein kinases.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoletic tumours of lymphoid lineage, including leukemia, acute lymphocite leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoletic tumours of myeloid lineage, including acute and chronic myelogenous leukemias, myelodysplastic syndrome and promyelocytic leukemia; tumours of mesenchymal origin, including fibrosarcoma and rhabdomyosarcoma; tumours of the central and peripheral nervous system, including astrocytoma, neuroblastoma, glioma and schwannomas; other tumours, including melanoma, seminoma, teratocarcinoma, osteosarcoma, xeroderma pigmentosum, keratoxanthoma, thyroid follicular cancer and Kaposi's sarcoma.

Due to the key role of PKs in the regulation of cellular proliferation, these pyrrolo[2,3-b]pyridine compounds are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention are also useful in the treatment of Alzheimer's disease, as suggested by the fact that cdk5 is involved in the phosphorylation of tau protein (J. Biochem., 117, 741-749, 1995).

The compounds of this invention, as modulators of apoptosis, are useful in the treatment of cancer, viral infections, prevention of AIDS development in HIV-infected individuals, autoimmune diseases and neurodegenerative disorders.

The compounds of this invention are also useful in inhibiting tumour angiogenesis and metastasis, as well as in the treatment of organ transplant rejection and host versus graft disease.

The compounds of the invention also act as inhibitor of other protein kinases, e.g., cyclin-dependent kinases (cdk) such as cdk2 and cdk5, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, PI3K, wee1 kinase, Src, Abl, Akt, MAPK, ILK, MK-2, IKK-2, Cdc7, Nek, and thus be effective in the treatment of diseases associated with other protein kinases.

The compounds of the invention are also useful in the treatment and prevention of radiotherapy-induced or chemotherapy-induced alopecia.

DETAILED DESCRIPTION OF THE INVENTION

Pyrrolo-pyridine derivatives are widely known in the art. As an example, the compound 3-carboxamido-pyrrolo[2,3-b]pyridine is reported as synthetic intermediate in Chemical Abstracts C.A. 93 (1980):168162.

Some other 3-carboxamido derivatives of pyrrolo-pyridine further N-substituted by indolyl groups are disclosed as 5-HT2C/2B antagonists (see WO 96/11929); the above 3-carboxamide derivatives further substituted by N-(isoquinolyl-ethyl-cyclohexyl) groups are disclosed as antipsychotic agents (see WO 00/24717; WO 00/21951; WO 00/21950; WO 98/50364); 3-carboxamido-pyrrolo-pyridine compounds N-substituted by azabicyclo rings are also disclosed as synthetic intermediates in the preparation of tropyl derivatives, possessing antitussive properties.

Moreover, 3-hydrazido pyrrolo-pyridine derivatives are disclosed as synthetic intermediates for preparing more complex protein kinase inhibitors, as reported in WO 00/71537.

7-Azaindoles as inhibitors of C-JUN N-terminal kinases and thus useful in the treatment of neurodegenerative disorders are also disclosed in WO 03/082868.

However, none of the pyrrolo-pyridine derivatives of the prior art resulted to bear an additional amino group, optionally further functionalised, in position 5 of the pyrrolo-pyridine skeleton.

Broad general formula pyrrolo[2,3-b]pyridine compounds endowed with therapeutic activity, also including protein kinase inhibitory activity, are also disclosed in WO 00/71537; WO 01/01986; WO 01/58869; WO 99/32111; WO 99/37637; WO 97/03069; WO 99/58496 and WO 95/28400.

3-Alkenyl-pyrrolo[2,3-b]pyridine derivatives as protein kinase inhibitors are also disclosed in WO 01/98299 in the name of the Applicant itself.

Accordingly, the present invention provides a method for treating conditions or diseases caused by and/or associated with an altered protein kinase activity, by administering to a mammal in need thereof an effective amount of a compound represented by formula (I)

(I)

wherein

R is selected from the group consisting of —$R^a$, —$COR^a$, —$CONR^aR^b$, —$SO_2R^a$ or —$COOR^a$;

$R_1$ is a group —$NR^cR^d$ or —$OR^c$;

wherein $R^a$, $R^b$, $R^c$ and $R^d$, are the same or different, and are each independently hydrogen or a group optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl or, taken together with the nitrogen atom to which they are bonded, either $R^a$ and $R^b$ as well as $R^c$ and $R^d$ may form an optionally substituted 4 to 7 membered heterocycle, optionally containing one additional ring heteroatom or heteroatomic group selected from S, O, N and NH;

or isomers, tautomers, carriers, metabolites, prodrugs, and pharmaceutically acceptable salts thereof.

In a preferred embodiment of the method described above, the disease caused by and/or associated with an altered protein kinase activity is selected from the group consisting of cancer, cell proliferative disorders, Alzheimer's disease, viral infections, autoimmune diseases and neurodegenerative disorders.

Specific types of cancer that the compounds of the present invention are useful for treating include, but are not limited to, carcinoma, squamous cell carcinoma, hematopoietic tumours of myeloid or lymphoid lineage, tumours of mesenchymal origin, tumours of the central and peripheral nervous system, melanoma, seminoma, teratocarcinoma, osteosarcoma, xeroderma pigmentosum, keratoxanthoma, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

The present invention further provides a compound represented by formula (I)

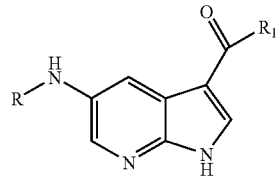

(I)

wherein

R is selected from the group consisting of —$R^a$, —$COR^a$, —$CONR^aR^b$, —$SO_2R^a$ or —$COOR^a$;

$R_1$ is a group —$NR^cR^d$ or —$OR^c$;

wherein $R^a$, $R^b$, $R^c$ and $R^d$, are the same or different, and are each independently hydrogen or a group optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl or, taken together with the nitrogen atom to which they are bonded, either $R^a$ and $R^b$ as well as $R^c$ and $R^d$ may form an optionally substituted 4 to 7 membered heterocycle, optionally containing one additional heteroatom or heteroatomic group selected from S, O, N and NH;

or isomers, tautomers, carriers, metabolites, prodrugs, and pharmaceutically acceptable salts thereof.

Unless otherwise specified, when referring to the compounds of formula (I) per se as well as to any pharmaceutical composition thereof or to any therapeutic method of treatment comprising them, the present invention includes all of the hydrates, solvates, complexes, metabolites and prodrugs of the compounds of this invention. Prodrugs are any covalently bonded compounds, which release the active parent drug according to formula (I) in vivo.

If a chiral center or another form of an isomeric center is present in a compound of the present invention, all forms of such isomer or isomers, including enantiomers and diastereomers, are intended to be covered herein. Compounds containing a chiral center can be used as a racemic mixture or as an enantiomerically enriched mixture, or the racemic mixture can be separated using well-known techniques and an individual enantiomer can be used alone. In cases wherein compounds exist in tautomeric forms, such as keto-enol tautomers, each tautomeric form is contemplated as being included within this invention whether existing in equilibrium or predominantly in one form.

In the present description, unless otherwise indicated, the term straight or branched $C_1$-$C_6$ alkyl includes any group such as, for instance, methyl, ethyl, n-propyl, isopropyl, n-butyl, isobutyl, sec-butyl, tert-butyl, n-pentyl, n-hexyl, and the like.

Examples of straight or branched $C_2$-$C_6$ alkenyl or alkynyl includes any of the unsaturated alkenyl or alkynyl groups with from 2 to 6 carbon atoms, for instance including but not limited to vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

The term $C_3$-$C_6$ cycloalkyl is defined as any 3 to 6 membered carbocyclic ring such as, for instance, cyclopropyl, cyclobutyl, cyclopentyl and cyclohexyl, and the like.

Unless otherwise specified, by aryl is intended a mono- or bi-cyclic, either carbocycle as well as heterocycle, with 1 or 2 ring moieties either fused or linked to each other by single bonds, wherein at least one of the carbocyclic or heterocyclic rings is aromatic but, it also includes 1 or 2 ring moieties wherein all of the rings is aromatic. Unless otherwise specified, the said heterocycle is a 4 to 7 membered ring with from 1 to 3 heteroatoms or heteroatomic groups selected among N, NH, O and S.

Non limiting examples of aryl groups of the invention are, for instance, phenyl, indanyl, biphenyl, α- or β-naphthyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, quinolinyl, isoquinolinyl, quinoxalinyl, benzofurazanyl, 1,2,3-triazolyl, 1-phenyl-1,2,3-triazolyl, and the like.

The term heterocycle (e.g. heterocyclyl) or heterocyclic group is a 4 to 7 membered heterocycle, which encompasses aromatic heterocyclic groups also known as heteroaryl groups and presently encompassed by the term aryl, as well as saturated or partially unsaturated heterocyclic groups, having with from 1 to 3 ring heteroatoms or heteroatomic groups selected among N, NH, O and S.

Examples of these 4 or 7 membered heterocyclic groups are, for instance, 1,3-dioxolane, pyran, pyrrolidine, pyrroline, imidazoline, imidazolidine, pyrazolidine, pyrazoline, piperidine, piperazine, morpholine, tetrahydrofuran, hexamethyleneimine, 1,4-hexahydrodiazepine, azetidine, and the like.

When referring to the compounds of formula (I) wherein R is a group —CONR$^a$R$^b$ and/or R$_1$ is a group —NR$^c$R$^d$ and R$^a$ and R$^b$ and/or R$^c$ and R$^d$ are taken together with the nitrogen atom to which they are bonded, they may also form an optionally substituted 4 to 7 membered heterocycle optionally containing one additional ring heteroatom or heteroatomic group among S, O, N or NH.

According to the meanings provided to R$^a$, R$^b$, R$^c$ and R$^d$, any of the above groups is unsubstituted or can be further optionally substituted in any of their free positions by one or more groups, for instance 1 to 6 groups, selected from: halogen, nitro, oxo groups (=O), carboxy, cyano, alkyl, polyfluorinated alkyl, alkenyl, alkynyl, cycloalkyl, cycloalkenyl; aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, aryloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents can, in addition, be further substituted by one or more of the aforementioned groups.

In the present description, unless otherwise specified, the term halogen is a fluorine, chlorine, bromine or iodine atom.

The term polyfluorinated alkyl is intend a straight or branched $C_1$-$C_6$ alkyl group as above defined, wherein more than one hydrogen atom is replaced by fluorine atoms such as, for instance, trifluoromethyl, 2,2,2-trifluoroethyl, 1,2-difluoroethyl, 1,1,1,3,3,3-hexafluoropropyl-2-yl, and the like.

From all of the above, it is clear to the skilled man that any group which name has been identified as a composite name such as, for instance, cycloalkylalkyl, arylalkyl, heterocyclylalkyl, alkoxy, alkylthio, aryloxy, arylalkyloxy, alkylcarbonyloxy and the like, has to be intended as conventionally construed from the parts to which it derives. So far, as an example, the term heterocyclyl-alkyl stands for a straight or branched alkyl group being further substituted by a heterocyclic group, as above defined.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention are preferably prepared from an inorganic acid or from an organic acid. Examples of such inorganic acids are hydrochloric, hydrobromic, hydroiodic, nitric, carbonic, sulfuric, and phosphoric acid. Appropriate organic acids are preferably selected from aliphatic, cycloaliphatic, aromatic, araliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts are preferably prepared by conventional means from the corresponding compounds of the present invention, for instance by reacting them with the appropriate acid or base.

A first class of preferred compounds of the invention is represented by the derivatives of formula (I) wherein R is a group —COR$^a$ and R$_1$ is a group —NR$^c$R$^d$, wherein R$^a$, R$^c$ and R$^d$ are as above defined.

Another class of preferred compounds is represented by the derivatives of formula (I) wherein R is a group —CONR$^a$R$^b$ and R$_1$ is a group —NR$^c$R$^d$, wherein R$^a$, R$^b$, R$^c$ and R$^d$ are as above defined.

Another class of preferred compounds is represented by the derivatives of formula (I) wherein R is a group —SO$_2$R$^a$ and R$_1$ is a group —NR$^c$R$^d$, wherein R$^a$, R$^c$ and R$^d$ are as above defined.

Another class of preferred compounds is represented by the derivatives of formula (I) wherein R is a group —COOR$^a$ and R$_1$ is a group —NR$^c$R$^d$, wherein R$^a$, R$^c$ and R$^d$ are as above defined.

Another class of preferred compounds is represented by the derivatives of formula (I) wherein R is as defined in formula (I) and R$_1$ is a group —OR$^c$, wherein R$^c$ is as above defined.

Another class of preferred compounds is represented by the derivatives of formula (I) wherein R is a group R$^a$ and R$_1$ is a group —NR$^c$R$^d$, wherein R$^a$, R$^c$ and R$^d$ are as above defined.

Preferably, within the above classes, R$^a$, R$^b$, R$^c$ and R$^d$ are selected, each independently, according to the meanings reported in tables I and II of the experimental section.

For a reference to specific examples of compounds of formula (I) of the invention, optionally in the form of pharmaceutically acceptable salts, see the experimental section.

As set forth above, it is a further object of the present invention a process for preparing the compounds of formula (I).

Therefore, the compounds of formula (I) and the pharmaceutically acceptable salts thereof are obtained using standard techniques known to one of ordinary skill in the art. For example, they are obtained by a process comprising:

a) reacting 1-(phenylsulfonyl)-1H-pyrrolo[2,3-b]pyridine-3-carboxylic acid methyl ester with tetrabutylammonium nitrate (TBAN) in the presence of trifluoroacetic anhydride (TFAA), so as to obtain a compound of formula (II)

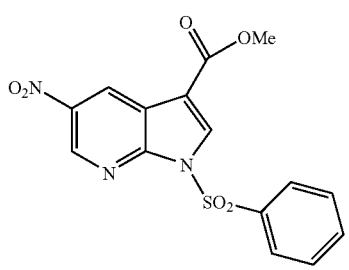

(II)

b) reacting the compound of formula (II) under basic or acidic hydrolysis conditions so as to obtain a compound of formula (III) or a salt thereof

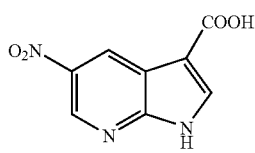

(III)

c) reacting the compound of formula (III) with a carboxy protecting agent, for instance an esterifying agent, so as to obtain a compound of formula

(IV)

wherein Alk stands for alkyl, for instance methyl;

d) reacting the compound of formula (IV) with tin(II) chloride and N-methyl-α-pyrrolidinone (NMP), so as to obtain a compound of formula (I)

(I)

wherein Alk is as above defined and, optionally, reacting it according to any one of the alternative steps (e.1), (e.2), (e.3) or (e.4)

e.1) with any one of the compounds of formula (V), (VI), (VII) or (VIII)

$R^a COZ$ (V);

$R^a NCO$ (VI);

$R^a SO_2 Z$ (VII);

$R^a COZ$ (VIII)

wherein $R^a$ is as above defined and Z is a halogen atom, so as to obtain a compound of formula (I)

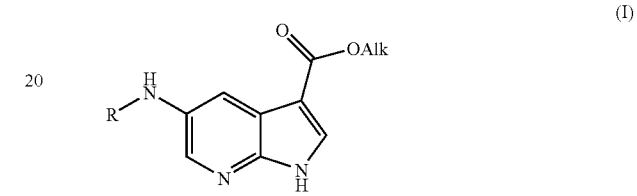

(I)

wherein Alk is as above defined and R is a group —$COR^a$, —$CONHR^a$, —$SO_2 R^a$ or —$COOR^a$, respectively; or e.2) with a suitable amine of formula (IX) in the presence of triphosgene or of a suitable chloroformate $HNR^a R^b$ (IX)

so as to obtain the above compound of formula (I) wherein R is a group —$CONR^a R^b$; or (e.3) with a suitable aldehyde or ketone derivative of formula (X) under reductive operative conditions $R^a$—CO—$R^a$ (X)

wherein each $R^a$ is the same or different as above defined, so as to obtain the above compound of formula (I) wherein R is a group —$CH(R^a)R^a$; or (e.4) with an aromatic iodide or bromide of formula (XI) or (XII)

$R^a$—I (XI)

$R^a$—Br (XII)

in the presence of a suitable palladium catalyst and of a ligand, so as to obtain a compound of formula (I) wherein R is $R^a$ and this latter represents a carbocyclic or heterocyclic aromatic group; and, optionally f) converting the compound of formula (I) being obtained according to any one of steps (d), (e.1), (e.2), (e.3) or (e.4) into another compound of formula (I) and/or into a pharmaceutically acceptable salt thereof.

The above process is an analogy process which can be carried out according to well-known methods.

According to step (a) of the process, the nitration of 1-(phenylsulfonyl)-1H-pyrrolo[2,3-b]pyridine-3-carboxylic acid methyl ester to yield the compound of formula (II) is carried out with tetrabutylammonium nitrate (TBAN) in the presence of trifluoroacetic anhydride (TFAA). The reaction is carried out in a suitable solvent, for instance a halogenated hydrocarbon such as dichloromethane, by working at a temperature ranging from 0° C. to room temperature and for a time varying from about 10 hours to about 30 hours.

According to step (b) of the process, the compound of formula (II) undergoes hydrolysis under basic or acidic conditions. Preferably, the reaction is carried out in the presence of aqueous sodium hydroxide and of 2,2,2-trifluoroethanol (TFE), at a temperature ranging from room temperature to about 90° C. and for a time of from 4 hours to one day. According to the operative conditions being employed, the compound of formula (III) could be obtained either in its acidic form or, alternatively, as a salt.

Preferably, the hydrolysis reaction is carried out under basic conditions, e.g. in the presence of sodium hydroxide, so as to obtain the corresponding disodium salt, as per the experimental section (see example 2).

According to step (c) of the process, the compound of formula (III) is esterified according to well-known operative conditions in the presence of suitable alcohols. As an example, this reaction is performed in the presence of methanol so as to get the corresponding carboxymethyl ester derivative of formula (II) wherein Alk stands for methyl.

Alternatively, the compound of formula (IV) of step (c) wherein Alk stands for methyl is prepared through the direct hydrolysis of the compound of formula (II) according to known methods, for instance in the presence of potassium trimethylsylanolate in tetrahydrofuran (THF) or of triethylamine (TEA) in methanol.

According to step (d) of the process, the nitro group of the compound of formula (IV) is reduced to the corresponding amino derivative. The reduction is preferably carried out in the presence of tin(II) chloride and NMP according to well-known methods. Clearly, any of the several methods known in the art to reduce nitro groups to amino groups, for instance comprising catalytic hydrogenation, can also be successfully employed as well.

From the above, it is clear to the skilled man that from the above reaction of step (d) a compound of formula (I) is obtained wherein R is a hydrogen atom and $R_1$ is a group —$OR^c$ wherein $R^c$ is just the alkyl group being introduced through step (c) of the process, e.g. methyl.

The compound of formula (I) thus obtained can optionally be then converted into a variety of derivatives of formula (I) by working as described in any one of steps from (e.1) to (e.4) of the process, according to well-known methods.

Typically, the compound of formula (I) of step (d), bearing an amino group in position 5, is reacted: with a compound of formula (V) so as to get the corresponding carboxamido derivative wherein R is —$COR^a$ and $R^a$ is as above defined; with a compound of formula (VI) so as to get the corresponding ureido derivative wherein R is —$CONHR^a$ and $R^a$ is as above defined; with a compound of formula (VII) so as to get a sulfonamido derivative wherein R is —$SO_2R^a$ and $R^a$ is as above defined; with a compound of formula (VIII) so as to get a carbamate derivative wherein R is —$COOR^a$ and $R^a$ is as above defined; with a compound of formula (IX) and triphosgene or a suitable chloroformate so as to get an ureido derivative wherein R is —$CONR^aR^b$ and $R^a$ and $R^b$ are as above defined; with a compound of formula (X) under reductive operative conditions so as to get a derivative wherein R is —$CH(R^a)R^a$ and each $R^a$, the same or different and independently from each other, is as above defined.

Any one of the above reactions is carried out according to conventional methods normally used in the preparation of functionalized amino derivatives, by starting from the corresponding amine.

Within the compounds of formula (V), (VII) or (VIII) of step (e.1), in particular, Z represents a halogen atom and, even more preferably, a chlorine atom.

In this respect, the compound of formula (I) of step (d) is dissolved in a suitable solvent such as dichloromethane, dimethylformamide, tetrahydrofuran, dioxane or the like, and a suitable base such as triethylamine, diisopropylethylamine, sodium carbonate or the like is added therein.

The compound of general formula (V), (VII) or (VIII) is then added and the mixture stirred for a time of about 2 hours to about 15 hours, at a temperature ranging from about 20° C. to about 80° C. When using an isocyanate of general formula (VI), the reaction conditions are the same as above except that the base may not be required. In all of these reactions, a suitable catalyst such as dimethylamino pyridine may be optionally used.

According to step (e.2) of the process, the compound of formula (I) obtained in step (d) may be reacted with an amine derivative of formula (IX) in the presence of triphosgene or of a suitable chloroformate such as, for instance, 4-nitrophenylchloroformate.

The reaction is carried out in a suitable solvent such as a halogenated hydrocarbon, preferably dichloromethane, in the presence of a base such as, for instance, diisopropylethylamine or triethylamine and by working at room temperature.

According to step (e.3) of the process, the compound of formula (I) of step (d) is reacted, under reductive conditions, with an aldehyde or ketone derivative of formula (X) so as to obtain the corresponding compound of formula (I) wherein R is as above defined. From the above, it is clear to the skilled man that by employing an aldehyde derivative of formula (X) wherein one of the two $R^a$ is a hydrogen atom, the corresponding derivative wherein R is —$CH_2R^a$ may be obtained. Likewise, by employing a ketone derivative, compounds having R as —$CH(R^a)R^a$ may be obtained, wherein each $R^a$ is, independently from each other, as set forth above but other than hydrogen.

According to step (e.4) of the process, the compound of formula (I) of step (d) is converted into the corresponding arylated derivative of formula (I) with R as $R^a$ and wherein $R^a$ is an aryl group, hence comprehensive of carbocyclic or heterocyclic aromatic groups.

The reaction is carried out according to known methods, with any suitable aryl iodide or bromide of formula (XI) or (XII) in the presence of a suitable catalyst, for instance a palladium catalyst like palladium acetate or $Pd_2(dba)_3$, and of a suitable ligand. For a general reference to the above arylation reaction and operative conditions thereof (also inclusive of solvents, catalysts and ligands) see, for instance, J. Am. Chem. Soc., (2003), 125, 6653-55; JOC (2001), 66, 2560-2565; and JOC (2002), 67, 6479-6486.

In addition to the above, it is clear to the skilled man that, whenever desired, any of the above compounds of formula (I) thus prepared may be further converted into other derivatives of formula (I), as set forth in step (f), by working according to conventional methods.

As an example, the compounds of formula (I)

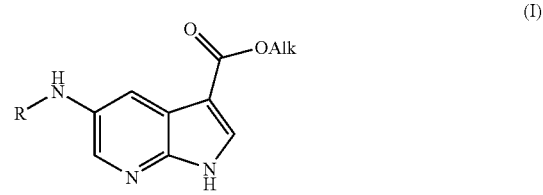

(I)

wherein R is any one of the aforementioned groups and Alk represents a given alkyl, for instance methyl, may be converted into the compounds of formula (I):

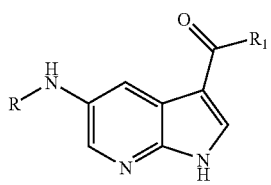
(I)

g) wherein R is as above defined and R₁ is —OR$^c$ with R$^c$ other than methyl, through transesterification reactions carried out according to well-known methods, for instance with a suitable compound of formula (XIII)

R$^c$—OH (XIII)

under acidic or basic conditions, optionally in the presence of suitable metal based catalysts, like dibutyltin oxide or titanium alkoxides such as, for instance, titanium(IV) ethoxide, titanium(IV) isopropoxide and the like;

h) wherein R is as above defined and R₁ is a group —OH, through acidic or basic hydrolysis.

As an additional example, the compounds of formula (I) wherein R is as above defined and R₁ is a group —OR$^c$ wherein R$^c$ is an alkyl group may be also converted into the corresponding amido derivatives of formula (I)

i) wherein R₁ is —NR$^c$R$^d$, with R$^c$ and R$^d$ as above defined, by treatment with ammonia or with a suitable amine of formula (XIV) or (XV)

R$^G$—NH2 (XIV);

R$^c$R$^d$NH (XV)

Optionally in the presence of suitable catalysts such as, for instance, 2-hydroxypyridine, potassium iodide, sodium cyanide or dimethylamino-pyridine.

Likewise, the compounds of formula (I) wherein R is as above defined and R₁ is a group —OR$^c$ wherein R$^c$ is hydrogen are optionally converted into the corresponding amido derivatives of formula (I) by working as set forth in step (i), optionally in the presence of a suitable condensing agent, for instance dicyclohexylcarbodilmide (DCC), 1-ethyl-3-(3'-dimethylaminopropyl)carbodiimide (EDC), O-benzotriazolyltetramethylisouronium tetrafluoroborate (TBTU) or benzotriazol-1-yloxytripyrrolidinophosphonium hexafluorophosphate (PyBOP).

From all of the above, it is also clear to the skilled person that if a compound of formula (I), prepared according to the above process, is obtained as an admixture of isomers, their separation into the single isomers of formula (I), carried out according to conventional techniques, is still within the scope of the present invention.

Likewise, the conversion into the free compound (I) of a corresponding salt thereof, according to well-known procedures in the art, is still within the scope of the invention.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

Likewise, the conversion of these latter into the free deprotected compounds may be carried out according to known procedures.

The starting materials of the process object of the present invention, comprehensive of any possible variant, as well as any reactant thereof, are known compounds and if not commercially available per se may be prepared according to well-known methods.

As an example, the compound 1-(phenylsulfonyl)-1H-pyrrolo[2,3-b]pyridine-3-carboxylic acid methyl ester may be prepared as described in Tetrahedron Letters 40 (1999), 5853-5854.

Likewise, the compounds of formula (V), (VI), (VII), (VIII), (IX), (X), (XII), (XIII), (XIV) and (XV) are known or easily obtained according to known methods.

The intermediate compound of formula (III) of the process represents a further object of the invention.

In addition to the above, the compounds of formula (I) of the invention are advantageously prepared according to combinatorial chemistry techniques widely known in the art, by accomplishing the aforementioned reactions between the intermediates in a serial manner and by working under solid-phase-synthesis (SPS) conditions.

As an example, the intermediate compounds of formula (III), being obtained according to step (b) of the process, can be easily supported onto a polymeric resin, for instance through the formation of a carboxamido group, and the intermediate thus supported may be subsequently reacted according to the remaining steps of the process.

Preferably, the above resin is a commercially available polystyrenic resin including, for instance, Wang resin, Trityl resin, Cl-trityl resin, Rink amide resin, Tentagel OH resin, formylic resin and derivatives thereof.

According to a preferred embodiment of the invention, the polystyrenic resin is a derivatized formyl polystyrenic resin which may be obtained by reacting a commercially available formyl polystyrenic resin, e.g. 4-(4-formyl-3-methoxyphenoxy)butyryl AM resin, with a suitable amino derivative under reductive conditions, for instance in the presence of sodium borohydride and derivatives thereof, substantially as follows:

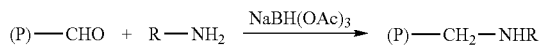

The reaction is preferably carried out in a suitable solvent such as dichloromethane and in the presence of acetic acid.

The polymer-supported-amino derivatives thus obtained, particularly those which are referable to as derivatized formyl polystyrenic resin above, are widely known in the art. In general, amines loaded onto formylpolystyrenic resins also known as Acid Sensitive MethoxyBenzaldehyde polystirene resins (AMEBA resin) are prepared by standard reductive amination in the presence of an excess of amine in TMOF/DCE and NaBH(OAc)₃ or AcOH/DMF and NaCNBH₃, for instance as reported in Tetrahedron Letters (1997), 38, 7151-7154; J. Am. Chem. Soc. (1998), 120, 5441; and Chem. Eur. J. (1999), 5, 2787.

Therefore, it is a further object of the present invention a process for preparing the compounds of formula (I), and the pharmaceutically acceptable salts thereof, which process comprises:

j) reacting the compound of formula (III), being prepared according to step (b), with a derivatized formyl polystyrenic resin of formula (XVI)

(P)—CH₂—NHR$^e$ (XVI)

wherein (P) is the resin and $R^c$ is as above defined, so as to obtain a compound of formula (XVII)

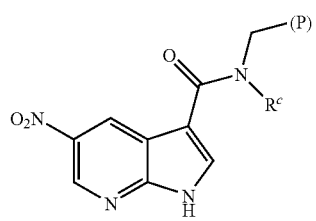

(XVII)

k) reacting the compound of formula (XVII) according to step (d) and, optionally, to any one of steps (e.1), (e.2), (e.3) or (e.4), so as to obtain a compound of formula (XVIII)

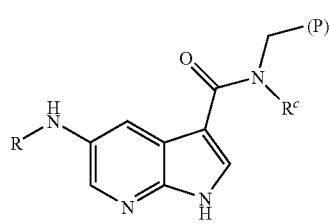

(XVIII)

wherein (P), R and $R^c$ are as above defined;

l) cleaving the resin from the compound of formula (XVIII) under acidic conditions so as to obtain a compound of formula (I) wherein R is as above defined and $R_1$ is a group —$NHR^c$ wherein $R^c$ is as above defined; and, optionally, m) converting the thus obtained compound of formula (I) into another compound of formula (I) and/or into a pharmaceutically acceptable salts thereof.

According to step (j) of the process, the reaction is performed in a suitable solvent, for instance N-methylpyrrolidone (NMP), dimethylformamide (DMF) or dichloromethane (DCM), in the presence of diisopropylethylamine (DIEA) and of a suitable condensing agent such as, for instance, 1-ethyl-3-(3'-dimethylaminopropyl)carbodiimide (EDC), dicyclohexylcarbodiimide (DCC), diisopropylcarbodiimide (DIC), dimethylaminopyridine (DMAP) or O-benzotriazolyl tetramethylisouronium tetrafluoroborate (TBTU).

According to step (k) of the process, the supported compound of formula (XVII) is first reduced as per step (d) of the process so as to obtain the amino derivative, and optionally further reacted as formerly indicated, so as to give rise to a variety of compounds functionalised in position 5 of the pyrrolo[2,3-b]pyridine ring. The operative conditions are essentially those formerly reported by working under homogeneous operative conditions.

Resin cleavage according to step (l) may be performed under acidic conditions in the presence of suitable acids such as, for instance, hydrochloric or trifluoroacetic acid.

Clearly, by working according to combinatorial chemistry techniques as formerly indicated, a plurality of compounds of formula (I) may be obtained.

Hence, it is a further object of the present invention a library of two or more compounds of formula (I)

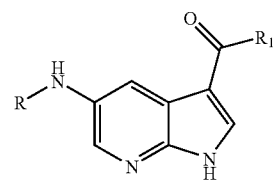

(I)

wherein

R is selected from the group consisting of —$R^a$, —$COR^a$, —$CONR^aR^b$, —$SO_2R^a$ or —$COOR^a$;

$R_1$ is a group —$NR^cR^d$ or —$OR^c$;

wherein $R^a$, $R^b$, $R^c$ and $R^d$, are the same or different, and are each independently hydrogen or a group optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl or, taken together with the nitrogen atom to which they are bonded, either $R^a$ and $R^b$ as well as $R^c$ and $R^d$ may form an optionally substituted 4 to 7 membered heterocycle, optionally containing one additional ring heteroatom or heteroatomic group selected from S, O, N or NH;

or isomers, tautomers, carriers, metabolites, prodrugs, and pharmaceutically acceptable salts thereof.

According to a preferred embodiment of the invention, the aforementioned library comprises the compounds of formula (I) wherein R is a group $R^a$ and $R_1$ is a group —$NR^cR^d$, wherein $R^a$, $R^b$ and $R^d$ are as above defined.

Within another embodiment the aforementioned library comprises compounds of formula (I) wherein R is a group —$COR^a$ and $R_1$ is a group —$NR^cR^d$, wherein $R^a$, $R^c$ and $R^d$ are as above defined.

Within another embodiment the aforementioned library comprises compounds of formula (I) wherein R is a group —$CONR^aR^b$ and $R_1$ is a group —$NR^cR^d$, wherein $R^a$, $R^b$, $R^c$ and $R^d$ are as above defined.

Within another embodiment the aforementioned library comprises compounds of formula (I) wherein R is a group —$SO_2R^a$ and $R_1$ is a group —$NR^cR^d$, wherein $R^a$, $R^c$ and $R^d$ are as above defined.

Within another embodiment the aforementioned library comprises compounds of formula (I) wherein R is a group —$COOR^a$ and $R_1$ is a group —$NR^cR^d$, wherein $R^a$, $R^c$ and $R^d$ are as above defined.

Within another embodiment the aforementioned library comprises compounds of formula (I) wherein R is as defined in formula (I) and $R_1$ is a group —$OR^c$, wherein $R^c$ is as above defined.

For a general reference to the above libraries of compounds of formula (I) see the experimental section.

From all of the above, it is clear to the skilled man that once a library of pyrrolo[2,3-b]pyridine derivatives is thus prepared, for instance consisting of a few thousands of compounds of formula (I), the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The compounds of formula (I) are active as protein kinase inhibitors and are therefore useful, for instance, to restrict the unregulated proliferation of tumour cells.
In therapy, they are useful in the treatment of various tumours, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of cdk2/Cyclin A Activity

Kinase reaction: 4 μM in house biotinylated histone H1 (Sigma #H-5505) substrate, 10 μM ATP (0.1 microCi $P^{33}\gamma$-ATP), 1.1 nM Cyclin A/CDK2 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: inhibitors were tested at different concentrations ranging from 0.0015 to 10 μM. Experimental data were analyzed by the computer program GraphPad Prizm using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki calculation:

Experimental method: Reaction was carried out in buffer (10 mM Tris, pH 7.5, 10 mM $MgCl_2$—, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq.1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + a \cdot Kb \cdot A + A \cdot B + \alpha \cdot \frac{Ka}{Ki} \cdot I \cdot \left(Kb + \frac{B}{\beta}\right)} \qquad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

In addition the selected compounds are characterized on a panel of ser/thre kinases strictly related to cell cycle (cdk2/cyclin E, cdk1/cyclin B1, cdk5/p25, cdk4/cyclin D1), and also for specificity on MAPK, PKA, EGFR, IGF1-R, Aurora-2 and Cdc 7.

Inhibition Assay of cdk2/Cyclin E Activity

Kinase reaction: 10 μM in house biotinylated histone H1 (Sigma #H-5505) substrate, 30 μM ATP (0.3 microCi $P^{33}\gamma$-ATP), 4 ng GST-Cyclin E/CDK2 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of cdk1/Cyclin B1 Activity

Kinase reaction: 4 μM in house biotinylated histone H1 (Sigma #H-5505) substrate, 20 μM ATP (0.2 microCi $P^{33}\gamma$-ATP), 3 ng Cyan B/CDK1 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After 20 min at r.t. incubation, reaction was stopped by 100 μl PBS+32 mM EDTA+0.1% Triton X-100+500 μM ATP, containing 1 mg SPA beads. Then a volume of 110 μl is transferred to Optiplate.

After 20 min. incubation for substrate capture, 100 μl 5M CsCl were added to allow statification of beads to the top of the Optiplate and let stand 4 hours before radioactivity counting in the Top-Count instrument.

IC50 determination: see above

Inhibition Assay of cdk5/p25 Activity

The inhibition assay of cdk5/p25 activity is performed according to the following protocol.

Kinase reaction: 10 μM biotinylated histone H1 (Sigma #H-5505) substrate, 30 μM ATP (0.3 microCi $P^{33}\gamma$-ATP), 15 ng CDK5/p25 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above
Inhibition Assay of cdk4/Cyclin D1 Activity

Kinase reaction: 0.4 uM μM mouse GST-Rb (769-921) (#sc-4112 from Santa Cruz) substrate, 10 μM ATP (0.5 μCi P$^{333}$γ-ATP), 100 ng of baculovirus expressed GST-cdk4/GST-Cyclin D1, suitable concentrations of inhibitor in a final volume of 50 μl buffer (TRIS HCl 10 mM pH 7.5, MgCl$_2$ 10 mM, 7.5 mM DTT+0.2 mg/ml BSA) were added to each well of a 96 U bottom well plate. After 40 min at 37° C. incubation, reaction was stopped by 20 μl EDTA 120 mM.

Capture: 60 μl were transferred from each well to Multi-Screen plate, to allow substrate binding to phosphocellulose filter. Plates were then washed 3 times with 150 μl/well PBS Ca$^{++}$/Mg$^{++}$ free and filtered by MultiScreen filtration system.

Detection: filters were allowed to dry at 37° C., then 100 μl/well scintillant were added and $^{33}$P labeled Rb fragment was detected by radioactivity counting in the Top-Count instrument.

IC50 determination: see above
Inhibition Assay of MAPK Activity

Kinase reaction: 10 μM in house biotinylated MBP (Sigma #M-1891) substrate, 15 μM ATP (0.15 microCi P$^{33}$γ-ATP), 30 ng GST-MAPK (Upstate Biothecnology #14-173), inhibitor in a final volume of 30 μl buffer (TRIS HCl 10 mM pH 7.5, MgCl$_2$ 10 mM, DTT 7.5 mM+0.2 mg/ml BSA) were added to each well of a 96 U bottom. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above
Inhibition Assay of PKA Activity

Kinase reaction: 10 μM in house biotinylated histone H1 (Sigma #H-5505) substrate, 10 μM ATP (0.2 microM P$^{33}$γ-ATP), 0.45 U PKA (Sigma #2645), inhibitor in a final volume of 30 μl buffer (TRIS HCl 10 mM pH 7.5, MgCl$_2$ 10 mM, DTT 7.5 mM+0.2 mg/ml BSA) were added to each well of a 96 U bottom. After incubation for 90 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above
Inhibition Assay of EGFR Activity

Kinase reaction: 10 μM in house biotinylated MBP (Sigma #M-1891) substrate, 2 μM ATP (0.04 microCi P$^{33}$γ-ATP), 36 ng insect cell expressed GST-EGFR, inhibitor in a final volume of 30 μl buffer (Hepes 50 mM pH 7.5, MgCl$_2$ 3 mM, MnCl$_2$ 3 mM, DTT 1 mM, NaVO$_3$ 3 μM, +0.2 mg/ml BSA) were added to each well of a 96 U bottom. After incubation for 20 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTI-PLATEs containing 100 μl of 5M CsCl. After 4 hours, the plates were read for 2 min in a Packard TOP-Count radioactivity reader.

IC50 determination: see above
Inhibition Assay of IGF1-R Activity

The inhibition assay of IGF1-R activity is performed according to the following protocol.

Enzyme activation: IGF1-R must be activated by auto-phosphorylation before starting the experiment. Just prior to the assay, a concentrated enzyme solution (694 nM) is incubated for half a hour at 28° C. in the presence of 100 μM ATP and then brought to the working dilution in the indicated buffer.

Kinase reaction: 10 μM biotinylated IRS1 peptide (PRIMM) substrate, 0-20 μM inhibitor, 6 μM ATP, 1 microCi $^{33}$P-ATP, and 6 nM GST-IGF1-R (pre-incubated for 30 min at room temperature with cold 60 μM cold ATP) in a final volume of 30 μl buffer (50 mM HEPES pH 7.9, 3 mM MnCl$_2$, 1 mM DTT, 3 μM NaVO$_3$) were added to each well of a 96 U bottom well plate. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

Inhibition Assay of Aurora-2 Activity

Kinase reaction: 8 μM biotinylated peptide (4 repeats of LRRWSLG), 10 μM ATP (0.5 uCi P$^{33}$γ-ATP), 7.5 ng Aurora 2, inhibitor in a final volume of 30 μl buffer (HEPES 50 mM pH 7.0, MgCl$_2$ 10 mM, 1 mM DTT, 0.2 mg/ml BSA, 3 μM orthovanadate) were added to each well of a 96 U bottom well plate. After 60 minutes at room temperature incubation, reaction was stopped and biotinylated peptide captured by adding 100 μl of bead suspension.

Stratification: 100 μl of CsCl2 5 M were added to each well and let stand 4 hour before radioactivity was counted in the Top-Count instrument.

IC50 determination: see above
Inhibition Assay of Cdc7/dbf4 Activity

The inhibition assay of Cdc7/dbf4 activity is performed according to the following protocol.

The Biotin-MCM2 substrate is trans-phosphorylated by the Cdc7/Dbf4 complex in the presence of ATP traced with γ$^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:

10 μl substrate (biotinylated MCM2, 6 μM final concentration)

10 μl enzyme (Cdc7/Dbf4, 17.9 nM final concentration)

10 μl test compound (12 increasing concentrations in the nM to μM range to generate a dose-response curve)

10 μl of a mixture of cold ATP (2 μM final concentration) and radioactive ATP (1/5000 molar ratio with cold ATP) was then used to start the reaction which was allowed to take place at 37° C.

Substrate, enzyme and ATP were diluted in 50 mM HEPES pH 7.9 containing 15 mM MgCl$_2$, 2 mM DTT, 3 μM NaVO$_3$, 2 mM glycerophosphate and 0.2 mg/ml BSA. The solvent for test compounds also contained 10% DMSO.

After incubation for 60 minutes, the reaction was stopped by adding to each well 100 μl of PBS pH 7.4 containing 50 mM EDTA, 1 mM cold ATP, 0.1% Triton X100 and 10 mg/ml streptavidin coated SPA beads.

After 20 min incubation, 110 μL of suspension were withdrawn and transferred into 96-well OPTIPLATEs containing 100 µl of 5M CsCl. After 4 hours, the plates were read for 2 min in a Packard TOP-Count radioactivity reader.

IC50 determination: see above.

The compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) preferably ranges from about 10 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

In addition, the compounds of the invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, rasraf signal transduction pathway inhibitors, cell cycle inhibitors, other cdks inhibitors, tubulin binding agents, topoisomerase I inhibitors, topoisomerase II inhibitors and the like, optionally within liposomal formulations thereof.

If formulated as a fixed dose, such combination products employ the compounds of this invention within the dosage range described above and the other pharmaceutically active agent within the approved dosage range.

Compounds of formula (I) can be used sequentially with known anticancer agents when a combination formulation is inappropriate.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms can contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulfates; and, in general, non-toxic and pharmacologically inactive substances used in pharmaceutical formulations. The pharmaceutical preparations are manufactured using known techniques, for example, by means of mixing, granulating, tabletting, sugar-coating, or film-coating processes.

The liquid dispersions for oral administration also includes e.g. syrups, emulsions and suspensions.

It is preferred that the syrups include, for example, saccharose or saccharose with glycerin and/or mannitol and/or sorbitol as carrier.

It is preferred that the suspensions and the emulsions contain as carrier, for example, a natural gum, agar, sodium alginate, pectin, methylcellulose, carboxymethylcellulose, or polyvinyl alcohol.

The suspension or solutions for intramuscular injections optionally and preferably contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions optionally and preferably contain as carrier, for example, sterile water or preferably they may be in the form of sterile, aqueous, isotonic saline solutions or they may contain as a carrier propylene glycol.

It is preferred that the suppositories contain together with the active compound a pharmaceutically acceptable carrier, e.g. cocoa butter, polyethylene glycol, a polyoxyethylene sorbitan fatty ester surfactant or lecithin.

The following examples are herewith intended to better illustrate the present invention without posing any limitation to it.

Experimental Section

General Methods

Flash Chromatography was performed on silica gel (Merck grade 9395, 60A). The high pressure liquid chromatography retention times (HPLC: r.t. values) were determined by:
Method 1 (HPLC_1):

Instrumentation: Hewlett Packard 1312A binary pump; Gilson 215 autosampler fitted with a 1 ml syringe, Polymer Labs PL1000 Evaporative Light Scattering Detector (ELSD), and a Micromass ZMD mass spectrometer operating in Electrospray positive ionisation mode. The LC eluent is split and approximately 200 µl/min enters the mass spectrometer, 800 µl/min to the ELS.

Chromatographic condition: HPLC mobile phases consisting of 0.1% trifluoroacetic acid in HPLC grade water (A) and 0.1% trifluoroacetic acid in HPLC grade acetonitrile (B). The HPLC gradient is shown in the table below

| Time (minutes) | % A | % B |
| --- | --- | --- |
| 0.0 | 100 | 0 |
| 1.8 | 5 | 95 |
| 2.1 | 5 | 95 |
| 2.3 | 100 | 0 |
| 2.4 | 100 | 0 |

| | |
| --- | --- |
| Run time: | 2.4 minutes (mins) |
| Flow rate: | 1 ml/min |
| Injection vol: | 3 µl |
| Column temperature: | ambient (20° C.) |
| Column: | 50 × 2.0 mm Hypersil C18 BDS; 5 µm |
| ELS Detector: | Nebuliser Temperature 80° C. |
| | Evaporation temperature 90° C. |
| | Gas Flow 1.5 l/hr |
| MS Detector: | m/z 150-800 at 0.5 secs/scan, |
| | 0.1 second interscan delay |
| | Cone voltage 25 V, Source Temp. 140° C. |
| | Drying Gas 350 l/hr |

ELSD retention times (HPLC r.t.) are given in minutes.
Mass are given as m/z ratio.

Method 2 (HPLC__2):

Instrumentation: Waters 2790 HPLC system equipped with a 996 Waters PDA detector and Micromass mod. ZQ single quadrupole mass spectrometer, equipped with an electrospray (ESI) ion source.

Chromatographic condition: RP18 Waters×Terra (4.6×50 mm, 3.5 μl) column; Mobile phase A was ammonium acetate 5 mM buffer (pH 5.5 with acetic acid/acetonitrile 95:5), and Mobile phase B was $H_2$/acetonitrile (5:95). Gradient from 10 to 90% B in 8 minutes, hold 90% B 2 minutes. UV detection at 220 nm and 254 nm. Flow rate 1 ml/min. Injection volume 10 μl. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

When necessary, the compounds have been purified by preparative HPLC on a Waters Symmetry C18 (19×50 mm, 5 μm) column using a Waters preparative HPLC 600 equipped with a 996 Waters PDA detector and a Micromass mod. ZQ single quadrupole mass spectrometer, electron spray ionization, positive mode. Mobile phase A was water 0.01% trifluoroacetic acid (TFA), and Mobile phase B was acetonitrile. Gradient from 10 to 90% B in 8 min, hold 90% B 2 min. Flow rate 20 ml/min.

1H-NMR spectrometry was performed on a Bruker AVANCE 400 MHz single bay instrument with gradients. It is equipped with a QNP probe (interchangeable 4 nuclei probe—1H, 13C, 19F and 31P) (NMR method 1) or on a Mercury VX 400 operating at 400.45 MHz equipped with a 5 mm double resonance probe [1H (15N-31P) ID_PFG Varian] (NMR method 2).

As formerly indicated, several pyrrolo-pyridine derivatives of formula (I) of the invention (also shortly identified as azaindoles) have been synthesized in parallel, according to combinatorial chemistry techniques.

In this respect, some compounds thus prepared have been conveniently and unambiguously identified, as per the coding system of tables III and from V to VIII, together with HPLC retention time (methods 1 and 2) and mass. Table IV, instead, refers to analytical NMR data for some representative compounds of formula (I) of the library.

Each code, which identifies a single specific compound of formula (I), consists of three units A-M-B.

A represents any substituent $R_1$— [see formula (I)] and is attached to the rest of the azaindole moiety through the carbon atom so as to get azaindole derivatives being substituted in position 3 (A-M-B); each A radical (substituent) is represented in the following table I.

B represents any substituent R— [see formula (I)] and is attached to the rest of the azaindole moiety through the nitrogen atom so as to get azaindole derivatives being substituted in position 5 (A-M-B); each B radical (substituent) is represented in the following table II.

M refers to the central core of the divalent 3-carboxy-azaindole moiety having the —N— group in position 5, substituted by groups A and B.

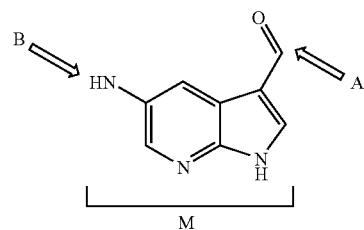

For ease of reference, each A or B groups of tables I and II has been identified with the proper chemical formula also indicating the point of attachment with the rest of the molecule M.

Just as an example, the compound A21-M-B10 of table V (see entry 3162) represents an azaindole M being substituted in position 5 by the group B10 and in position 3 (through the —NH— group) by the group A21; likewise, the compound A10-M-B70 of table III (see entry 2083) represents an azaindole M being substituted in position 5 by the group B70 and in position 3 (through the —NH— group) by the group A10:

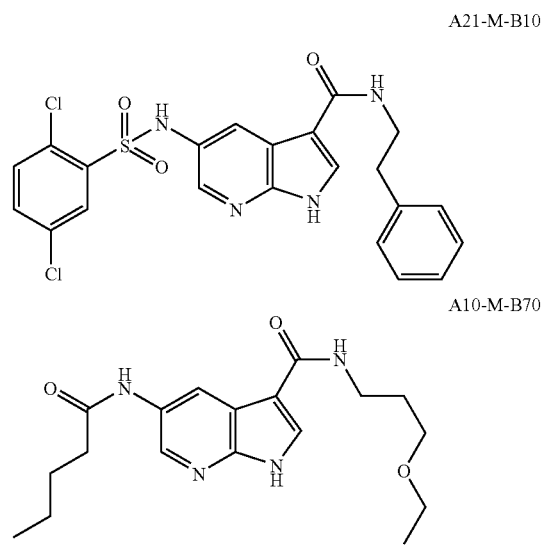

TABLE I

| A groups | |
|---|---|
| Fragment | Code |
| ![cyclohexyl-NH-M] | A1 |
| ![M-NH-benzyl] | A2 |

TABLE I-continued
| A groups | |
|---|---|
| Fragment | Code |
| 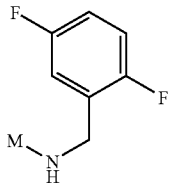 | A3 |
| 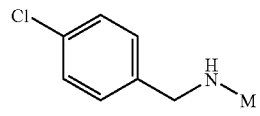 | A4 |
| 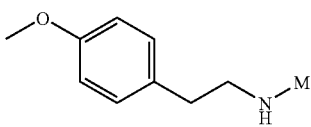 | A5 |
| 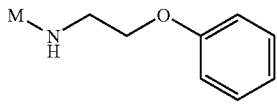 | A6 |
| 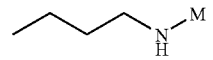 | A7 |
| 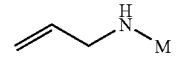 | A8 |
| 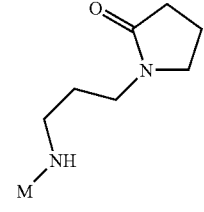 | A9 |
| 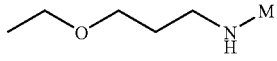 | A10 |
| 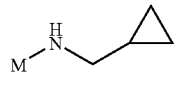 | A11 |
| 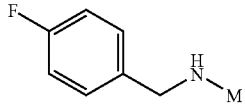 | A12 |
| 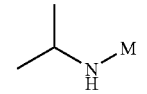 | A13 |
| 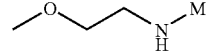 | A14 |
| 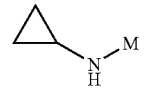 | A15 |
| 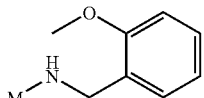 | A16 |
| 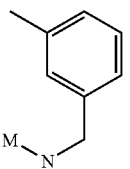 | A17 |
| 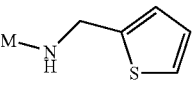 | A18 |
| 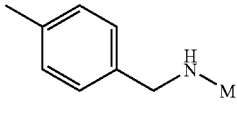 | A19 |
| 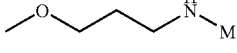 | A20 |
| 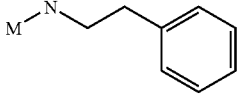 | A21 |
| 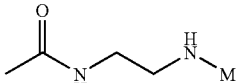 | A22 |
| 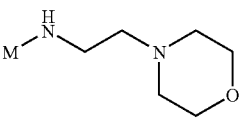 | A23 |
| 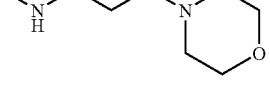 | A24 |
| 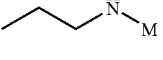 | A25 |
| 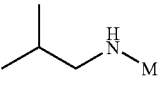 | A26 |
| 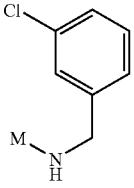 | A27 |

TABLE I-continued
A groups
| Fragment | Code |
|---|---|
| 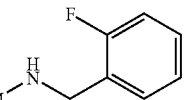 | A28 |
| 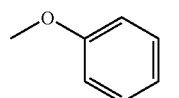 | A29 |
| 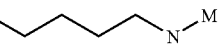 | A30 |
| 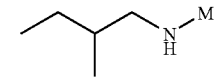 | A31 |
| 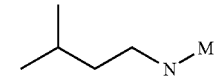 | A32 |
| 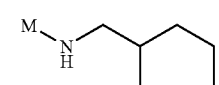 | A33 |
| 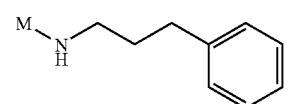 | A34 |
| 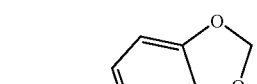 | A35 |
| 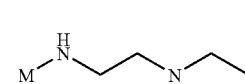 | A36 |
| 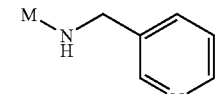 | A37 |
| 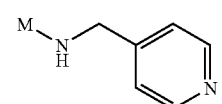 | A38 |
| 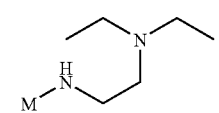 | A39 |
| 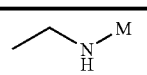 | A40 |
| 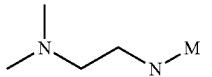 | A41 |
| 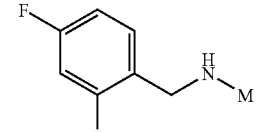 | A42 |
| 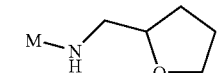 | A43 |
| 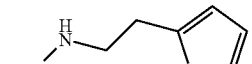 | A44 |
| 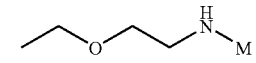 | A45 |
| 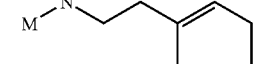 | A46 |
| 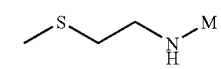 | A47 |
| 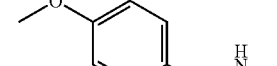 | A48 |
| 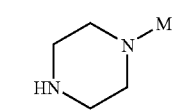 | A50 |
|  | A51 |
| 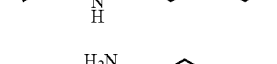 | A52 |
| 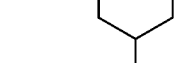 | A53 |

TABLE I-continued

A groups

| Fragment | Code |
|---|---|
| (structure) | A54 |
| (structure) | A55 |
| (structure) | A56 |
| (structure) | A57 |
| (structure) | A58 |

TABLE II

B groups

| Fragment | Code |
|---|---|
| (structure) | B1 |
| (structure) | B2 |
| (structure) | B3 |
| (structure) | B4 |
| (structure) | B5 |

TABLE II-continued

B groups

| Fragment | Code |
|---|---|
| (structure) | B6 |
| (structure) | B7 |
| (structure) | B8 |
| (structure) | B9 |
| (structure) | B10 |
| (structure) | B11 |
| (structure) | B12 |
| (structure) | B13 |
| (structure) | B14 |

TABLE II-continued

B groups

| Fragment | Code |
|---|---|
| phenylsulfonyl (M-SO₂-C₆H₅) | B15 |
| 4-fluorophenylsulfonyl | B16 |
| 5-bromothiophene-2-sulfonyl | B17 |
| naphthalene-1-sulfonyl | B18 |
| naphthalene-2-sulfonyl | B19 |
| 3,5-dichlorophenylsulfonyl | B20 |
| isopropylsulfonyl | B21 |
| 3,4-dimethoxyphenylsulfonyl | B22 |
| 3,4-dichlorophenylsulfonyl | B23 |
| 2-fluorophenylsulfonyl | B24 |
| benzoyl | B25 |
| pivaloyl (2,2-dimethylpropanoyl) | B26 |
| phenylacetyl | B27 |
| cyclohexanecarbonyl | B28 |
| acetyl | B29 |
| 3-cyclopentylpropanoyl | B30 |
| 3-chlorobenzoyl | B31 |
| 2-(4-methoxyphenyl)acetyl | B32 |
| butanoyl | B33 |
| 3-(trifluoromethyl)benzoyl | B34 |

TABLE II-continued

B groups

| Fragment | Code |
|---|---|
| (benzo[d][1,3]dioxol-5-yl)carbonyl- | B35 |
| (4-tert-butylphenyl)carbonyl- | B36 |
| propanoyl- | B37 |
| (isoxazol-5-yl)carbonyl- | B38 |
| phenoxyacetyl- | B39 |
| (4-methylphenyl)carbonyl- | B40 |
| 3,3-dimethylbutanoyl- | B41 |
| (4-fluorophenyl)carbonyl- | B42 |
| (2,4,6-trichlorophenyl)carbonyl- | B43 |
| (thiophen-2-yl)carbonyl- | B44 |
| (3,4-dimethoxyphenyl)acetyl- | B45 |
| cyclopropanecarbonyl- | B46 |
| (4-methoxyphenyl)carbonyl- | B47 |
| (3,5-difluorophenyl)carbonyl- | B48 |
| (2-methoxyphenyl)carbonyl- | B49 |
| (3,5-dimethylisoxazol-4-yl)carbonyl- | B50 |
| isobutyryl- | B51 |
| 3-methylbutanoyl- | B52 |
| (2,4-dimethoxyphenyl)carbonyl- | B53 |
| (2-fluorophenyl)carbonyl- | B54 |

TABLE II-continued
B groups
| Fragment | Code |
|---|---|
| 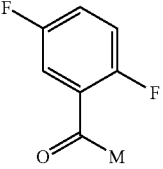 | B55 |
| 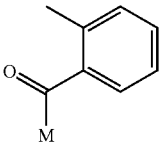 | B56 |
| 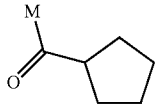 | B57 |
| 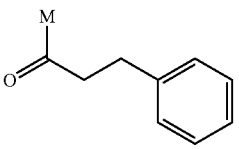 | B58 |
| 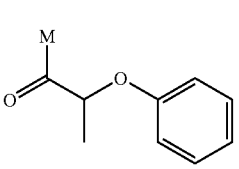 | B59 |
| 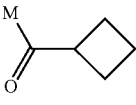 | B60 |
| 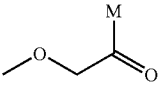 | B61 |
| 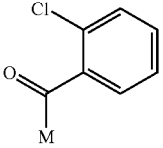 | B62 |
| 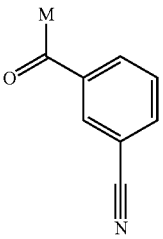 | B63 |
| 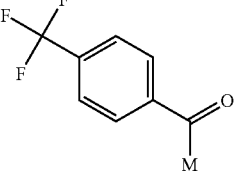 | B64 |
| 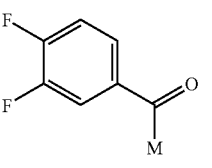 | B65 |
| 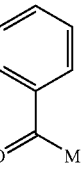 | B66 |
| 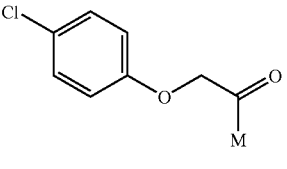 | B67 |
| 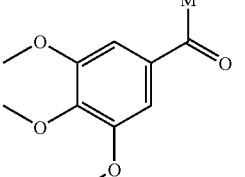 | B68 |
| 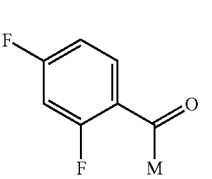 | B69 |
| 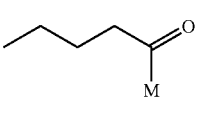 | B70 |
| 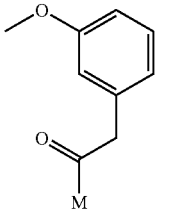 | B71 |

TABLE II-continued
| B groups | |
|---|---|
| Fragment | Code |
| 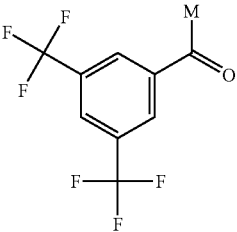 | B72 |
| 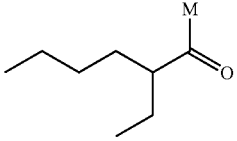 | B73 |
| 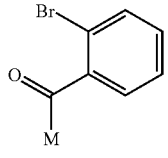 | B74 |
| 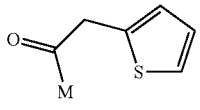 | B75 |
| 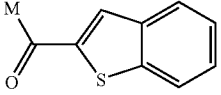 | B76 |
| 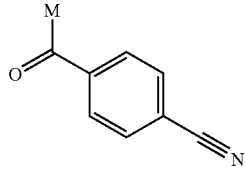 | B77 |
| 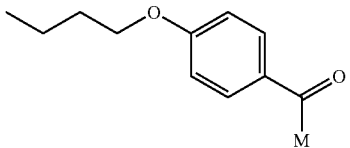 | B78 |
| 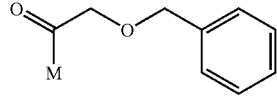 | B79 |
| 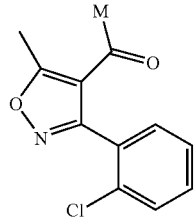 | B80 |
TABLE II-continued
| B groups | |
|---|---|
| Fragment | Code |
| 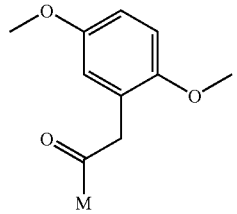 | B81 |
| 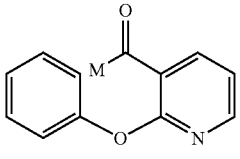 | B82 |
| 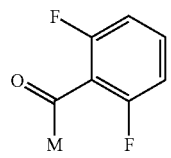 | B83 |
| 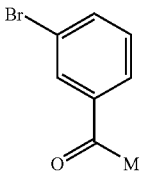 | B84 |
| 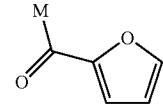 | B85 |
| 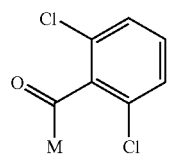 | B86 |
| 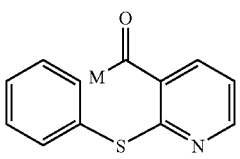 | B87 |
| 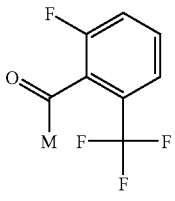 | B88 |

TABLE II-continued

B groups

| Fragment | Code |
|---|---|
| (4-chlorophenyl-5-propyl-pyrazole-4-carbonyl, M at carbonyl) | B89 |
| 4-fluorophenylacetyl (M) | B90 |
| cyclopentylacetyl (M) | B91 |
| 4-phenoxybutanoyl (M) | B92 |
| 4-chlorophenylacetyl (M) | B93 |
| 3,5-dichlorobenzoyl (M) | B94 |
| 5-bromopyridine-3-carbonyl (M) | B95 |
| piperidine-1-carbonyl (M) | B96 |
| N-propyl carbamoyl (M) | B97 |
| N-benzyl carbamoyl (M) | B98 |
| piperazine-1-carbonyl (NH free) (M) | B99 |
| N-[3-(imidazol-1-yl)propyl] carbamoyl (M) | B100 |
| N-(4-fluorobenzyl) carbamoyl (M) | B101 |
| N-(pentan-3-yl) carbamoyl (M) | B102 |
| N-butyl carbamoyl (M) | B103 |
| N-(4-methylbenzyl) carbamoyl (M) | B104 |
| N-[2-(trifluoromethyl)benzyl] carbamoyl (M) | B105 |
| N-(2-fluorobenzyl) carbamoyl (M) | B106 |
| N-(2-methylbenzyl) carbamoyl (M) | B107 |
| N-[5-(diethylamino)pentan-2-yl] carbamoyl (M) | B108 |

TABLE II-continued

B groups

| Fragment | Code |
|---|---|
| (structure) | B109 |
| (structure) | B110 |
| (structure) | B111 |
| (structure) | B112 |
| (structure) | B113 |
| (structure) | B114 |
| (structure) | B115 |
| (structure) | B116 |
| (structure) | B117 |
| (structure) | B118 |
| (structure) | B119 |
| (structure) | B120 |
| (structure) | B121 |
| (structure) | B122 |
| (structure) | B123 |
| (structure) | B124 |
| (structure) | B125 |
| (structure) | B126 |
| (structure) | B127 |
| (structure) | B128 |

TABLE II-continued

B groups

| Fragment | Code |
|---|---|
| (furan-2-yl-carbonyl-piperazine-carbonyl-M) | B129 |
| (M-C(O)-NH-CH2CH2-imidazolidin-2-one) | B130 |
| (M-C(O)-thiomorpholine) | B131 |
| (M-C(O)-piperazine-N-benzyl) | B132 |
| (M-C(O)-N(ethyl)-CH2-pyridin-4-yl) | B133 |
| (M-C(O)-4-(piperidin-1-yl)piperidine) | B134 |
| (ethoxy-CH2CH2CH2-NH-C(O)-M) | B135 |
| (M-C(O)-NH-2-methylcyclohexyl) | B136 |
| (3-hydroxy-piperidine-1-C(O)-M) | B137 |
| (M-C(O)-NH-CH2CH2CH2-N(ethyl)2) | B138 |
| (3,5-dimethyl-piperazine-C(O)-M) | B139 |
| (isopropoxy-CH2CH2CH2-NH-C(O)-M) | B140 |
| (M-C(O)-NH-CH2CH2-N(isopropyl)2) | B141 |
| (HO-CH2CH2-N-piperazine-C(O)-M) | B142 |
| ((CH3)2N-CH2CH2CH2-NH-C(O)-M) | B143 |
| (pentyl-NH-C(O)-M) | B144 |
| H | B145 |
| (M-C(O)-CHF-phenyl) | B146 |
| (4-Cl-phenyl-cyclopropyl-C(O)-M) | B147 |
| ((CH3)2N-C(O)-CH2CH2-C(O)-M) | B148 |

TABLE II-continued

B groups

| Fragment | Code |
|---|---|
| (structure) | B149 |
| (structure) | B150 |
| (structure) | B151 |
| (structure) | B152 |
| (structure) | B153 |
| (structure) | B154 |
| (structure) | B155 |

Example 1

Preparation of methyl 5-nitro-1-(phenylsulfonyl)-1H-pyrrolo[2,3-b]pyridine-3-carboxylate To an ice-cooled solution of 187.7 g (0.616 mol) of tetrabutylammonium nitrate in 2.07 L of dichloromethane, trifluoroacetic anhydride (85.7 mL, 0.616 mol) was added dropwise over a period of 25 minutes, under nitrogen. This mixture was slowly transferred, via cannula, to a preformed solution of 150.0 g (0.474 mol) of 1-(phenylsulfonyl)-1H-pyrrolo[2,3-b]pyridine-3-carboxylic acid methyl ester in 2.7 L of dichloromethane at +4° C. The reaction mixture was stirred at +4° C. for 4 hours and then kept at this temperature for additional 23 hours. The cold reaction mass was poured in 2.3 L of water and stirred for 1 hour. The aqueous layer was separated and extracted again with 1 L of dichloromethane. The combined organic extracts were concentrated under vacuum to a thick yellow suspension, which was treated with 1.05 L of methanol. The slurry was cooled at 0° C. and stirred for further 1 hour before it was filtered, washed with methanol and dried to afford 128 g of pure title compound as a woolly yellow solid (Yield=74.7%). m.p.=195-196° C.

$^1$H-NMR-method 2 (DMSO): 3.91 (s, 3H), 7.64-7.69 (m, 2H), 7.76-7.81 (m, 1H), 8.25-8.27 (m, 2H), 8.74 (s, 1H), 8.96 (d, 1H, J=2.58 Hz), 9.27 (d, 1H, J=2.58 Hz).

Example 2

Preparation of disodium 5-nitro-1H-pyrrolo[2,3-b]pyridine-3-carboxylate

To a suspension of 95.7 g (0.265 mol) of the compound of example 1 in 1.34 L of 2,2,2-trifluoroethanol, 0.545 L of 17% NaOH were added over a period of 40 minutes under vigorous stirring. The yellow-orange mixture was heated at reflux for 16 hours and then it was cooled to 0° C. and stirred for 2 additional hours. The precipitate was filtered off, washed with acetone and dried to afford 79.8 g of the title compound as an orange crystalline solid (Yield=93.1% as tetrahydrate). m.p.>230° C.

$^1$H-NMR-method 2 (DMSO): 7.83 (bs, 1H), 8.89 (d, 1H, J=2.80 Hz), 9.07 (bs, 1H).

Example 3

Preparation of 5-nitro-1H-pyrrolo[2,3-b]pyridine-3-carboxylic acid

To a clear solution of the compound of example 2 (88.10 g, 0.35 mol) in 2.65 L of water, it was added dropwise concentrated HCl (52.6 mL, 0.526 mol) diluted with 105 mL of water over a period of 50 minutes under efficient stirring at ambient temperature. The resulting suspension was cooled at +4° C. and stirred for further 1 hour. The precipitate was filtered off, washed with water and finally dried to give 55.6 g of the title compound as a light-yellow powder (Yield=98.5% (title 95%)).

m.p.=282-285° C. dec.

$^1$H-NMR-method 2 (DMSO): 8.41 (d, 1H, J=2.83 Hz), 9.00 (d, 1H, J=2.59 Hz), 9.16 (d, 1H, J=2.59 Hz), 12.5-13.0 (bs, 1H), 13.14 (s, 1H).

Example 4

Loading of Isoamylamine (Corresponding to Fragment A32 of Table I) onto Acid Sensitive Methoxy Benzaldehyde Polystyrene Resin (AMEBA Resin)

4-(4-Formyl-3-methoxyphenoxy)butyryl AM resin [copoly(styrene-1% dvb) 100-200 mesh] (1.5 g, 1 eq, loading 0.94 mmol/g) was swollen in DCM and then filtered. A mixture of THF/DCM (4:1, 15 ml), isoamylamine (6 eq.) and AcOH (6 eq.) were added. After 15 minutes, NaBH(OAc)$_3$ was added and the reaction was shaken over night at room

Example 5

Preparation of A32-M-B47

Step (a): Loading of the 7-Azaindole Scaffold (Title Compound of Example 3) onto the Resin of Example 4

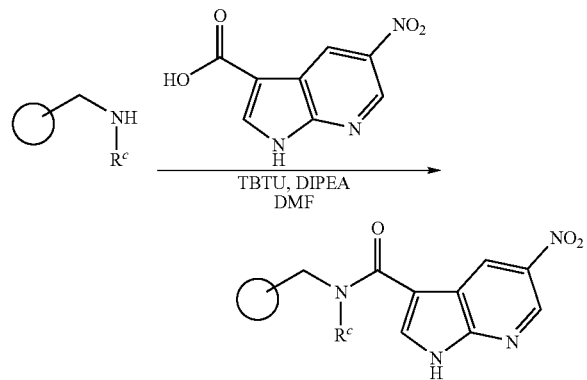

To the resin of example 4 (10 g, 0.77 mmol/g, 7.7 mmol) in anhydrous DMF (100 ml) it was added 3-carboxy-5-nitro-7-azaindole (2.39 g, 11.55 mmol), TBTU (3.71 g, 11.55 mmol) and DIPEA (2.92 g, 23.10 mmol). The reaction mixture was shaken at room temperature for 20 hours and then the resin was isolated by filtration. The resin was washed sequentially with DMF (100 ml), DCM (100 ml), DMF (100 ml), DCM (100 ml), MeOH (100 ml), DCM (100 ml), MeOH (100 ml), DCM (100 ml), MeOH (100 ml) and TBME (100 ml×2) and dried in vacuo to give the resin bound 7-azaindole (11.30 g).

Resin Loading Check

Resin loading check was carried out to demonstrate the complete loading of the building block onto the resin and that no oligomerization has occurred whilst coupling with TBTU. Benzoyl chloride was used in order to cap unreacted resin loaded amine (i.e. isoamylamine, for example 5) and to acylate the 1-NH azaindole. The absence of benzamide (i.e. isoamylbenzamide, for example 5) in the cleaved mixture demonstrates the quantitative loading of the scaffold onto the resin. The presence of 1-N-benzoylazaindole or of 1-NH-azaindole, demonstrate that no homocoupling of the 3-carboxy-5-nitro-7-azaindole has occurred during the resin loading step.

To the resin obtained following the procedure described in example 5 (step a) (0.035 g, 0.027 mmol) in DCM (1 ml), DIPEA (0.035 g, 0.265 mmol) and benzoyl chloride (0.038 g, 0.265 mmol) were added. The reaction mixture was shaken for 4 hours and the resin isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (1 ml of 60% TFA/DCM for 20 minutes) to give an off white solid (0.008 g, 80%). LCMS (shows a mixture of the 1-N-benzoylated azaindole and the 1-NH azaindole): m/z 277 [M+H]$^+$, m/z 318 [M+MeCN+H]$^+$ (17% purity at 215 nm) and m/z 381 [M+H]$^+$, m/z 422 [M+MeCN+H]$^+$ and m/z 761 [2M+H]$^+$ at r.t. 2.04 min (74% purity at 215 nm).

Step b: Reduction of Nitro Group

To the resin obtained in step (a) (11 g, 7.5 mmol) in NMP (100 ml), tin(II) chloride dihydrate (15.94 g, 77 mmol) was added. The reaction mixture was shaken at room temperature for 20 hours and then the resin was isolated by filtration. The resin was washed sequentially with DMF (100 ml), DCM (100 ml), DMF (100 ml), DCM (100 ml), MeOH (100 ml), water (100 ml), MeOH (100 ml), DCM (100 ml), MeOH (100 ml), DCM (100 ml), MeOH (100 ml), TBME (100 ml×2) and dried in vacuo to give the resin bound azaindole (11.05 g). 0.01 g of resin were cleaved with 1 ml of 60% TFA/DCM for 20 minutes, to give an off-white solid (0.0014 g, 74%). LCMS: m/z 247 [M+H]$^+$ and m/z 288 [M+MeCN+H]$^+$ at r.t. 1.35 min (96% purity at 215 nm).

Step c: Capping with Acid Chlorides

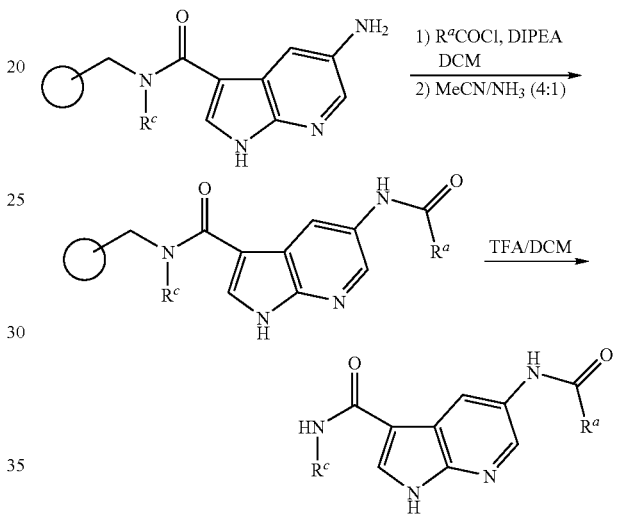

To the resin of step (b) (0.11 g, 0.075 mmol) in DCM (1 ml), it was added Hunig's base (0.050 g, 0.385 mmol) followed by 4-methoxybenzoyl chloride (corresponding to fragment B47 of Table II, 0.065 g, 0.385 mmol). The reaction mixture was shaken at room temperature for 20 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried.

The resin was shaken in an acetonitrile/ammonia solution (1 ml, 4:1) for 4 hours and then isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (60% TFA/DCM, 3×(3×0.5 ml)) to give an off white solid (0.016 g, 55%) of formula (I) corresponding to A32-M-B47 (see entry 964 of table III below).

$^1$H NMR-method 1 (MeOH d-4): 8.75 (1H, d, 2.3 Hz), 8.67 (1H, s), 7.97 (1H, s), 7.85 (2H, d, 8.8 Hz), 6.92 (2H, d, 8.9 Hz), 3.75 (3H, s), 3.39 (2H, t, 7.5 Hz), 1.62-1.52 (1H, m), 1.44-1.37 (2H, m), 0.85 (6H, d, 6.6 Hz), indole and amide NHs were not observed;

LCMS (HPLC_1): m/z 381 [M+]$^+$ at r.t. 1.24 min (100% by ELS detection).

Following the procedure described above, that is by starting from any suitable amino derivative being supported onto the resin according to example 4, and by working as per previous steps from (a) to (c) of example 5 in the presence of any suitable acyl chloride derivative, the following compounds of table III (i.e. library) were prepared:

TABLE III

| Entry | Compound | HPLC method | r.t. (min) | [M + H]+ |
|---|---|---|---|---|
| 1 | A12-M-B25 | HPLC_1 | 1.24 | 389 |
| 2 | A12-M-B26 | HPLC_1 | 1.21 | 369 |
| 3 | A12-M-B27 | HPLC_1 | 1.25 | 403 |
| 4 | A12-M-B28 | HPLC_1 | 1.3 | 395 |
| 5 | A12-M-B29 | HPLC_1 | 1 | 327 |
| 6 | A12-M-B30 | HPLC_1 | 1.39 | 409 |
| 7 | A12-M-B31 | HPLC_1 | 1.34 | 423 |
| 8 | A12-M-B32 | HPLC_1 | 1.25 | 433 |
| 9 | A12-M-B33 | HPLC_1 | 1.14 | 355 |
| 10 | A12-M-B34 | HPLC_1 | 1.39 | 457 |
| 11 | A12-M-B35 | HPLC_1 | 1.24 | 433 |
| 12 | A12-M-B36 | HPLC_1 | 1.49 | 445 |
| 13 | A13-M-B25 | HPLC_1 | 1.05 | 323 |
| 14 | A13-M-B26 | HPLC_1 | 1.01 | 303 |
| 15 | A13-M-B27 | HPLC_1 | 1.09 | 337 |
| 16 | A13-M-B28 | HPLC_1 | 1.12 | 329 |
| 17 | A13-M-B29 | HPLC_1 | 0.79 | 261 |
| 18 | A13-M-B30 | HPLC_1 | 1.24 | 343 |
| 19 | A13-M-B31 | HPLC_1 | 1.18 | 357 |
| 20 | A13-M-B32 | HPLC_1 | 1.08 | 367 |
| 21 | A13-M-B33 | HPLC_1 | 0.94 | 289 |
| 22 | A13-M-B34 | HPLC_1 | 1.25 | 391 |
| 23 | A13-M-B35 | HPLC_1 | 1.06 | 367 |
| 24 | A13-M-B36 | HPLC_1 | 1.36 | 379 |
| 25 | A14-M-B25 | HPLC_1 | 0.97 | 339 |
| 26 | A14-M-B26 | HPLC_1 | 0.92 | 319 |
| 27 | A14-M-B27 | HPLC_1 | 1 | 353 |
| 28 | A14-M-B28 | HPLC_1 | 1.04 | 345 |
| 29 | A14-M-B30 | HPLC_1 | 1.16 | 359 |
| 30 | A14-M-B31 | HPLC_1 | 1.1 | 373 |
| 31 | A14-M-B32 | HPLC_1 | 1 | 383 |
| 32 | A14-M-B33 | HPLC_1 | 0.86 | 305 |
| 33 | A14-M-B34 | HPLC_1 | 1.17 | 407 |
| 34 | A14-M-B35 | HPLC_1 | 0.98 | 383 |
| 35 | A14-M-B36 | HPLC_1 | 1.28 | 395 |
| 36 | A15-M-B25 | HPLC_1 | 0.99 | 321 |
| 37 | A15-M-B26 | HPLC_1 | 0.95 | 301 |
| 38 | A15-M-B27 | HPLC_1 | 1.02 | 335 |
| 39 | A15-M-B28 | HPLC_1 | 1.06 | 327 |
| 40 | A15-M-B29 | HPLC_1 | 0.74 | 259 |
| 41 | A15-M-B30 | HPLC_1 | 1.18 | 341 |
| 42 | A15-M-B31 | HPLC_1 | 1.13 | 355 |
| 43 | A15-M-B32 | HPLC_1 | 1.03 | 365 |
| 44 | A15-M-B33 | HPLC_1 | 0.87 | 287 |
| 45 | A15-M-B34 | HPLC_1 | 1.2 | 389 |
| 46 | A15-M-B35 | HPLC_1 | 1 | 365 |
| 47 | A15-M-B36 | HPLC_1 | 1.3 | 377 |
| 48 | A16-M-B25 | HPLC_1 | 1.23 | 401 |
| 49 | A16-M-B28 | HPLC_1 | 1.29 | 407 |
| 50 | A16-M-B29 | HPLC_1 | 1 | 339 |
| 51 | A16-M-B30 | HPLC_1 | 1.39 | 421 |
| 52 | A16-M-B31 | HPLC_1 | 1.34 | 435 |
| 53 | A16-M-B32 | HPLC_1 | 1.24 | 445 |
| 54 | A16-M-B33 | HPLC_1 | 1.14 | 367 |
| 55 | A16-M-B34 | HPLC_1 | 1.39 | 469 |
| 56 | A17-M-B25 | HPLC_1 | 1.27 | 385 |
| 57 | A17-M-B26 | HPLC_1 | 1.26 | 365 |
| 58 | A17-M-B27 | HPLC_1 | 1.29 | 399 |
| 59 | A17-M-B28 | HPLC_1 | 1.34 | 391 |
| 60 | A17-M-B29 | HPLC_1 | 1.05 | 323 |
| 61 | A17-M-B30 | HPLC_1 | 1.43 | 405 |
| 62 | A17-M-B31 | HPLC_1 | 1.38 | 419 |
| 63 | A17-M-B32 | HPLC_1 | 1.29 | 429 |
| 64 | A17-M-B33 | HPLC_1 | 1.18 | 351 |
| 65 | A17-M-B34 | HPLC_1 | 1.43 | 453 |
| 66 | A17-M-B35 | HPLC_1 | 1.28 | 429 |
| 67 | A12-M-B37 | HPLC_1 | 1.07 | 341 |
| 68 | A12-M-B38 | HPLC_1 | 1.11 | 380 |
| 69 | A13-M-B39 | HPLC_1 | 1.14 | 353 |
| 70 | A13-M-B40 | HPLC_1 | 1.14 | 337 |
| 71 | A13-M-B41 | HPLC_1 | 1.09 | 317 |
| 72 | A13-M-B42 | HPLC_1 | 1.1 | 341 |
| 73 | A13-M-B43 | HPLC_1 | 1.27 | 425 |
| 74 | A13-M-B44 | HPLC_1 | 1.03 | 329 |
| 75 | A13-M-B45 | HPLC_1 | 1.02 | 397 |
| 76 | A13-M-B46 | HPLC_1 | 0.9 | 287 |
| 77 | A13-M-B47 | HPLC_1 | 1.08 | 353 |
| 78 | A13-M-B37 | HPLC_1 | 0.86 | 275 |
| 79 | A13-M-B38 | HPLC_1 | 0.9 | 314 |
| 80 | A14-M-B39 | HPLC_1 | 1.06 | 369 |
| 81 | A14-M-B40 | HPLC_1 | 1.05 | 353 |
| 82 | A14-M-B41 | HPLC_1 | 1 | 333 |
| 83 | A14-M-B42 | HPLC_1 | 1.02 | 357 |
| 84 | A14-M-B43 | HPLC_1 | 1.18 | 441 |
| 85 | A14-M-B44 | HPLC_1 | 0.94 | 345 |
| 86 | A14-M-B45 | HPLC_1 | 0.94 | 413 |
| 87 | A14-M-B46 | HPLC_1 | 0.83 | 303 |
| 88 | A14-M-B47 | HPLC_1 | 0.99 | 369 |
| 89 | A14-M-B37 | HPLC_1 | 0.77 | 291 |
| 90 | A14-M-B38 | HPLC_1 | 0.81 | 330 |
| 91 | A15-M-B39 | HPLC_1 | 1.09 | 351 |
| 92 | A15-M-B41 | HPLC_1 | 1.03 | 315 |
| 93 | A15-M-B42 | HPLC_1 | 1.04 | 339 |
| 94 | A15-M-B44 | HPLC_1 | 0.97 | 327 |
| 95 | A15-M-B45 | HPLC_1 | 0.96 | 395 |
| 96 | A15-M-B46 | HPLC_1 | 0.84 | 285 |
| 97 | A15-M-B47 | HPLC_1 | 1.02 | 351 |
| 98 | A15-M-B37 | HPLC_1 | 0.79 | 273 |
| 99 | A15-M-B38 | HPLC_1 | 0.84 | 312 |
| 100 | A16-M-B40 | HPLC_1 | 1.3 | 415 |
| 101 | A16-M-B41 | HPLC_1 | 1.27 | 395 |
| 102 | A16-M-B42 | HPLC_1 | 1.27 | 419 |
| 103 | A16-M-B44 | HPLC_1 | 1.22 | 407 |
| 104 | A16-M-B45 | HPLC_1 | 1.18 | 475 |
| 105 | A16-M-B46 | HPLC_1 | 1.11 | 365 |
| 106 | A16-M-B47 | HPLC_1 | 1.24 | 431 |
| 107 | A16-M-B37 | HPLC_1 | 1.07 | 353 |
| 108 | A17-M-B39 | HPLC_1 | 1.34 | 415 |
| 109 | A17-M-B41 | HPLC_1 | 1.32 | 379 |
| 110 | A17-M-B42 | HPLC_1 | 1.32 | 403 |
| 111 | A17-M-B43 | HPLC_1 | 1.45 | 487 |
| 112 | A17-M-B44 | HPLC_1 | 1.27 | 391 |
| 113 | A17-M-B45 | HPLC_1 | 1.22 | 459 |
| 114 | A17-M-B46 | HPLC_1 | 1.16 | 349 |
| 115 | A17-M-B47 | HPLC_1 | 1.29 | 415 |
| 116 | A17-M-B37 | HPLC_1 | 1.12 | 337 |
| 117 | A17-M-B38 | HPLC_1 | 1.15 | 376 |
| 118 | A18-M-B45 | HPLC_1 | 1.13 | 451 |
| 119 | A18-M-B37 | HPLC_1 | 1 | 329 |
| 120 | A12-M-B48 | HPLC_1 | 1.33 | 425 |
| 121 | A12-M-B49 | HPLC_1 | 1.29 | 419 |
| 122 | A12-M-B50 | HPLC_1 | 1.16 | 408 |
| 123 | A12-M-B51 | HPLC_1 | 1.14 | 355 |
| 124 | A12-M-B52 | HPLC_1 | 1.21 | 369 |
| 125 | A12-M-B53 | HPLC_1 | 1.31 | 449 |
| 126 | A12-M-B54 | HPLC_1 | 1.24 | 407 |
| 127 | A12-M-B55 | HPLC_1 | 1.28 | 425 |
| 128 | A12-M-B56 | HPLC_1 | 1.27 | 403 |
| 129 | A12-M-B57 | HPLC_1 | 1.24 | 381 |
| 130 | A12-M-B58 | HPLC_1 | 1.3 | 417 |
| 131 | A13-M-B48 | HPLC_1 | 1.17 | 359 |
| 132 | A13-M-B49 | HPLC_1 | 1.11 | 353 |
| 133 | A13-M-B50 | HPLC_1 | 0.97 | 342 |
| 134 | A13-M-B51 | HPLC_1 | 0.93 | 289 |
| 135 | A13-M-B52 | HPLC_1 | 1.02 | 303 |
| 136 | A13-M-B53 | HPLC_1 | 1.15 | 383 |
| 137 | A13-M-B54 | HPLC_1 | 1.06 | 341 |
| 138 | A13-M-B55 | HPLC_1 | 1.1 | 359 |
| 139 | A13-M-B56 | HPLC_1 | 1.09 | 337 |
| 140 | A13-M-B58 | HPLC_1 | 1.14 | 351 |
| 141 | A14-M-B48 | HPLC_1 | 1.08 | 375 |
| 142 | A14-M-B49 | HPLC_1 | 1.03 | 369 |
| 143 | A14-M-B50 | HPLC_1 | 0.88 | 358 |
| 144 | A14-M-B51 | HPLC_1 | 0.85 | 305 |
| 145 | A14-M-B52 | HPLC_1 | 0.94 | 319 |
| 146 | A14-M-B54 | HPLC_1 | 0.97 | 357 |
| 147 | A14-M-B55 | HPLC_1 | 1.01 | 375 |
| 148 | A14-M-B56 | HPLC_1 | 1 | 353 |
| 149 | A14-M-B57 | HPLC_1 | 0.97 | 331 |

TABLE III-continued

| Entry | Compound | HPLC method | r.t. (min) | [M + H]+ |
|---|---|---|---|---|
| 150 | A14-M-B58 | HPLC_1 | 1.07 | 367 |
| 151 | A15-M-B48 | HPLC_1 | 1.11 | 357 |
| 152 | A19-M-B58 | HPLC_1 | 1.34 | 413 |
| 153 | A20-M-B48 | HPLC_1 | 1.12 | 389 |
| 154 | A20-M-B49 | HPLC_1 | 1.07 | 383 |
| 155 | A15-M-B51 | HPLC_1 | 0.87 | 287 |
| 156 | A15-M-B52 | HPLC_1 | 0.96 | 301 |
| 157 | A15-M-B55 | HPLC_1 | 1.04 | 357 |
| 158 | A15-M-B56 | HPLC_1 | 1.03 | 335 |
| 159 | A15-M-B57 | HPLC_1 | 0.99 | 313 |
| 160 | A15-M-B58 | HPLC_1 | 1.09 | 349 |
| 161 | A16-M-B52 | HPLC_1 | 1.21 | 381 |
| 162 | A16-M-B54 | HPLC_1 | 1.24 | 419 |
| 163 | A16-M-B57 | HPLC_1 | 1.24 | 393 |
| 164 | A17-M-B50 | HPLC_1 | 1.2 | 404 |
| 165 | A17-M-B51 | HPLC_1 | 1.19 | 351 |
| 166 | A17-M-B52 | HPLC_1 | 1.25 | 365 |
| 167 | A17-M-B54 | HPLC_1 | 1.29 | 403 |
| 168 | A17-M-B56 | HPLC_1 | 1.31 | 399 |
| 169 | A17-M-B57 | HPLC_1 | 1.29 | 377 |
| 170 | A17-M-B58 | HPLC_1 | 1.34 | 413 |
| 171 | A12-M-B59 | HPLC_1 | 1.33 | 433 |
| 172 | A12-M-B60 | HPLC_1 | 1.17 | 367 |
| 173 | A12-M-B61 | HPLC_1 | 1.05 | 357 |
| 174 | A13-M-B59 | HPLC_1 | 1.17 | 367 |
| 175 | A13-M-B62 | HPLC_1 | 1.08 | 357 |
| 176 | A13-M-B63 | HPLC_1 | 1.07 | 348 |
| 177 | A13-M-B60 | HPLC_1 | 0.98 | 301 |
| 178 | A13-M-B64 | HPLC_1 | 1.27 | 391 |
| 179 | A13-M-B65 | HPLC_1 | 1.17 | 359 |
| 180 | A13-M-B61 | HPLC_1 | 0.84 | 291 |
| 181 | A13-M-B66 | HPLC_1 | 1.12 | 341 |
| 182 | A14-M-B59 | HPLC_1 | 1.09 | 383 |
| 183 | A14-M-B62 | HPLC_1 | 0.99 | 373 |
| 184 | A14-M-B67 | HPLC_1 | 1.17 | 403 |
| 185 | A14-M-B60 | HPLC_1 | 0.9 | 317 |
| 186 | A14-M-B64 | HPLC_1 | 1.19 | 407 |
| 187 | A14-M-B65 | HPLC_1 | 1.08 | 375 |
| 188 | A14-M-B61 | HPLC_1 | 0.76 | 307 |
| 189 | A14-M-B68 | HPLC_1 | 1.01 | 429 |
| 190 | A14-M-B69 | HPLC_1 | 1.02 | 375 |
| 191 | A14-M-B66 | HPLC_1 | 1.03 | 357 |
| 192 | A14-M-B70 | HPLC_1 | 0.96 | 319 |
| 193 | A15-M-B59 | HPLC_1 | 1.12 | 365 |
| 194 | A15-M-B62 | HPLC_1 | 1.02 | 355 |
| 195 | A15-M-B63 | HPLC_1 | 1.01 | 346 |
| 196 | A15-M-B60 | HPLC_1 | 0.92 | 299 |
| 197 | A15-M-B61 | HPLC_1 | 0.78 | 289 |
| 198 | A15-M-B68 | HPLC_1 | 1.03 | 411 |
| 199 | A15-M-B66 | HPLC_1 | 1.05 | 339 |
| 200 | A15-M-B70 | HPLC_1 | 0.99 | 301 |
| 201 | A17-M-B59 | HPLC_1 | 1.36 | 429 |
| 202 | A17-M-B62 | HPLC_1 | 1.3 | 419 |
| 203 | A17-M-B60 | HPLC_1 | 1.22 | 363 |
| 204 | A17-M-B68 | HPLC_1 | 1.29 | 475 |
| 205 | A17-M-B69 | HPLC_1 | 1.33 | 421 |
| 206 | A17-M-B36 | HPLC_1 | 1.52 | 441 |
| 207 | A18-M-B27 | HPLC_1 | 1.2 | 391 |
| 208 | A18-M-B28 | HPLC_1 | 1.24 | 383 |
| 209 | A18-M-B29 | HPLC_1 | 0.92 | 315 |
| 210 | A18-M-B32 | HPLC_1 | 1.19 | 421 |
| 211 | A18-M-B33 | HPLC_1 | 1.07 | 343 |
| 212 | A18-M-B34 | HPLC_1 | 1.36 | 445 |
| 213 | A18-M-B35 | HPLC_1 | 1.18 | 421 |
| 214 | A12-M-B39 | HPLC_1 | 1.3 | 419 |
| 215 | A12-M-B40 | HPLC_1 | 1.3 | 403 |
| 216 | A12-M-B41 | HPLC_1 | 1.27 | 383 |
| 217 | A12-M-B42 | HPLC_1 | 1.27 | 407 |
| 218 | A12-M-B43 | HPLC_1 | 1.41 | 491 |
| 219 | A12-M-B44 | HPLC_1 | 1.22 | 395 |
| 220 | A12-M-B45 | HPLC_1 | 1.19 | 463 |
| 221 | A12-M-B46 | HPLC_1 | 1.11 | 353 |
| 222 | A12-M-B47 | HPLC_1 | 1.25 | 419 |
| 223 | A21-M-B34 | HPLC_1 | 1.37 | 453 |
| 224 | A21-M-B35 | HPLC_1 | 1.24 | 429 |
| 225 | A19-M-B26 | HPLC_1 | 1.26 | 365 |
| 226 | A19-M-B27 | HPLC_1 | 1.29 | 399 |
| 227 | A19-M-B28 | HPLC_1 | 1.33 | 391 |
| 228 | A17-M-B66 | HPLC_1 | 1.32 | 403 |
| 229 | A17-M-B70 | HPLC_1 | 1.26 | 365 |
| 230 | A18-M-B62 | HPLC_1 | 1.2 | 411 |
| 231 | A18-M-B63 | HPLC_1 | 1.19 | 402 |
| 232 | A18-M-B64 | HPLC_1 | 1.37 | 445 |
| 233 | A18-M-B68 | HPLC_1 | 1.2 | 467 |
| 234 | A18-M-B66 | HPLC_1 | 1.23 | 395 |
| 235 | A12-M-B71 | HPLC_1 | 1.24 | 433 |
| 236 | A12-M-B72 | HPLC_1 | 1.52 | 525 |
| 237 | A12-M-B73 | HPLC_1 | 1.38 | 411 |
| 238 | A12-M-B74 | HPLC_1 | 1.24 | 467 |
| 239 | A12-M-B75 | HPLC_1 | 1.21 | 409 |
| 240 | A12-M-B76 | HPLC_1 | 1.37 | 445 |
| 241 | A12-M-B77 | HPLC_1 | 1.22 | 414 |
| 242 | A12-M-B78 | HPLC_1 | 1.46 | 461 |
| 243 | A12-M-B79 | HPLC_1 | 1.28 | 433 |
| 244 | A12-M-B80 | HPLC_1 | 1.32 | 504 |
| 245 | A13-M-B81 | HPLC_1 | 1.08 | 397 |
| 246 | A13-M-B71 | HPLC_1 | 1.07 | 367 |
| 247 | A13-M-B72 | HPLC_1 | 1.4 | 459 |
| 248 | A13-M-B73 | HPLC_1 | 1.22 | 345 |
| 249 | A13-M-B74 | HPLC_1 | 1.07 | 401 |
| 250 | A13-M-B75 | HPLC_1 | 1.02 | 343 |
| 251 | A13-M-B76 | HPLC_1 | 1.22 | 379 |
| 252 | A13-M-B77 | HPLC_1 | 1.04 | 348 |
| 253 | A13-M-B78 | HPLC_1 | 1.33 | 395 |
| 254 | A13-M-B79 | HPLC_1 | 1.12 | 367 |
| 255 | A13-M-B80 | HPLC_1 | 1.16 | 438 |
| 256 | A14-M-B81 | HPLC_1 | 1 | 413 |
| 257 | A14-M-B71 | HPLC_1 | 0.99 | 383 |
| 258 | A14-M-B72 | HPLC_1 | 1.32 | 475 |
| 259 | A14-M-B73 | HPLC_1 | 1.14 | 361 |
| 260 | A14-M-B74 | HPLC_1 | 0.98 | 417 |
| 261 | A14-M-B75 | HPLC_1 | 0.95 | 359 |
| 262 | A14-M-B76 | HPLC_1 | 1.14 | 395 |
| 263 | A14-M-B77 | HPLC_1 | 0.95 | 364 |
| 264 | A14-M-B78 | HPLC_1 | 1.26 | 411 |
| 265 | A14-M-B79 | HPLC_1 | 1.04 | 383 |
| 266 | A14-M-B82 | HPLC_1 | 1.06 | 432 |
| 267 | A14-M-B80 | HPLC_1 | 1.08 | 454 |
| 268 | A15-M-B81 | HPLC_1 | 1.03 | 395 |
| 269 | A15-M-B71 | HPLC_1 | 1.02 | 365 |
| 270 | A15-M-B72 | HPLC_1 | 1.35 | 457 |
| 271 | A15-M-B73 | HPLC_1 | 1.17 | 343 |
| 272 | A15-M-B75 | HPLC_1 | 0.97 | 341 |
| 273 | A15-M-B76 | HPLC_1 | 1.17 | 377 |
| 274 | A15-M-B77 | HPLC_1 | 0.98 | 346 |
| 275 | A15-M-B79 | HPLC_1 | 1.07 | 365 |
| 276 | A15-M-B80 | HPLC_1 | 1.11 | 436 |
| 277 | A16-M-B81 | HPLC_1 | 1.24 | 475 |
| 278 | A16-M-B71 | HPLC_1 | 1.24 | 445 |
| 279 | A16-M-B72 | HPLC_1 | 1.52 | 537 |
| 280 | A16-M-B73 | HPLC_1 | 1.39 | 423 |
| 281 | A16-M-B74 | HPLC_1 | 1.24 | 479 |
| 282 | A16-M-B78 | HPLC_1 | 1.46 | 473 |
| 283 | A16-M-B80 | HPLC_1 | 1.32 | 516 |
| 284 | A17-M-B81 | HPLC_1 | 1.28 | 459 |
| 285 | A17-M-B71 | HPLC_1 | 1.27 | 429 |
| 286 | A17-M-B72 | HPLC_1 | 1.56 | 521 |
| 287 | A17-M-B73 | HPLC_1 | 1.42 | 407 |
| 288 | A17-M-B74 | HPLC_1 | 1.28 | 463 |
| 289 | A17-M-B75 | HPLC_1 | 1.25 | 405 |
| 290 | A17-M-B76 | HPLC_1 | 1.41 | 441 |
| 291 | A17-M-B77 | HPLC_1 | 1.25 | 410 |
| 292 | A17-M-B78 | HPLC_1 | 1.5 | 457 |
| 293 | A17-M-B79 | HPLC_1 | 1.32 | 429 |
| 294 | A17-M-B80 | HPLC_1 | 1.36 | 500 |
| 295 | A18-M-B75 | HPLC_1 | 1.15 | 397 |
| 296 | A18-M-B77 | HPLC_1 | 1.16 | 402 |
| 297 | A18-M-B79 | HPLC_1 | 1.23 | 421 |
| 298 | A18-M-B80 | HPLC_1 | 1.27 | 492 |
| 299 | A12-M-B83 | HPLC_1 | 1.24 | 425 |
| 300 | A12-M-B84 | HPLC_1 | 1.34 | 467 |
| 301 | A12-M-B85 | HPLC_1 | 1.14 | 379 |
| 302 | A12-M-B86 | HPLC_1 | 1.27 | 457 |
| 303 | A12-M-B87 | HPLC_1 | 1.3 | 498 |

TABLE III-continued

| Entry | Compound | HPLC method | r.t. (min) | [M + H]+ |
|---|---|---|---|---|
| 304 | A12-M-B88 | HPLC_1 | 1.29 | 475 |
| 305 | A12-M-B89 | HPLC_1 | 1.44 | 531 |
| 306 | A12-M-B90 | HPLC_1 | 1.27 | 421 |
| 307 | A12-M-B91 | HPLC_1 | 1.29 | 395 |
| 308 | A12-M-B92 | HPLC_1 | 1.33 | 447 |
| 309 | A13-M-B83 | HPLC_1 | 1.07 | 359 |
| 310 | A13-M-B84 | HPLC_1 | 1.21 | 401 |
| 311 | A13-M-B85 | HPLC_1 | 0.97 | 313 |
| 312 | A13-M-B86 | HPLC_1 | 1.14 | 391 |
| 313 | A13-M-B87 | HPLC_1 | 1.16 | 432 |
| 314 | A13-M-B89 | HPLC_1 | 1.37 | 465 |
| 315 | A19-M-B29 | HPLC_1 | 1.07 | 323 |
| 316 | A13-M-B90 | HPLC_1 | 1.13 | 355 |
| 317 | A13-M-B93 | HPLC_1 | 1.21 | 371 |
| 318 | A13-M-B91 | HPLC_1 | 1.14 | 329 |
| 319 | A14-M-B83 | HPLC_1 | 0.98 | 375 |
| 320 | A14-M-B84 | HPLC_1 | 1.14 | 417 |
| 321 | A14-M-B94 | HPLC_1 | 1.24 | 407 |
| 322 | A14-M-B85 | HPLC_1 | 0.88 | 329 |
| 323 | A14-M-B86 | HPLC_1 | 1.05 | 407 |
| 324 | A14-M-B87 | HPLC_1 | 1.08 | 448 |
| 325 | A14-M-B89 | HPLC_1 | 1.31 | 481 |
| 326 | A14-M-B93 | HPLC_1 | 1.13 | 387 |
| 327 | A14-M-B91 | HPLC_1 | 1.07 | 345 |
| 328 | A14-M-B92 | HPLC_1 | 1.13 | 397 |
| 329 | A15-M-B86 | HPLC_1 | 1.08 | 389 |
| 330 | A15-M-B89 | HPLC_1 | 1.33 | 463 |
| 331 | A15-M-B90 | HPLC_1 | 1.07 | 353 |
| 332 | A15-M-B93 | HPLC_1 | 1.15 | 369 |
| 333 | A15-M-B91 | HPLC_1 | 1.09 | 327 |
| 334 | A16-M-B85 | HPLC_1 | 1.14 | 391 |
| 335 | A17-M-B85 | HPLC_1 | 1.18 | 375 |
| 336 | A17-M-B86 | HPLC_1 | 1.31 | 453 |
| 337 | A17-M-B87 | HPLC_1 | 1.32 | 494 |
| 338 | A17-M-B89 | HPLC_1 | 1.48 | 527 |
| 339 | A19-M-B30 | HPLC_1 | 1.42 | 405 |
| 340 | A19-M-B31 | HPLC_1 | 1.36 | 419 |
| 341 | A19-M-B32 | HPLC_1 | 1.29 | 429 |
| 342 | A19-M-B33 | HPLC_1 | 1.19 | 351 |
| 343 | A19-M-B34 | HPLC_1 | 1.4 | 453 |
| 344 | A19-M-B36 | HPLC_1 | 1.48 | 441 |
| 345 | A20-M-B25 | HPLC_1 | 1.02 | 353 |
| 346 | A19-M-B48 | HPLC_1 | 1.37 | 421 |
| 347 | A19-M-B49 | HPLC_1 | 1.33 | 415 |
| 348 | A19-M-B51 | HPLC_1 | 1.19 | 351 |
| 349 | A19-M-B52 | HPLC_1 | 1.26 | 365 |
| 350 | A19-M-B53 | HPLC_1 | 1.35 | 445 |
| 351 | A19-M-B55 | HPLC_1 | 1.32 | 421 |
| 352 | A19-M-B56 | HPLC_1 | 1.31 | 399 |
| 353 | A19-M-B57 | HPLC_1 | 1.28 | 377 |
| 354 | A22-M-B26 | HPLC_1 | 0.88 | 346 |
| 355 | A22-M-B27 | HPLC_1 | 0.95 | 380 |
| 356 | A22-M-B30 | HPLC_1 | 1.09 | 386 |
| 357 | A22-M-B32 | HPLC_1 | 0.96 | 410 |
| 358 | A22-M-B33 | HPLC_1 | 0.82 | 332 |
| 359 | A23-M-B25 | HPLC_1 | 0.92 | 394 |
| 360 | A23-M-B26 | HPLC_1 | 0.88 | 374 |
| 361 | A23-M-B28 | HPLC_1 | 0.99 | 400 |
| 362 | A23-M-B30 | HPLC_1 | 1.09 | 414 |
| 363 | A23-M-B31 | HPLC_1 | 1.04 | 428 |
| 364 | A23-M-B32 | HPLC_1 | 0.96 | 438 |
| 365 | A23-M-B33 | HPLC_1 | 0.81 | 360 |
| 366 | A23-M-B34 | HPLC_1 | 1.1 | 462 |
| 367 | A23-M-B35 | HPLC_1 | 0.93 | 438 |
| 368 | A23-M-B36 | HPLC_1 | 1.19 | 450 |
| 369 | A24-M-B25 | HPLC_1 | 0.92 | 408 |
| 370 | A24-M-B26 | HPLC_1 | 0.88 | 388 |
| 371 | A24-M-B28 | HPLC_1 | 0.98 | 414 |
| 372 | A24-M-B30 | HPLC_1 | 1.09 | 428 |
| 373 | A24-M-B31 | HPLC_1 | 1.04 | 442 |
| 374 | A24-M-B32 | HPLC_1 | 0.96 | 452 |
| 375 | A24-M-B33 | HPLC_1 | 0.82 | 374 |
| 376 | A24-M-B34 | HPLC_1 | 1.1 | 476 |
| 377 | A24-M-B35 | HPLC_1 | 0.94 | 452 |
| 378 | A24-M-B36 | HPLC_1 | 1.19 | 464 |
| 379 | A25-M-B25 | HPLC_1 | 1.08 | 323 |
| 380 | A25-M-B26 | HPLC_1 | 1.04 | 303 |
| 381 | A25-M-B27 | HPLC_1 | 1.11 | 337 |
| 382 | A25-M-B28 | HPLC_1 | 1.14 | 329 |
| 383 | A25-M-B29 | HPLC_1 | 0.82 | 261 |
| 384 | A25-M-B30 | HPLC_1 | 1.25 | 343 |
| 385 | A25-M-B31 | HPLC_1 | 1.2 | 357 |
| 386 | A25-M-B32 | HPLC_1 | 1.11 | 367 |
| 387 | A25-M-B33 | HPLC_1 | 0.97 | 289 |
| 388 | A25-M-B34 | HPLC_1 | 1.27 | 391 |
| 389 | A25-M-B35 | HPLC_1 | 1.1 | 367 |
| 390 | A25-M-B36 | HPLC_1 | 1.36 | 379 |
| 391 | A21-M-B25 | HPLC_1 | 1.24 | 385 |
| 392 | A21-M-B26 | HPLC_1 | 1.23 | 365 |
| 393 | A21-M-B27 | HPLC_1 | 1.26 | 399 |
| 394 | A21-M-B28 | HPLC_1 | 1.31 | 391 |
| 395 | A21-M-B29 | HPLC_1 | 1.03 | 323 |
| 396 | A21-M-B30 | HPLC_1 | 1.38 | 405 |
| 397 | A21-M-B31 | HPLC_1 | 1.33 | 419 |
| 398 | A21-M-B32 | HPLC_1 | 1.25 | 429 |
| 399 | A21-M-B33 | HPLC_1 | 1.16 | 351 |
| 400 | A20-M-B26 | HPLC_1 | 0.99 | 333 |
| 401 | A20-M-B28 | HPLC_1 | 1.09 | 359 |
| 402 | A20-M-B29 | HPLC_1 | 0.79 | 291 |
| 403 | A20-M-B30 | HPLC_1 | 1.19 | 373 |
| 404 | A20-M-B31 | HPLC_1 | 1.14 | 387 |
| 405 | A20-M-B32 | HPLC_1 | 1.06 | 397 |
| 406 | A20-M-B33 | HPLC_1 | 0.92 | 319 |
| 407 | A20-M-B34 | HPLC_1 | 1.2 | 421 |
| 408 | A20-M-B35 | HPLC_1 | 1.03 | 397 |
| 409 | A20-M-B36 | HPLC_1 | 1.29 | 409 |
| 410 | A22-M-B39 | HPLC_1 | 0.99 | 396 |
| 411 | A22-M-B40 | HPLC_1 | 0.99 | 380 |
| 412 | A22-M-B41 | HPLC_1 | 0.94 | 360 |
| 413 | A22-M-B43 | HPLC_1 | 1.09 | 468 |
| 414 | A22-M-B44 | HPLC_1 | 0.89 | 372 |
| 415 | A22-M-B45 | HPLC_1 | 0.89 | 440 |
| 416 | A22-M-B37 | HPLC_1 | 0.74 | 318 |
| 417 | A22-M-B38 | HPLC_1 | 0.77 | 357 |
| 418 | A25-M-B39 | HPLC_1 | 1.15 | 353 |
| 419 | A25-M-B40 | HPLC_1 | 1.16 | 337 |
| 420 | A25-M-B41 | HPLC_1 | 1.11 | 317 |
| 421 | A25-M-B42 | HPLC_1 | 1.12 | 341 |
| 422 | A25-M-B43 | HPLC_1 | 1.27 | 425 |
| 423 | A25-M-B44 | HPLC_1 | 1.05 | 329 |
| 424 | A25-M-B45 | HPLC_1 | 1.03 | 397 |
| 425 | A25-M-B46 | HPLC_1 | 0.92 | 287 |
| 426 | A25-M-B47 | HPLC_1 | 1.1 | 353 |
| 427 | A25-M-B37 | HPLC_1 | 0.88 | 275 |
| 428 | A25-M-B38 | HPLC_1 | 0.92 | 314 |
| 429 | A21-M-B39 | HPLC_1 | 1.31 | 415 |
| 430 | A21-M-B40 | HPLC_1 | 1.31 | 399 |
| 431 | A21-M-B41 | HPLC_1 | 1.28 | 379 |
| 432 | A21-M-B42 | HPLC_1 | 1.29 | 403 |
| 433 | A21-M-B43 | HPLC_1 | 1.42 | 487 |
| 434 | A21-M-B44 | HPLC_1 | 1.22 | 391 |
| 435 | A21-M-B45 | HPLC_1 | 1.19 | 459 |
| 436 | A21-M-B46 | HPLC_1 | 1.13 | 349 |
| 437 | A21-M-B47 | HPLC_1 | 1.27 | 415 |
| 438 | A21-M-B37 | HPLC_1 | 1.08 | 337 |
| 439 | A21-M-B38 | HPLC_1 | 1.12 | 376 |
| 440 | A19-M-B39 | HPLC_1 | 1.34 | 415 |
| 441 | A19-M-B40 | HPLC_1 | 1.34 | 399 |
| 442 | A19-M-B41 | HPLC_1 | 1.32 | 379 |
| 443 | A19-M-B42 | HPLC_1 | 1.32 | 403 |
| 444 | A19-M-B43 | HPLC_1 | 1.45 | 487 |
| 445 | A19-M-B44 | HPLC_1 | 1.27 | 391 |
| 446 | A19-M-B45 | HPLC_1 | 1.23 | 459 |
| 447 | A19-M-B46 | HPLC_1 | 1.17 | 349 |
| 448 | A19-M-B47 | HPLC_1 | 1.29 | 415 |
| 449 | A19-M-B37 | HPLC_1 | 1.12 | 337 |
| 450 | A19-M-B38 | HPLC_1 | 1.16 | 376 |
| 451 | A20-M-B39 | HPLC_1 | 1.09 | 383 |
| 452 | A20-M-B40 | HPLC_1 | 1.09 | 367 |
| 453 | A20-M-B41 | HPLC_1 | 1.04 | 347 |
| 454 | A20-M-B42 | HPLC_1 | 1.05 | 371 |
| 455 | A20-M-B43 | HPLC_1 | 1.2 | 455 |
| 456 | A20-M-B44 | HPLC_1 | 0.99 | 359 |
| 457 | A20-M-B45 | HPLC_1 | 0.98 | 427 |

TABLE III-continued

| Entry | Compound | HPLC method | r.t. (min) | [M + H]+ |
|---|---|---|---|---|
| 458 | A20-M-B46 | HPLC_1 | 0.87 | 317 |
| 459 | A20-M-B47 | HPLC_1 | 1.04 | 383 |
| 460 | A20-M-B38 | HPLC_1 | 0.87 | 344 |
| 461 | A22-M-B58 | HPLC_1 | 1 | 394 |
| 462 | A23-M-B48 | HPLC_1 | 1.16 | 430 |
| 463 | A23-M-B50 | HPLC_1 | 0.93 | 413 |
| 464 | A23-M-B51 | HPLC_1 | 0.96 | 360 |
| 465 | A23-M-B55 | HPLC_1 | 1.07 | 430 |
| 466 | A25-M-B48 | HPLC_1 | 1.18 | 359 |
| 467 | A25-M-B49 | HPLC_1 | 1.13 | 353 |
| 468 | A25-M-B50 | HPLC_1 | 0.98 | 342 |
| 469 | A25-M-B51 | HPLC_1 | 0.95 | 289 |
| 470 | A25-M-B52 | HPLC_1 | 1.03 | 303 |
| 471 | A25-M-B53 | HPLC_1 | 1.17 | 383 |
| 472 | A25-M-B54 | HPLC_1 | 1.07 | 341 |
| 473 | A25-M-B55 | HPLC_1 | 1.11 | 359 |
| 474 | A25-M-B56 | HPLC_1 | 1.1 | 337 |
| 475 | A25-M-B57 | HPLC_1 | 1.07 | 315 |
| 476 | A25-M-B58 | HPLC_1 | 1.15 | 351 |
| 477 | A21-M-B48 | HPLC_1 | 1.34 | 421 |
| 478 | A21-M-B49 | HPLC_1 | 1.29 | 415 |
| 479 | A21-M-B50 | HPLC_1 | 1.17 | 404 |
| 480 | A21-M-B51 | HPLC_1 | 1.14 | 351 |
| 481 | A21-M-B52 | HPLC_1 | 1.22 | 365 |
| 482 | A21-M-B53 | HPLC_1 | 1.31 | 445 |
| 483 | A21-M-B54 | HPLC_1 | 1.24 | 403 |
| 484 | A21-M-B55 | HPLC_1 | 1.28 | 421 |
| 485 | A21-M-B56 | HPLC_1 | 1.27 | 399 |
| 486 | A21-M-B57 | HPLC_1 | 1.25 | 377 |
| 487 | A21-M-B58 | HPLC_1 | 1.32 | 413 |
| 488 | A20-M-B57 | HPLC_1 | 1.01 | 345 |
| 489 | A20-M-B58 | HPLC_1 | 1.1 | 381 |
| 490 | A22-M-B59 | HPLC_1 | 1.01 | 410 |
| 491 | A22-M-B63 | HPLC_1 | 0.9 | 391 |
| 492 | A22-M-B60 | HPLC_1 | 0.82 | 344 |
| 493 | A22-M-B64 | HPLC_1 | 1.11 | 434 |
| 494 | A22-M-B65 | HPLC_1 | 0.99 | 402 |
| 495 | A22-M-B68 | HPLC_1 | 0.93 | 456 |
| 496 | A22-M-B70 | HPLC_1 | 0.88 | 346 |
| 497 | A23-M-B59 | HPLC_1 | 1.02 | 438 |
| 498 | A23-M-B62 | HPLC_1 | 0.92 | 428 |
| 499 | A23-M-B67 | HPLC_1 | 1.1 | 458 |
| 500 | A23-M-B63 | HPLC_1 | 0.91 | 419 |
| 501 | A23-M-B64 | HPLC_1 | 1.11 | 462 |
| 502 | A23-M-B65 | HPLC_1 | 1 | 430 |
| 503 | A23-M-B61 | HPLC_1 | 0.71 | 362 |
| 504 | A23-M-B68 | HPLC_1 | 0.94 | 484 |
| 505 | A23-M-B69 | HPLC_1 | 0.94 | 430 |
| 506 | A23-M-B66 | HPLC_1 | 0.95 | 412 |
| 507 | A23-M-B70 | HPLC_1 | 0.89 | 374 |
| 508 | A24-M-B59 | HPLC_1 | 1.02 | 452 |
| 509 | A24-M-B62 | HPLC_1 | 0.93 | 442 |
| 510 | A24-M-B67 | HPLC_1 | 1.1 | 472 |
| 511 | A24-M-B63 | HPLC_1 | 0.92 | 433 |
| 512 | A24-M-B64 | HPLC_1 | 1.12 | 476 |
| 513 | A24-M-B65 | HPLC_1 | 1 | 444 |
| 514 | A24-M-B68 | HPLC_1 | 0.94 | 498 |
| 515 | A24-M-B69 | HPLC_1 | 0.95 | 444 |
| 516 | A24-M-B66 | HPLC_1 | 0.96 | 426 |
| 517 | A24-M-B70 | HPLC_1 | 0.89 | 388 |
| 518 | A25-M-B59 | HPLC_1 | 1.18 | 367 |
| 519 | A25-M-B62 | HPLC_1 | 1.09 | 357 |
| 520 | A25-M-B67 | HPLC_1 | 1.26 | 387 |
| 521 | A25-M-B63 | HPLC_1 | 1.08 | 348 |
| 522 | A25-M-B60 | HPLC_1 | 0.99 | 301 |
| 523 | A25-M-B64 | HPLC_1 | 1.27 | 391 |
| 524 | A25-M-B65 | HPLC_1 | 1.17 | 359 |
| 525 | A25-M-B61 | HPLC_1 | 0.84 | 291 |
| 526 | A25-M-B68 | HPLC_1 | 1.09 | 413 |
| 527 | A25-M-B69 | HPLC_1 | 1.11 | 359 |
| 528 | A25-M-B66 | HPLC_1 | 1.12 | 341 |
| 529 | A25-M-B70 | HPLC_1 | 1.05 | 303 |
| 530 | A21-M-B59 | HPLC_1 | 1.34 | 429 |
| 531 | A21-M-B62 | HPLC_1 | 1.27 | 419 |
| 532 | A21-M-B63 | HPLC_1 | 1.24 | 410 |
| 533 | A21-M-B60 | HPLC_1 | 1.18 | 363 |
| 534 | A21-M-B64 | HPLC_1 | 1.41 | 453 |
| 535 | A21-M-B65 | HPLC_1 | 1.33 | 421 |
| 536 | A21-M-B61 | HPLC_1 | 1.06 | 353 |
| 537 | A21-M-B68 | HPLC_1 | 1.25 | 475 |
| 538 | A21-M-B69 | HPLC_1 | 1.29 | 421 |
| 539 | A21-M-B66 | HPLC_1 | 1.29 | 403 |
| 540 | A21-M-B70 | HPLC_1 | 1.23 | 365 |
| 541 | A19-M-B59 | HPLC_1 | 1.37 | 429 |
| 542 | A19-M-B67 | HPLC_1 | 1.43 | 449 |
| 543 | A19-M-B63 | HPLC_1 | 1.28 | 410 |
| 544 | A19-M-B60 | HPLC_1 | 1.22 | 363 |
| 545 | A19-M-B64 | HPLC_1 | 1.44 | 453 |
| 546 | A19-M-B65 | HPLC_1 | 1.36 | 421 |
| 547 | A19-M-B61 | HPLC_1 | 1.09 | 353 |
| 548 | A19-M-B68 | HPLC_1 | 1.28 | 475 |
| 549 | A19-M-B69 | HPLC_1 | 1.32 | 421 |
| 550 | A19-M-B66 | HPLC_1 | 1.32 | 403 |
| 551 | A19-M-B70 | HPLC_1 | 1.27 | 365 |
| 552 | A20-M-B59 | HPLC_1 | 1.12 | 397 |
| 553 | A20-M-B62 | HPLC_1 | 1.03 | 387 |
| 554 | A20-M-B67 | HPLC_1 | 1.2 | 417 |
| 555 | A20-M-B63 | HPLC_1 | 1.01 | 378 |
| 556 | A20-M-B60 | HPLC_1 | 0.93 | 331 |
| 557 | A20-M-B64 | HPLC_1 | 1.22 | 421 |
| 558 | A20-M-B65 | HPLC_1 | 1.11 | 389 |
| 559 | A20-M-B61 | HPLC_1 | 0.79 | 321 |
| 560 | A20-M-B68 | HPLC_1 | 1.03 | 443 |
| 561 | A20-M-B69 | HPLC_1 | 1.05 | 389 |
| 562 | A20-M-B66 | HPLC_1 | 1.05 | 371 |
| 563 | A20-M-B70 | HPLC_1 | 0.99 | 333 |
| 564 | A22-M-B81 | HPLC_1 | 0.97 | 440 |
| 565 | A22-M-B71 | HPLC_1 | 0.95 | 410 |
| 566 | A22-M-B72 | HPLC_1 | 1.25 | 502 |
| 567 | A22-M-B78 | HPLC_1 | 1.21 | 438 |
| 568 | A22-M-B79 | HPLC_1 | 0.99 | 410 |
| 569 | A22-M-B82 | HPLC_1 | 1.01 | 459 |
| 570 | A22-M-B80 | HPLC_1 | 1.03 | 481 |
| 571 | A23-M-B81 | HPLC_1 | 0.99 | 468 |
| 572 | A23-M-B71 | HPLC_1 | 0.97 | 438 |
| 573 | A23-M-B72 | HPLC_1 | 1.26 | 530 |
| 574 | A23-M-B73 | HPLC_1 | 1.09 | 416 |
| 575 | A23-M-B74 | HPLC_1 | 0.94 | 472 |
| 576 | A24-M-B82 | HPLC_1 | 1.02 | 501 |
| 577 | A24-M-B80 | HPLC_1 | 1.04 | 523 |
| 578 | A25-M-B81 | HPLC_1 | 1.12 | 397 |
| 579 | A25-M-B71 | HPLC_1 | 1.11 | 367 |
| 580 | A25-M-B73 | HPLC_1 | 1.27 | 345 |
| 581 | A25-M-B74 | HPLC_1 | 1.1 | 401 |
| 582 | A25-M-B75 | HPLC_1 | 1.06 | 343 |
| 583 | A25-M-B76 | HPLC_1 | 1.26 | 379 |
| 584 | A25-M-B77 | HPLC_1 | 1.07 | 348 |
| 585 | A25-M-B78 | HPLC_1 | 1.37 | 395 |
| 586 | A25-M-B79 | HPLC_1 | 1.16 | 367 |
| 587 | A25-M-B82 | HPLC_1 | 1.19 | 416 |
| 588 | A25-M-B80 | HPLC_1 | 1.21 | 438 |
| 589 | A21-M-B81 | HPLC_1 | 1.27 | 459 |
| 590 | A21-M-B71 | HPLC_1 | 1.27 | 429 |
| 591 | A21-M-B74 | HPLC_1 | 1.27 | 463 |
| 592 | A21-M-B75 | HPLC_1 | 1.24 | 405 |
| 593 | A21-M-B76 | HPLC_1 | 1.4 | 441 |
| 594 | A21-M-B77 | HPLC_1 | 1.24 | 410 |
| 595 | A21-M-B78 | HPLC_1 | 1.5 | 457 |
| 596 | A21-M-B79 | HPLC_1 | 1.31 | 429 |
| 597 | A21-M-B80 | HPLC_1 | 1.35 | 500 |
| 598 | A19-M-B81 | HPLC_1 | 1.31 | 459 |
| 599 | A19-M-B71 | HPLC_1 | 1.3 | 429 |
| 600 | A19-M-B72 | HPLC_1 | 1.58 | 521 |
| 601 | A19-M-B74 | HPLC_1 | 1.31 | 463 |
| 602 | A19-M-B75 | HPLC_1 | 1.28 | 405 |
| 603 | A19-M-B76 | HPLC_1 | 1.44 | 441 |
| 604 | A19-M-B77 | HPLC_1 | 1.28 | 410 |
| 605 | A19-M-B78 | HPLC_1 | 1.53 | 457 |
| 606 | A19-M-B79 | HPLC_1 | 1.34 | 429 |
| 607 | A19-M-B82 | HPLC_1 | 1.38 | 478 |
| 608 | A19-M-B80 | HPLC_1 | 1.38 | 500 |
| 609 | A20-M-B81 | HPLC_1 | 1.06 | 427 |
| 610 | A20-M-B71 | HPLC_1 | 1.05 | 397 |
| 611 | A20-M-B72 | HPLC_1 | 1.37 | 489 |

TABLE III-continued

| Entry | Compound | HPLC method | r.t. (min) | [M + H]+ |
|---|---|---|---|---|
| 612 | A20-M-B73 | HPLC_1 | 1.2 | 375 |
| 613 | A20-M-B74 | HPLC_1 | 1.04 | 431 |
| 614 | A20-M-B75 | HPLC_1 | 1 | 373 |
| 615 | A20-M-B76 | HPLC_1 | 1.2 | 409 |
| 616 | A20-M-B77 | HPLC_1 | 1.02 | 378 |
| 617 | A20-M-B78 | HPLC_1 | 1.31 | 425 |
| 618 | A20-M-B79 | HPLC_1 | 1.1 | 397 |
| 619 | A20-M-B82 | HPLC_1 | 1.12 | 446 |
| 620 | A20-M-B80 | HPLC_1 | 1.14 | 468 |
| 621 | A22-M-B85 | HPLC_1 | 0.8 | 356 |
| 622 | A22-M-B86 | HPLC_1 | 0.95 | 434 |
| 623 | A22-M-B87 | HPLC_1 | 0.99 | 475 |
| 624 | A22-M-B88 | HPLC_1 | 0.97 | 452 |
| 625 | A22-M-B89 | HPLC_1 | 1.21 | 508 |
| 626 | A22-M-B90 | HPLC_1 | 0.97 | 398 |
| 627 | A22-M-B93 | HPLC_1 | 1.04 | 414 |
| 628 | A22-M-B92 | HPLC_1 | 1.04 | 424 |
| 629 | A23-M-B83 | HPLC_1 | 0.92 | 430 |
| 630 | A23-M-B94 | HPLC_1 | 1.19 | 462 |
| 631 | A23-M-B86 | HPLC_1 | 0.99 | 462 |
| 632 | A23-M-B87 | HPLC_1 | 1.03 | 503 |
| 633 | A23-M-B90 | HPLC_1 | 1.01 | 426 |
| 634 | A24-M-B83 | HPLC_1 | 0.93 | 444 |
| 635 | A24-M-B86 | HPLC_1 | 0.98 | 476 |
| 636 | A25-M-B83 | HPLC_1 | 1.05 | 359 |
| 637 | A25-M-B84 | HPLC_1 | 1.21 | 401 |
| 638 | A25-M-B94 | HPLC_1 | 1.32 | 391 |
| 639 | A25-M-B85 | HPLC_1 | 0.95 | 313 |
| 640 | A25-M-B86 | HPLC_1 | 1.12 | 391 |
| 641 | A25-M-B88 | HPLC_1 | 1.15 | 409 |
| 642 | A25-M-B89 | HPLC_1 | 1.38 | 465 |
| 643 | A25-M-B90 | HPLC_1 | 1.12 | 355 |
| 644 | A25-M-B93 | HPLC_1 | 1.19 | 371 |
| 645 | A25-M-B91 | HPLC_1 | 1.13 | 329 |
| 646 | A25-M-B92 | HPLC_1 | 1.19 | 381 |
| 647 | A21-M-B83 | HPLC_1 | 1.24 | 421 |
| 648 | A21-M-B84 | HPLC_1 | 1.37 | 463 |
| 649 | A21-M-B94 | HPLC_1 | 1.47 | 453 |
| 650 | A21-M-B85 | HPLC_1 | 1.13 | 375 |
| 651 | A21-M-B86 | HPLC_1 | 1.3 | 453 |
| 652 | A21-M-B87 | HPLC_1 | 1.32 | 494 |
| 653 | A21-M-B89 | HPLC_1 | 1.5 | 527 |
| 654 | A21-M-B90 | HPLC_1 | 1.28 | 417 |
| 655 | A21-M-B93 | HPLC_1 | 1.35 | 433 |
| 656 | A21-M-B91 | HPLC_1 | 1.3 | 391 |
| 657 | A21-M-B92 | HPLC_1 | 1.34 | 443 |
| 658 | A19-M-B83 | HPLC_1 | 1.27 | 421 |
| 659 | A19-M-B84 | HPLC_1 | 1.4 | 463 |
| 660 | A19-M-B85 | HPLC_1 | 1.17 | 375 |
| 661 | A19-M-B86 | HPLC_1 | 1.34 | 453 |
| 662 | A19-M-B87 | HPLC_1 | 1.34 | 494 |
| 663 | A19-M-B88 | HPLC_1 | 1.35 | 471 |
| 664 | A26-M-B25 | HPLC_1 | 1.1 | 337 |
| 665 | A26-M-B26 | HPLC_1 | 1.08 | 317 |
| 666 | A26-M-B27 | HPLC_1 | 1.13 | 351 |
| 667 | A26-M-B28 | HPLC_1 | 1.17 | 343 |
| 668 | A26-M-B29 | HPLC_1 | 0.87 | 275 |
| 669 | A26-M-B30 | HPLC_1 | 1.27 | 357 |
| 670 | A26-M-B31 | HPLC_1 | 1.22 | 371 |
| 671 | A26-M-B32 | HPLC_1 | 1.13 | 381 |
| 672 | A26-M-B33 | HPLC_1 | 1.01 | 303 |
| 673 | A26-M-B34 | HPLC_1 | 1.28 | 405 |
| 674 | A26-M-B35 | HPLC_1 | 1.12 | 381 |
| 675 | A26-M-B36 | HPLC_1 | 1.37 | 393 |
| 676 | A27-M-B25 | HPLC_1 | 1.25 | 405 |
| 677 | A27-M-B26 | HPLC_1 | 1.24 | 385 |
| 678 | A27-M-B27 | HPLC_1 | 1.27 | 419 |
| 679 | A27-M-B28 | HPLC_1 | 1.31 | 411 |
| 680 | A27-M-B29 | HPLC_1 | 1.05 | 343 |
| 681 | A27-M-B30 | HPLC_1 | 1.39 | 425 |
| 682 | A27-M-B31 | HPLC_1 | 1.35 | 439 |
| 683 | A27-M-B32 | HPLC_1 | 1.26 | 449 |
| 684 | A27-M-B33 | HPLC_1 | 1.17 | 371 |
| 685 | A27-M-B34 | HPLC_1 | 1.4 | 473 |
| 686 | A27-M-B35 | HPLC_1 | 1.25 | 449 |
| 687 | A27-M-B36 | HPLC_1 | 1.48 | 461 |
| 688 | A28-M-B25 | HPLC_1 | 1.19 | 389 |
| 689 | A28-M-B26 | HPLC_1 | 1.16 | 369 |
| 690 | A28-M-B27 | HPLC_1 | 1.2 | 403 |
| 691 | A28-M-B28 | HPLC_1 | 1.24 | 395 |
| 692 | A28-M-B29 | HPLC_1 | 0.97 | 327 |
| 693 | A28-M-B30 | HPLC_1 | 1.33 | 409 |
| 694 | A28-M-B31 | HPLC_1 | 1.29 | 423 |
| 695 | A28-M-B32 | HPLC_1 | 1.2 | 433 |
| 696 | A28-M-B33 | HPLC_1 | 1.09 | 355 |
| 697 | A28-M-B34 | HPLC_1 | 1.34 | 457 |
| 698 | A28-M-B35 | HPLC_1 | 1.19 | 433 |
| 699 | A28-M-B36 | HPLC_1 | 1.43 | 445 |
| 700 | A29-M-B25 | HPLC_1 | 1.18 | 401 |
| 701 | A29-M-B26 | HPLC_1 | 1.15 | 381 |
| 702 | A29-M-B27 | HPLC_1 | 1.19 | 415 |
| 703 | A29-M-B28 | HPLC_1 | 1.23 | 407 |
| 704 | A29-M-B29 | HPLC_1 | 0.96 | 339 |
| 705 | A29-M-B30 | HPLC_1 | 1.32 | 421 |
| 706 | A29-M-B31 | HPLC_1 | 1.27 | 435 |
| 707 | A29-M-B32 | HPLC_1 | 1.19 | 445 |
| 708 | A29-M-B33 | HPLC_1 | 1.09 | 367 |
| 709 | A29-M-B34 | HPLC_1 | 1.33 | 469 |
| 710 | A29-M-B35 | HPLC_1 | 1.18 | 445 |
| 711 | A29-M-B36 | HPLC_1 | 1.41 | 457 |
| 712 | A30-M-B25 | HPLC_1 | 1.28 | 365 |
| 713 | A30-M-B26 | HPLC_1 | 1.26 | 345 |
| 714 | A30-M-B27 | HPLC_1 | 1.3 | 379 |
| 715 | A30-M-B28 | HPLC_1 | 1.34 | 371 |
| 716 | A30-M-B29 | HPLC_1 | 1.08 | 303 |
| 717 | A30-M-B30 | HPLC_1 | 1.43 | 385 |
| 718 | A30-M-B31 | HPLC_1 | 1.38 | 399 |
| 719 | A30-M-B32 | HPLC_1 | 1.29 | 409 |
| 720 | A30-M-B33 | HPLC_1 | 1.2 | 331 |
| 721 | A30-M-B34 | HPLC_1 | 1.43 | 433 |
| 722 | A31-M-B31 | HPLC_1 | 1.29 | 385 |
| 723 | A31-M-B32 | HPLC_1 | 1.2 | 395 |
| 724 | A31-M-B33 | HPLC_1 | 1.09 | 317 |
| 725 | A31-M-B34 | HPLC_1 | 1.35 | 419 |
| 726 | A31-M-B35 | HPLC_1 | 1.19 | 395 |
| 727 | A31-M-B36 | HPLC_1 | 1.44 | 407 |
| 728 | A32-M-B25 | HPLC_1 | 1.2 | 351 |
| 729 | A32-M-B26 | HPLC_1 | 1.17 | 331 |
| 730 | A32-M-B27 | HPLC_1 | 1.21 | 365 |
| 731 | A32-M-B28 | HPLC_1 | 1.25 | 357 |
| 732 | A32-M-B29 | HPLC_1 | 0.98 | 289 |
| 733 | A32-M-B30 | HPLC_1 | 1.34 | 371 |
| 734 | A32-M-B31 | HPLC_1 | 1.3 | 385 |
| 735 | A32-M-B32 | HPLC_1 | 1.21 | 395 |
| 736 | A32-M-B33 | HPLC_1 | 1.1 | 317 |
| 737 | A32-M-B34 | HPLC_1 | 1.35 | 419 |
| 738 | A32-M-B35 | HPLC_1 | 1.2 | 395 |
| 739 | A32-M-B36 | HPLC_1 | 1.45 | 407 |
| 740 | A26-M-B39 | HPLC_1 | 1.2 | 367 |
| 741 | A26-M-B40 | HPLC_1 | 1.21 | 351 |
| 742 | A26-M-B41 | HPLC_1 | 1.16 | 331 |
| 743 | A26-M-B42 | HPLC_1 | 1.18 | 355 |
| 744 | A26-M-B44 | HPLC_1 | 1.12 | 343 |
| 745 | A26-M-B45 | HPLC_1 | 1.08 | 411 |
| 746 | A26-M-B46 | HPLC_1 | 0.99 | 301 |
| 747 | A26-M-B47 | HPLC_1 | 1.15 | 367 |
| 748 | A26-M-B37 | HPLC_1 | 0.95 | 289 |
| 749 | A26-M-B38 | HPLC_1 | 0.99 | 328 |
| 750 | A27-M-B40 | HPLC_1 | 1.36 | 419 |
| 751 | A27-M-B41 | HPLC_1 | 1.33 | 399 |
| 752 | A27-M-B42 | HPLC_1 | 1.33 | 423 |
| 753 | A27-M-B43 | HPLC_1 | 1.47 | 507 |
| 754 | A27-M-B44 | HPLC_1 | 1.28 | 411 |
| 755 | A27-M-B45 | HPLC_1 | 1.24 | 479 |
| 756 | A27-M-B46 | HPLC_1 | 1.18 | 369 |
| 757 | A27-M-B47 | HPLC_1 | 1.31 | 435 |
| 758 | A27-M-B37 | HPLC_1 | 1.14 | 357 |
| 759 | A28-M-B39 | HPLC_1 | 1.29 | 419 |
| 760 | A28-M-B40 | HPLC_1 | 1.29 | 403 |
| 761 | A28-M-B41 | HPLC_1 | 1.26 | 383 |
| 762 | A28-M-B42 | HPLC_1 | 1.26 | 407 |
| 763 | A28-M-B43 | HPLC_1 | 1.4 | 491 |
| 764 | A28-M-B44 | HPLC_1 | 1.2 | 395 |
| 765 | A28-M-B45 | HPLC_1 | 1.17 | 463 |

TABLE III-continued

| Entry | Compound | HPLC method | r.t. (min) | [M + H]+ |
|---|---|---|---|---|
| 766 | A28-M-B46 | HPLC_1 | 1.09 | 353 |
| 767 | A28-M-B47 | HPLC_1 | 1.24 | 419 |
| 768 | A28-M-B37 | HPLC_1 | 1.05 | 341 |
| 769 | A29-M-B39 | HPLC_1 | 1.28 | 431 |
| 770 | A29-M-B40 | HPLC_1 | 1.28 | 415 |
| 771 | A29-M-B41 | HPLC_1 | 1.24 | 395 |
| 772 | A29-M-B42 | HPLC_1 | 1.25 | 419 |
| 773 | A29-M-B43 | HPLC_1 | 1.39 | 503 |
| 774 | A29-M-B44 | HPLC_1 | 1.19 | 407 |
| 775 | A29-M-B45 | HPLC_1 | 1.16 | 475 |
| 776 | A29-M-B46 | HPLC_1 | 1.09 | 365 |
| 777 | A29-M-B47 | HPLC_1 | 1.22 | 431 |
| 778 | A29-M-B37 | HPLC_1 | 1.05 | 353 |
| 779 | A30-M-B39 | HPLC_1 | 1.39 | 395 |
| 780 | A30-M-B40 | HPLC_1 | 1.39 | 379 |
| 781 | A30-M-B41 | HPLC_1 | 1.36 | 359 |
| 782 | A30-M-B42 | HPLC_1 | 1.36 | 383 |
| 783 | A30-M-B43 | HPLC_1 | 1.49 | 467 |
| 784 | A30-M-B44 | HPLC_1 | 1.31 | 371 |
| 785 | A30-M-B45 | HPLC_1 | 1.27 | 439 |
| 786 | A30-M-B46 | HPLC_1 | 1.21 | 329 |
| 787 | A30-M-B47 | HPLC_1 | 1.34 | 395 |
| 788 | A30-M-B37 | HPLC_1 | 1.17 | 317 |
| 789 | A33-M-B39 | HPLC_1 | 1.37 | 407 |
| 790 | A33-M-B40 | HPLC_1 | 1.37 | 391 |
| 791 | A33-M-B41 | HPLC_1 | 1.34 | 371 |
| 792 | A33-M-B42 | HPLC_1 | 1.34 | 395 |
| 793 | A33-M-B43 | HPLC_1 | 1.48 | 479 |
| 794 | A33-M-B44 | HPLC_1 | 1.3 | 383 |
| 795 | A33-M-B45 | HPLC_1 | 1.25 | 451 |
| 796 | A33-M-B46 | HPLC_1 | 1.18 | 341 |
| 797 | A33-M-B47 | HPLC_1 | 1.32 | 407 |
| 798 | A33-M-B37 | HPLC_1 | 1.14 | 329 |
| 799 | A31-M-B39 | HPLC_1 | 1.29 | 381 |
| 800 | A31-M-B40 | HPLC_1 | 1.29 | 365 |
| 801 | A31-M-B41 | HPLC_1 | 1.25 | 345 |
| 802 | A31-M-B42 | HPLC_1 | 1.26 | 369 |
| 803 | A31-M-B43 | HPLC_1 | 1.41 | 453 |
| 804 | A31-M-B44 | HPLC_1 | 1.2 | 357 |
| 805 | A31-M-B45 | HPLC_1 | 1.16 | 425 |
| 806 | A31-M-B46 | HPLC_1 | 1.08 | 315 |
| 807 | A31-M-B47 | HPLC_1 | 1.24 | 381 |
| 808 | A31-M-B37 | HPLC_1 | 1.04 | 303 |
| 809 | A32-M-B39 | HPLC_1 | 1.29 | 381 |
| 810 | A26-M-B52 | HPLC_1 | 1.07 | 317 |
| 811 | A26-M-B53 | HPLC_1 | 1.18 | 397 |
| 812 | A26-M-B54 | HPLC_1 | 1.11 | 355 |
| 813 | A26-M-B55 | HPLC_1 | 1.15 | 373 |
| 814 | A26-M-B56 | HPLC_1 | 1.14 | 351 |
| 815 | A26-M-B57 | HPLC_1 | 1.1 | 329 |
| 816 | A26-M-B58 | HPLC_1 | 1.18 | 365 |
| 817 | A27-M-B48 | HPLC_1 | 1.34 | 441 |
| 818 | A27-M-B49 | HPLC_1 | 1.3 | 435 |
| 819 | A27-M-B50 | HPLC_1 | 1.18 | 424 |
| 820 | A27-M-B51 | HPLC_1 | 1.17 | 371 |
| 821 | A27-M-B52 | HPLC_1 | 1.23 | 385 |
| 822 | A27-M-B53 | HPLC_1 | 1.32 | 465 |
| 823 | A27-M-B54 | HPLC_1 | 1.26 | 423 |
| 824 | A27-M-B55 | HPLC_1 | 1.29 | 441 |
| 825 | A27-M-B56 | HPLC_1 | 1.28 | 419 |
| 826 | A27-M-B57 | HPLC_1 | 1.26 | 397 |
| 827 | A27-M-B58 | HPLC_1 | 1.31 | 433 |
| 828 | A28-M-B48 | HPLC_1 | 1.28 | 425 |
| 829 | A28-M-B49 | HPLC_1 | 1.23 | 419 |
| 830 | A28-M-B50 | HPLC_1 | 1.11 | 408 |
| 831 | A28-M-B51 | HPLC_1 | 1.09 | 355 |
| 832 | A28-M-B52 | HPLC_1 | 1.16 | 369 |
| 833 | A28-M-B54 | HPLC_1 | 1.19 | 407 |
| 834 | A28-M-B55 | HPLC_1 | 1.23 | 425 |
| 835 | A28-M-B56 | HPLC_1 | 1.22 | 403 |
| 836 | A28-M-B57 | HPLC_1 | 1.19 | 381 |
| 837 | A28-M-B58 | HPLC_1 | 1.25 | 417 |
| 838 | A29-M-B48 | HPLC_1 | 1.26 | 437 |
| 839 | A29-M-B49 | HPLC_1 | 1.22 | 431 |
| 840 | A29-M-B50 | HPLC_1 | 1.11 | 420 |
| 841 | A29-M-B51 | HPLC_1 | 1.08 | 367 |
| 842 | A29-M-B52 | HPLC_1 | 1.14 | 381 |
| 843 | A29-M-B53 | HPLC_1 | 1.24 | 461 |
| 844 | A29-M-B54 | HPLC_1 | 1.17 | 419 |
| 845 | A29-M-B55 | HPLC_1 | 1.21 | 437 |
| 846 | A29-M-B56 | HPLC_1 | 1.2 | 415 |
| 847 | A29-M-B57 | HPLC_1 | 1.17 | 393 |
| 848 | A29-M-B58 | HPLC_1 | 1.23 | 429 |
| 849 | A30-M-B48 | HPLC_1 | 1.37 | 401 |
| 850 | A30-M-B49 | HPLC_1 | 1.33 | 395 |
| 851 | A30-M-B50 | HPLC_1 | 1.22 | 384 |
| 852 | A30-M-B51 | HPLC_1 | 1.2 | 331 |
| 853 | A30-M-B52 | HPLC_1 | 1.26 | 345 |
| 854 | A30-M-B53 | HPLC_1 | 1.35 | 425 |
| 855 | A30-M-B54 | HPLC_1 | 1.29 | 383 |
| 856 | A30-M-B55 | HPLC_1 | 1.32 | 401 |
| 857 | A30-M-B56 | HPLC_1 | 1.31 | 379 |
| 858 | A30-M-B57 | HPLC_1 | 1.29 | 357 |
| 859 | A30-M-B58 | HPLC_1 | 1.34 | 393 |
| 860 | A33-M-B48 | HPLC_1 | 1.36 | 413 |
| 861 | A33-M-B49 | HPLC_1 | 1.32 | 407 |
| 862 | A33-M-B50 | HPLC_1 | 1.2 | 396 |
| 863 | A33-M-B51 | HPLC_1 | 1.17 | 343 |
| 864 | A33-M-B52 | HPLC_1 | 1.24 | 357 |
| 865 | A33-M-B53 | HPLC_1 | 1.33 | 437 |
| 866 | A33-M-B54 | HPLC_1 | 1.27 | 395 |
| 867 | A33-M-B55 | HPLC_1 | 1.31 | 413 |
| 868 | A33-M-B58 | HPLC_1 | 1.33 | 405 |
| 869 | A31-M-B48 | HPLC_1 | 1.28 | 387 |
| 870 | A31-M-B49 | HPLC_1 | 1.23 | 381 |
| 871 | A31-M-B50 | HPLC_1 | 1.11 | 370 |
| 872 | A31-M-B51 | HPLC_1 | 1.09 | 317 |
| 873 | A31-M-B52 | HPLC_1 | 1.15 | 331 |
| 874 | A31-M-B53 | HPLC_1 | 1.25 | 411 |
| 875 | A31-M-B54 | HPLC_1 | 1.19 | 369 |
| 876 | A31-M-B55 | HPLC_1 | 1.23 | 387 |
| 877 | A31-M-B56 | HPLC_1 | 1.21 | 365 |
| 878 | A31-M-B57 | HPLC_1 | 1.18 | 343 |
| 879 | A31-M-B58 | HPLC_1 | 1.25 | 379 |
| 880 | A32-M-B48 | HPLC_1 | 1.29 | 387 |
| 881 | A32-M-B49 | HPLC_1 | 1.24 | 381 |
| 882 | A32-M-B50 | HPLC_1 | 1.12 | 370 |
| 883 | A32-M-B51 | HPLC_1 | 1.1 | 317 |
| 884 | A32-M-B52 | HPLC_1 | 1.16 | 331 |
| 885 | A32-M-B53 | HPLC_1 | 1.26 | 411 |
| 886 | A32-M-B54 | HPLC_1 | 1.2 | 369 |
| 887 | A32-M-B55 | HPLC_1 | 1.23 | 387 |
| 888 | A32-M-B56 | HPLC_1 | 1.22 | 365 |
| 889 | A32-M-B57 | HPLC_1 | 1.19 | 343 |
| 890 | A32-M-B58 | HPLC_1 | 1.26 | 379 |
| 891 | A26-M-B59 | HPLC_1 | 1.24 | 381 |
| 892 | A26-M-B62 | HPLC_1 | 1.16 | 371 |
| 893 | A26-M-B67 | HPLC_1 | 1.32 | 401 |
| 894 | A26-M-B63 | HPLC_1 | 1.14 | 362 |
| 895 | A26-M-B60 | HPLC_1 | 1.06 | 315 |
| 896 | A26-M-B64 | HPLC_1 | 1.33 | 405 |
| 897 | A26-M-B65 | HPLC_1 | 1.23 | 373 |
| 898 | A20-M-B50 | HPLC_1 | 0.92 | 372 |
| 899 | A20-M-B51 | HPLC_1 | 0.89 | 319 |
| 900 | A20-M-B52 | HPLC_1 | 0.97 | 333 |
| 901 | A20-M-B53 | HPLC_1 | 1.1 | 413 |
| 902 | A20-M-B54 | HPLC_1 | 1.01 | 371 |
| 903 | A20-M-B55 | HPLC_1 | 1.05 | 389 |
| 904 | A20-M-B56 | HPLC_1 | 1.04 | 367 |
| 905 | A23-M-B75 | HPLC_1 | 0.91 | 414 |
| 906 | A23-M-B76 | HPLC_1 | 1.1 | 450 |
| 907 | A23-M-B77 | HPLC_1 | 0.92 | 419 |
| 908 | A23-M-B78 | HPLC_1 | 1.22 | 466 |
| 909 | A23-M-B79 | HPLC_1 | 1 | 438 |
| 910 | A23-M-B82 | HPLC_1 | 1.02 | 487 |
| 911 | A23-M-B80 | HPLC_1 | 1.04 | 509 |
| 912 | A24-M-B81 | HPLC_1 | 0.98 | 482 |
| 913 | A24-M-B71 | HPLC_1 | 0.97 | 452 |
| 914 | A24-M-B73 | HPLC_1 | 1.09 | 430 |
| 915 | A24-M-B74 | HPLC_1 | 0.94 | 486 |
| 916 | A24-M-B75 | HPLC_1 | 0.92 | 428 |
| 917 | A24-M-B76 | HPLC_1 | 1.11 | 464 |
| 918 | A24-M-B77 | HPLC_1 | 0.92 | 433 |
| 919 | A24-M-B78 | HPLC_1 | 1.21 | 480 |

TABLE III-continued

| Entry | Compound | HPLC method | r.t. (min) | [M + H]+ |
|---|---|---|---|---|
| 920 | A24-M-B79 | HPLC_1 | 1.01 | 452 |
| 921 | A19-M-B89 | HPLC_1 | 1.53 | 527 |
| 922 | A19-M-B90 | HPLC_1 | 1.31 | 417 |
| 923 | A19-M-B93 | HPLC_1 | 1.38 | 433 |
| 924 | A19-M-B91 | HPLC_1 | 1.33 | 391 |
| 925 | A19-M-B92 | HPLC_1 | 1.37 | 443 |
| 926 | A20-M-B83 | HPLC_1 | 0.99 | 389 |
| 927 | A20-M-B84 | HPLC_1 | 1.14 | 431 |
| 928 | A20-M-B94 | HPLC_1 | 1.25 | 421 |
| 929 | A20-M-B85 | HPLC_1 | 0.9 | 343 |
| 930 | A20-M-B86 | HPLC_1 | 1.06 | 421 |
| 931 | A20-M-B87 | HPLC_1 | 1.09 | 462 |
| 932 | A20-M-B88 | HPLC_1 | 1.08 | 439 |
| 933 | A20-M-B89 | HPLC_1 | 1.32 | 495 |
| 934 | A20-M-B90 | HPLC_1 | 1.06 | 385 |
| 935 | A20-M-B93 | HPLC_1 | 1.14 | 401 |
| 936 | A20-M-B91 | HPLC_1 | 1.07 | 359 |
| 937 | A20-M-B92 | HPLC_1 | 1.13 | 411 |
| 938 | A30-M-B35 | HPLC_1 | 1.28 | 409 |
| 939 | A30-M-B36 | HPLC_1 | 1.52 | 421 |
| 940 | A33-M-B25 | HPLC_1 | 1.27 | 377 |
| 941 | A33-M-B26 | HPLC_1 | 1.25 | 357 |
| 942 | A33-M-B27 | HPLC_1 | 1.28 | 391 |
| 943 | A33-M-B29 | HPLC_1 | 1.06 | 315 |
| 944 | A33-M-B30 | HPLC_1 | 1.41 | 397 |
| 945 | A33-M-B31 | HPLC_1 | 1.37 | 411 |
| 946 | A33-M-B32 | HPLC_1 | 1.28 | 421 |
| 947 | A33-M-B33 | HPLC_1 | 1.18 | 343 |
| 948 | A33-M-B34 | HPLC_1 | 1.42 | 445 |
| 949 | A33-M-B35 | HPLC_1 | 1.27 | 421 |
| 950 | A33-M-B36 | HPLC_1 | 1.51 | 433 |
| 951 | A31-M-B25 | HPLC_1 | 1.18 | 351 |
| 952 | A31-M-B26 | HPLC_1 | 1.16 | 331 |
| 953 | A31-M-B27 | HPLC_1 | 1.2 | 365 |
| 954 | A31-M-B28 | HPLC_1 | 1.24 | 357 |
| 955 | A31-M-B29 | HPLC_1 | 0.96 | 289 |
| 956 | A31-M-B30 | HPLC_1 | 1.34 | 371 |
| 957 | A32-M-B40 | HPLC_1 | 1.3 | 365 |
| 958 | A32-M-B41 | HPLC_1 | 1.26 | 345 |
| 959 | A32-M-B42 | HPLC_1 | 1.27 | 369 |
| 960 | A32-M-B43 | HPLC_1 | 1.41 | 453 |
| 961 | A32-M-B44 | HPLC_1 | 1.21 | 357 |
| 962 | A32-M-B45 | HPLC_1 | 1.17 | 425 |
| 963 | A32-M-B46 | HPLC_1 | 1.1 | 315 |
| 964 | A32-M-B47 | HPLC_1 | 1.24 | 381 |
| 965 | A32-M-B37 | HPLC_1 | 1.05 | 303 |
| 966 | A28-M-B59 | HPLC_1 | 1.32 | 433 |
| 967 | A28-M-B62 | HPLC_1 | 1.25 | 423 |
| 968 | A28-M-B67 | HPLC_1 | 1.39 | 453 |
| 969 | A28-M-B60 | HPLC_1 | 1.16 | 367 |
| 970 | A28-M-B64 | HPLC_1 | 1.4 | 457 |
| 971 | A28-M-B65 | HPLC_1 | 1.32 | 425 |
| 972 | A28-M-B61 | HPLC_1 | 1.03 | 357 |
| 973 | A28-M-B68 | HPLC_1 | 1.23 | 479 |
| 974 | A28-M-B69 | HPLC_1 | 1.27 | 425 |
| 975 | A28-M-B66 | HPLC_1 | 1.27 | 407 |
| 976 | A28-M-B70 | HPLC_1 | 1.21 | 369 |
| 977 | A29-M-B59 | HPLC_1 | 1.31 | 445 |
| 978 | A29-M-B62 | HPLC_1 | 1.24 | 435 |
| 979 | A29-M-B63 | HPLC_1 | 1.22 | 426 |
| 980 | A29-M-B60 | HPLC_1 | 1.14 | 379 |
| 981 | A29-M-B64 | HPLC_1 | 1.39 | 469 |
| 982 | A29-M-B65 | HPLC_1 | 1.3 | 437 |
| 983 | A29-M-B61 | HPLC_1 | 1.02 | 369 |
| 984 | A29-M-B68 | HPLC_1 | 1.22 | 491 |
| 985 | A29-M-B69 | HPLC_1 | 1.25 | 437 |
| 986 | A29-M-B66 | HPLC_1 | 1.26 | 419 |
| 987 | A29-M-B70 | HPLC_1 | 1.19 | 381 |
| 988 | A30-M-B59 | HPLC_1 | 1.42 | 409 |
| 989 | A30-M-B62 | HPLC_1 | 1.36 | 399 |
| 990 | A30-M-B67 | HPLC_1 | 1.47 | 429 |
| 991 | A30-M-B63 | HPLC_1 | 1.34 | 390 |
| 992 | A30-M-B60 | HPLC_1 | 1.27 | 343 |
| 993 | A30-M-B64 | HPLC_1 | 1.49 | 433 |
| 994 | A30-M-B65 | HPLC_1 | 1.42 | 401 |
| 995 | A30-M-B61 | HPLC_1 | 1.14 | 333 |
| 996 | A30-M-B68 | HPLC_1 | 1.33 | 455 |
| 997 | A30-M-B69 | HPLC_1 | 1.37 | 401 |
| 998 | A30-M-B66 | HPLC_1 | 1.38 | 383 |
| 999 | A30-M-B70 | HPLC_1 | 1.32 | 345 |
| 1000 | A33-M-B59 | HPLC_1 | 1.41 | 421 |
| 1001 | A33-M-B62 | HPLC_1 | 1.34 | 411 |
| 1002 | A33-M-B67 | HPLC_1 | 1.47 | 441 |
| 1003 | A33-M-B63 | HPLC_1 | 1.32 | 402 |
| 1004 | A33-M-B60 | HPLC_1 | 1.25 | 355 |
| 1005 | A33-M-B64 | HPLC_1 | 1.48 | 445 |
| 1006 | A33-M-B65 | HPLC_1 | 1.4 | 413 |
| 1007 | A33-M-B61 | HPLC_1 | 1.12 | 345 |
| 1008 | A33-M-B68 | HPLC_1 | 1.32 | 467 |
| 1009 | A33-M-B69 | HPLC_1 | 1.36 | 413 |
| 1010 | A33-M-B66 | HPLC_1 | 1.36 | 395 |
| 1011 | A33-M-B70 | HPLC_1 | 1.29 | 357 |
| 1012 | A31-M-B59 | HPLC_1 | 1.33 | 395 |
| 1013 | A31-M-B62 | HPLC_1 | 1.24 | 385 |
| 1014 | A31-M-B67 | HPLC_1 | 1.39 | 415 |
| 1015 | A31-M-B63 | HPLC_1 | 1.23 | 376 |
| 1016 | A31-M-B60 | HPLC_1 | 1.15 | 329 |
| 1017 | A31-M-B65 | HPLC_1 | 1.32 | 387 |
| 1018 | A31-M-B61 | HPLC_1 | 1.02 | 319 |
| 1019 | A31-M-B68 | HPLC_1 | 1.23 | 441 |
| 1020 | A31-M-B69 | HPLC_1 | 1.27 | 387 |
| 1021 | A31-M-B66 | HPLC_1 | 1.27 | 369 |
| 1022 | A31-M-B70 | HPLC_1 | 1.2 | 331 |
| 1023 | A32-M-B59 | HPLC_1 | 1.33 | 395 |
| 1024 | A32-M-B62 | HPLC_1 | 1.26 | 385 |
| 1025 | A32-M-B67 | HPLC_1 | 1.39 | 415 |
| 1026 | A32-M-B63 | HPLC_1 | 1.24 | 376 |
| 1027 | A32-M-B60 | HPLC_1 | 1.16 | 329 |
| 1028 | A32-M-B64 | HPLC_1 | 1.42 | 419 |
| 1029 | A32-M-B65 | HPLC_1 | 1.32 | 387 |
| 1030 | A32-M-B61 | HPLC_1 | 1.04 | 319 |
| 1031 | A32-M-B68 | HPLC_1 | 1.24 | 441 |
| 1032 | A32-M-B69 | HPLC_1 | 1.28 | 387 |
| 1033 | A32-M-B66 | HPLC_1 | 1.28 | 369 |
| 1034 | A32-M-B70 | HPLC_1 | 1.22 | 331 |
| 1035 | A26-M-B81 | HPLC_1 | 1.18 | 411 |
| 1036 | A26-M-B71 | HPLC_1 | 1.17 | 381 |
| 1037 | A26-M-B72 | HPLC_1 | 1.48 | 473 |
| 1038 | A26-M-B73 | HPLC_1 | 1.33 | 359 |
| 1039 | A26-M-B74 | HPLC_1 | 1.17 | 415 |
| 1040 | A26-M-B75 | HPLC_1 | 1.13 | 357 |
| 1041 | A26-M-B76 | HPLC_1 | 1.33 | 393 |
| 1042 | A26-M-B77 | HPLC_1 | 1.14 | 362 |
| 1043 | A26-M-B78 | HPLC_1 | 1.43 | 409 |
| 1044 | A26-M-B79 | HPLC_1 | 1.22 | 381 |
| 1045 | A26-M-B82 | HPLC_1 | 1.25 | 430 |
| 1046 | A26-M-B80 | HPLC_1 | 1.26 | 452 |
| 1047 | A27-M-B81 | HPLC_1 | 1.33 | 479 |
| 1048 | A27-M-B71 | HPLC_1 | 1.32 | 449 |
| 1049 | A27-M-B72 | HPLC_1 | 1.59 | 541 |
| 1050 | A27-M-B73 | HPLC_1 | 1.47 | 427 |
| 1051 | A27-M-B74 | HPLC_1 | 1.34 | 483 |
| 1052 | A27-M-B75 | HPLC_1 | 1.3 | 425 |
| 1053 | A27-M-B76 | HPLC_1 | 1.46 | 461 |
| 1054 | A29-M-B73 | HPLC_1 | 1.39 | 423 |
| 1055 | A29-M-B74 | HPLC_1 | 1.24 | 479 |
| 1056 | A29-M-B75 | HPLC_1 | 1.21 | 421 |
| 1057 | A29-M-B76 | HPLC_1 | 1.38 | 457 |
| 1058 | A29-M-B77 | HPLC_1 | 1.22 | 426 |
| 1059 | A29-M-B78 | HPLC_1 | 1.47 | 473 |
| 1060 | A29-M-B79 | HPLC_1 | 1.29 | 445 |
| 1061 | A29-M-B80 | HPLC_1 | 1.32 | 516 |
| 1062 | A30-M-B81 | HPLC_1 | 1.36 | 439 |
| 1063 | A30-M-B71 | HPLC_1 | 1.35 | 409 |
| 1064 | A30-M-B73 | HPLC_1 | 1.5 | 387 |
| 1065 | A30-M-B74 | HPLC_1 | 1.37 | 443 |
| 1066 | A30-M-B75 | HPLC_1 | 1.33 | 385 |
| 1067 | A30-M-B76 | HPLC_1 | 1.49 | 421 |
| 1068 | A30-M-B77 | HPLC_1 | 1.33 | 390 |
| 1069 | A30-M-B78 | HPLC_1 | 1.57 | 437 |
| 1070 | A30-M-B79 | HPLC_1 | 1.4 | 409 |
| 1071 | A30-M-B80 | HPLC_1 | 1.44 | 480 |
| 1072 | A33-M-B81 | HPLC_1 | 1.34 | 451 |
| 1073 | A33-M-B71 | HPLC_1 | 1.34 | 421 |

TABLE III-continued

| Entry | Compound | HPLC method | r.t. (min) | [M + H]+ |
|---|---|---|---|---|
| 1074 | A33-M-B73 | HPLC_1 | 1.49 | 399 |
| 1075 | A33-M-B75 | HPLC_1 | 1.31 | 397 |
| 1076 | A33-M-B76 | HPLC_1 | 1.47 | 433 |
| 1077 | A33-M-B77 | HPLC_1 | 1.32 | 402 |
| 1078 | A33-M-B79 | HPLC_1 | 1.39 | 421 |
| 1079 | A33-M-B82 | HPLC_1 | 1.42 | 470 |
| 1080 | A33-M-B80 | HPLC_1 | 1.42 | 492 |
| 1081 | A31-M-B81 | HPLC_1 | 1.25 | 425 |
| 1082 | A31-M-B71 | HPLC_1 | 1.25 | 395 |
| 1083 | A31-M-B72 | HPLC_1 | 1.55 | 487 |
| 1084 | A31-M-B73 | HPLC_1 | 1.4 | 373 |
| 1085 | A31-M-B74 | HPLC_1 | 1.26 | 429 |
| 1086 | A31-M-B75 | HPLC_1 | 1.22 | 371 |
| 1087 | A31-M-B76 | HPLC_1 | 1.4 | 407 |
| 1088 | A31-M-B77 | HPLC_1 | 1.23 | 376 |
| 1089 | A31-M-B78 | HPLC_1 | 1.49 | 423 |
| 1090 | A31-M-B79 | HPLC_1 | 1.29 | 395 |
| 1091 | A31-M-B82 | HPLC_1 | 1.34 | 444 |
| 1092 | A31-M-B80 | HPLC_1 | 1.34 | 466 |
| 1093 | A32-M-B81 | HPLC_1 | 1.26 | 425 |
| 1094 | A32-M-B71 | HPLC_1 | 1.26 | 395 |
| 1095 | A32-M-B72 | HPLC_1 | 1.55 | 487 |
| 1096 | A32-M-B73 | HPLC_1 | 1.42 | 373 |
| 1097 | A32-M-B74 | HPLC_1 | 1.27 | 429 |
| 1098 | A32-M-B75 | HPLC_1 | 1.23 | 371 |
| 1099 | A32-M-B76 | HPLC_1 | 1.4 | 407 |
| 1100 | A32-M-B77 | HPLC_1 | 1.24 | 376 |
| 1101 | A32-M-B78 | HPLC_1 | 1.49 | 423 |
| 1102 | A32-M-B79 | HPLC_1 | 1.31 | 395 |
| 1103 | A32-M-B82 | HPLC_1 | 1.34 | 444 |
| 1104 | A32-M-B80 | HPLC_1 | 1.35 | 466 |
| 1105 | A26-M-B83 | HPLC_1 | 1.13 | 373 |
| 1106 | A26-M-B84 | HPLC_1 | 1.28 | 415 |
| 1107 | A26-M-B94 | HPLC_1 | 1.39 | 405 |
| 1108 | A26-M-B85 | HPLC_1 | 1.02 | 327 |
| 1109 | A26-M-B86 | HPLC_1 | 1.2 | 405 |
| 1110 | A26-M-B87 | HPLC_1 | 1.22 | 446 |
| 1111 | A26-M-B89 | HPLC_1 | 1.44 | 479 |
| 1112 | A26-M-B90 | HPLC_1 | 1.19 | 369 |
| 1113 | A26-M-B93 | HPLC_1 | 1.26 | 385 |
| 1114 | A26-M-B91 | HPLC_1 | 1.2 | 343 |
| 1115 | A27-M-B83 | HPLC_1 | 1.3 | 441 |
| 1116 | A27-M-B84 | HPLC_1 | 1.43 | 483 |
| 1117 | A27-M-B94 | HPLC_1 | 1.53 | 473 |
| 1118 | A27-M-B85 | HPLC_1 | 1.2 | 395 |
| 1119 | A27-M-B86 | HPLC_1 | 1.36 | 473 |
| 1120 | A27-M-B87 | HPLC_1 | 1.37 | 514 |
| 1121 | A27-M-B88 | HPLC_1 | 1.37 | 491 |
| 1122 | A27-M-B89 | HPLC_1 | 1.56 | 547 |
| 1123 | A27-M-B93 | HPLC_1 | 1.41 | 453 |
| 1124 | A27-M-B91 | HPLC_1 | 1.37 | 411 |
| 1125 | A27-M-B92 | HPLC_1 | 1.39 | 463 |
| 1126 | A28-M-B83 | HPLC_1 | 1.23 | 425 |
| 1127 | A28-M-B84 | HPLC_1 | 1.36 | 467 |
| 1128 | A28-M-B94 | HPLC_1 | 1.47 | 457 |
| 1129 | A28-M-B85 | HPLC_1 | 1.12 | 379 |
| 1130 | A28-M-B86 | HPLC_1 | 1.29 | 457 |
| 1131 | A28-M-B87 | HPLC_1 | 1.3 | 498 |
| 1132 | A28-M-B88 | HPLC_1 | 1.31 | 475 |
| 1133 | A28-M-B89 | HPLC_1 | 1.51 | 531 |
| 1134 | A28-M-B91 | HPLC_1 | 1.29 | 395 |
| 1135 | A28-M-B92 | HPLC_1 | 1.34 | 447 |
| 1136 | A29-M-B83 | HPLC_1 | 1.21 | 437 |
| 1137 | A29-M-B84 | HPLC_1 | 1.34 | 479 |
| 1138 | A29-M-B85 | HPLC_1 | 1.11 | 391 |
| 1139 | A29-M-B87 | HPLC_1 | 1.29 | 510 |
| 1140 | A29-M-B88 | HPLC_1 | 1.29 | 487 |
| 1141 | A29-M-B89 | HPLC_1 | 1.49 | 543 |
| 1142 | A30-M-B89 | HPLC_1 | 1.59 | 507 |
| 1143 | A30-M-B90 | HPLC_1 | 1.37 | 397 |
| 1144 | A30-M-B93 | HPLC_1 | 1.43 | 413 |
| 1145 | A30-M-B91 | HPLC_1 | 1.39 | 371 |
| 1146 | A30-M-B92 | HPLC_1 | 1.42 | 423 |
| 1147 | A33-M-B83 | HPLC_1 | 1.32 | 413 |
| 1148 | A33-M-B84 | HPLC_1 | 1.45 | 455 |
| 1149 | A33-M-B94 | HPLC_1 | 1.55 | 445 |
| 1150 | A33-M-B85 | HPLC_1 | 1.21 | 367 |
| 1151 | A33-M-B86 | HPLC_1 | 1.38 | 445 |
| 1152 | A33-M-B87 | HPLC_1 | 1.39 | 486 |
| 1153 | A33-M-B88 | HPLC_1 | 1.39 | 463 |
| 1154 | A33-M-B89 | HPLC_1 | 1.59 | 519 |
| 1155 | A33-M-B90 | HPLC_1 | 1.35 | 409 |
| 1156 | A33-M-B93 | HPLC_1 | 1.42 | 425 |
| 1157 | A33-M-B91 | HPLC_1 | 1.38 | 383 |
| 1158 | A33-M-B92 | HPLC_1 | 1.41 | 435 |
| 1159 | A31-M-B83 | HPLC_1 | 1.22 | 387 |
| 1160 | A31-M-B84 | HPLC_1 | 1.36 | 429 |
| 1161 | A31-M-B94 | HPLC_1 | 1.47 | 419 |
| 1162 | A31-M-B85 | HPLC_1 | 1.12 | 341 |
| 1163 | A31-M-B86 | HPLC_1 | 1.29 | 419 |
| 1164 | A31-M-B87 | HPLC_1 | 1.3 | 460 |
| 1165 | A31-M-B89 | HPLC_1 | 1.51 | 493 |
| 1166 | A31-M-B90 | HPLC_1 | 1.27 | 383 |
| 1167 | A31-M-B93 | HPLC_1 | 1.34 | 399 |
| 1168 | A31-M-B91 | HPLC_1 | 1.29 | 357 |
| 1169 | A31-M-B92 | HPLC_1 | 1.33 | 409 |
| 1170 | A32-M-B83 | HPLC_1 | 1.24 | 387 |
| 1171 | A32-M-B94 | HPLC_1 | 1.47 | 419 |
| 1172 | A32-M-B85 | HPLC_1 | 1.12 | 341 |
| 1173 | A32-M-B86 | HPLC_1 | 1.3 | 419 |
| 1174 | A32-M-B87 | HPLC_1 | 1.32 | 460 |
| 1175 | A32-M-B88 | HPLC_1 | 1.32 | 437 |
| 1176 | A32-M-B89 | HPLC_1 | 1.52 | 493 |
| 1177 | A32-M-B90 | HPLC_1 | 1.28 | 383 |
| 1178 | A32-M-B93 | HPLC_1 | 1.35 | 399 |
| 1179 | A32-M-B91 | HPLC_1 | 1.3 | 357 |
| 1180 | A32-M-B92 | HPLC_1 | 1.34 | 409 |
| 1181 | A34-M-B25 | HPLC_1 | 1.3 | 399 |
| 1182 | A34-M-B27 | HPLC_1 | 1.32 | 413 |
| 1183 | A34-M-B28 | HPLC_1 | 1.36 | 405 |
| 1184 | A34-M-B29 | HPLC_1 | 1.09 | 337 |
| 1185 | A34-M-B30 | HPLC_1 | 1.45 | 419 |
| 1186 | A34-M-B32 | HPLC_1 | 1.32 | 443 |
| 1187 | A34-M-B33 | HPLC_1 | 1.21 | 365 |
| 1188 | A34-M-B34 | HPLC_1 | 1.45 | 467 |
| 1189 | A34-M-B36 | HPLC_1 | 1.54 | 455 |
| 1190 | A35-M-B25 | HPLC_1 | 1.19 | 415 |
| 1191 | A35-M-B26 | HPLC_1 | 1.16 | 395 |
| 1192 | A35-M-B27 | HPLC_1 | 1.21 | 429 |
| 1193 | A35-M-B28 | HPLC_1 | 1.25 | 421 |
| 1194 | A35-M-B29 | HPLC_1 | 0.97 | 353 |
| 1195 | A35-M-B30 | HPLC_1 | 1.35 | 435 |
| 1196 | A35-M-B31 | HPLC_1 | 1.31 | 449 |
| 1197 | A35-M-B32 | HPLC_1 | 1.21 | 459 |
| 1198 | A35-M-B33 | HPLC_1 | 1.09 | 381 |
| 1199 | A36-M-B26 | HPLC_1 | 0.93 | 372 |
| 1200 | A36-M-B33 | HPLC_1 | 0.87 | 358 |
| 1201 | A36-M-B36 | HPLC_1 | 1.26 | 448 |
| 1202 | A37-M-B25 | HPLC_1 | 0.92 | 372 |
| 1203 | A37-M-B26 | HPLC_1 | 0.87 | 352 |
| 1204 | A37-M-B27 | HPLC_1 | 0.94 | 386 |
| 1205 | A37-M-B28 | HPLC_1 | 0.97 | 378 |
| 1206 | A37-M-B29 | HPLC_1 | 0.7 | 310 |
| 1207 | A37-M-B30 | HPLC_1 | 1.07 | 392 |
| 1208 | A37-M-B31 | HPLC_1 | 1.02 | 406 |
| 1209 | A37-M-B32 | HPLC_1 | 0.96 | 416 |
| 1210 | A37-M-B33 | HPLC_1 | 0.81 | 338 |
| 1211 | A37-M-B34 | HPLC_1 | 1.09 | 440 |
| 1212 | A37-M-B35 | HPLC_1 | 0.92 | 416 |
| 1213 | A37-M-B36 | HPLC_1 | 1.19 | 428 |
| 1214 | A38-M-B25 | HPLC_1 | 0.9 | 372 |
| 1215 | A38-M-B26 | HPLC_1 | 0.85 | 352 |
| 1216 | A38-M-B27 | HPLC_1 | 0.93 | 386 |
| 1217 | A38-M-B28 | HPLC_1 | 0.97 | 378 |
| 1218 | A38-M-B29 | HPLC_1 | 0.69 | 310 |
| 1219 | A38-M-B30 | HPLC_1 | 1.06 | 392 |
| 1220 | A38-M-B31 | HPLC_1 | 1.02 | 406 |
| 1221 | A38-M-B32 | HPLC_1 | 0.94 | 416 |
| 1222 | A38-M-B33 | HPLC_1 | 0.8 | 338 |
| 1223 | A38-M-B34 | HPLC_1 | 1.08 | 440 |
| 1224 | A38-M-B35 | HPLC_1 | 0.92 | 416 |
| 1225 | A39-M-B26 | HPLC_1 | 0.91 | 360 |
| 1226 | A39-M-B32 | HPLC_1 | 0.99 | 424 |
| 1227 | A34-M-B39 | HPLC_1 | 1.37 | 429 |

TABLE III-continued

| Entry | Compound | HPLC method | r.t. (min) | [M + H]+ |
|---|---|---|---|---|
| 1228 | A34-M-B42 | HPLC_1 | 1.37 | 417 |
| 1229 | A34-M-B43 | HPLC_1 | 1.37 | 501 |
| 1230 | A34-M-B95 | HPLC_1 | 1.37 | 478 |
| 1231 | A34-M-B44 | HPLC_1 | 1.37 | 405 |
| 1232 | A34-M-B45 | HPLC_1 | 1.37 | 473 |
| 1233 | A34-M-B46 | HPLC_1 | 1.37 | 363 |
| 1234 | A34-M-B47 | HPLC_1 | 1.37 | 429 |
| 1235 | A34-M-B37 | HPLC_1 | 1.37 | 351 |
| 1236 | A34-M-B38 | HPLC_1 | 1.37 | 390 |
| 1237 | A35-M-B39 | HPLC_1 | 1.37 | 445 |
| 1238 | A35-M-B40 | HPLC_1 | 1.37 | 429 |
| 1239 | A35-M-B41 | HPLC_1 | 1.37 | 409 |
| 1240 | A35-M-B42 | HPLC_1 | 1.37 | 433 |
| 1241 | A35-M-B43 | HPLC_1 | 1.37 | 517 |
| 1242 | A35-M-B95 | HPLC_1 | 1.37 | 494 |
| 1243 | A35-M-B44 | HPLC_1 | 1.37 | 421 |
| 1244 | A35-M-B45 | HPLC_1 | 1.37 | 489 |
| 1245 | A35-M-B46 | HPLC_1 | 1.37 | 379 |
| 1246 | A35-M-B47 | HPLC_1 | 1.37 | 445 |
| 1247 | A35-M-B37 | HPLC_1 | 1.37 | 367 |
| 1248 | A40-M-B40 | HPLC_1 | 1.37 | 323 |
| 1249 | A40-M-B44 | HPLC_1 | 1.37 | 315 |
| 1250 | A40-M-B46 | HPLC_1 | 1.37 | 273 |
| 1251 | A40-M-B47 | HPLC_1 | 1.37 | 339 |
| 1252 | A40-M-B37 | HPLC_1 | 1.37 | 261 |
| 1253 | A41-M-B95 | HPLC_1 | 1.37 | 431 |
| 1254 | A41-M-B45 | HPLC_1 | 1.37 | 426 |
| 1255 | A36-M-B43 | HPLC_1 | 1.37 | 494 |
| 1256 | A36-M-B95 | HPLC_1 | 1.37 | 471 |
| 1257 | A36-M-B45 | HPLC_1 | 1.37 | 466 |
| 1258 | A36-M-B46 | HPLC_1 | 1.37 | 356 |
| 1259 | A36-M-B37 | HPLC_1 | 1.37 | 344 |
| 1260 | A37-M-B40 | HPLC_1 | 1.37 | 386 |
| 1261 | A37-M-B41 | HPLC_1 | 1.37 | 366 |
| 1262 | A37-M-B42 | HPLC_1 | 1.37 | 390 |
| 1263 | A37-M-B95 | HPLC_1 | 1.37 | 451 |
| 1264 | A37-M-B44 | HPLC_1 | 1.37 | 378 |
| 1265 | A37-M-B45 | HPLC_1 | 1.37 | 446 |
| 1266 | A37-M-B46 | HPLC_1 | 1.37 | 336 |
| 1267 | A37-M-B47 | HPLC_1 | 1.37 | 402 |
| 1268 | A37-M-B37 | HPLC_1 | 1.37 | 324 |
| 1269 | A38-M-B39 | HPLC_1 | 1.37 | 402 |
| 1270 | A38-M-B40 | HPLC_1 | 1.37 | 386 |
| 1271 | A38-M-B41 | HPLC_1 | 1.37 | 366 |
| 1272 | A38-M-B42 | HPLC_1 | 1.37 | 390 |
| 1273 | A38-M-B95 | HPLC_1 | 1.37 | 451 |
| 1274 | A38-M-B44 | HPLC_1 | 1.37 | 378 |
| 1275 | A38-M-B45 | HPLC_1 | 1.37 | 446 |
| 1276 | A38-M-B47 | HPLC_1 | 1.37 | 402 |
| 1277 | A38-M-B37 | HPLC_1 | 1.37 | 324 |
| 1278 | A39-M-B43 | HPLC_1 | 1.37 | 482 |
| 1279 | A39-M-B95 | HPLC_1 | 1.37 | 459 |
| 1280 | A39-M-B45 | HPLC_1 | 1.37 | 454 |
| 1281 | A39-M-B46 | HPLC_1 | 1.37 | 344 |
| 1282 | A39-M-B37 | HPLC_1 | 1.37 | 332 |
| 1283 | A34-M-B48 | HPLC_1 | 1.4 | 435 |
| 1284 | A34-M-B49 | HPLC_1 | 1.36 | 429 |
| 1285 | A34-M-B51 | HPLC_1 | 1.23 | 365 |
| 1286 | A34-M-B52 | HPLC_1 | 1.29 | 379 |
| 1287 | A32-M-B38 | HPLC_1 | 1.1 | 342 |
| 1288 | A26-M-B48 | HPLC_1 | 1.21 | 373 |
| 1289 | A26-M-B49 | HPLC_1 | 1.16 | 367 |
| 1290 | A26-M-B50 | HPLC_1 | 1.03 | 356 |
| 1291 | A26-M-B51 | HPLC_1 | 1 | 303 |
| 1292 | A26-M-B61 | HPLC_1 | 0.93 | 305 |
| 1293 | A26-M-B68 | HPLC_1 | 1.15 | 427 |
| 1294 | A26-M-B69 | HPLC_1 | 1.18 | 373 |
| 1295 | A26-M-B66 | HPLC_1 | 1.19 | 355 |
| 1296 | A26-M-B70 | HPLC_1 | 1.12 | 317 |
| 1297 | A27-M-B59 | HPLC_1 | 1.39 | 449 |
| 1298 | A27-M-B62 | HPLC_1 | 1.32 | 439 |
| 1299 | A27-M-B67 | HPLC_1 | 1.44 | 469 |
| 1300 | A27-M-B63 | HPLC_1 | 1.31 | 430 |
| 1301 | A27-M-B60 | HPLC_1 | 1.24 | 383 |
| 1302 | A27-M-B64 | HPLC_1 | 1.46 | 473 |
| 1303 | A27-M-B65 | HPLC_1 | 1.38 | 441 |
| 1304 | A27-M-B61 | HPLC_1 | 1.12 | 373 |
| 1305 | A27-M-B68 | HPLC_1 | 1.3 | 495 |
| 1306 | A27-M-B69 | HPLC_1 | 1.34 | 441 |
| 1307 | A27-M-B66 | HPLC_1 | 1.35 | 423 |
| 1308 | A27-M-B70 | HPLC_1 | 1.29 | 385 |
| 1309 | A27-M-B77 | HPLC_1 | 1.31 | 430 |
| 1310 | A27-M-B78 | HPLC_1 | 1.54 | 477 |
| 1311 | A27-M-B79 | HPLC_1 | 1.37 | 449 |
| 1312 | A28-M-B81 | HPLC_1 | 1.26 | 463 |
| 1313 | A28-M-B71 | HPLC_1 | 1.25 | 433 |
| 1314 | A28-M-B73 | HPLC_1 | 1.4 | 411 |
| 1315 | A28-M-B74 | HPLC_1 | 1.26 | 467 |
| 1316 | A28-M-B75 | HPLC_1 | 1.22 | 409 |
| 1317 | A28-M-B76 | HPLC_1 | 1.4 | 445 |
| 1318 | A28-M-B77 | HPLC_1 | 1.23 | 414 |
| 1319 | A28-M-B78 | HPLC_1 | 1.49 | 461 |
| 1320 | A28-M-B79 | HPLC_1 | 1.3 | 433 |
| 1321 | A28-M-B80 | HPLC_1 | 1.34 | 504 |
| 1322 | A29-M-B81 | HPLC_1 | 1.25 | 475 |
| 1323 | A29-M-B71 | HPLC_1 | 1.24 | 445 |
| 1324 | A29-M-B90 | HPLC_1 | 1.27 | 433 |
| 1325 | A29-M-B93 | HPLC_1 | 1.33 | 449 |
| 1326 | A29-M-B91 | HPLC_1 | 1.28 | 407 |
| 1327 | A29-M-B92 | HPLC_1 | 1.32 | 459 |
| 1328 | A30-M-B83 | HPLC_1 | 1.34 | 401 |
| 1329 | A30-M-B84 | HPLC_1 | 1.46 | 443 |
| 1330 | A30-M-B94 | HPLC_1 | 1.56 | 433 |
| 1331 | A30-M-B85 | HPLC_1 | 1.24 | 355 |
| 1332 | A30-M-B86 | HPLC_1 | 1.39 | 433 |
| 1333 | A30-M-B87 | HPLC_1 | 1.4 | 474 |
| 1334 | A30-M-B88 | HPLC_1 | 1.41 | 451 |
| 1335 | A35-M-B34 | HPLC_1 | 1.36 | 483 |
| 1336 | A35-M-B36 | HPLC_1 | 1.44 | 471 |
| 1337 | A40-M-B25 | HPLC_1 | 0.99 | 309 |
| 1338 | A40-M-B28 | HPLC_1 | 1.05 | 315 |
| 1339 | A40-M-B31 | HPLC_1 | 1.11 | 343 |
| 1340 | A41-M-B26 | HPLC_1 | 0.87 | 332 |
| 1341 | A34-M-B53 | HPLC_1 | 1.37 | 459 |
| 1342 | A34-M-B54 | HPLC_1 | 1.32 | 417 |
| 1343 | A34-M-B55 | HPLC_1 | 1.35 | 435 |
| 1344 | A34-M-B57 | HPLC_1 | 1.32 | 391 |
| 1345 | A34-M-B58 | HPLC_1 | 1.37 | 427 |
| 1346 | A35-M-B48 | HPLC_1 | 1.29 | 451 |
| 1347 | A35-M-B49 | HPLC_1 | 1.25 | 445 |
| 1348 | A35-M-B50 | HPLC_1 | 1.13 | 434 |
| 1349 | A35-M-B51 | HPLC_1 | 1.11 | 381 |
| 1350 | A35-M-B52 | HPLC_1 | 1.17 | 395 |
| 1351 | A35-M-B53 | HPLC_1 | 1.27 | 475 |
| 1352 | A35-M-B54 | HPLC_1 | 1.2 | 433 |
| 1353 | A35-M-B55 | HPLC_1 | 1.24 | 451 |
| 1354 | A35-M-B56 | HPLC_1 | 1.23 | 429 |
| 1355 | A35-M-B57 | HPLC_1 | 1.21 | 407 |
| 1356 | A35-M-B58 | HPLC_1 | 1.27 | 443 |
| 1357 | A40-M-B58 | HPLC_1 | 1.1 | 337 |
| 1358 | A41-M-B51 | HPLC_1 | 0.79 | 318 |
| 1359 | A41-M-B52 | HPLC_1 | 0.87 | 332 |
| 1360 | A41-M-B53 | HPLC_1 | 1 | 412 |
| 1361 | A41-M-B57 | HPLC_1 | 0.9 | 344 |
| 1362 | A41-M-B58 | HPLC_1 | 0.99 | 380 |
| 1363 | A36-M-B51 | HPLC_1 | 0.86 | 358 |
| 1364 | A36-M-B52 | HPLC_1 | 0.94 | 372 |
| 1365 | A36-M-B53 | HPLC_1 | 1.06 | 452 |
| 1366 | A36-M-B56 | HPLC_1 | 1 | 406 |
| 1367 | A36-M-B57 | HPLC_1 | 0.97 | 384 |
| 1368 | A36-M-B58 | HPLC_1 | 1.06 | 420 |
| 1369 | A37-M-B48 | HPLC_1 | 1 | 408 |
| 1370 | A37-M-B49 | HPLC_1 | 0.97 | 402 |
| 1371 | A37-M-B50 | HPLC_1 | 0.83 | 391 |
| 1372 | A37-M-B51 | HPLC_1 | 0.8 | 338 |
| 1373 | A37-M-B52 | HPLC_1 | 0.88 | 352 |
| 1374 | A37-M-B54 | HPLC_1 | 0.91 | 390 |
| 1375 | A37-M-B55 | HPLC_1 | 0.94 | 408 |
| 1376 | A37-M-B57 | HPLC_1 | 0.91 | 364 |
| 1377 | A37-M-B58 | HPLC_1 | 1 | 400 |
| 1378 | A38-M-B48 | HPLC_1 | 1 | 408 |
| 1379 | A38-M-B49 | HPLC_1 | 0.96 | 402 |
| 1380 | A38-M-B50 | HPLC_1 | 0.82 | 391 |
| 1381 | A38-M-B51 | HPLC_1 | 0.79 | 338 |

TABLE III-continued

| Entry | Compound | HPLC method | r.t. (min) | [M + H]+ |
|---|---|---|---|---|
| 1382 | A38-M-B52 | HPLC_1 | 0.87 | 352 |
| 1383 | A38-M-B53 | HPLC_1 | 1 | 432 |
| 1384 | A38-M-B54 | HPLC_1 | 0.9 | 390 |
| 1385 | A38-M-B55 | HPLC_1 | 0.94 | 408 |
| 1386 | A38-M-B56 | HPLC_1 | 0.94 | 386 |
| 1387 | A38-M-B57 | HPLC_1 | 0.91 | 364 |
| 1388 | A38-M-B58 | HPLC_1 | 0.99 | 400 |
| 1389 | A39-M-B51 | HPLC_1 | 0.84 | 346 |
| 1390 | A39-M-B57 | HPLC_1 | 0.96 | 372 |
| 1391 | A39-M-B58 | HPLC_1 | 1.04 | 408 |
| 1392 | A34-M-B59 | HPLC_1 | 1.39 | 443 |
| 1393 | A34-M-B68 | HPLC_1 | 1.31 | 489 |
| 1394 | A34-M-B69 | HPLC_1 | 1.35 | 435 |
| 1395 | A34-M-B70 | HPLC_1 | 1.29 | 379 |
| 1396 | A35-M-B59 | HPLC_1 | 1.29 | 459 |
| 1397 | A35-M-B62 | HPLC_1 | 1.22 | 449 |
| 1398 | A35-M-B64 | HPLC_1 | 1.37 | 483 |
| 1399 | A35-M-B65 | HPLC_1 | 1.28 | 451 |
| 1400 | A35-M-B66 | HPLC_1 | 1.24 | 433 |
| 1401 | A41-M-B60 | HPLC_1 | 0.84 | 330 |
| 1402 | A41-M-B70 | HPLC_1 | 0.89 | 332 |
| 1403 | A36-M-B68 | HPLC_1 | 0.99 | 482 |
| 1404 | A37-M-B59 | HPLC_1 | 1.01 | 416 |
| 1405 | A37-M-B62 | HPLC_1 | 0.92 | 406 |
| 1406 | A37-M-B67 | HPLC_1 | 1.09 | 436 |
| 1407 | A37-M-B63 | HPLC_1 | 0.92 | 397 |
| 1408 | A37-M-B60 | HPLC_1 | 0.84 | 350 |
| 1409 | A37-M-B64 | HPLC_1 | 1.1 | 440 |
| 1410 | A37-M-B65 | HPLC_1 | 1 | 408 |
| 1411 | A37-M-B61 | HPLC_1 | 0.73 | 340 |
| 1412 | A37-M-B68 | HPLC_1 | 0.94 | 462 |
| 1413 | A37-M-B69 | HPLC_1 | 0.94 | 408 |
| 1414 | A38-M-B59 | HPLC_1 | 1 | 416 |
| 1415 | A38-M-B62 | HPLC_1 | 0.92 | 406 |
| 1416 | A38-M-B67 | HPLC_1 | 1.08 | 436 |
| 1417 | A38-M-B63 | HPLC_1 | 0.91 | 397 |
| 1418 | A38-M-B60 | HPLC_1 | 0.84 | 350 |
| 1419 | A38-M-B64 | HPLC_1 | 1.09 | 440 |
| 1420 | A38-M-B65 | HPLC_1 | 0.99 | 408 |
| 1421 | A38-M-B61 | HPLC_1 | 0.72 | 340 |
| 1422 | A38-M-B68 | HPLC_1 | 0.94 | 462 |
| 1423 | A38-M-B69 | HPLC_1 | 0.94 | 408 |
| 1424 | A38-M-B66 | HPLC_1 | 0.95 | 390 |
| 1425 | A38-M-B70 | HPLC_1 | 0.9 | 352 |
| 1426 | A39-M-B67 | HPLC_1 | 1.13 | 444 |
| 1427 | A39-M-B61 | HPLC_1 | 0.75 | 348 |
| 1428 | A39-M-B70 | HPLC_1 | 0.93 | 360 |
| 1429 | A34-M-B81 | HPLC_1 | 1.33 | 473 |
| 1430 | A34-M-B72 | HPLC_1 | 1.56 | 535 |
| 1431 | A34-M-B78 | HPLC_1 | 1.52 | 471 |
| 1432 | A34-M-B80 | HPLC_1 | 1.4 | 514 |
| 1433 | A35-M-B73 | HPLC_1 | 1.37 | 437 |
| 1434 | A35-M-B78 | HPLC_1 | 1.44 | 487 |
| 1435 | A35-M-B80 | HPLC_1 | 1.3 | 530 |
| 1436 | A41-M-B73 | HPLC_1 | 1.09 | 374 |
| 1437 | A41-M-B75 | HPLC_1 | 0.9 | 372 |
| 1438 | A41-M-B76 | HPLC_1 | 1.09 | 408 |
| 1439 | A36-M-B81 | HPLC_1 | 1.02 | 466 |
| 1440 | A36-M-B71 | HPLC_1 | 1.02 | 436 |
| 1441 | A36-M-B72 | HPLC_1 | 1.3 | 528 |
| 1442 | A36-M-B75 | HPLC_1 | 0.97 | 412 |
| 1443 | A36-M-B76 | HPLC_1 | 1.14 | 448 |
| 1444 | A36-M-B78 | HPLC_1 | 1.25 | 464 |
| 1445 | A36-M-B82 | HPLC_1 | 1.07 | 485 |
| 1446 | A36-M-B80 | HPLC_1 | 1.09 | 507 |
| 1447 | A37-M-B81 | HPLC_1 | 0.97 | 446 |
| 1448 | A37-M-B71 | HPLC_1 | 0.96 | 416 |
| 1449 | A37-M-B72 | HPLC_1 | 1.24 | 508 |
| 1450 | A37-M-B73 | HPLC_1 | 1.09 | 394 |
| 1451 | A37-M-B74 | HPLC_1 | 0.94 | 450 |
| 1452 | A37-M-B75 | HPLC_1 | 0.91 | 392 |
| 1453 | A37-M-B76 | HPLC_1 | 1.09 | 428 |
| 1454 | A37-M-B77 | HPLC_1 | 0.91 | 397 |
| 1455 | A37-M-B78 | HPLC_1 | 1.19 | 444 |
| 1456 | A37-M-B80 | HPLC_1 | 1.03 | 487 |
| 1457 | A38-M-B81 | HPLC_1 | 0.97 | 446 |
| 1458 | A38-M-B71 | HPLC_1 | 0.96 | 416 |
| 1459 | A38-M-B72 | HPLC_1 | 1.23 | 508 |
| 1460 | A38-M-B73 | HPLC_1 | 1.08 | 394 |
| 1461 | A38-M-B74 | HPLC_1 | 0.94 | 450 |
| 1462 | A38-M-B75 | HPLC_1 | 0.91 | 392 |
| 1463 | A38-M-B76 | HPLC_1 | 1.09 | 428 |
| 1464 | A38-M-B77 | HPLC_1 | 0.92 | 397 |
| 1465 | A38-M-B78 | HPLC_1 | 1.19 | 444 |
| 1466 | A38-M-B79 | HPLC_1 | 1 | 416 |
| 1467 | A38-M-B82 | HPLC_1 | 1 | 465 |
| 1468 | A39-M-B75 | HPLC_1 | 0.96 | 400 |
| 1469 | A39-M-B76 | HPLC_1 | 1.13 | 436 |
| 1470 | A39-M-B78 | HPLC_1 | 1.24 | 452 |
| 1471 | A39-M-B82 | HPLC_1 | 1.06 | 473 |
| 1472 | A34-M-B83 | HPLC_1 | 1.31 | 435 |
| 1473 | A34-M-B87 | HPLC_1 | 1.37 | 508 |
| 1474 | A34-M-B90 | HPLC_1 | 1.34 | 431 |
| 1475 | A34-M-B93 | HPLC_1 | 1.41 | 447 |
| 1476 | A34-M-B92 | HPLC_1 | 1.4 | 457 |
| 1477 | A35-M-B83 | HPLC_1 | 1.19 | 451 |
| 1478 | A35-M-B85 | HPLC_1 | 1.09 | 405 |
| 1479 | A35-M-B87 | HPLC_1 | 1.27 | 524 |
| 1480 | A35-M-B88 | HPLC_1 | 1.27 | 501 |
| 1481 | A35-M-B89 | HPLC_1 | 1.47 | 557 |
| 1482 | A35-M-B93 | HPLC_1 | 1.31 | 463 |
| 1483 | A35-M-B92 | HPLC_1 | 1.3 | 473 |
| 1484 | A41-M-B89 | HPLC_1 | 1.22 | 494 |
| 1485 | A36-M-B86 | HPLC_1 | 1.02 | 460 |
| 1486 | A36-M-B87 | HPLC_1 | 1.05 | 501 |
| 1487 | A36-M-B89 | HPLC_1 | 1.27 | 534 |
| 1488 | A37-M-B83 | HPLC_1 | 0.9 | 408 |
| 1489 | A37-M-B84 | HPLC_1 | 1.04 | 450 |
| 1490 | A37-M-B85 | HPLC_1 | 0.82 | 362 |
| 1491 | A37-M-B87 | HPLC_1 | 0.99 | 481 |
| 1492 | A37-M-B88 | HPLC_1 | 0.97 | 458 |
| 1493 | A37-M-B89 | HPLC_1 | 1.2 | 514 |
| 1494 | A37-M-B90 | HPLC_1 | 0.97 | 404 |
| 1495 | A37-M-B93 | HPLC_1 | 1.04 | 420 |
| 1496 | A37-M-B91 | HPLC_1 | 0.97 | 378 |
| 1497 | A37-M-B92 | HPLC_1 | 1.04 | 430 |
| 1498 | A38-M-B83 | HPLC_1 | 0.89 | 408 |
| 1499 | A38-M-B84 | HPLC_1 | 1.04 | 450 |
| 1500 | A38-M-B94 | HPLC_1 | 1.12 | 440 |
| 1501 | A38-M-B85 | HPLC_1 | 0.82 | 362 |
| 1502 | A38-M-B87 | HPLC_1 | 0.98 | 481 |
| 1503 | A38-M-B90 | HPLC_1 | 0.96 | 404 |
| 1504 | A38-M-B92 | HPLC_1 | 1.04 | 430 |
| 1505 | A39-M-B86 | HPLC_1 | 1 | 448 |
| 1506 | A39-M-B90 | HPLC_1 | 1.01 | 412 |
| 1507 | A42-M-B25 | HPLC_1 | 1.26 | 407 |
| 1508 | A42-M-B26 | HPLC_1 | 1.25 | 387 |
| 1509 | A42-M-B27 | HPLC_1 | 1.29 | 421 |
| 1510 | A42-M-B28 | HPLC_1 | 1.33 | 413 |
| 1511 | A42-M-B29 | HPLC_1 | 1.06 | 345 |
| 1512 | A42-M-B30 | HPLC_1 | 1.4 | 427 |
| 1513 | A42-M-B32 | HPLC_1 | 1.28 | 451 |
| 1514 | A42-M-B33 | HPLC_1 | 1.18 | 373 |
| 1515 | A42-M-B34 | HPLC_1 | 1.39 | 475 |
| 1516 | A42-M-B36 | HPLC_1 | 1.49 | 463 |
| 1517 | A43-M-B25 | HPLC_1 | 1.04 | 365 |
| 1518 | A43-M-B26 | HPLC_1 | 1.01 | 345 |
| 1519 | A43-M-B28 | HPLC_1 | 1.11 | 371 |
| 1520 | A43-M-B29 | HPLC_1 | 0.8 | 303 |
| 1521 | A43-M-B30 | HPLC_1 | 1.22 | 385 |
| 1522 | A43-M-B32 | HPLC_1 | 1.07 | 409 |
| 1523 | A43-M-B33 | HPLC_1 | 0.94 | 331 |
| 1524 | A43-M-B34 | HPLC_1 | 1.23 | 433 |
| 1525 | A43-M-B36 | HPLC_1 | 1.33 | 421 |
| 1526 | A44-M-B25 | HPLC_1 | 1.22 | 391 |
| 1527 | A44-M-B29 | HPLC_1 | 1 | 329 |
| 1528 | A44-M-B32 | HPLC_1 | 1.24 | 435 |
| 1529 | A45-M-B25 | HPLC_1 | 1.06 | 353 |
| 1530 | A45-M-B26 | HPLC_1 | 1.02 | 333 |
| 1531 | A45-M-B27 | HPLC_1 | 1.08 | 367 |
| 1532 | A45-M-B29 | HPLC_1 | 0.82 | 291 |
| 1533 | A45-M-B30 | HPLC_1 | 1.22 | 373 |
| 1534 | A45-M-B32 | HPLC_1 | 1.09 | 397 |
| 1535 | A45-M-B33 | HPLC_1 | 0.96 | 319 |

TABLE III-continued

| Entry | Compound | HPLC method | r.t. (min) | [M + H]+ |
|---|---|---|---|---|
| 1536 | A45-M-B34 | HPLC_1 | 1.25 | 421 |
| 1537 | A45-M-B36 | HPLC_1 | 1.33 | 409 |
| 1538 | A46-M-B25 | HPLC_1 | 1.21 | 389 |
| 1539 | A46-M-B27 | HPLC_1 | 1.22 | 403 |
| 1540 | A46-M-B29 | HPLC_1 | 0.97 | 327 |
| 1541 | A1-M-B26 | HPLC_1 | 1.22 | 343 |
| 1542 | A1-M-B29 | HPLC_1 | 1.01 | 301 |
| 1543 | A1-M-B30 | HPLC_1 | 1.4 | 383 |
| 1544 | A1-M-B33 | HPLC_1 | 1.14 | 329 |
| 1545 | A1-M-B34 | HPLC_1 | 1.41 | 431 |
| 1546 | A1-M-B36 | HPLC_1 | 1.5 | 419 |
| 1547 | A2-M-B25 | HPLC_1 | 1.22 | 371 |
| 1548 | A2-M-B29 | HPLC_1 | 0.98 | 309 |
| 1549 | A2-M-B31 | HPLC_1 | 1.33 | 405 |
| 1550 | A2-M-B32 | HPLC_1 | 1.24 | 415 |
| 1551 | A2-M-B33 | HPLC_1 | 1.12 | 337 |
| 1552 | A2-M-B35 | HPLC_1 | 1.23 | 415 |
| 1553 | A2-M-B36 | HPLC_1 | 1.48 | 427 |
| 1554 | A42-M-B39 | HPLC_1 | 1.33 | 437 |
| 1555 | A42-M-B40 | HPLC_1 | 1.34 | 421 |
| 1556 | A42-M-B41 | HPLC_1 | 1.3 | 401 |
| 1557 | A42-M-B43 | HPLC_1 | 1.44 | 509 |
| 1558 | A42-M-B44 | HPLC_1 | 1.26 | 413 |
| 1559 | A42-M-B45 | HPLC_1 | 1.22 | 481 |
| 1560 | A42-M-B46 | HPLC_1 | 1.15 | 371 |
| 1561 | A42-M-B47 | HPLC_1 | 1.28 | 437 |
| 1562 | A42-M-B37 | HPLC_1 | 1.11 | 359 |
| 1563 | A42-M-B38 | HPLC_1 | 1.14 | 398 |
| 1564 | A43-M-B39 | HPLC_1 | 1.11 | 395 |
| 1565 | A43-M-B40 | HPLC_1 | 1.12 | 379 |
| 1566 | A43-M-B41 | HPLC_1 | 1.07 | 359 |
| 1567 | A43-M-B42 | HPLC_1 | 1.08 | 383 |
| 1568 | A43-M-B43 | HPLC_1 | 1.23 | 467 |
| 1569 | A43-M-B95 | HPLC_1 | 1.05 | 444 |
| 1570 | A43-M-B44 | HPLC_1 | 1.02 | 371 |
| 1571 | A43-M-B45 | HPLC_1 | 1 | 439 |
| 1572 | A43-M-B46 | HPLC_1 | 0.9 | 329 |
| 1573 | A43-M-B47 | HPLC_1 | 1.07 | 395 |
| 1574 | A43-M-B37 | HPLC_1 | 0.86 | 317 |
| 1575 | A43-M-B38 | HPLC_1 | 0.89 | 356 |
| 1576 | A44-M-B39 | HPLC_1 | 1.28 | 421 |
| 1577 | A44-M-B46 | HPLC_1 | 1.1 | 355 |
| 1578 | A45-M-B39 | HPLC_1 | 1.12 | 383 |
| 1579 | A45-M-B40 | HPLC_1 | 1.13 | 367 |
| 1580 | A45-M-B41 | HPLC_1 | 1.08 | 347 |
| 1581 | A45-M-B42 | HPLC_1 | 1.09 | 371 |
| 1582 | A45-M-B43 | HPLC_1 | 1.24 | 455 |
| 1583 | A45-M-B95 | HPLC_1 | 1.05 | 432 |
| 1584 | A45-M-B44 | HPLC_1 | 1.02 | 359 |
| 1585 | A45-M-B45 | HPLC_1 | 1.01 | 427 |
| 1586 | A45-M-B46 | HPLC_1 | 0.91 | 317 |
| 1587 | A45-M-B47 | HPLC_1 | 1.07 | 383 |
| 1588 | A45-M-B37 | HPLC_1 | 0.86 | 305 |
| 1589 | A45-M-B38 | HPLC_1 | 0.89 | 344 |
| 1590 | A46-M-B39 | HPLC_1 | 1.32 | 419 |
| 1591 | A46-M-B41 | HPLC_1 | 1.3 | 383 |
| 1592 | A46-M-B46 | HPLC_1 | 1.2 | 353 |
| 1593 | A1-M-B39 | HPLC_1 | 1.31 | 393 |
| 1594 | A1-M-B40 | HPLC_1 | 1.31 | 377 |
| 1595 | A1-M-B41 | HPLC_1 | 1.27 | 357 |
| 1596 | A1-M-B42 | HPLC_1 | 1.28 | 381 |
| 1597 | A1-M-B43 | HPLC_1 | 1.42 | 465 |
| 1598 | A1-M-B95 | HPLC_1 | 1.24 | 442 |
| 1599 | A1-M-B44 | HPLC_1 | 1.23 | 369 |
| 1600 | A1-M-B45 | HPLC_1 | 1.19 | 437 |
| 1601 | A1-M-B46 | HPLC_1 | 1.11 | 327 |
| 1602 | A1-M-B47 | HPLC_1 | 1.26 | 393 |
| 1603 | A2-M-B39 | HPLC_1 | 1.29 | 401 |
| 1604 | A2-M-B40 | HPLC_1 | 1.29 | 385 |
| 1605 | A2-M-B41 | HPLC_1 | 1.25 | 365 |
| 1606 | A2-M-B43 | HPLC_1 | 1.4 | 473 |
| 1607 | A2-M-B95 | HPLC_1 | 1.22 | 450 |
| 1608 | A2-M-B44 | HPLC_1 | 1.2 | 377 |
| 1609 | A2-M-B45 | HPLC_1 | 1.17 | 445 |
| 1610 | A2-M-B46 | HPLC_1 | 1.09 | 335 |
| 1611 | A2-M-B47 | HPLC_1 | 1.24 | 401 |
| 1612 | A2-M-B37 | HPLC_1 | 1.05 | 323 |
| 1613 | A2-M-B38 | HPLC_1 | 1.08 | 362 |
| 1614 | A42-M-B48 | HPLC_1 | 1.35 | 443 |
| 1615 | A42-M-B49 | HPLC_1 | 1.3 | 437 |
| 1616 | A42-M-B51 | HPLC_1 | 1.14 | 373 |
| 1617 | A42-M-B52 | HPLC_1 | 1.21 | 387 |
| 1618 | A42-M-B54 | HPLC_1 | 1.25 | 425 |
| 1619 | A42-M-B57 | HPLC_1 | 1.24 | 399 |
| 1620 | A42-M-B58 | HPLC_1 | 1.32 | 435 |
| 1621 | A43-M-B48 | HPLC_1 | 1.11 | 401 |
| 1622 | A43-M-B49 | HPLC_1 | 1.06 | 395 |
| 1623 | A43-M-B50 | HPLC_1 | 0.94 | 384 |
| 1624 | A43-M-B51 | HPLC_1 | 0.91 | 331 |
| 1625 | A43-M-B52 | HPLC_1 | 0.98 | 345 |
| 1626 | A43-M-B54 | HPLC_1 | 1.02 | 383 |
| 1627 | A43-M-B55 | HPLC_1 | 1.05 | 401 |
| 1628 | A43-M-B56 | HPLC_1 | 1.04 | 379 |
| 1629 | A43-M-B57 | HPLC_1 | 1.01 | 357 |
| 1630 | A43-M-B58 | HPLC_1 | 1.09 | 393 |
| 1631 | A44-M-B48 | HPLC_1 | 1.3 | 427 |
| 1632 | A44-M-B51 | HPLC_1 | 1.09 | 357 |
| 1633 | A44-M-B53 | HPLC_1 | 1.27 | 451 |
| 1634 | A44-M-B54 | HPLC_1 | 1.2 | 409 |
| 1635 | A45-M-B48 | HPLC_1 | 1.12 | 389 |
| 1636 | A45-M-B49 | HPLC_1 | 1.07 | 383 |
| 1637 | A45-M-B50 | HPLC_1 | 0.94 | 372 |
| 1638 | A45-M-B51 | HPLC_1 | 0.91 | 319 |
| 1639 | A45-M-B52 | HPLC_1 | 0.99 | 333 |
| 1640 | A45-M-B53 | HPLC_1 | 1.1 | 413 |
| 1641 | A45-M-B54 | HPLC_1 | 1.02 | 371 |
| 1642 | A45-M-B55 | HPLC_1 | 1.06 | 389 |
| 1643 | A45-M-B56 | HPLC_1 | 1.05 | 367 |
| 1644 | A45-M-B57 | HPLC_1 | 1.02 | 345 |
| 1645 | A45-M-B58 | HPLC_1 | 1.09 | 381 |
| 1646 | A46-M-B53 | HPLC_1 | 1.27 | 449 |
| 1647 | A46-M-B55 | HPLC_1 | 1.22 | 425 |
| 1648 | A46-M-B57 | HPLC_1 | 1.2 | 381 |
| 1649 | A46-M-B58 | HPLC_1 | 1.24 | 417 |
| 1650 | A1-M-B48 | HPLC_1 | 1.32 | 399 |
| 1651 | A1-M-B49 | HPLC_1 | 1.27 | 393 |
| 1652 | A1-M-B50 | HPLC_1 | 1.13 | 382 |
| 1653 | A1-M-B51 | HPLC_1 | 1.1 | 329 |
| 1654 | A1-M-B52 | HPLC_1 | 1.17 | 343 |
| 1655 | A1-M-B53 | HPLC_1 | 1.29 | 423 |
| 1656 | A1-M-B54 | HPLC_1 | 1.21 | 381 |
| 1657 | A1-M-B55 | HPLC_1 | 1.26 | 399 |
| 1658 | A1-M-B57 | HPLC_1 | 1.2 | 355 |
| 1659 | A1-M-B58 | HPLC_1 | 1.28 | 391 |
| 1660 | A2-M-B49 | HPLC_1 | 1.24 | 401 |
| 1661 | A2-M-B50 | HPLC_1 | 1.11 | 390 |
| 1662 | A2-M-B51 | HPLC_1 | 1.09 | 337 |
| 1663 | A2-M-B52 | HPLC_1 | 1.15 | 351 |
| 1664 | A2-M-B53 | HPLC_1 | 1.27 | 431 |
| 1665 | A2-M-B54 | HPLC_1 | 1.19 | 389 |
| 1666 | A2-M-B55 | HPLC_1 | 1.24 | 407 |
| 1667 | A2-M-B57 | HPLC_1 | 1.19 | 363 |
| 1668 | A2-M-B58 | HPLC_1 | 1.26 | 399 |
| 1669 | A42-M-B59 | HPLC_1 | 1.36 | 451 |
| 1670 | A42-M-B62 | HPLC_1 | 1.29 | 441 |
| 1671 | A42-M-B67 | HPLC_1 | 1.42 | 471 |
| 1672 | A42-M-B63 | HPLC_1 | 1.27 | 432 |
| 1673 | A42-M-B60 | HPLC_1 | 1.21 | 385 |
| 1674 | A42-M-B61 | HPLC_1 | 1.08 | 375 |
| 1675 | A42-M-B69 | HPLC_1 | 1.31 | 443 |
| 1676 | A42-M-B70 | HPLC_1 | 1.25 | 387 |
| 1677 | A43-M-B59 | HPLC_1 | 1.14 | 409 |
| 1678 | A43-M-B63 | HPLC_1 | 1.04 | 390 |
| 1679 | A43-M-B60 | HPLC_1 | 0.96 | 343 |
| 1680 | A43-M-B64 | HPLC_1 | 1.24 | 433 |
| 1681 | A43-M-B65 | HPLC_1 | 1.14 | 401 |
| 1682 | A43-M-B61 | HPLC_1 | 0.83 | 333 |
| 1683 | A43-M-B68 | HPLC_1 | 1.06 | 455 |
| 1684 | A43-M-B69 | HPLC_1 | 1.07 | 401 |
| 1685 | A43-M-B66 | HPLC_1 | 1.08 | 383 |
| 1686 | A43-M-B70 | HPLC_1 | 1.02 | 345 |
| 1687 | A44-M-B60 | HPLC_1 | 1.16 | 369 |
| 1688 | A44-M-B69 | HPLC_1 | 1.26 | 427 |
| 1689 | A44-M-B70 | HPLC_1 | 1.21 | 371 |

TABLE III-continued

| Entry | Compound | HPLC method | r.t. (min) | [M + H]+ |
|---|---|---|---|---|
| 1690 | A45-M-B59 | HPLC_1 | 1.15 | 397 |
| 1691 | A45-M-B62 | HPLC_1 | 1.06 | 387 |
| 1692 | A45-M-B67 | HPLC_1 | 1.23 | 417 |
| 1693 | A45-M-B63 | HPLC_1 | 1.05 | 378 |
| 1694 | A45-M-B60 | HPLC_1 | 0.97 | 331 |
| 1695 | A45-M-B64 | HPLC_1 | 1.24 | 421 |
| 1696 | A45-M-B65 | HPLC_1 | 1.14 | 389 |
| 1697 | A45-M-B61 | HPLC_1 | 0.82 | 321 |
| 1698 | A45-M-B68 | HPLC_1 | 1.07 | 443 |
| 1699 | A45-M-B69 | HPLC_1 | 1.08 | 389 |
| 1700 | A45-M-B66 | HPLC_1 | 1.09 | 371 |
| 1701 | A45-M-B70 | HPLC_1 | 1.02 | 333 |
| 1702 | A46-M-B59 | HPLC_1 | 1.31 | 433 |
| 1703 | A46-M-B62 | HPLC_1 | 1.27 | 423 |
| 1704 | A46-M-B67 | HPLC_1 | 1.38 | 453 |
| 1705 | A46-M-B63 | HPLC_1 | 1.27 | 414 |
| 1706 | A46-M-B70 | HPLC_1 | 1.27 | 369 |
| 1707 | A1-M-B59 | HPLC_1 | 1.33 | 407 |
| 1708 | A1-M-B62 | HPLC_1 | 1.26 | 397 |
| 1709 | A1-M-B67 | HPLC_1 | 1.39 | 427 |
| 1710 | A1-M-B63 | HPLC_1 | 1.24 | 388 |
| 1711 | A1-M-B60 | HPLC_1 | 1.17 | 341 |
| 1712 | A1-M-B64 | HPLC_1 | 1.41 | 431 |
| 1713 | A1-M-B65 | HPLC_1 | 1.32 | 399 |
| 1714 | A1-M-B61 | HPLC_1 | 1.04 | 331 |
| 1715 | A1-M-B68 | HPLC_1 | 1.25 | 453 |
| 1716 | A1-M-B66 | HPLC_1 | 1.28 | 381 |
| 1717 | A1-M-B70 | HPLC_1 | 1.22 | 343 |
| 1718 | A2-M-B59 | HPLC_1 | 1.31 | 415 |
| 1719 | A2-M-B62 | HPLC_1 | 1.23 | 405 |
| 1720 | A2-M-B67 | HPLC_1 | 1.37 | 435 |
| 1721 | A2-M-B60 | HPLC_1 | 1.15 | 349 |
| 1722 | A2-M-B64 | HPLC_1 | 1.38 | 439 |
| 1723 | A2-M-B61 | HPLC_1 | 1.02 | 339 |
| 1724 | A2-M-B68 | HPLC_1 | 1.22 | 461 |
| 1725 | A2-M-B69 | HPLC_1 | 1.25 | 407 |
| 1726 | A2-M-B66 | HPLC_1 | 1.26 | 389 |
| 1727 | A2-M-B70 | HPLC_1 | 1.2 | 351 |
| 1728 | A42-M-B81 | HPLC_1 | 1.25 | 481 |
| 1729 | A42-M-B71 | HPLC_1 | 1.24 | 451 |
| 1730 | A42-M-B72 | HPLC_1 | 1.51 | 543 |
| 1731 | A42-M-B73 | HPLC_1 | 1.38 | 429 |
| 1732 | A42-M-B74 | HPLC_1 | 1.25 | 485 |
| 1733 | A42-M-B75 | HPLC_1 | 1.22 | 427 |
| 1734 | A42-M-B76 | HPLC_1 | 1.37 | 463 |
| 1735 | A42-M-B77 | HPLC_1 | 1.22 | 432 |
| 1736 | A42-M-B78 | HPLC_1 | 1.46 | 479 |
| 1737 | A42-M-B79 | HPLC_1 | 1.29 | 451 |
| 1738 | A42-M-B82 | HPLC_1 | 1.31 | 500 |
| 1739 | A42-M-B80 | HPLC_1 | 1.32 | 522 |
| 1740 | A47-M-B77 | HPLC_1 | 1.05 | 380 |
| 1741 | A43-M-B81 | HPLC_1 | 1.05 | 439 |
| 1742 | A43-M-B71 | HPLC_1 | 1.04 | 409 |
| 1743 | A43-M-B73 | HPLC_1 | 1.18 | 387 |
| 1744 | A43-M-B75 | HPLC_1 | 1.01 | 385 |
| 1745 | A43-M-B76 | HPLC_1 | 1.19 | 421 |
| 1746 | A43-M-B77 | HPLC_1 | 1.01 | 390 |
| 1747 | A43-M-B78 | HPLC_1 | 1.28 | 437 |
| 1748 | A43-M-B79 | HPLC_1 | 1.08 | 409 |
| 1749 | A43-M-B80 | HPLC_1 | 1.12 | 480 |
| 1750 | A44-M-B71 | HPLC_1 | 1.2 | 435 |
| 1751 | A44-M-B75 | HPLC_1 | 1.18 | 411 |
| 1752 | A44-M-B78 | HPLC_1 | 1.43 | 463 |
| 1753 | A45-M-B81 | HPLC_1 | 1.06 | 427 |
| 1754 | A45-M-B71 | HPLC_1 | 1.05 | 397 |
| 1755 | A45-M-B72 | HPLC_1 | 1.35 | 489 |
| 1756 | A45-M-B73 | HPLC_1 | 1.19 | 375 |
| 1757 | A45-M-B74 | HPLC_1 | 1.04 | 431 |
| 1758 | A45-M-B75 | HPLC_1 | 1.01 | 373 |
| 1759 | A45-M-B76 | HPLC_1 | 1.19 | 409 |
| 1760 | A45-M-B77 | HPLC_1 | 1.01 | 378 |
| 1761 | A45-M-B78 | HPLC_1 | 1.29 | 425 |
| 1762 | A45-M-B79 | HPLC_1 | 1.09 | 397 |
| 1763 | A45-M-B82 | HPLC_1 | 1.12 | 446 |
| 1764 | A45-M-B80 | HPLC_1 | 1.13 | 468 |
| 1765 | A46-M-B77 | HPLC_1 | 1.22 | 414 |
| 1766 | A46-M-B78 | HPLC_1 | 1.49 | 461 |
| 1767 | A46-M-B82 | HPLC_1 | 1.29 | 482 |
| 1768 | A1-M-B81 | HPLC_1 | 1.22 | 437 |
| 1769 | A1-M-B71 | HPLC_1 | 1.22 | 407 |
| 1770 | A1-M-B72 | HPLC_1 | 1.51 | 499 |
| 1771 | A1-M-B73 | HPLC_1 | 1.36 | 385 |
| 1772 | A1-M-B74 | HPLC_1 | 1.23 | 441 |
| 1773 | A1-M-B76 | HPLC_1 | 1.35 | 419 |
| 1774 | A1-M-B79 | HPLC_1 | 1.26 | 407 |
| 1775 | A1-M-B80 | HPLC_1 | 1.3 | 478 |
| 1776 | A2-M-B81 | HPLC_1 | 1.2 | 445 |
| 1777 | A2-M-B71 | HPLC_1 | 1.2 | 415 |
| 1778 | A2-M-B72 | HPLC_1 | 1.48 | 507 |
| 1779 | A2-M-B74 | HPLC_1 | 1.2 | 449 |
| 1780 | A2-M-B75 | HPLC_1 | 1.17 | 391 |
| 1781 | A2-M-B76 | HPLC_1 | 1.33 | 427 |
| 1782 | A2-M-B77 | HPLC_1 | 1.17 | 396 |
| 1783 | A2-M-B78 | HPLC_1 | 1.42 | 443 |
| 1784 | A2-M-B79 | HPLC_1 | 1.24 | 415 |
| 1785 | A2-M-B82 | HPLC_1 | 1.27 | 464 |
| 1786 | A2-M-B80 | HPLC_1 | 1.27 | 486 |
| 1787 | A42-M-B83 | HPLC_1 | 1.25 | 443 |
| 1788 | A42-M-B94 | HPLC_1 | 1.47 | 475 |
| 1789 | A42-M-B85 | HPLC_1 | 1.14 | 397 |
| 1790 | A42-M-B86 | HPLC_1 | 1.31 | 475 |
| 1791 | A42-M-B87 | HPLC_1 | 1.32 | 516 |
| 1792 | A42-M-B88 | HPLC_1 | 1.32 | 493 |
| 1793 | A42-M-B89 | HPLC_1 | 1.49 | 549 |
| 1794 | A42-M-B90 | HPLC_1 | 1.29 | 439 |
| 1795 | A42-M-B93 | HPLC_1 | 1.36 | 455 |
| 1796 | A43-M-B83 | HPLC_1 | 1.01 | 401 |
| 1797 | A43-M-B84 | HPLC_1 | 1.15 | 443 |
| 1798 | A43-M-B94 | HPLC_1 | 1.26 | 433 |
| 1799 | A43-M-B85 | HPLC_1 | 0.93 | 355 |
| 1800 | A43-M-B86 | HPLC_1 | 1.07 | 433 |
| 1801 | A43-M-B88 | HPLC_1 | 1.09 | 451 |
| 1802 | A43-M-B89 | HPLC_1 | 1.32 | 507 |
| 1803 | A43-M-B90 | HPLC_1 | 1.06 | 397 |
| 1804 | A43-M-B93 | HPLC_1 | 1.13 | 413 |
| 1805 | A43-M-B91 | HPLC_1 | 1.07 | 371 |
| 1806 | A43-M-B92 | HPLC_1 | 1.13 | 423 |
| 1807 | A44-M-B85 | HPLC_1 | 1.09 | 381 |
| 1808 | A44-M-B87 | HPLC_1 | 1.27 | 500 |
| 1809 | A45-M-B83 | HPLC_1 | 1.01 | 389 |
| 1810 | A45-M-B84 | HPLC_1 | 1.15 | 431 |
| 1811 | A45-M-B94 | HPLC_1 | 1.27 | 421 |
| 1812 | A45-M-B85 | HPLC_1 | 0.92 | 343 |
| 1813 | A45-M-B86 | HPLC_1 | 1.07 | 421 |
| 1814 | A45-M-B87 | HPLC_1 | 1.1 | 462 |
| 1815 | A45-M-B88 | HPLC_1 | 1.09 | 439 |
| 1816 | A45-M-B90 | HPLC_1 | 1.07 | 385 |
| 1817 | A45-M-B93 | HPLC_1 | 1.14 | 401 |
| 1818 | A45-M-B91 | HPLC_1 | 1.08 | 359 |
| 1819 | A45-M-B92 | HPLC_1 | 1.14 | 411 |
| 1820 | A46-M-B85 | HPLC_1 | 1.07 | 379 |
| 1821 | A1-M-B85 | HPLC_1 | 1.11 | 353 |
| 1822 | A1-M-B86 | HPLC_1 | 1.28 | 431 |
| 1823 | A1-M-B87 | HPLC_1 | 1.29 | 472 |
| 1824 | A1-M-B90 | HPLC_1 | 1.26 | 395 |
| 1825 | A1-M-B93 | HPLC_1 | 1.32 | 411 |
| 1826 | A2-M-B83 | HPLC_1 | 1.18 | 407 |
| 1827 | A2-M-B94 | HPLC_1 | 1.4 | 439 |
| 1828 | A2-M-B85 | HPLC_1 | 1.08 | 361 |
| 1829 | A2-M-B86 | HPLC_1 | 1.24 | 439 |
| 1830 | A2-M-B87 | HPLC_1 | 1.25 | 480 |
| 1831 | A2-M-B88 | HPLC_1 | 1.26 | 457 |
| 1832 | A7-M-B25 | HPLC_1 | 1.16 | 337 |
| 1833 | A7-M-B26 | HPLC_1 | 1.14 | 317 |
| 1834 | A7-M-B27 | HPLC_1 | 1.19 | 351 |
| 1835 | A7-M-B28 | HPLC_1 | 1.23 | 343 |
| 1836 | A7-M-B29 | HPLC_1 | 0.92 | 275 |
| 1837 | A7-M-B30 | HPLC_1 | 1.34 | 357 |
| 1838 | A7-M-B32 | HPLC_1 | 1.19 | 381 |
| 1839 | A7-M-B33 | HPLC_1 | 1.06 | 303 |
| 1840 | A8-M-B25 | HPLC_1 | 1.04 | 321 |
| 1841 | A8-M-B26 | HPLC_1 | 1.01 | 301 |
| 1842 | A8-M-B27 | HPLC_1 | 1.07 | 335 |
| 1843 | A8-M-B28 | HPLC_1 | 1.12 | 327 |

TABLE III-continued

| Entry | Compound | HPLC method | r.t. (min) | [M + H]+ |
|---|---|---|---|---|
| 1844 | A8-M-B29 | HPLC_1 | 0.78 | 259 |
| 1845 | A8-M-B30 | HPLC_1 | 1.23 | 341 |
| 1846 | A8-M-B32 | HPLC_1 | 1.08 | 365 |
| 1847 | A8-M-B33 | HPLC_1 | 0.93 | 287 |
| 1848 | A8-M-B34 | HPLC_1 | 1.24 | 389 |
| 1849 | A8-M-B35 | HPLC_1 | 1.06 | 365 |
| 1850 | A8-M-B36 | HPLC_1 | 1.35 | 377 |
| 1851 | A11-M-B25 | HPLC_1 | 1.11 | 335 |
| 1852 | A11-M-B26 | HPLC_1 | 1.07 | 315 |
| 1853 | A11-M-B27 | HPLC_1 | 1.13 | 349 |
| 1854 | A11-M-B28 | HPLC_1 | 1.17 | 341 |
| 1855 | A11-M-B29 | HPLC_1 | 0.85 | 273 |
| 1856 | A11-M-B30 | HPLC_1 | 1.28 | 355 |
| 1857 | A11-M-B32 | HPLC_1 | 1.13 | 379 |
| 1858 | A11-M-B33 | HPLC_1 | 1 | 301 |
| 1859 | A11-M-B34 | HPLC_1 | 1.29 | 403 |
| 1860 | A11-M-B36 | HPLC_1 | 1.4 | 391 |
| 1861 | A4-M-B26 | HPLC_1 | 1.29 | 385 |
| 1862 | A4-M-B27 | HPLC_1 | 1.32 | 419 |
| 1863 | A4-M-B28 | HPLC_1 | 1.37 | 411 |
| 1864 | A4-M-B29 | HPLC_1 | 1.1 | 343 |
| 1865 | A4-M-B30 | HPLC_1 | 1.46 | 425 |
| 1866 | A4-M-B33 | HPLC_1 | 1.22 | 371 |
| 1867 | A4-M-B34 | HPLC_1 | 1.46 | 473 |
| 1868 | A4-M-B36 | HPLC_1 | 1.56 | 461 |
| 1869 | A3-M-B25 | HPLC_1 | 1.26 | 407 |
| 1870 | A3-M-B26 | HPLC_1 | 1.24 | 387 |
| 1871 | A3-M-B27 | HPLC_1 | 1.27 | 421 |
| 1872 | A3-M-B28 | HPLC_1 | 1.32 | 413 |
| 1873 | A3-M-B29 | HPLC_1 | 1.03 | 345 |
| 1874 | A3-M-B30 | HPLC_1 | 1.41 | 427 |
| 1875 | A3-M-B32 | HPLC_1 | 1.27 | 451 |
| 1876 | A3-M-B33 | HPLC_1 | 1.16 | 373 |
| 1877 | A3-M-B34 | HPLC_1 | 1.42 | 475 |
| 1878 | A3-M-B36 | HPLC_1 | 97.72 | 463 |
| 1879 | A5-M-B25 | HPLC_1 | 1.24 | 415 |
| 1880 | A5-M-B26 | HPLC_1 | 1.22 | 395 |
| 1881 | A5-M-B27 | HPLC_1 | 1.26 | 429 |
| 1882 | A5-M-B29 | HPLC_1 | 1.02 | 353 |
| 1883 | A5-M-B32 | HPLC_1 | 1.26 | 459 |
| 1884 | A5-M-B33 | HPLC_1 | 1.15 | 381 |
| 1885 | A5-M-B35 | HPLC_1 | 1.24 | 459 |
| 1886 | A9-M-B25 | HPLC_1 | 0.99 | 406 |
| 1887 | A9-M-B26 | HPLC_1 | 0.95 | 386 |
| 1888 | A9-M-B27 | HPLC_1 | 1.02 | 420 |
| 1889 | A9-M-B28 | HPLC_1 | 1.05 | 412 |
| 1890 | A9-M-B29 | HPLC_1 | 0.78 | 344 |
| 1891 | A9-M-B30 | HPLC_1 | 1.16 | 426 |
| 1892 | A9-M-B31 | HPLC_1 | 1.11 | 440 |
| 1893 | A9-M-B32 | HPLC_1 | 1.02 | 450 |
| 1894 | A9-M-B33 | HPLC_1 | 0.89 | 372 |
| 1895 | A9-M-B36 | HPLC_1 | 1.27 | 462 |
| 1896 | A10-M-B25 | HPLC_1 | 1.07 | 367 |
| 1897 | A10-M-B27 | HPLC_1 | 1.1 | 381 |
| 1898 | A10-M-B28 | HPLC_1 | 1.14 | 373 |
| 1899 | A10-M-B29 | HPLC_1 | 0.84 | 305 |
| 1900 | A10-M-B30 | HPLC_1 | 1.25 | 387 |
| 1901 | A10-M-B31 | HPLC_1 | 1.2 | 401 |
| 1902 | A10-M-B32 | HPLC_1 | 1.1 | 411 |
| 1903 | A10-M-B33 | HPLC_1 | 0.97 | 333 |
| 1904 | A10-M-B34 | HPLC_1 | 1.26 | 435 |
| 1905 | A10-M-B35 | HPLC_1 | 1.09 | 411 |
| 1906 | A10-M-B36 | HPLC_1 | 1.36 | 423 |
| 1907 | A7-M-B39 | HPLC_1 | 1.2 | 367 |
| 1908 | A7-M-B44 | HPLC_1 | 1.1 | 343 |
| 1909 | A7-M-B46 | HPLC_1 | 1 | 301 |
| 1910 | A7-M-B38 | HPLC_1 | 1.01 | 328 |
| 1911 | A8-M-B39 | HPLC_1 | 1.09 | 351 |
| 1912 | A8-M-B40 | HPLC_1 | 1.09 | 335 |
| 1913 | A8-M-B44 | HPLC_1 | 1 | 327 |
| 1914 | A8-M-B45 | HPLC_1 | 0.99 | 395 |
| 1915 | A8-M-B46 | HPLC_1 | 0.89 | 285 |
| 1916 | A8-M-B47 | HPLC_1 | 1.04 | 351 |
| 1917 | A8-M-B38 | HPLC_1 | 0.89 | 312 |
| 1918 | A11-M-B44 | HPLC_1 | 1.05 | 341 |
| 1919 | A11-M-B46 | HPLC_1 | 0.94 | 299 |
| 1920 | A11-M-B47 | HPLC_1 | 1.09 | 365 |
| 1921 | A4-M-B40 | HPLC_1 | 1.32 | 419 |
| 1922 | A4-M-B41 | HPLC_1 | 1.28 | 399 |
| 1923 | A4-M-B44 | HPLC_1 | 1.24 | 411 |
| 1924 | A4-M-B45 | HPLC_1 | 1.2 | 479 |
| 1925 | A4-M-B46 | HPLC_1 | 1.15 | 369 |
| 1926 | A3-M-B39 | HPLC_1 | 1.27 | 437 |
| 1927 | A3-M-B41 | HPLC_1 | 1.23 | 401 |
| 1928 | A3-M-B43 | HPLC_1 | 1.35 | 509 |
| 1929 | A3-M-B44 | HPLC_1 | 1.19 | 413 |
| 1930 | A3-M-B45 | HPLC_1 | 1.16 | 481 |
| 1931 | A3-M-B46 | HPLC_1 | 1.09 | 371 |
| 1932 | A3-M-B47 | HPLC_1 | 1.21 | 437 |
| 1933 | A3-M-B37 | HPLC_1 | 1.06 | 359 |
| 1934 | A5-M-B39 | HPLC_1 | 1.23 | 445 |
| 1935 | A5-M-B40 | HPLC_1 | 1.22 | 429 |
| 1936 | A5-M-B45 | HPLC_1 | 1.14 | 489 |
| 1937 | A5-M-B46 | HPLC_1 | 1.08 | 379 |
| 1938 | A9-M-B39 | HPLC_1 | 1.02 | 436 |
| 1939 | A9-M-B44 | HPLC_1 | 0.96 | 412 |
| 1940 | A9-M-B46 | HPLC_1 | 0.86 | 370 |
| 1941 | A10-M-B39 | HPLC_1 | 1.09 | 397 |
| 1942 | A10-M-B42 | HPLC_1 | 1.07 | 385 |
| 1943 | A10-M-B95 | HPLC_1 | 1.02 | 446 |
| 1944 | A10-M-B44 | HPLC_1 | 1.02 | 373 |
| 1945 | A10-M-B46 | HPLC_1 | 0.93 | 331 |
| 1946 | A10-M-B47 | HPLC_1 | 1.05 | 397 |
| 1947 | A10-M-B37 | HPLC_1 | 0.9 | 319 |
| 1948 | A10-M-B38 | HPLC_1 | 0.92 | 358 |
| 1949 | A7-M-B49 | HPLC_1 | 1.18 | 367 |
| 1950 | A7-M-B51 | HPLC_1 | 1.02 | 303 |
| 1951 | A7-M-B52 | HPLC_1 | 1.09 | 317 |
| 1952 | A7-M-B54 | HPLC_1 | 1.13 | 355 |
| 1953 | A7-M-B55 | HPLC_1 | 1.16 | 373 |
| 1954 | A7-M-B57 | HPLC_1 | 1.12 | 329 |
| 1955 | A8-M-B48 | HPLC_1 | 1.11 | 357 |
| 1956 | A8-M-B49 | HPLC_1 | 1.07 | 351 |
| 1957 | A8-M-B50 | HPLC_1 | 0.93 | 340 |
| 1958 | A8-M-B51 | HPLC_1 | 0.9 | 287 |
| 1959 | A8-M-B52 | HPLC_1 | 0.98 | 301 |
| 1960 | A8-M-B54 | HPLC_1 | 1.01 | 339 |
| 1961 | A8-M-B55 | HPLC_1 | 1.05 | 357 |
| 1962 | A8-M-B57 | HPLC_1 | 1.01 | 313 |
| 1963 | A8-M-B58 | HPLC_1 | 1.1 | 349 |
| 1964 | A11-M-B48 | HPLC_1 | 1.17 | 371 |
| 1965 | A11-M-B49 | HPLC_1 | 1.12 | 365 |
| 1966 | A11-M-B50 | HPLC_1 | 0.99 | 354 |
| 1967 | A11-M-B51 | HPLC_1 | 0.96 | 301 |
| 1968 | A11-M-B52 | HPLC_1 | 1.03 | 315 |
| 1969 | A11-M-B54 | HPLC_1 | 1.07 | 353 |
| 1970 | A11-M-B55 | HPLC_1 | 1.11 | 371 |
| 1971 | A4-M-B49 | HPLC_1 | 1.3 | 435 |
| 1972 | A4-M-B50 | HPLC_1 | 1.19 | 424 |
| 1973 | A4-M-B51 | HPLC_1 | 1.18 | 371 |
| 1974 | A4-M-B52 | HPLC_1 | 1.23 | 385 |
| 1975 | A4-M-B53 | HPLC_1 | 1.32 | 465 |
| 1976 | A4-M-B54 | HPLC_1 | 1.26 | 423 |
| 1977 | A4-M-B55 | HPLC_1 | 1.3 | 441 |
| 1978 | A4-M-B56 | HPLC_1 | 1.29 | 419 |
| 1979 | A4-M-B57 | HPLC_1 | 1.27 | 397 |
| 1980 | A4-M-B58 | HPLC_1 | 1.32 | 433 |
| 1981 | A3-M-B48 | HPLC_1 | 1.3 | 443 |
| 1982 | A3-M-B49 | HPLC_1 | 1.26 | 437 |
| 1983 | A3-M-B50 | HPLC_1 | 1.14 | 426 |
| 1984 | A3-M-B51 | HPLC_1 | 1.12 | 373 |
| 1985 | A3-M-B52 | HPLC_1 | 1.18 | 387 |
| 1986 | A3-M-B54 | HPLC_1 | 1.21 | 425 |
| 1987 | A3-M-B55 | HPLC_1 | 1.25 | 443 |
| 1988 | A3-M-B56 | HPLC_1 | 1.24 | 421 |
| 1989 | A3-M-B57 | HPLC_1 | 1.21 | 399 |
| 1990 | A3-M-B58 | HPLC_1 | 1.27 | 435 |
| 1991 | A5-M-B51 | HPLC_1 | 1.11 | 381 |
| 1992 | A5-M-B52 | HPLC_1 | 1.17 | 395 |
| 1993 | A5-M-B53 | HPLC_1 | 1.25 | 475 |
| 1994 | A5-M-B54 | HPLC_1 | 1.19 | 433 |
| 1995 | A5-M-B57 | HPLC_1 | 1.19 | 407 |
| 1996 | A5-M-B58 | HPLC_1 | 1.26 | 443 |
| 1997 | A9-M-B49 | HPLC_1 | 1.01 | 436 |

TABLE III-continued

| Entry | Compound | HPLC method | r.t. (min) | [M + H]+ |
|---|---|---|---|---|
| 1998 | A9-M-B50 | HPLC_1 | 0.89 | 425 |
| 1999 | A9-M-B51 | HPLC_1 | 0.88 | 372 |
| 2000 | A9-M-B52 | HPLC_1 | 0.94 | 386 |
| 2001 | A9-M-B53 | HPLC_1 | 1.04 | 466 |
| 2002 | A9-M-B54 | HPLC_1 | 0.96 | 424 |
| 2003 | A9-M-B55 | HPLC_1 | 0.99 | 442 |
| 2004 | A9-M-B56 | HPLC_1 | 0.99 | 420 |
| 2005 | A9-M-B57 | HPLC_1 | 0.96 | 398 |
| 2006 | A9-M-B58 | HPLC_1 | 1.04 | 434 |
| 2007 | A10-M-B48 | HPLC_1 | 1.13 | 403 |
| 2008 | A10-M-B49 | HPLC_1 | 1.09 | 397 |
| 2009 | A10-M-B50 | HPLC_1 | 0.96 | 386 |
| 2010 | A10-M-B51 | HPLC_1 | 0.94 | 333 |
| 2011 | A10-M-B52 | HPLC_1 | 1.01 | 347 |
| 2012 | A10-M-B53 | HPLC_1 | 1.12 | 427 |
| 2013 | A10-M-B54 | HPLC_1 | 1.04 | 385 |
| 2014 | A10-M-B55 | HPLC_1 | 1.08 | 403 |
| 2015 | A10-M-B56 | HPLC_1 | 1.07 | 381 |
| 2016 | A10-M-B57 | HPLC_1 | 1.04 | 359 |
| 2017 | A10-M-B58 | HPLC_1 | 1.12 | 395 |
| 2018 | A7-M-B59 | HPLC_1 | 1.2 | 381 |
| 2019 | A7-M-B67 | HPLC_1 | 1.27 | 401 |
| 2020 | A7-M-B63 | HPLC_1 | 1.12 | 362 |
| 2021 | A7-M-B60 | HPLC_1 | 1.05 | 315 |
| 2022 | A7-M-B64 | HPLC_1 | 1.29 | 405 |
| 2023 | A7-M-B65 | HPLC_1 | 1.19 | 373 |
| 2024 | A7-M-B69 | HPLC_1 | 1.15 | 373 |
| 2025 | A7-M-B66 | HPLC_1 | 1.15 | 355 |
| 2026 | A7-M-B70 | HPLC_1 | 1.09 | 317 |
| 2027 | A8-M-B59 | HPLC_1 | 1.11 | 365 |
| 2028 | A8-M-B62 | HPLC_1 | 1.03 | 355 |
| 2029 | A8-M-B67 | HPLC_1 | 1.18 | 385 |
| 2030 | A8-M-B63 | HPLC_1 | 1.02 | 346 |
| 2031 | A8-M-B60 | HPLC_1 | 0.94 | 299 |
| 2032 | A8-M-B64 | HPLC_1 | 1.2 | 389 |
| 2033 | A8-M-B65 | HPLC_1 | 1.09 | 357 |
| 2034 | A8-M-B61 | HPLC_1 | 0.82 | 289 |
| 2035 | A8-M-B68 | HPLC_1 | 1.04 | 411 |
| 2036 | A8-M-B69 | HPLC_1 | 1.05 | 357 |
| 2037 | A8-M-B70 | HPLC_1 | 1 | 301 |
| 2038 | A11-M-B59 | HPLC_1 | 1.16 | 379 |
| 2039 | A11-M-B62 | HPLC_1 | 1.08 | 369 |
| 2040 | A4-M-B59 | HPLC_1 | 1.33 | 449 |
| 2041 | A4-M-B62 | HPLC_1 | 1.28 | 439 |
| 2042 | A4-M-B64 | HPLC_1 | 1.39 | 473 |
| 2043 | A4-M-B65 | HPLC_1 | 1.32 | 441 |
| 2044 | A4-M-B61 | HPLC_1 | 1.09 | 373 |
| 2045 | A4-M-B68 | HPLC_1 | 1.26 | 495 |
| 2046 | A4-M-B69 | HPLC_1 | 1.28 | 441 |
| 2047 | A4-M-B66 | HPLC_1 | 1.29 | 423 |
| 2048 | A4-M-B70 | HPLC_1 | 1.23 | 385 |
| 2049 | A3-M-B59 | HPLC_1 | 1.29 | 451 |
| 2050 | A3-M-B62 | HPLC_1 | 1.22 | 441 |
| 2051 | A3-M-B67 | HPLC_1 | 1.34 | 471 |
| 2052 | A3-M-B60 | HPLC_1 | 1.14 | 385 |
| 2053 | A3-M-B64 | HPLC_1 | 1.35 | 475 |
| 2054 | A3-M-B65 | HPLC_1 | 1.28 | 443 |
| 2055 | A3-M-B61 | HPLC_1 | 1.02 | 375 |
| 2056 | A3-M-B68 | HPLC_1 | 1.2 | 497 |
| 2057 | A3-M-B69 | HPLC_1 | 1.25 | 443 |
| 2058 | A3-M-B66 | HPLC_1 | 1.25 | 425 |
| 2059 | A3-M-B70 | HPLC_1 | 1.19 | 387 |
| 2060 | A5-M-B59 | HPLC_1 | 1.27 | 459 |
| 2061 | A5-M-B60 | HPLC_1 | 1.12 | 393 |
| 2062 | A5-M-B64 | HPLC_1 | 1.34 | 483 |
| 2063 | A5-M-B68 | HPLC_1 | 1.18 | 505 |
| 2064 | A5-M-B69 | HPLC_1 | 1.2 | 451 |
| 2065 | A5-M-B66 | HPLC_1 | 1.22 | 433 |
| 2066 | A5-M-B70 | HPLC_1 | 1.16 | 395 |
| 2067 | A9-M-B59 | HPLC_1 | 1.04 | 450 |
| 2068 | A9-M-B67 | HPLC_1 | 1.1 | 470 |
| 2069 | A9-M-B60 | HPLC_1 | 0.89 | 384 |
| 2070 | A9-M-B64 | HPLC_1 | 1.12 | 474 |
| 2071 | A9-M-B61 | HPLC_1 | 0.82 | 374 |
| 2072 | A9-M-B68 | HPLC_1 | 0.98 | 496 |
| 2073 | A9-M-B66 | HPLC_1 | 1 | 424 |
| 2074 | A9-M-B70 | HPLC_1 | 0.94 | 386 |
| 2075 | A10-M-B59 | HPLC_1 | 1.12 | 411 |
| 2076 | A10-M-B67 | HPLC_1 | 1.21 | 431 |
| 2077 | A10-M-B63 | HPLC_1 | 1.04 | 392 |
| 2078 | A10-M-B60 | HPLC_1 | 0.98 | 345 |
| 2079 | A10-M-B64 | HPLC_1 | 1.21 | 435 |
| 2080 | A10-M-B68 | HPLC_1 | 1.05 | 457 |
| 2081 | A10-M-B69 | HPLC_1 | 1.07 | 403 |
| 2082 | A10-M-B66 | HPLC_1 | 1.07 | 385 |
| 2083 | A10-M-B70 | HPLC_1 | 1.02 | 347 |
| 2084 | A7-M-B81 | HPLC_1 | 1.16 | 411 |
| 2085 | A7-M-B71 | HPLC_1 | 1.15 | 381 |
| 2086 | A7-M-B72 | HPLC_1 | 1.45 | 473 |
| 2087 | A7-M-B76 | HPLC_1 | 1.29 | 393 |
| 2088 | A7-M-B77 | HPLC_1 | 1.13 | 362 |
| 2089 | A7-M-B78 | HPLC_1 | 1.39 | 409 |
| 2090 | A7-M-B79 | HPLC_1 | 1.2 | 381 |
| 2091 | A7-M-B82 | HPLC_1 | 1.23 | 430 |
| 2092 | A7-M-B80 | HPLC_1 | 1.23 | 452 |
| 2093 | A8-M-B81 | HPLC_1 | 1.06 | 395 |
| 2094 | A8-M-B72 | HPLC_1 | 1.36 | 457 |
| 2095 | A8-M-B73 | HPLC_1 | 1.2 | 343 |
| 2096 | A8-M-B74 | HPLC_1 | 1.05 | 399 |
| 2097 | A8-M-B75 | HPLC_1 | 1.01 | 341 |
| 2098 | A8-M-B76 | HPLC_1 | 1.2 | 377 |
| 2099 | A8-M-B77 | HPLC_1 | 1.02 | 346 |
| 2100 | A8-M-B78 | HPLC_1 | 1.3 | 393 |
| 2101 | A8-M-B79 | HPLC_1 | 1.1 | 365 |
| 2102 | A8-M-B82 | HPLC_1 | 1.13 | 414 |
| 2103 | A8-M-B80 | HPLC_1 | 1.14 | 436 |
| 2104 | A11-M-B81 | HPLC_1 | 1.11 | 409 |
| 2105 | A11-M-B72 | HPLC_1 | 1.4 | 471 |
| 2106 | A11-M-B73 | HPLC_1 | 1.25 | 357 |
| 2107 | A11-M-B77 | HPLC_1 | 1.07 | 360 |
| 2108 | A11-M-B78 | HPLC_1 | 1.34 | 407 |
| 2109 | A11-M-B79 | HPLC_1 | 1.15 | 379 |
| 2110 | A11-M-B82 | HPLC_1 | 1.18 | 428 |
| 2111 | A4-M-B81 | HPLC_1 | 1.29 | 479 |
| 2112 | A4-M-B72 | HPLC_1 | 1.54 | 541 |
| 2113 | A4-M-B73 | HPLC_1 | 1.42 | 427 |
| 2114 | A4-M-B74 | HPLC_1 | 1.29 | 483 |
| 2115 | A4-M-B75 | HPLC_1 | 1.26 | 425 |
| 2116 | A4-M-B76 | HPLC_1 | 1.4 | 461 |
| 2117 | A4-M-B77 | HPLC_1 | 1.26 | 430 |
| 2118 | A4-M-B78 | HPLC_1 | 1.49 | 477 |
| 2119 | A4-M-B79 | HPLC_1 | 1.32 | 449 |
| 2120 | A4-M-B80 | HPLC_1 | 1.35 | 520 |
| 2121 | A3-M-B72 | HPLC_1 | 1.5 | 543 |
| 2122 | A3-M-B73 | HPLC_1 | 1.38 | 429 |
| 2123 | A3-M-B76 | HPLC_1 | 1.36 | 463 |
| 2124 | A3-M-B77 | HPLC_1 | 1.21 | 432 |
| 2125 | A3-M-B78 | HPLC_1 | 1.45 | 479 |
| 2126 | A3-M-B79 | HPLC_1 | 1.28 | 451 |
| 2127 | A3-M-B80 | HPLC_1 | 1.31 | 522 |
| 2128 | A5-M-B71 | HPLC_1 | 1.22 | 459 |
| 2129 | A5-M-B74 | HPLC_1 | 1.22 | 493 |
| 2130 | A5-M-B75 | HPLC_1 | 1.19 | 435 |
| 2131 | A5-M-B77 | HPLC_1 | 1.19 | 440 |
| 2132 | A5-M-B78 | HPLC_1 | 1.43 | 487 |
| 2133 | A5-M-B80 | HPLC_1 | 1.29 | 530 |
| 2134 | A9-M-B73 | HPLC_1 | 1.12 | 428 |
| 2135 | A9-M-B78 | HPLC_1 | 1.22 | 478 |
| 2136 | A9-M-B79 | HPLC_1 | 1.03 | 450 |
| 2137 | A10-M-B81 | HPLC_1 | 1.08 | 441 |
| 2138 | A10-M-B72 | HPLC_1 | 1.37 | 503 |
| 2139 | A10-M-B77 | HPLC_1 | 1.04 | 392 |
| 2140 | A10-M-B80 | HPLC_1 | 1.15 | 482 |
| 2141 | A7-M-B83 | HPLC_1 | 1.16 | 373 |
| 2142 | A7-M-B86 | HPLC_1 | 1.23 | 405 |
| 2143 | A7-M-B89 | HPLC_1 | 1.46 | 479 |
| 2144 | A7-M-B90 | HPLC_1 | 1.22 | 369 |
| 2145 | A8-M-B83 | HPLC_1 | 1.04 | 357 |
| 2146 | A8-M-B94 | HPLC_1 | 1.31 | 389 |
| 2147 | A8-M-B85 | HPLC_1 | 0.93 | 311 |
| 2148 | A8-M-B86 | HPLC_1 | 1.12 | 389 |
| 2149 | A8-M-B87 | HPLC_1 | 1.14 | 430 |
| 2150 | A8-M-B88 | HPLC_1 | 1.14 | 407 |
| 2151 | A8-M-B89 | HPLC_1 | 1.38 | 463 |

TABLE III-continued

| Entry | Compound | HPLC method | r.t. (min) | [M + H]+ |
|---|---|---|---|---|
| 2152 | A8-M-B90 | HPLC_1 | 1.11 | 353 |
| 2153 | A8-M-B93 | HPLC_1 | 1.19 | 369 |
| 2154 | A11-M-B83 | HPLC_1 | 1.1 | 371 |
| 2155 | A11-M-B84 | HPLC_1 | 1.25 | 413 |
| 2156 | A11-M-B85 | HPLC_1 | 1 | 325 |
| 2157 | A11-M-B90 | HPLC_1 | 1.17 | 367 |
| 2158 | A11-M-B93 | HPLC_1 | 1.24 | 383 |
| 2159 | A11-M-B91 | HPLC_1 | 1.18 | 341 |
| 2160 | A4-M-B83 | HPLC_1 | 1.31 | 441 |
| 2161 | A4-M-B84 | HPLC_1 | 1.44 | 483 |
| 2162 | A4-M-B94 | HPLC_1 | 1.54 | 473 |
| 2163 | A4-M-B85 | HPLC_1 | 1.22 | 395 |
| 2164 | A4-M-B86 | HPLC_1 | 1.37 | 473 |
| 2165 | A4-M-B87 | HPLC_1 | 1.38 | 514 |
| 2166 | A4-M-B88 | HPLC_1 | 1.38 | 491 |
| 2167 | A4-M-B89 | HPLC_1 | 1.57 | 547 |
| 2168 | A4-M-B90 | HPLC_1 | 1.35 | 437 |
| 2169 | A3-M-B83 | HPLC_1 | 1.26 | 443 |
| 2170 | A3-M-B84 | HPLC_1 | 1.39 | 485 |
| 2171 | A3-M-B94 | HPLC_1 | 1.49 | 475 |
| 2172 | A3-M-B85 | HPLC_1 | 1.16 | 397 |
| 2173 | A3-M-B86 | HPLC_1 | 1.32 | 475 |
| 2174 | A3-M-B87 | HPLC_1 | 1.33 | 516 |
| 2175 | A3-M-B88 | HPLC_1 | 1.33 | 493 |
| 2176 | A3-M-B89 | HPLC_1 | 1.53 | 549 |
| 2177 | A3-M-B90 | HPLC_1 | 1.3 | 439 |
| 2178 | A3-M-B93 | HPLC_1 | 1.37 | 455 |
| 2179 | A5-M-B83 | HPLC_1 | 1.24 | 451 |
| 2180 | A5-M-B84 | HPLC_1 | 1.37 | 493 |
| 2181 | A5-M-B85 | HPLC_1 | 1.14 | 405 |
| 2182 | A5-M-B87 | HPLC_1 | 1.32 | 524 |
| 2183 | A5-M-B89 | HPLC_1 | 1.51 | 557 |
| 2184 | A5-M-B90 | HPLC_1 | 1.29 | 447 |
| 2185 | A5-M-B93 | HPLC_1 | 1.35 | 463 |
| 2186 | A5-M-B91 | HPLC_1 | 1.31 | 421 |
| 2187 | A5-M-B92 | HPLC_1 | 1.34 | 473 |
| 2188 | A9-M-B83 | HPLC_1 | 0.98 | 442 |
| 2189 | A9-M-B84 | HPLC_1 | 1.13 | 484 |
| 2190 | A9-M-B94 | HPLC_1 | 1.23 | 474 |
| 2191 | A9-M-B85 | HPLC_1 | 0.89 | 396 |
| 2192 | A9-M-B86 | HPLC_1 | 1.04 | 474 |
| 2193 | A9-M-B87 | HPLC_1 | 1.08 | 515 |
| 2194 | A9-M-B89 | HPLC_1 | 1.29 | 548 |
| 2195 | A9-M-B90 | HPLC_1 | 1.05 | 438 |
| 2196 | A9-M-B93 | HPLC_1 | 1.12 | 454 |
| 2197 | A48-M-B28 | HPLC_1 | 1.27 | 407 |
| 2198 | A48-M-B33 | HPLC_1 | 1.1 | 367 |
| 2199 | A16-M-B27 | HPLC_1 | 1.25 | 415 |
| 2200 | A48-M-B44 | HPLC_1 | 1.18 | 407 |
| 2201 | A48-M-B45 | HPLC_1 | 1.16 | 475 |
| 2202 | A48-M-B46 | HPLC_1 | 1.08 | 365 |
| 2203 | A48-M-B47 | HPLC_1 | 1.22 | 431 |
| 2204 | A48-M-B37 | HPLC_1 | 1.03 | 353 |
| 2205 | A15-M-B40 | HPLC_1 | 1.08 | 335 |
| 2206 | A16-M-B39 | HPLC_1 | 1.3 | 431 |
| 2207 | A16-M-B43 | HPLC_1 | 1.42 | 503 |
| 2208 | A17-M-B40 | HPLC_1 | 1.34 | 399 |
| 2209 | A18-M-B39 | HPLC_1 | 1.25 | 407 |
| 2210 | A18-M-B40 | HPLC_1 | 1.25 | 391 |
| 2211 | A18-M-B42 | HPLC_1 | 1.22 | 395 |
| 2212 | A18-M-B46 | HPLC_1 | 1.04 | 341 |
| 2213 | A18-M-B47 | HPLC_1 | 1.19 | 407 |
| 2214 | A48-M-B50 | HPLC_1 | 1.13 | 420 |
| 2215 | A48-M-B51 | HPLC_1 | 1.1 | 367 |
| 2216 | A48-M-B52 | HPLC_1 | 1.18 | 381 |
| 2217 | A48-M-B54 | HPLC_1 | 1.21 | 419 |
| 2218 | A48-M-B55 | HPLC_1 | 1.24 | 437 |
| 2219 | A48-M-B57 | HPLC_1 | 1.2 | 393 |
| 2220 | A14-M-B53 | HPLC_1 | 1.07 | 399 |
| 2221 | A15-M-B49 | HPLC_1 | 1.06 | 351 |
| 2222 | A15-M-B50 | HPLC_1 | 0.91 | 340 |
| 2223 | A16-M-B48 | HPLC_1 | 1.34 | 437 |
| 2224 | A16-M-B49 | HPLC_1 | 1.29 | 431 |
| 2225 | A16-M-B50 | HPLC_1 | 1.16 | 420 |
| 2226 | A16-M-B51 | HPLC_1 | 1.14 | 367 |
| 2227 | A16-M-B53 | HPLC_1 | 1.31 | 461 |
| 2228 | A16-M-B55 | HPLC_1 | 1.28 | 437 |
| 2229 | A16-M-B56 | HPLC_1 | 1.27 | 415 |
| 2230 | A16-M-B58 | HPLC_1 | 1.3 | 429 |
| 2231 | A17-M-B48 | HPLC_1 | 1.37 | 421 |
| 2232 | A17-M-B53 | HPLC_1 | 1.35 | 445 |
| 2233 | A18-M-B48 | HPLC_1 | 1.28 | 413 |
| 2234 | A18-M-B50 | HPLC_1 | 1.1 | 396 |
| 2235 | A18-M-B51 | HPLC_1 | 1.07 | 343 |
| 2236 | A18-M-B54 | HPLC_1 | 1.19 | 395 |
| 2237 | A18-M-B55 | HPLC_1 | 1.22 | 413 |
| 2238 | A18-M-B56 | HPLC_1 | 1.22 | 391 |
| 2239 | A18-M-B57 | HPLC_1 | 1.18 | 369 |
| 2240 | A12-M-B62 | HPLC_1 | 1.26 | 423 |
| 2241 | A12-M-B67 | HPLC_1 | 1.39 | 453 |
| 2242 | A15-M-B64 | HPLC_1 | 1.22 | 389 |
| 2243 | A15-M-B65 | HPLC_1 | 1.11 | 357 |
| 2244 | A16-M-B59 | HPLC_1 | 1.33 | 445 |
| 2245 | A16-M-B62 | HPLC_1 | 1.26 | 435 |
| 2246 | A16-M-B60 | HPLC_1 | 1.18 | 379 |
| 2247 | A16-M-B61 | HPLC_1 | 1.05 | 369 |
| 2248 | A16-M-B68 | HPLC_1 | 1.24 | 491 |
| 2249 | A16-M-B70 | HPLC_1 | 1.23 | 381 |
| 2250 | A18-M-B59 | HPLC_1 | 1.29 | 421 |
| 2251 | A18-M-B65 | HPLC_1 | 1.27 | 413 |
| 2252 | A18-M-B69 | HPLC_1 | 1.23 | 413 |
| 2253 | A48-M-B73 | HPLC_1 | 1.35 | 423 |
| 2254 | A48-M-B74 | HPLC_1 | 1.21 | 479 |
| 2255 | A48-M-B76 | HPLC_1 | 1.34 | 457 |
| 2256 | A15-M-B78 | HPLC_1 | 1.29 | 393 |
| 2257 | A15-M-B82 | HPLC_1 | 1.1 | 414 |
| 2258 | A16-M-B75 | HPLC_1 | 1.21 | 421 |
| 2259 | A16-M-B77 | HPLC_1 | 1.21 | 426 |
| 2260 | A16-M-B82 | HPLC_1 | 1.31 | 494 |
| 2261 | A18-M-B72 | HPLC_1 | 1.48 | 513 |
| 2262 | A18-M-B73 | HPLC_1 | 1.34 | 399 |
| 2263 | A18-M-B74 | HPLC_1 | 1.19 | 455 |
| 2264 | A12-M-B93 | HPLC_1 | 1.34 | 437 |
| 2265 | A13-M-B92 | HPLC_1 | 1.2 | 381 |
| 2266 | A15-M-B92 | HPLC_1 | 1.15 | 379 |
| 2267 | A16-M-B83 | HPLC_1 | 1.24 | 437 |
| 2268 | A16-M-B87 | HPLC_1 | 1.3 | 510 |
| 2269 | A16-M-B89 | HPLC_1 | 1.49 | 543 |
| 2270 | A16-M-B90 | HPLC_1 | 1.28 | 433 |
| 2271 | A16-M-B91 | HPLC_1 | 1.29 | 407 |
| 2272 | A17-M-B92 | HPLC_1 | 1.37 | 443 |
| 2273 | A18-M-B90 | HPLC_1 | 1.23 | 409 |
| 2274 | A21-M-B36 | HPLC_1 | 1.44 | 441 |
| 2275 | A20-M-B37 | HPLC_1 | 0.83 | 305 |
| 2276 | A19-M-B50 | HPLC_1 | 1.2 | 404 |
| 2277 | A22-M-B67 | HPLC_1 | 1.09 | 430 |
| 2278 | A21-M-B67 | HPLC_1 | 1.39 | 449 |
| 2279 | A22-M-B75 | HPLC_1 | 0.9 | 386 |
| 2280 | A22-M-B77 | HPLC_1 | 0.91 | 391 |
| 2281 | A21-M-B82 | HPLC_1 | 1.34 | 478 |
| 2282 | A25-M-B87 | HPLC_1 | 1.15 | 432 |
| 2283 | A19-M-B94 | HPLC_1 | 1.5 | 453 |
| 2284 | A33-M-B28 | HPLC_1 | 1.32 | 383 |
| 2285 | A27-M-B39 | HPLC_1 | 1.36 | 435 |
| 2286 | A33-M-B38 | HPLC_1 | 1.19 | 368 |
| 2287 | A31-M-B38 | HPLC_1 | 1.09 | 342 |
| 2288 | A28-M-B53 | HPLC_1 | 1.25 | 449 |
| 2289 | A33-M-B57 | HPLC_1 | 1.27 | 369 |
| 2290 | A28-M-B63 | HPLC_1 | 1.23 | 414 |
| 2291 | A29-M-B67 | HPLC_1 | 1.37 | 465 |
| 2292 | A27-M-B82 | HPLC_1 | 1.4 | 498 |
| 2293 | A29-M-B82 | HPLC_1 | 1.32 | 494 |
| 2294 | A30-M-B82 | HPLC_1 | 1.43 | 458 |
| 2295 | A33-M-B74 | HPLC_1 | 1.35 | 455 |
| 2296 | A27-M-B90 | HPLC_1 | 1.34 | 437 |
| 2297 | A28-M-B90 | HPLC_1 | 1.27 | 421 |
| 2298 | A28-M-B93 | HPLC_1 | 1.34 | 437 |
| 2299 | A29-M-B94 | HPLC_1 | 1.44 | 469 |
| 2300 | A29-M-B86 | HPLC_1 | 1.27 | 469 |
| 2301 | A34-M-B35 | HPLC_1 | 1.31 | 443 |
| 2302 | A35-M-B35 | HPLC_1 | 1.2 | 459 |
| 2303 | A40-M-B30 | HPLC_1 | 1.17 | 329 |
| 2304 | A40-M-B33 | HPLC_1 | 0.87 | 275 |
| 2305 | A40-M-B34 | HPLC_1 | 1.19 | 377 |

TABLE III-continued

| Entry | Compound | HPLC method | r.t. (min) | [M + H]+ |
|---|---|---|---|---|
| 2306 | A40-M-B35 | HPLC_1 | 1 | 353 |
| 2307 | A40-M-B36 | HPLC_1 | 1.29 | 365 |
| 2308 | A34-M-B40 | HPLC_1 | 1.37 | 413 |
| 2309 | A35-M-B38 | HPLC_1 | 1.37 | 406 |
| 2310 | A40-M-B42 | HPLC_1 | 1.37 | 327 |
| 2311 | A40-M-B48 | HPLC_1 | 1.11 | 345 |
| 2312 | A40-M-B49 | HPLC_1 | 1.07 | 339 |
| 2313 | A40-M-B51 | HPLC_1 | 0.88 | 275 |
| 2314 | A40-M-B52 | HPLC_1 | 0.97 | 289 |
| 2315 | A40-M-B53 | HPLC_1 | 1.1 | 369 |
| 2316 | A40-M-B57 | HPLC_1 | 1.01 | 301 |
| 2317 | A36-M-B49 | HPLC_1 | 1.02 | 422 |
| 2318 | A37-M-B53 | HPLC_1 | 1 | 432 |
| 2319 | A39-M-B55 | HPLC_1 | 0.99 | 416 |
| 2320 | A34-M-B60 | HPLC_1 | 1.24 | 377 |
| 2321 | A34-M-B61 | HPLC_1 | 1.12 | 367 |
| 2322 | A35-M-B60 | HPLC_1 | 1.12 | 393 |
| 2323 | A35-M-B61 | HPLC_1 | 1.01 | 383 |
| 2324 | A35-M-B68 | HPLC_1 | 1.2 | 505 |
| 2325 | A35-M-B69 | HPLC_1 | 1.24 | 451 |
| 2326 | A40-M-B62 | HPLC_1 | 1.01 | 343 |
| 2327 | A40-M-B70 | HPLC_1 | 0.97 | 289 |
| 2328 | A41-M-B59 | HPLC_1 | 1.01 | 396 |
| 2329 | A36-M-B67 | HPLC_1 | 1.15 | 456 |
| 2330 | A37-M-B66 | HPLC_1 | 0.94 | 390 |
| 2331 | A37-M-B70 | HPLC_1 | 0.9 | 352 |
| 2332 | A39-M-B62 | HPLC_1 | 0.97 | 414 |
| 2333 | A34-M-B71 | HPLC_1 | 1.32 | 443 |
| 2334 | A34-M-B75 | HPLC_1 | 1.3 | 419 |
| 2335 | A34-M-B77 | HPLC_1 | 1.3 | 424 |
| 2336 | A35-M-B71 | HPLC_1 | 1.23 | 459 |
| 2337 | A35-M-B72 | HPLC_1 | 1.48 | 551 |
| 2338 | A35-M-B75 | HPLC_1 | 1.2 | 435 |
| 2339 | A35-M-B77 | HPLC_1 | 1.2 | 440 |
| 2340 | A40-M-B74 | HPLC_1 | 1.04 | 387 |
| 2341 | A40-M-B77 | HPLC_1 | 1.01 | 334 |
| 2342 | A39-M-B72 | HPLC_1 | 1.29 | 516 |
| 2343 | A39-M-B73 | HPLC_1 | 1.14 | 402 |
| 2344 | A39-M-B80 | HPLC_1 | 1.08 | 495 |
| 2345 | A34-M-B85 | HPLC_1 | 1.21 | 389 |
| 2346 | A35-M-B84 | HPLC_1 | 1.32 | 493 |
| 2347 | A35-M-B91 | HPLC_1 | 1.26 | 421 |
| 2348 | A40-M-B84 | HPLC_1 | 1.14 | 387 |
| 2349 | A37-M-B94 | HPLC_1 | 1.13 | 440 |
| 2350 | A38-M-B93 | HPLC_1 | 1.04 | 420 |
| 2351 | A38-M-B91 | HPLC_1 | 0.97 | 378 |
| 2352 | A39-M-B87 | HPLC_1 | 1.03 | 489 |
| 2353 | A43-M-B27 | HPLC_1 | 1.07 | 379 |
| 2354 | A43-M-B35 | HPLC_1 | 1.05 | 409 |
| 2355 | A44-M-B26 | HPLC_1 | 1.2 | 371 |
| 2356 | A44-M-B27 | HPLC_1 | 1.24 | 405 |
| 2357 | A44-M-B31 | HPLC_1 | 1.32 | 425 |
| 2358 | A44-M-B33 | HPLC_1 | 1.14 | 357 |
| 2359 | A44-M-B36 | HPLC_1 | 1.44 | 447 |
| 2360 | A45-M-B28 | HPLC_1 | 1.12 | 359 |
| 2361 | A45-M-B35 | HPLC_1 | 1.07 | 397 |
| 2362 | A46-M-B26 | HPLC_1 | 1.19 | 369 |
| 2363 | A46-M-B31 | HPLC_1 | 1.54 | 423 |
| 2364 | A46-M-B32 | HPLC_1 | 1.39 | 433 |
| 2365 | A46-M-B34 | HPLC_1 | 1.49 | 457 |
| 2366 | A1-M-B25 | HPLC_1 | 1.24 | 363 |
| 2367 | A1-M-B27 | HPLC_1 | 1.27 | 377 |
| 2368 | A1-M-B28 | HPLC_1 | 1.3 | 369 |
| 2369 | A1-M-B31 | HPLC_1 | 1.36 | 397 |
| 2370 | A2-M-B26 | HPLC_1 | 1.19 | 351 |
| 2371 | A42-M-B95 | HPLC_1 | 1.27 | 486 |
| 2372 | A47-M-B45 | HPLC_1 | 1.04 | 429 |
| 2373 | A47-M-B47 | HPLC_1 | 1.11 | 385 |
| 2374 | A44-M-B40 | HPLC_1 | 1.29 | 405 |
| 2375 | A44-M-B41 | HPLC_1 | 1.26 | 385 |
| 2376 | A44-M-B42 | HPLC_1 | 1.26 | 409 |
| 2377 | A44-M-B43 | HPLC_1 | 1.4 | 493 |
| 2378 | A44-M-B44 | HPLC_1 | 1.2 | 397 |
| 2379 | A44-M-B45 | HPLC_1 | 1.17 | 465 |
| 2380 | A44-M-B47 | HPLC_1 | 1.24 | 421 |
| 2381 | A44-M-B37 | HPLC_1 | 1.06 | 343 |
| 2382 | A46-M-B42 | HPLC_1 | 1.32 | 407 |
| 2383 | A46-M-B43 | HPLC_1 | 1.41 | 491 |
| 2384 | A46-M-B44 | HPLC_1 | 1.29 | 395 |
| 2385 | A46-M-B45 | HPLC_1 | 1.22 | 463 |
| 2386 | A46-M-B37 | HPLC_1 | 1.15 | 341 |
| 2387 | A46-M-B38 | HPLC_1 | 1.13 | 380 |
| 2388 | A1-M-B38 | HPLC_1 | 1.11 | 354 |
| 2389 | A2-M-B42 | HPLC_1 | 1.25 | 389 |
| 2390 | A42-M-B53 | HPLC_1 | 1.32 | 467 |
| 2391 | A42-M-B55 | HPLC_1 | 1.29 | 443 |
| 2392 | A47-M-B58 | HPLC_1 | 1.14 | 383 |
| 2393 | A43-M-B53 | HPLC_1 | 1.09 | 425 |
| 2394 | A44-M-B49 | HPLC_1 | 1.25 | 421 |
| 2395 | A44-M-B52 | HPLC_1 | 1.16 | 371 |
| 2396 | A44-M-B55 | HPLC_1 | 1.24 | 427 |
| 2397 | A44-M-B57 | HPLC_1 | 1.2 | 383 |
| 2398 | A44-M-B58 | HPLC_1 | 1.27 | 419 |
| 2399 | A46-M-B49 | HPLC_1 | 1.24 | 419 |
| 2400 | A46-M-B50 | HPLC_1 | 1.08 | 408 |
| 2401 | A46-M-B51 | HPLC_1 | 1.08 | 355 |
| 2402 | A46-M-B52 | HPLC_1 | 1.14 | 369 |
| 2403 | A46-M-B54 | HPLC_1 | 1.18 | 407 |
| 2404 | A46-M-B56 | HPLC_1 | 1.21 | 403 |
| 2405 | A2-M-B48 | HPLC_1 | 1.29 | 407 |
| 2406 | A42-M-B65 | HPLC_1 | 1.35 | 443 |
| 2407 | A42-M-B66 | HPLC_1 | 1.31 | 425 |
| 2408 | A47-M-B68 | HPLC_1 | 1.11 | 445 |
| 2409 | A43-M-B62 | HPLC_1 | 1.05 | 399 |
| 2410 | A43-M-B67 | HPLC_1 | 1.22 | 429 |
| 2411 | A44-M-B59 | HPLC_1 | 1.32 | 435 |
| 2412 | A44-M-B64 | HPLC_1 | 1.39 | 459 |
| 2413 | A44-M-B65 | HPLC_1 | 1.31 | 427 |
| 2414 | A44-M-B61 | HPLC_1 | 1.03 | 359 |
| 2415 | A46-M-B60 | HPLC_1 | 1.24 | 367 |
| 2416 | A46-M-B64 | HPLC_1 | 1.42 | 457 |
| 2417 | A46-M-B65 | HPLC_1 | 1.36 | 425 |
| 2418 | A46-M-B69 | HPLC_1 | 1.29 | 425 |
| 2419 | A46-M-B66 | HPLC_1 | 1.32 | 407 |
| 2420 | A1-M-B69 | HPLC_1 | 1.28 | 399 |
| 2421 | A47-M-B76 | HPLC_1 | 1.23 | 411 |
| 2422 | A47-M-B79 | HPLC_1 | 1.13 | 399 |
| 2423 | A43-M-B74 | HPLC_1 | 1.03 | 443 |
| 2424 | A43-M-B82 | HPLC_1 | 1.11 | 458 |
| 2425 | A44-M-B81 | HPLC_1 | 1.21 | 465 |
| 2426 | A44-M-B73 | HPLC_1 | 1.35 | 413 |
| 2427 | A44-M-B74 | HPLC_1 | 1.21 | 469 |
| 2428 | A44-M-B76 | HPLC_1 | 1.34 | 447 |
| 2429 | A44-M-B77 | HPLC_1 | 1.18 | 416 |
| 2430 | A44-M-B79 | HPLC_1 | 1.24 | 435 |
| 2431 | A44-M-B80 | HPLC_1 | 1.28 | 506 |
| 2432 | A46-M-B81 | HPLC_1 | 1.24 | 463 |
| 2433 | A46-M-B71 | HPLC_1 | 1.24 | 433 |
| 2434 | A46-M-B72 | HPLC_1 | 1.5 | 525 |
| 2435 | A46-M-B74 | HPLC_1 | 1.24 | 467 |
| 2436 | A46-M-B80 | HPLC_1 | 1.28 | 504 |
| 2437 | A1-M-B77 | HPLC_1 | 1.2 | 388 |
| 2438 | A1-M-B78 | HPLC_1 | 1.45 | 435 |
| 2439 | A1-M-B82 | HPLC_1 | 1.3 | 456 |
| 2440 | A42-M-B91 | HPLC_1 | 1.31 | 413 |
| 2441 | A43-M-B87 | HPLC_1 | 1.09 | 474 |
| 2442 | A44-M-B83 | HPLC_1 | 1.19 | 427 |
| 2443 | A44-M-B84 | HPLC_1 | 1.33 | 469 |
| 2444 | A44-M-B89 | HPLC_1 | 1.45 | 533 |
| 2445 | A44-M-B90 | HPLC_1 | 1.23 | 423 |
| 2446 | A44-M-B93 | HPLC_1 | 1.3 | 439 |
| 2447 | A45-M-B89 | HPLC_1 | 1.32 | 495 |
| 2448 | A46-M-B83 | HPLC_1 | 1.15 | 425 |
| 2449 | A46-M-B84 | HPLC_1 | 1.32 | 467 |
| 2450 | A46-M-B94 | HPLC_1 | 1.42 | 457 |
| 2451 | A46-M-B86 | HPLC_1 | 1.21 | 457 |
| 2452 | A46-M-B87 | HPLC_1 | 1.22 | 498 |
| 2453 | A46-M-B89 | HPLC_1 | 1.48 | 531 |
| 2454 | A46-M-B90 | HPLC_1 | 1.2 | 421 |
| 2455 | A46-M-B93 | HPLC_1 | 1.28 | 437 |
| 2456 | A46-M-B91 | HPLC_1 | 1.24 | 395 |
| 2457 | A46-M-B92 | HPLC_1 | 1.28 | 447 |
| 2458 | A1-M-B83 | HPLC_1 | 1.21 | 399 |
| 2459 | A1-M-B84 | HPLC_1 | 1.35 | 441 |

TABLE III-continued

| Entry | Compound | HPLC method | r.t. (min) | [M + H]+ |
|---|---|---|---|---|
| 2460 | A1-M-B94 | HPLC_1 | 1.45 | 431 |
| 2461 | A1-M-B91 | HPLC_1 | 1.27 | 369 |
| 2462 | A2-M-B84 | HPLC_1 | 1.32 | 449 |
| 2463 | A2-M-B89 | HPLC_1 | 1.44 | 513 |
| 2464 | A2-M-B90 | HPLC_1 | 1.23 | 403 |
| 2465 | A2-M-B93 | HPLC_1 | 1.3 | 419 |
| 2466 | A7-M-B31 | HPLC_1 | 1.29 | 371 |
| 2467 | A7-M-B35 | HPLC_1 | 1.17 | 381 |
| 2468 | A8-M-B31 | HPLC_1 | 1.18 | 355 |
| 2469 | A11-M-B35 | HPLC_1 | 1.12 | 379 |
| 2470 | A4-M-B25 | HPLC_1 | 1.31 | 405 |
| 2471 | A4-M-B31 | HPLC_1 | 1.42 | 439 |
| 2472 | A4-M-B32 | HPLC_1 | 1.32 | 449 |
| 2473 | A4-M-B35 | HPLC_1 | 1.31 | 449 |
| 2474 | A3-M-B31 | HPLC_1 | 1.37 | 441 |
| 2475 | A5-M-B28 | HPLC_1 | 1.3 | 421 |
| 2476 | A5-M-B30 | HPLC_1 | 1.39 | 435 |
| 2477 | A5-M-B34 | HPLC_1 | 1.4 | 483 |
| 2478 | A5-M-B36 | HPLC_1 | 1.48 | 471 |
| 2479 | A10-M-B26 | HPLC_1 | 1.04 | 347 |
| 2480 | A7-M-B40 | HPLC_1 | 1.19 | 351 |
| 2481 | A7-M-B42 | HPLC_1 | 1.16 | 355 |
| 2482 | A7-M-B45 | HPLC_1 | 1.08 | 411 |
| 2483 | A7-M-B37 | HPLC_1 | 0.97 | 289 |
| 2484 | A8-M-B41 | HPLC_1 | 1.04 | 315 |
| 2485 | A8-M-B42 | HPLC_1 | 1.06 | 339 |
| 2486 | A8-M-B43 | HPLC_1 | 1.21 | 423 |
| 2487 | A8-M-B37 | HPLC_1 | 0.85 | 273 |
| 2488 | A11-M-B39 | HPLC_1 | 1.14 | 365 |
| 2489 | A11-M-B41 | HPLC_1 | 1.1 | 329 |
| 2490 | A11-M-B42 | HPLC_1 | 1.1 | 353 |
| 2491 | A11-M-B43 | HPLC_1 | 1.24 | 437 |
| 2492 | A11-M-B45 | HPLC_1 | 1.03 | 409 |
| 2493 | A11-M-B37 | HPLC_1 | 0.92 | 287 |
| 2494 | A11-M-B38 | HPLC_1 | 0.94 | 326 |
| 2495 | A4-M-B39 | HPLC_1 | 1.31 | 435 |
| 2496 | A4-M-B42 | HPLC_1 | 1.28 | 423 |
| 2497 | A4-M-B43 | HPLC_1 | 1.39 | 507 |
| 2498 | A4-M-B47 | HPLC_1 | 1.25 | 435 |
| 2499 | A4-M-B38 | HPLC_1 | 1.15 | 396 |
| 2500 | A3-M-B42 | HPLC_1 | 1.24 | 425 |
| 2501 | A5-M-B41 | HPLC_1 | 1.22 | 409 |
| 2502 | A5-M-B42 | HPLC_1 | 1.22 | 433 |
| 2503 | A5-M-B47 | HPLC_1 | 1.19 | 445 |
| 2504 | A5-M-B37 | HPLC_1 | 1.04 | 367 |
| 2505 | A5-M-B38 | HPLC_1 | 1.07 | 406 |
| 2506 | A9-M-B41 | HPLC_1 | 0.99 | 400 |
| 2507 | A9-M-B43 | HPLC_1 | 1.11 | 508 |
| 2508 | A9-M-B95 | HPLC_1 | 0.95 | 485 |
| 2509 | A9-M-B45 | HPLC_1 | 0.94 | 480 |
| 2510 | A9-M-B37 | HPLC_1 | 0.85 | 358 |
| 2511 | A10-M-B41 | HPLC_1 | 1.07 | 361 |
| 2512 | A10-M-B45 | HPLC_1 | 1.01 | 441 |
| 2513 | A7-M-B48 | HPLC_1 | 1.22 | 373 |
| 2514 | A7-M-B50 | HPLC_1 | 1.04 | 356 |
| 2515 | A7-M-B53 | HPLC_1 | 1.2 | 397 |
| 2516 | A7-M-B58 | HPLC_1 | 1.19 | 365 |
| 2517 | A8-M-B53 | HPLC_1 | 1.1 | 381 |
| 2518 | A8-M-B56 | HPLC_1 | 1.05 | 335 |
| 2519 | A11-M-B53 | HPLC_1 | 1.15 | 395 |
| 2520 | A11-M-B56 | HPLC_1 | 1.1 | 349 |
| 2521 | A11-M-B57 | HPLC_1 | 1.07 | 327 |
| 2522 | A11-M-B58 | HPLC_1 | 1.15 | 363 |
| 2523 | A4-M-B48 | HPLC_1 | 1.35 | 441 |
| 2524 | A3-M-B53 | HPLC_1 | 1.28 | 467 |
| 2525 | A5-M-B48 | HPLC_1 | 1.28 | 451 |
| 2526 | A5-M-B49 | HPLC_1 | 1.23 | 445 |
| 2527 | A5-M-B50 | HPLC_1 | 1.12 | 434 |
| 2528 | A5-M-B55 | HPLC_1 | 1.23 | 451 |
| 2529 | A9-M-B48 | HPLC_1 | 1.05 | 442 |
| 2530 | A7-M-B62 | HPLC_1 | 1.13 | 371 |
| 2531 | A7-M-B61 | HPLC_1 | 0.94 | 305 |
| 2532 | A7-M-B68 | HPLC_1 | 1.12 | 427 |
| 2533 | A8-M-B66 | HPLC_1 | 1.06 | 339 |
| 2534 | A11-M-B67 | HPLC_1 | 1.21 | 399 |
| 2535 | A11-M-B63 | HPLC_1 | 1.08 | 360 |
| 2536 | A11-M-B60 | HPLC_1 | 1 | 313 |
| 2537 | A11-M-B65 | HPLC_1 | 1.15 | 371 |
| 2538 | A11-M-B61 | HPLC_1 | 0.9 | 303 |
| 2539 | A11-M-B69 | HPLC_1 | 1.1 | 371 |
| 2540 | A11-M-B66 | HPLC_1 | 1.11 | 353 |
| 2541 | A11-M-B70 | HPLC_1 | 1.04 | 315 |
| 2542 | A4-M-B63 | HPLC_1 | 1.27 | 430 |
| 2543 | A4-M-B60 | HPLC_1 | 1.2 | 383 |
| 2544 | A5-M-B62 | HPLC_1 | 1.19 | 449 |
| 2545 | A5-M-B67 | HPLC_1 | 1.32 | 479 |
| 2546 | A5-M-B63 | HPLC_1 | 1.18 | 440 |
| 2547 | A5-M-B61 | HPLC_1 | 1.02 | 383 |
| 2548 | A9-M-B62 | HPLC_1 | 0.97 | 440 |
| 2549 | A9-M-B63 | HPLC_1 | 0.97 | 431 |
| 2550 | A9-M-B65 | HPLC_1 | 1.03 | 442 |
| 2551 | A10-M-B62 | HPLC_1 | 1.06 | 401 |
| 2552 | A10-M-B65 | HPLC_1 | 1.12 | 403 |
| 2553 | A10-M-B61 | HPLC_1 | 0.86 | 335 |
| 2554 | A7-M-B75 | HPLC_1 | 1.12 | 357 |
| 2555 | A11-M-B71 | HPLC_1 | 1.1 | 379 |
| 2556 | A11-M-B74 | HPLC_1 | 1.1 | 413 |
| 2557 | A11-M-B75 | HPLC_1 | 1.07 | 355 |
| 2558 | A11-M-B80 | HPLC_1 | 1.19 | 450 |
| 2559 | A4-M-B71 | HPLC_1 | 1.28 | 449 |
| 2560 | A4-M-B82 | HPLC_1 | 1.35 | 498 |
| 2561 | A3-M-B81 | HPLC_1 | 1.24 | 481 |
| 2562 | A3-M-B71 | HPLC_1 | 1.23 | 451 |
| 2563 | A3-M-B82 | HPLC_1 | 1.31 | 500 |
| 2564 | A5-M-B81 | HPLC_1 | 1.22 | 489 |
| 2565 | A5-M-B72 | HPLC_1 | 1.48 | 551 |
| 2566 | A5-M-B79 | HPLC_1 | 1.26 | 459 |
| 2567 | A5-M-B82 | HPLC_1 | 1.28 | 508 |
| 2568 | A9-M-B81 | HPLC_1 | 1.01 | 480 |
| 2569 | A9-M-B71 | HPLC_1 | 1 | 450 |
| 2570 | A9-M-B75 | HPLC_1 | 0.96 | 426 |
| 2571 | A9-M-B77 | HPLC_1 | 0.97 | 431 |
| 2572 | A9-M-B80 | HPLC_1 | 1.07 | 521 |
| 2573 | A10-M-B74 | HPLC_1 | 1.07 | 445 |
| 2574 | A10-M-B76 | HPLC_1 | 1.21 | 423 |
| 2575 | A10-M-B78 | HPLC_1 | 1.31 | 439 |
| 2576 | A10-M-B82 | HPLC_1 | 1.14 | 460 |
| 2577 | A7-M-B84 | HPLC_1 | 1.3 | 415 |
| 2578 | A7-M-B85 | HPLC_1 | 1.06 | 327 |
| 2579 | A7-M-B87 | HPLC_1 | 1.25 | 446 |
| 2580 | A7-M-B93 | HPLC_1 | 1.29 | 385 |
| 2581 | A7-M-B92 | HPLC_1 | 1.28 | 395 |
| 2582 | A8-M-B91 | HPLC_1 | 1.12 | 327 |
| 2583 | A8-M-B92 | HPLC_1 | 1.19 | 379 |
| 2584 | A11-M-B94 | HPLC_1 | 1.36 | 403 |
| 2585 | A11-M-B89 | HPLC_1 | 1.42 | 477 |
| 2586 | A11-M-B92 | HPLC_1 | 1.24 | 393 |
| 2587 | A4-M-B93 | HPLC_1 | 1.42 | 453 |
| 2588 | A4-M-B91 | HPLC_1 | 1.38 | 411 |
| 2589 | A4-M-B92 | HPLC_1 | 1.4 | 463 |
| 2590 | A3-M-B91 | HPLC_1 | 1.33 | 413 |
| 2591 | A5-M-B94 | HPLC_1 | 1.46 | 483 |
| 2592 | A9-M-B91 | HPLC_1 | 1.06 | 412 |
| 2593 | A9-M-B92 | HPLC_1 | 1.12 | 464 |
| 2594 | A10-M-B92 | HPLC_1 | 1.2 | 425 |
| 2595 | A10-M-B83 | HPLC_1 | 1.07 | 403 |
| 2596 | A10-M-B84 | HPLC_1 | 1.22 | 445 |
| 2597 | A10-M-B94 | HPLC_1 | 1.33 | 435 |
| 2598 | A10-M-B85 | HPLC_1 | 0.97 | 357 |
| 2599 | A10-M-B86 | HPLC_1 | 1.14 | 435 |
| 2600 | A10-M-B87 | HPLC_1 | 1.17 | 476 |
| 2601 | A10-M-B89 | HPLC_1 | 1.39 | 509 |
| 2602 | A10-M-B90 | HPLC_1 | 1.14 | 399 |
| 2603 | A10-M-B93 | HPLC_1 | 1.21 | 415 |
| 2604 | A10-M-B91 | HPLC_1 | 1.15 | 373 |
| 2605 | A48-M-B38 | HPLC_1 | 1.08 | 392 |
| 2606 | A16-M-B38 | HPLC_1 | 1.11 | 392 |
| 2607 | A15-M-B53 | HPLC_1 | 1.1 | 381 |
| 2608 | A15-M-B54 | HPLC_1 | 0.99 | 339 |
| 2609 | A17-M-B49 | HPLC_1 | 1.33 | 415 |
| 2610 | A17-M-B55 | HPLC_1 | 1.32 | 421 |
| 2611 | A12-M-B63 | HPLC_1 | 1.24 | 414 |
| 2612 | A12-M-B64 | HPLC_1 | 1.4 | 457 |
| 2613 | A12-M-B66 | HPLC_1 | 1.28 | 407 |

TABLE III-continued

| Entry | Compound | HPLC method | r.t. (min) | [M + H]+ |
|---|---|---|---|---|
| 2614 | A48-M-B60 | HPLC_1 | 1.14 | 379 |
| 2615 | A48-M-B61 | HPLC_1 | 1.01 | 369 |
| 2616 | A48-M-B68 | HPLC_1 | 1.22 | 491 |
| 2617 | A48-M-B69 | HPLC_1 | 1.25 | 437 |
| 2618 | A16-M-B64 | HPLC_1 | 1.41 | 469 |
| 2619 | A16-M-B65 | HPLC_1 | 1.32 | 437 |
| 2620 | A16-M-B69 | HPLC_1 | 1.28 | 437 |
| 2621 | A16-M-B66 | HPLC_1 | 1.28 | 419 |
| 2622 | A17-M-B67 | HPLC_1 | 1.43 | 449 |
| 2623 | A17-M-B65 | HPLC_1 | 1.36 | 421 |
| 2624 | A17-M-B61 | HPLC_1 | 1.09 | 353 |
| 2625 | A18-M-B61 | HPLC_1 | 0.97 | 345 |
| 2626 | A12-M-B82 | HPLC_1 | 1.31 | 482 |
| 2627 | A13-M-B82 | HPLC_1 | 1.14 | 416 |
| 2628 | A15-M-B74 | HPLC_1 | 1.01 | 399 |
| 2629 | A17-M-B82 | HPLC_1 | 1.35 | 478 |
| 2630 | A12-M-B94 | HPLC_1 | 1.42 | 457 |
| 2631 | A48-M-B87 | HPLC_1 | 1.28 | 510 |
| 2632 | A14-M-B90 | HPLC_1 | 1.05 | 371 |
| 2633 | A15-M-B83 | HPLC_1 | 1.01 | 357 |
| 2634 | A15-M-B84 | HPLC_1 | 1.16 | 399 |
| 2635 | A15-M-B94 | HPLC_1 | 1.27 | 389 |
| 2636 | A15-M-B87 | HPLC_1 | 1.11 | 430 |
| 2637 | A16-M-B86 | HPLC_1 | 1.29 | 469 |
| 2638 | A17-M-B94 | HPLC_1 | 1.48 | 453 |
| 2639 | A17-M-B90 | HPLC_1 | 1.31 | 417 |
| 2640 | A18-M-B83 | HPLC_1 | 1.18 | 413 |
| 2641 | A18-M-B85 | HPLC_1 | 1.08 | 367 |
| 2642 | A18-M-B91 | HPLC_1 | 1.25 | 383 |
| 2643 | A27-M-B38 | HPLC_1 | 1.17 | 396 |
| 2644 | A28-M-B38 | HPLC_1 | 1.09 | 380 |
| 2645 | A29-M-B38 | HPLC_1 | 1.08 | 392 |
| 2646 | A33-M-B56 | HPLC_1 | 1.3 | 391 |
| 2647 | A27-M-B80 | HPLC_1 | 1.4 | 520 |
| 2648 | A28-M-B82 | HPLC_1 | 1.33 | 482 |
| 2649 | A33-M-B78 | HPLC_1 | 1.56 | 449 |
| 2650 | A34-M-B26 | HPLC_1 | 1.28 | 379 |
| 2651 | A34-M-B31 | HPLC_1 | 1.41 | 433 |
| 2652 | A40-M-B95 | HPLC_1 | 1.37 | 388 |
| 2653 | A34-M-B50 | HPLC_1 | 1.25 | 418 |
| 2654 | A40-M-B50 | HPLC_1 | 0.92 | 328 |
| 2655 | A40-M-B54 | HPLC_1 | 1 | 327 |
| 2656 | A40-M-B55 | HPLC_1 | 1.05 | 345 |
| 2657 | A40-M-B56 | HPLC_1 | 1.04 | 323 |
| 2658 | A34-M-B67 | HPLC_1 | 1.45 | 463 |
| 2659 | A34-M-B63 | HPLC_1 | 1.31 | 424 |
| 2660 | A34-M-B64 | HPLC_1 | 1.46 | 467 |
| 2661 | A34-M-B65 | HPLC_1 | 1.39 | 435 |
| 2662 | A34-M-B66 | HPLC_1 | 1.35 | 417 |
| 2663 | A35-M-B67 | HPLC_1 | 1.36 | 479 |
| 2664 | A35-M-B63 | HPLC_1 | 1.19 | 440 |
| 2665 | A40-M-B59 | HPLC_1 | 1.1 | 353 |
| 2666 | A40-M-B63 | HPLC_1 | 0.99 | 334 |
| 2667 | A40-M-B60 | HPLC_1 | 0.92 | 287 |
| 2668 | A40-M-B64 | HPLC_1 | 1.19 | 377 |
| 2669 | A40-M-B65 | HPLC_1 | 1.09 | 345 |
| 2670 | A40-M-B68 | HPLC_1 | 1.01 | 399 |
| 2671 | A40-M-B69 | HPLC_1 | 1.03 | 345 |
| 2672 | A40-M-B66 | HPLC_1 | 1.03 | 327 |
| 2673 | A36-M-B59 | HPLC_1 | 1.07 | 436 |
| 2674 | A34-M-B76 | HPLC_1 | 1.43 | 455 |
| 2675 | A34-M-B82 | HPLC_1 | 1.39 | 492 |
| 2676 | A35-M-B76 | HPLC_1 | 1.35 | 471 |
| 2677 | A35-M-B82 | HPLC_1 | 1.29 | 508 |
| 2678 | A40-M-B72 | HPLC_1 | 1.37 | 445 |
| 2679 | A40-M-B73 | HPLC_1 | 1.21 | 331 |
| 2680 | A40-M-B78 | HPLC_1 | 1.31 | 381 |
| 2681 | A40-M-B82 | HPLC_1 | 1.13 | 402 |
| 2682 | A40-M-B80 | HPLC_1 | 1.14 | 424 |
| 2683 | A37-M-B82 | HPLC_1 | 1.02 | 465 |
| 2684 | A39-M-B74 | HPLC_1 | 0.99 | 458 |
| 2685 | A34-M-B84 | HPLC_1 | 1.43 | 477 |
| 2686 | A34-M-B86 | HPLC_1 | 1.37 | 467 |
| 2687 | A34-M-B91 | HPLC_1 | 1.37 | 405 |
| 2688 | A35-M-B94 | HPLC_1 | 1.43 | 483 |
| 2689 | A35-M-B86 | HPLC_1 | 1.25 | 483 |
| 2690 | A35-M-B90 | HPLC_1 | 1.24 | 447 |
| 2691 | A40-M-B83 | HPLC_1 | 0.98 | 345 |
| 2692 | A40-M-B85 | HPLC_1 | 0.89 | 299 |
| 2693 | A40-M-B87 | HPLC_1 | 1.08 | 418 |
| 2694 | A40-M-B91 | HPLC_1 | 1.06 | 315 |
| 2695 | A40-M-B92 | HPLC_1 | 1.12 | 367 |
| 2696 | A41-M-B87 | HPLC_1 | 0.99 | 461 |
| 2697 | A42-M-B31 | HPLC_1 | 1.37 | 441 |
| 2698 | A47-M-B32 | HPLC_1 | 1.13 | 399 |
| 2699 | A47-M-B35 | HPLC_1 | 1.1 | 399 |
| 2700 | A43-M-B31 | HPLC_1 | 1.16 | 399 |
| 2701 | A44-M-B28 | HPLC_1 | 1.29 | 397 |
| 2702 | A44-M-B30 | HPLC_1 | 1.37 | 411 |
| 2703 | A44-M-B34 | HPLC_1 | 1.37 | 459 |
| 2704 | A44-M-B35 | HPLC_1 | 1.22 | 435 |
| 2705 | A45-M-B31 | HPLC_1 | 1.17 | 387 |
| 2706 | A46-M-B30 | HPLC_1 | 1.34 | 409 |
| 2707 | A46-M-B35 | HPLC_1 | 1.44 | 433 |
| 2708 | A1-M-B32 | HPLC_1 | 1.25 | 407 |
| 2709 | A1-M-B35 | HPLC_1 | 1.25 | 407 |
| 2710 | A2-M-B27 | HPLC_1 | 1.24 | 385 |
| 2711 | A2-M-B28 | HPLC_1 | 1.29 | 377 |
| 2712 | A2-M-B34 | HPLC_1 | 1.39 | 439 |
| 2713 | A42-M-B42 | HPLC_1 | 1.3 | 425 |
| 2714 | A44-M-B95 | HPLC_1 | 1.24 | 470 |
| 2715 | A44-M-B38 | HPLC_1 | 1.09 | 382 |
| 2716 | A47-M-B57 | HPLC_1 | 1.06 | 347 |
| 2717 | A44-M-B50 | HPLC_1 | 1.12 | 410 |
| 2718 | A46-M-B48 | HPLC_1 | 1.29 | 425 |
| 2719 | A42-M-B64 | HPLC_1 | 1.43 | 475 |
| 2720 | A42-M-B68 | HPLC_1 | 1.27 | 497 |
| 2721 | A47-M-B62 | HPLC_1 | 1.11 | 389 |
| 2722 | A47-M-B63 | HPLC_1 | 1.09 | 380 |
| 2723 | A47-M-B64 | HPLC_1 | 1.28 | 423 |
| 2724 | A47-M-B65 | HPLC_1 | 1.19 | 391 |
| 2725 | A47-M-B61 | HPLC_1 | 0.87 | 323 |
| 2726 | A44-M-B62 | HPLC_1 | 1.24 | 425 |
| 2727 | A44-M-B67 | HPLC_1 | 1.38 | 455 |
| 2728 | A44-M-B63 | HPLC_1 | 1.22 | 416 |
| 2729 | A44-M-B68 | HPLC_1 | 1.23 | 481 |
| 2730 | A46-M-B68 | HPLC_1 | 1.27 | 479 |
| 2731 | A2-M-B63 | HPLC_1 | 1.22 | 396 |
| 2732 | A2-M-B65 | HPLC_1 | 1.3 | 407 |
| 2733 | A47-M-B71 | HPLC_1 | 1.09 | 399 |
| 2734 | A47-M-B72 | HPLC_1 | 1.39 | 491 |
| 2735 | A47-M-B74 | HPLC_1 | 1.09 | 433 |
| 2736 | A44-M-B82 | HPLC_1 | 1.27 | 484 |
| 2737 | A46-M-B73 | HPLC_1 | 1.39 | 411 |
| 2738 | A42-M-B84 | HPLC_1 | 1.38 | 485 |
| 2739 | A44-M-B94 | HPLC_1 | 1.42 | 459 |
| 2740 | A44-M-B86 | HPLC_1 | 1.25 | 459 |
| 2741 | A44-M-B91 | HPLC_1 | 1.25 | 397 |
| 2742 | A44-M-B92 | HPLC_1 | 1.29 | 449 |
| 2743 | A1-M-B92 | HPLC_1 | 1.32 | 421 |
| 2744 | A2-M-B91 | HPLC_1 | 1.25 | 377 |
| 2745 | A2-M-B92 | HPLC_1 | 1.29 | 429 |
| 2746 | A7-M-B36 | HPLC_1 | 1.44 | 393 |
| 2747 | A5-M-B31 | HPLC_1 | 1.35 | 449 |
| 2748 | A9-M-B34 | HPLC_1 | 1.17 | 474 |
| 2749 | A7-M-B95 | HPLC_1 | 1.11 | 416 |
| 2750 | A7-M-B47 | HPLC_1 | 1.14 | 367 |
| 2751 | A8-M-B95 | HPLC_1 | 1 | 400 |
| 2752 | A11-M-B95 | HPLC_1 | 1.06 | 414 |
| 2753 | A4-M-B37 | HPLC_1 | 1.12 | 357 |
| 2754 | A3-M-B40 | HPLC_1 | 1.27 | 421 |
| 2755 | A3-M-B38 | HPLC_1 | 1.08 | 398 |
| 2756 | A5-M-B95 | HPLC_1 | 1.17 | 494 |
| 2757 | A5-M-B44 | HPLC_1 | 1.16 | 421 |
| 2758 | A9-M-B42 | HPLC_1 | 0.99 | 424 |
| 2759 | A9-M-B38 | HPLC_1 | 0.85 | 397 |
| 2760 | A7-M-B56 | HPLC_1 | 1.16 | 351 |
| 2761 | A5-M-B56 | HPLC_1 | 1.22 | 429 |
| 2762 | A5-M-B65 | HPLC_1 | 1.26 | 451 |
| 2763 | A9-M-B69 | HPLC_1 | 0.99 | 442 |
| 2764 | A5-M-B73 | HPLC_1 | 1.35 | 437 |
| 2765 | A5-M-B76 | HPLC_1 | 1.34 | 471 |
| 2766 | A9-M-B74 | HPLC_1 | 0.99 | 484 |
| 2767 | A9-M-B76 | HPLC_1 | 1.13 | 462 |

TABLE III-continued

| Entry | Compound | HPLC method | r.t. (min) | [M + H]⁺ |
|---|---|---|---|---|
| 2768 | A9-M-B82 | HPLC_1 | 1.05 | 499 |
| 2769 | A7-M-B94 | HPLC_1 | 1.42 | 405 |
| 2770 | A8-M-B84 | HPLC_1 | 1.2 | 399 |
| 2771 | A11-M-B86 | HPLC_1 | 1.17 | 403 |
| 2772 | A11-M-B87 | HPLC_1 | 1.2 | 444 |
| 2773 | A5-M-B86 | HPLC_1 | 1.31 | 483 |
| 2774 | A2-M-B146 | HPLC_2 | 4.87 | 403 |
| 2775 | A2-M-B147 | HPLC_2 | 5.76 | 445 |
| 2776 | A2-M-B148 | HPLC_2 | 3.16 | 394 |
| 2777 | A2-M-B149 | HPLC_2 | 4.88 | 429 |
| 2778 | A2-M-B150 | HPLC_2 | 4.15 | 369 |
| 2779 | A2-M-B151 | HPLC_2 | 4.47 | 456 |
| 2780 | A2-M-B152 | HPLC_2 | 5.6 | 454 |
| 2781 | A2-M-B153 | HPLC_2 | 6.06 | 453 |
| 2782 | A2-M-B154 | HPLC_2 | 5.8 | 438 |
| 2783 | A2-M-B155 | HPLC_2 | 4.76 | 439 |
| 2784 | A15-M-B146 | HPLC_2 | 3.68 | 353 |
| 2785 | A15-M-B147 | HPLC_2 | 4.69 | 395 |
| 2786 | A15-M-B148 | HPLC_2 | 2 | 344 |
| 2787 | A15-M-B149 | HPLC_2 | 3.68 | 379 |
| 2788 | A15-M-B150 | HPLC_2 | 2.87 | 319 |
| 2789 | A15-M-B151 | HPLC_2 | 3.38 | 406 |
| 2790 | A15-M-B152 | HPLC_2 | 4.55 | 404 |
| 2791 | A15-M-B153 | HPLC_2 | 5.08 | 403 |
| 2792 | A15-M-B154 | HPLC_2 | 4.72 | 388 |
| 2793 | A15-M-B155 | HPLC_2 | 3.65 | 389 |
| 2794 | A57-M-B146 | HPLC_2 | 5.15 | 435 |
| 2795 | A57-M-B147 | HPLC_2 | 5.97 | 477 |
| 2796 | A57-M-B148 | HPLC_2 | 3.54 | 426 |
| 2797 | A57-M-B149 | HPLC_2 | 5.14 | 461 |
| 2798 | A57-M-B150 | HPLC_2 | 4.52 | 401 |
| 2799 | A57-M-B151 | HPLC_2 | 4.74 | 488 |
| 2800 | A57-M-B152 | HPLC_2 | 5.84 | 486 |
| 2801 | A57-M-B153 | HPLC_2 | 6.27 | 485 |
| 2802 | A57-M-B154 | HPLC_2 | 5.98 | 470 |
| 2803 | A57-M-B155 | HPLC_2 | 5.02 | 471 |
| 2804 | A58-M-B146 | HPLC_2 | 2.62 | 453 |
| 2805 | A58-M-B147 | HPLC_2 | 3.58 | 495 |
| 2806 | A58-M-B148 | HPLC_2 | 1.21 | 444 |
| 2807 | A58-M-B149 | HPLC_2 | 2.67 | 479 |
| 2808 | A58-M-B150 | HPLC_2 | 1.97 | 419 |
| 2809 | A58-M-B151 | HPLC_2 | 2.51 | 506 |
| 2810 | A58-M-B152 | HPLC_2 | 3.5 | 504 |
| 2811 | A58-M-B153 | HPLC_2 | 3.96 | 503 |
| 2812 | A58-M-B154 | HPLC_2 | 3.56 | 488 |
| 2813 | A58-M-B155 | HPLC_2 | 2.74 | 489 |

For entries from 2774 to 2813 of Table III, also 1H-NMR were run (NMR-method 2) and data are reported in the following Table IV

TABLE IV

| Entry | Compound | ¹H NMR (400 MHz, DMSO-D6) δ ppm |
|---|---|---|
| 2774 | A2-M-B146 | 4.45 (d, J = 5.98 Hz, 2 H) 6.06 (s, 1 H) 7.25 (s, 5 H) 7.45 (s, 3 H) 7.56 (s, 2 H) 8.17 (d, J = 2.32 Hz, 1 H) 8.46 (d, J = 2.44 Hz, 1 H) 8.53 (t, J = 5.86 Hz, 1 H) 8.71 (d, J = 2.44 Hz, 1 H) 10.46 (s, 1 H) 12.04 (s, 1 H) |
| 2775 | A2-M-B147 | 1.09 (dd, J = 4.02, 2.80 Hz, 2 H) 1.47 (dd, J = 4.15, 2.80 Hz, 2 H) 4.45 (d, J = 5.97 Hz, 2 H) 7.18-7.35 (m, 5 H) 7.40 (m, 4 H) 8.12 (d, J = 2.93 Hz, 1 H) 8.32 (d, J = 2.44 Hz, 1 H) 8.48-8.52 (m, 2 H) 9.09 (s, 1 H) 11.94 (s, 1 H) |
| 2776 | A2-M-B148 | 2.55 (m, 4 H) 2.80 (s, 3 H) 2.98 (s, 3 H) 4.46 (d, J = 5.85 Hz, 2 H) 7.18-7.33 (m, 5 H) 8.13 (d, J = 2.93 Hz, 1 H) 8.41 (d, J = 2.44 Hz, 1 H) 8.49 (t, 1 H) 8.68 (d, J = 2.32 Hz, 1 H) 9.97 (s, 1 H) 11.93 (s, 1 H) |
| 2777 | A2-M-B149 | 4.48 (d, J = 5.97 Hz, 2 H) 7.18-7.36 (m, 5 H) 8.20 (d, J = 2.80 Hz, 1 H) 8.38 (dd, J = 6.95, 1.59 Hz, 1 H) 8.53-8.59 (m, 2 H) 8.69 (d, J = 2.32 Hz, 1 H) 8.90 (d, J = 2.44 Hz, 1 H) 9.37 (m, 1 H) 10.70 (s, 1 H) 12.07 (s, 1 H) |
| 2778 | A2-M-B150 | 1.21 (d, J = 7.44 Hz, 3 H) 2.65 (q, J = 7.82 Hz, 2 H) 3.31 (s, 2 H) 4.45 (d, J = 6.10 Hz, 2 H) 7.18-7.34 (m, 5 H) 8.15 (d, J = 3.05 Hz, 1 H) 8.41 (d, J = 2.44 Hz, 1 H) 8.52 (d, J = 6.10 Hz, 1 H) 8.68 (d, J = 2.44 Hz, 1 H) 10.11 (s, 1 H) |
| 2779 | A2-M-B151 | 3.24 (m, 2 H) 3.73 (m, 4 H) 4.48 (d, J = 5.97 Hz, 2 H) 7.03 (d, J = 9.02 Hz, 2 H) 7.19-7.36 (m, 5 H) 7.91 (d, J = 9.02 Hz, 2 H) 8.15 (d, J = 2.80 Hz, 1 H) 8.52 (t, 1 H) 8.60 (d, J = 2.44 Hz, 1 H) 8.78 (d, J = 2.44 Hz, 1 H) 10.04 (s, 1 |
| 2780 | A2-M-B152 | 1.91 (m, 4 H) 3.16 (m, 4 H) 3.47 (s, 2 H) 4.46 (d, J = 5.97 Hz, 2 H) 6.44-6.50 (m, 2 H) 7.11-7.15 (m, 2 H) 7.18-7.34 (m, 5 H) 8.13 (d, J = 2.19 Hz, 1 H) 8.43 (d, J = 2.44 Hz, 1 H) 8.50 (t, J = 6.10 Hz, 1 H) 8.64 (d, J = 2.32 Hz, 1 H |
| 2781 | A2-M-B153 | 1.30-3.25 (m, 11 H) 4.46 (d, J = 5.85 Hz, 2 H) 7.05-7.33 (m, 10 H) 8.13 (d, J = 2.80 Hz, 1 H) 8.42 (d, J = 2.32 Hz, 1 H) 8.50 (t, J = 5.98 Hz, 1 H) 8.68 (d, J = 2.44 Hz, 1 H) 9.93 (s, 1 H) 11.95 (s, 1 H) |
| 2782 | A2-M-B154 | 4.47 (d, J = 5.97 Hz, 2 H) 7.18-7.35 (m, 5 H) 7.48 (s, 1 H) 7.51-7.60 (m, 3 H) 7.96 (s, 2 H) 8.20 (s, 1 H) 8.48-8.59 (m, 2 H) 8.88 (d, J = 2.44 Hz, 1 H) 10.83 (s, 1 H) 12.11 (s, 1 H) |
| 2783 | A2-M-B155 | 2.07 (m, 2 H) 2.66 (dd, J = 5.97 Hz, 2 H) 3.02 (dd, J = 5.97 Hz, 2 H) 4.46 (d, J = 5.97 Hz, 2 H) 7.18-7.36 (m, 5 H) 7.52 (d, J = 8.17 Hz, 1 H) 8.14 (dd, J = 5.85, 2.07 Hz, 1 H) 8.17 (d, J = 2.44 Hz, 1 H) 8.49-8.57 (m, 2 H) 8.62 (d, J = |
| 2784 | A15-M-B146 | 0.45-0.70 (m, 4 H) 2.64-2.80 (m, 1 H) 6.01 (d, J = 47.56 Hz, 1 H) 7.38-7.58 (m, 5 H) 7.96 (d, J = 3.78 Hz, 1 H) 8.05 (d, J = 3.05 Hz, 1 H) 8.45 (d, J = 2.44 Hz, 1 H) 8.67 (d, J = 2.32 Hz, 1 H) 10.46 (s, 1 H) 11.97 (s, 1 H) |
| 2785 | A15-M-B147 | 0.47-0.51 (m, 2 H) 0.63-0.68 (m, 2H) 1.09 (q, J = 2.68 Hz, 2 H) 1.47 (q, J = 2.68 Hz, 2 H) 2.75 (m, 1 H) 7.38-7.45 (m, 4 H) 7.93 (d, J = 3.78 Hz, 1 H) 8.02 (s, 1 H) 8.30 (d, J = 2.44 Hz, 1 H) 8.46 (d, J = 2.44 Hz, 1 H) 9.10 (s, 1 H) |
| 2786 | A15-M-B148 | 0.47-0.53 (m, 3 H) 0.63-0.69 (m, 2 H) 2.53-2.64 (m, 4 H) 2.73-2.80 (m, 4 H) 2.98 (s, 3 H) 7.92 (d, J = 3.41 Hz, 1 H) 8.03 (d, J = 2.93 Hz, 1 H) 8.41 (d, J = 2.44 Hz, 1 H) 8.64 (d, J = 2.44 Hz, 1 H) 9.96 (s, 1 H) 11.88 (s, 1 H) |
| 2787 | A15-M-B149 | 0.49-0.55 (m, 2 H) 0.65-0.71 (m, 2 H) 2.76-2.84 (m, 1 H) 7.99 (d, J = 3.66 Hz, 1 H) 8.09 (s, 1 H) 8.38 (dd, J = 6.95, 1.59 Hz, 1 H) 8.54 (dd, J = 7.93, 0.61 Hz, 1 H) 8.86 (dd, J = 73.65, 2.44 Hz, 2 H) 9.38 (d, J = 0.61 Hz, 1 H) 10.7 |
| 2788 | A15-M-B150 | 0.47-0.53 (m, 2 H) 0.63-0.69 (m, 2 H) 1.21 (t, J = 7.32 Hz, 1 H) 2.64 (q, J = 7.32 Hz, 2 H) 2.73-2.81 (m, 1 H) 7.95 (d, J = 3.66 Hz, 1 H) 8.04 (d, J = 2.93 Hz, 1 H) 8.40 (d, J = 2.44 Hz, 1 H) 8.64 (d, J = 2.32 Hz, 1 H) 10.11 (s, 1 H) |
| 2789 | A15-M-B151 | 0.48-0.54 (m, 2 H) 0.64-0.70 (m, 2 H) 2.74-2.83 (m, 1 H) 3.20-3.30 (m, 4 H) 3.74 (m, 4 H) 7.03 (d, J = 9.15 Hz, 2 H) 7.90-7.97 (m, 3 H) 8.05 (s, 1 H) 8.58 (d, J = 2.44 Hz, 1 H) 8.74 (d, J = 2.44 Hz, 1 H) 10.04 (s, 1 H) 11.92 (s, |
| 2790 | A15-M-B152 | 0.47-0.51 (m, 2 H) 0.63-0.69 (m, 2 H) 1.91 (m, 4 H) 2.71-2.80 (m, 1 H) 3.11-3.20 (m, 4 H) 3.47 (s, 2 H) 6.40-6.51 (m, 2 H) 7.13 (d, J = 8.66 Hz, 2 H) 7.92 (d, J = 2.32 Hz, 1 H) 8.02 (d, J = 2.93 Hz, 1 H) 8.43 (d, J = 2.44 Hz, 1 H) |
| 2791 | A15-M-B153 | 0.47-0.51 (m, 2 H) 0.63-0.69 (m, 2 H)1.32-1.90 (m, 6 H) 2.18-2.29 (m, 1 H) 2.32-2.41 (m, 2 H) 2.70-2.92 (m, 3 H) 7.05-7.22 (m, 4 H) 7.93 (d, J = 3.66 Hz, 1 H) 8.02 (d, J = 2.93 Hz, 1 H) 8.42 (d, J = 2.44 Hz, 1 H) 8.64 (d, J = 2.44 |
| 2792 | A15-M-B154 | 0.47-0.51 (m, 2 H) 0.63-0.69 (m, 2 H) 2.75-2.82 (m, 1 H) 7.49 (s, 1 H) 7.51-7.59 (m, 3 H) 7.93-8.0 (m, 3 H) 8.09 (d, J = 2.44 Hz, 1 H) 8.56 (d, J = 2.44 Hz, 1 H) 8.84 (d, J = 2.44 Hz, 1 H) 10.83 (s, 1 H) 12.04 (s, 1 H) |
| 2793 | A15-M-B155 | 0.47-0.51 (m, 2 H) 0.63-0.69 (m, 2 H) 2.02-2.12 (m, 2 H) 2.66 (t, J = 7.07 Hz, 2 H) 2.75-2.83 (m, 1 H) 3.02 (t, J = 5.97 Hz, 2 H) 7.53 (d, J = 8.05 Hz, 1 H) 7.97 (d, J = 3.66 Hz, 1 H) 8.07 (s, 1 H) 8.15 (dd, J = 5.98, 2.07 Hz, 1 H) |

TABLE IV-continued

| Entry | Compound | $^1$H NMR (400 MHz, DMSO-D6) δ ppm |
|---|---|---|
| 2794 | A57-M-B146 | 2.81 (t, J = 7.07 Hz, 2 H) 3.38-3.46 (m, 2 H) 6.01 (d, J = 47.43 Hz, 1 H) 7.04-7.12 (m, 2 H) 7.23-7.29 (m, 2 H) 7.40-7.49 (m, 5 H) 8.03-8.1 (m, 2 H) 8.45 (d, J = 2.44 Hz, 1 H) 8.68 (d, J = 2.44 Hz, 1 H) 10.45 (s, 1 H) 11.99 (s, 1 H |
| 2795 | A57-M-B147 | 1.09 (q, J = 2.68, 2.68 Hz, 2 H) 1.47 (q, J = 2.68, 2.68 Hz, 2 H) 2.80 (t, J = 7.19 Hz, 2 H) 3.38-3.46 (m, 2 H) 7.03-7.12 (m, 2 H) 7.22-7.28 (m, 2 H) 7.37-7.46 (m, 4 H) 8.01-8.06 (m, 2 H) 8.31 (d, J = 2.44 Hz, 1 H) 8.47 (d, J = 2.32 Hz, 1 |
| 2796 | A57-M-B148 | 2.53-2.68 (m, 4 H) 2.76-2.85 (m, 5 H) 2.98 (s, 3 H) 3.44 (s, 2 H) 7.04-7.13 (m, 2 H) 7.22-7.30 (m, 2 H) 7.99-8.07 (m, 2 H) 8.39 (d, J = 2.32 Hz, 1 H) 8.67 (d, J = 2.32 Hz, 1 H) 9.96 (s, 1 H) 11.89 (s, 1 H) |
| 2798 | A57-M-B150 | 1.21 (t, J = 7.44 Hz, 3 H) 2.64 (q, J = 7.32 Hz, 2 H) 2.81 (t, J = 7.19 Hz, 2 H) 3.31 (s, 2H) 3.38-3.48 (m, 2 H) 7.03-7.13 (m, 2 H) 7.23-7.33 (m, 2 H) 8.02-8.09 (m, 2 H) 8.39 (d, J = 2.44 Hz, 1 H) 8.66 (d, J = 2.44 Hz, 1 H) 10.10 (s |
| 2799 | A57-M-B151 | 2.82 (t, J = 7.07 Hz, 2 H) 3.24 (m, 4 H) 3.29-3.49 (m, 2 H) 3.74 (m, 4 H) 7.03 (d, 9.15 Hz, 2 H 7.09 (m, 2 H) 7.24-7.3 (m, 2 H) 7.91 (d, J = 8.90 Hz, 2 H) 8.03-8.08 (m, 2 H) 8.58 (d, J = 2.44 Hz, 1 H) 8.76 (d, J = 2.44 Hz, 1 H) 10. |
| 2800 | A57-M-B152 | 1.88-1.94 (m, 4 H) 2.81 (t, J = 6.95 Hz, 2 H) 3.12-3.19 (m, 4 H) 3.37-3.45 (m, 2 H) 3.47 (s, 2 H) 6.49 (d, J = 8.66 Hz, 2 H) 7.02-7.17 (m, 4 H) 7.23-7.29 (m, 2 H) 8.0-8.07 (m, 2 H) 8.41 (d, J = 2.32 Hz, 1 H) 8.62 (d, J = 2.44 Hz, |
| 2801 | A57-M-B153 | 1.29-3.52 (m, 15 H) 7.03-7.32 (m, 8 H) 8.01-8.06 (m, 2 H) 8.40 (d, J = 2.32 Hz, 1 H) 8.66 (d, J = 2.32 Hz, 1 H) 9.92 (s, 1 H) 11.90 (s, 1 H) |
| 2802 | A57-M-B154 | 2.83 (t, J = 7.32 Hz, 2 H) 3.40-3.50 (m, 2H) 7.06-7.13 (m, 2 H) 7.25-7.31 (m, 2 H) 7.49 (s, 1 H) 7.52-7.6 (m, 3 H) 7.94-7.98 (m, 2 H) 8.5-8.12 (m, 2 H) 8.56 (d, J = 2.44 Hz, 1 H) 8.85 (d, J = 2.44 Hz, 1 H) 10.83 (s, 1 H) 12.05 (s |
| 2803 | A57-M-B155 | 2.03-2.11 (m, 2 H) 2.66 (t, J = 7.07 Hz, 2 H) 2.82 (t, J = 7.19 Hz, 2 H) 3.02 (t, J = 5.97 Hz, 2 H) 3.41-3.49 (m, 2 H) 7.05-7.13 (m, 2 H) 7.24-7.30 (m, 2 H) 7.53 (d, J = 8.17 Hz, 1 H) 8.05-8.09 (m, 2 H) 8.15 (dd, J = 5.97, 1.95 Hz, |
| 2804 | A58-M-B146 | 1.5-3.5 (m, 17 H) 6.01 (d, J = 47.43 Hz, 1 H) 7.37-7.58 (m, 5 H) 7.94 (br.s, 1 H) 8.08 (d, J = 2.93 Hz, 1 H) 8.42 (d, J = 2.32 Hz, 1 H) 8.72 (d, 1 H) 10.47 (s, 1 H) 12.03 (s, 1 H) |
| 2805 | A58-M-B147 | 1.10 (q, J = 2.68 Hz, 2 H) 1.46 (q, J = 2.68 Hz, 2 H) 1.50-3.50 (m, 17 H) 7.36-7.49 (m, 4 H) 7.96 (br.s., 1 H) 8.03 (d, J = 2.93 Hz, 1 H) 8.28 (d, J = 2.44 Hz, 1 H) 8.49 (d, J = 2.20 Hz, 1 H) 9.09 (s, 1 H) 11.92 (s, 1 H) |
| 2806 | A58-M-B148 | 1H NMR (400 MHz, DMSO-D6) d ppm1.5-3.59 (m, 27 H) 7.93 (br.s, 1 H) 8.04 (d, J = 2.80 Hz, 1 H) 8.35 (d, J = 2.44 Hz, 1 H) 8.70 (s, 1 H) 9.97 (s, 1 H) 11.93 (s, 1 H) |
| 2807 | A58-M-B149 | 1.57-3.57 (m, 17 H) 7.93 (br.s, 2H) 8.12 (d, J = 3.05 Hz, 1 H) 8.37 (dd, J = 6.95, 1.59 Hz, 1 H) 8.55 (dd, J = 7.93, 0.61 Hz, 1 H) 8.64 (d, J = 2.44 Hz, 1 H) 8.90 (s, 1 H) 9.37 (s, 1 H) 10.70 (s, 1 H) 12.05 (s, 1 H) |
| 2808 | A58-M-B150 | 1.21 (t, J = 7.32 Hz, 3 H) 1.57-3.57 (m, 17 H) 7.96 (br.s, 1 H) 8.08 (d, J = 3.05 Hz, 1 H) 8.34 (d, J = 2.44 Hz, 1 H) 8.72 (d, 1 H) 10.12 (s, 1 H) 11.98 (s, 1 H) |
| 2809 | A58-M-B151 | 1.57-3.57 (m, 21 H) 3.74 (m, 4 H) 7.03 (d, J = 9.15 Hz, 2 H) 7.90 (d, J = 9.02 Hz, 2 H) 8.07 (d, J = 3.05 Hz, 1 H) 8.54 (d, J = 2.44 Hz, 1 H) 8.79 (br.s., 1 H) 10.04 (s, 1 H) 11.96 (s, 1 H) |
| 2810 | A58-M-B152 | 1.57-3.57 (m, 27 H) 6.49 (d, J = 8.66 Hz, 2 H) 7.13 (d, J = 8.54 Hz, 2 H) 8.00 (m, 2 H) 8.37 (d, J = 2.44 Hz, 1 H) 8.66 (d, J = 2.32 Hz, 1 H) 10.06 (s, 1 H) 11.94 (s, 1 H) |
| 2811 | A58-M-B153 | 1.28-3.41 (m, 28 H) 7.06-7.21 (m, 4 H) 7.94 (br.s., 1 H) 8.05 (d, J = 2.93 Hz, 1 H) 8.36 (d, J = 2.44 Hz, 1 H) 8.70 (s, 1 H) 9.93 (s, 1 H) 11.94 (s, 1 H) |
| 2812 | A58-M-B154 | 1.57-3.57 (m, 17 H) 7.47 (s, 1 H) 7.52-7.61 (m, 3 H) 7.94-7.99 (m, 2 H) 8.07 (br.s, 1 H) 8.11 (d, 1 H) 8.54 (d, 1 H) 8.87 (d, 1 H) 10.84 (s, 1 H) 12.10 (s, 1 H) |
| 2813 | A58-M-B155 | 1.57-3.57 (m, J = 311.67 Hz, 23 H) 7.53 (d, J = 8.17 Hz, 1 H) 7.98 (br.s, 1 H) 8.09 (d, J = 2.93 Hz, 1 H) 8.14 (dd, J = 5.85, 2.07 Hz, 1 H) 8.52 (d, J = 1.95 Hz, 1 H) 8.56 (d, J = 2.32 Hz, 1 H) 8.83 (s, 1 H) 10.49 (s, 1 H) 12.01 (s, 1H) |

Example 6

Preparation of A32-M-B13

By working as described in examples 4 and 5 and by carrying out the capping reaction with 2-trifluoromethylbenzene sulfonyl chloride (corresponding to fragment B13 of Table II) in place of the acyl chloride derivative, the title compound was obtained according to the following operative conditions To the resin being obtained in step (b) of example 5 (0.11 g, 0.075 mmol) in DCM (1 ml), pyridine (0.030 g, 0.385 mmol), DMAP (0.001 g, 0.0077 mmol) and 2-trifluoromethylbenzene sulfonyl chloride (0.094 g, 0.385 mmol) were added. The reaction mixture was shaken at room temperature for 20 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (60% TFA/DCM, 3×(3×0.5 ml)) to give an off white solid (0.02 g, 55%) corresponding to the compound A32-M-B13 (see entry 3364 of table V below).

LCMS (HPLC_1): m/z 455 [M+H]$^+$ and 496 [M+MeCN+H]$^+$ at r.t. 1.36 min (97.5% by ELS detection).

By working according to any previous example, that is to say by starting from any suitable resin supported amino derivative and by carrying out the capping reaction with any suitable sulfonyl chloride derivative, the following compounds of Table V (i.e. library) were thus obtained.

TABLE V

| Entry | Compound | HPLC method | r.t. (min) | [M + H]$^+$ |
|---|---|---|---|---|
| 2814 | A1-M-B1 | HPLC_1 | 1.03 | 337 |
| 2815 | A2-M-B1 | HPLC_1 | 1.01 | 345 |
| 2816 | A3-M-B1 | HPLC_1 | 1.06 | 381 |
| 2817 | A4-M-B1 | HPLC_1 | 1.13 | 379 |
| 2818 | A5-M-B1 | HPLC_1 | 1.05 | 389 |
| 2819 | A6-M-B1 | HPLC_1 | 1.07 | 375 |
| 2820 | A1-M-B2 | HPLC_1 | 1.28 | 413 |
| 2821 | A2-M-B2 | HPLC_1 | 1.25 | 421 |
| 2822 | A7-M-B2 | HPLC_1 | 1.21 | 387 |
| 2823 | A8-M-B2 | HPLC_1 | 1.1 | 371 |
| 2824 | A4-M-B2 | HPLC_1 | 1.34 | 455 |
| 2825 | A5-M-B2 | HPLC_1 | 1.27 | 465 |
| 2826 | A9-M-B2 | HPLC_1 | 1.02 | 456 |
| 2827 | A6-M-B2 | HPLC_1 | 1.29 | 451 |
| 2828 | A10-M-B2 | HPLC_1 | 1.12 | 417 |
| 2829 | A1-M-B3 | HPLC_1 | 1.32 | 433 |
| 2830 | A2-M-B3 | HPLC_1 | 1.29 | 441 |
| 2831 | A8-M-B3 | HPLC_1 | 1.15 | 391 |
| 2832 | A4-M-B3 | HPLC_1 | 1.38 | 475 |
| 2833 | A5-M-B3 | HPLC_1 | 1.31 | 485 |
| 2834 | A9-M-B3 | HPLC_1 | 1.07 | 476 |
| 2835 | A10-M-B3 | HPLC_1 | 1.16 | 437 |
| 2836 | A1-M-B4 | HPLC_1 | 1.07 | 351 |
| 2837 | A2-M-B4 | HPLC_1 | 1.05 | 359 |
| 2838 | A7-M-B4 | HPLC_1 | 0.99 | 325 |
| 2839 | A8-M-B4 | HPLC_1 | 0.86 | 309 |
| 2840 | A3-M-B4 | HPLC_1 | 1.1 | 395 |

TABLE V-continued

| Entry | Compound | HPLC method | r.t. (min) | [M + H]+ |
|---|---|---|---|---|
| 2841 | A4-M-B4 | HPLC_1 | 1.16 | 393 |
| 2842 | A9-M-B4 | HPLC_1 | 0.82 | 394 |
| 2843 | A6-M-B4 | HPLC_1 | 1.1 | 389 |
| 2844 | A1-M-B5 | HPLC_1 | 1.24 | 459 |
| 2845 | A2-M-B5 | HPLC_1 | 1.21 | 467 |
| 2846 | A7-M-B5 | HPLC_1 | 1.17 | 433 |
| 2847 | A8-M-B5 | HPLC_1 | 1.05 | 417 |
| 2848 | A3-M-B5 | HPLC_1 | 1.25 | 503 |
| 2849 | A4-M-B5 | HPLC_1 | 1.3 | 501 |
| 2850 | A9-M-B5 | HPLC_1 | 0.98 | 502 |
| 2851 | A6-M-B5 | HPLC_1 | 1.24 | 497 |
| 2852 | A10-M-B5 | HPLC_1 | 1.07 | 463 |
| 2853 | A1-M-B6 | HPLC_1 | 1.24 | 429 |
| 2854 | A2-M-B6 | HPLC_1 | 1.21 | 437 |
| 2855 | A7-M-B6 | HPLC_1 | 1.17 | 403 |
| 2856 | A8-M-B6 | HPLC_1 | 1.06 | 387 |
| 2857 | A3-M-B6 | HPLC_1 | 1.25 | 473 |
| 2858 | A4-M-B6 | HPLC_1 | 1.3 | 471 |
| 2859 | A5-M-B6 | HPLC_1 | 1.23 | 481 |
| 2860 | A9-M-B6 | HPLC_1 | 0.99 | 472 |
| 2861 | A10-M-B6 | HPLC_1 | 1.08 | 433 |
| 2862 | A1-M-B7 | HPLC_1 | 1.45 | 455 |
| 2863 | A2-M-B7 | HPLC_1 | 1.42 | 463 |
| 2864 | A7-M-B7 | HPLC_1 | 1.39 | 429 |
| 2865 | A8-M-B7 | HPLC_1 | 1.29 | 413 |
| 2866 | A3-M-B7 | HPLC_1 | 1.44 | 499 |
| 2867 | A4-M-B7 | HPLC_1 | 1.49 | 497 |
| 2868 | A5-M-B7 | HPLC_1 | 1.43 | 507 |
| 2869 | A9-M-B7 | HPLC_1 | 1.19 | 498 |
| 2870 | A6-M-B7 | HPLC_1 | 1.44 | 493 |
| 2871 | A10-M-B7 | HPLC_1 | 1.3 | 459 |
| 2872 | A1-M-B8 | HPLC_1 | 1.26 | 433 |
| 2873 | A2-M-B8 | HPLC_1 | 1.24 | 441 |
| 2874 | A7-M-B8 | HPLC_1 | 1.19 | 407 |
| 2875 | A8-M-B8 | HPLC_1 | 1.08 | 391 |
| 2876 | A3-M-B8 | HPLC_1 | 1.27 | 477 |
| 2877 | A4-M-B8 | HPLC_1 | 1.33 | 475 |
| 2878 | A6-M-B8 | HPLC_1 | 1.27 | 471 |
| 2879 | A10-M-B8 | HPLC_1 | 1.1 | 437 |
| 2880 | A1-M-B9 | HPLC_1 | 1.27 | 435 |
| 2881 | A2-M-B9 | HPLC_1 | 1.24 | 443 |
| 2882 | A7-M-B9 | HPLC_1 | 1.2 | 409 |
| 2883 | A8-M-B9 | HPLC_1 | 1.09 | 393 |
| 2884 | A3-M-B9 | HPLC_1 | 1.29 | 479 |
| 2885 | A4-M-B9 | HPLC_1 | 1.33 | 477 |
| 2886 | A11-M-B9 | HPLC_1 | 1.14 | 407 |
| 2887 | A5-M-B9 | HPLC_1 | 1.27 | 487 |
| 2888 | A9-M-B9 | HPLC_1 | 1.01 | 478 |
| 2889 | A6-M-B9 | HPLC_1 | 1.29 | 473 |
| 2890 | A10-M-B9 | HPLC_1 | 1.11 | 439 |
| 2891 | A2-M-B10 | HPLC_1 | 1.33 | 475 |
| 2892 | A7-M-B10 | HPLC_1 | 1.29 | 441 |
| 2893 | A8-M-B10 | HPLC_1 | 1.19 | 425 |
| 2894 | A3-M-B10 | HPLC_1 | 1.37 | 511 |
| 2895 | A4-M-B10 | HPLC_1 | 1.41 | 509 |
| 2896 | A11-M-B10 | HPLC_1 | 1.24 | 439 |
| 2897 | A6-M-B10 | HPLC_1 | 1.36 | 505 |
| 2898 | A10-M-B10 | HPLC_1 | 1.2 | 471 |
| 2899 | A1-M-B11 | HPLC_1 | 1.15 | 365 |
| 2900 | A2-M-B11 | HPLC_1 | 1.13 | 373 |
| 2901 | A8-M-B11 | HPLC_1 | 0.94 | 323 |
| 2902 | A3-M-B12 | HPLC_1 | 1.42 | 485 |
| 2903 | A11-M-B12 | HPLC_1 | 1.3 | 413 |
| 2904 | A5-M-B12 | HPLC_1 | 1.41 | 493 |
| 2905 | A9-M-B12 | HPLC_1 | 1.17 | 484 |
| 2906 | A10-M-B12 | HPLC_1 | 1.27 | 445 |
| 2907 | A1-M-B13 | HPLC_1 | 1.33 | 467 |
| 2908 | A2-M-B13 | HPLC_1 | 1.3 | 475 |
| 2909 | A7-M-B13 | HPLC_1 | 1.27 | 441 |
| 2910 | A8-M-B13 | HPLC_1 | 1.17 | 425 |
| 2911 | A3-M-B13 | HPLC_1 | 1.34 | 511 |
| 2912 | A4-M-B13 | HPLC_1 | 1.39 | 509 |
| 2913 | A11-M-B13 | HPLC_1 | 1.21 | 439 |
| 2914 | A9-M-B13 | HPLC_1 | 1.08 | 510 |
| 2915 | A6-M-B13 | HPLC_1 | 1.34 | 505 |
| 2916 | A10-M-B13 | HPLC_1 | 1.18 | 471 |
| 2917 | A1-M-B14 | HPLC_1 | 1.23 | 379 |
| 2918 | A2-M-B14 | HPLC_1 | 1.2 | 387 |
| 2919 | A7-M-B14 | HPLC_1 | 1.16 | 353 |
| 2920 | A8-M-B14 | HPLC_1 | 1.03 | 337 |
| 2921 | A11-M-B14 | HPLC_1 | 1.09 | 351 |
| 2922 | A5-M-B14 | HPLC_1 | 1.22 | 431 |
| 2923 | A9-M-B14 | HPLC_1 | 0.97 | 422 |
| 2924 | A6-M-B14 | HPLC_1 | 1.24 | 417 |
| 2925 | A10-M-B14 | HPLC_1 | 1.06 | 383 |
| 2926 | A1-M-B15 | HPLC_1 | 1.22 | 399 |
| 2927 | A2-M-B15 | HPLC_1 | 1.2 | 407 |
| 2928 | A7-M-B15 | HPLC_1 | 1.15 | 373 |
| 2929 | A8-M-B15 | HPLC_1 | 1.03 | 357 |
| 2930 | A3-M-B15 | HPLC_1 | 1.24 | 443 |
| 2931 | A4-M-B15 | HPLC_1 | 1.29 | 441 |
| 2932 | A11-M-B15 | HPLC_1 | 1.09 | 371 |
| 2933 | A5-M-B15 | HPLC_1 | 1.22 | 451 |
| 2934 | A9-M-B15 | HPLC_1 | 0.97 | 442 |
| 2935 | A6-M-B15 | HPLC_1 | 1.24 | 437 |
| 2936 | A10-M-B15 | HPLC_1 | 1.06 | 403 |
| 2937 | A1-M-B16 | HPLC_1 | 1.26 | 417 |
| 2938 | A2-M-B16 | HPLC_1 | 1.24 | 425 |
| 2939 | A11-M-B16 | HPLC_1 | 1.14 | 389 |
| 2940 | A5-M-B16 | HPLC_1 | 1.26 | 469 |
| 2941 | A9-M-B16 | HPLC_1 | 1.01 | 460 |
| 2942 | A6-M-B16 | HPLC_1 | 1.28 | 455 |
| 2943 | A10-M-B16 | HPLC_1 | 1.11 | 421 |
| 2944 | A1-M-B17 | HPLC_1 | 1.34 | 483 |
| 2945 | A2-M-B17 | HPLC_1 | 1.3 | 491 |
| 2946 | A7-M-B17 | HPLC_1 | 1.27 | 457 |
| 2947 | A8-M-B17 | HPLC_1 | 1.17 | 441 |
| 2948 | A3-M-B17 | HPLC_1 | 1.34 | 527 |
| 2949 | A4-M-B17 | HPLC_1 | 1.39 | 525 |
| 2950 | A11-M-B17 | HPLC_1 | 1.21 | 455 |
| 2951 | A6-M-B17 | HPLC_1 | 1.34 | 521 |
| 2952 | A10-M-B17 | HPLC_1 | 1.17 | 487 |
| 2953 | A1-M-B18 | HPLC_1 | 1.34 | 449 |
| 2954 | A2-M-B18 | HPLC_1 | 1.31 | 457 |
| 2955 | A7-M-B18 | HPLC_1 | 1.27 | 423 |
| 2956 | A8-M-B18 | HPLC_1 | 1.17 | 407 |
| 2957 | A3-M-B18 | HPLC_1 | 1.35 | 493 |
| 2958 | A11-M-B18 | HPLC_1 | 1.22 | 421 |
| 2959 | A6-M-B18 | HPLC_1 | 1.34 | 487 |
| 2960 | A10-M-B18 | HPLC_1 | 1.19 | 453 |
| 2961 | A7-M-B19 | HPLC_1 | 1.29 | 423 |
| 2962 | A8-M-B19 | HPLC_1 | 1.19 | 407 |
| 2963 | A11-M-B19 | HPLC_1 | 1.24 | 421 |
| 2964 | A5-M-B19 | HPLC_1 | 1.34 | 501 |
| 2965 | A9-M-B19 | HPLC_1 | 1.11 | 492 |
| 2966 | A6-M-B19 | HPLC_1 | 1.35 | 487 |
| 2967 | A10-M-B19 | HPLC_1 | 1.2 | 453 |
| 2968 | A1-M-B20 | HPLC_1 | 1.42 | 467 |
| 2969 | A2-M-B20 | HPLC_1 | 1.39 | 475 |
| 2970 | A7-M-B20 | HPLC_1 | 1.36 | 441 |
| 2971 | A8-M-B20 | HPLC_1 | 1.25 | 425 |
| 2972 | A3-M-B20 | HPLC_1 | 1.42 | 511 |
| 2973 | A4-M-B20 | HPLC_1 | 1.47 | 509 |
| 2974 | A11-M-B20 | HPLC_1 | 1.3 | 439 |
| 2975 | A5-M-B20 | HPLC_1 | 1.41 | 519 |
| 2976 | A9-M-B20 | HPLC_1 | 1.17 | 510 |
| 2977 | A6-M-B20 | HPLC_1 | 1.42 | 505 |
| 2978 | A10-M-B20 | HPLC_1 | 1.27 | 471 |
| 2979 | A1-M-B21 | HPLC_1 | 1.12 | 365 |
| 2980 | A2-M-B21 | HPLC_1 | 1.09 | 373 |
| 2981 | A7-M-B21 | HPLC_1 | 1.04 | 339 |
| 2982 | A8-M-B21 | HPLC_1 | 0.91 | 323 |
| 2983 | A3-M-B21 | HPLC_1 | 1.14 | 409 |
| 2984 | A4-M-B21 | HPLC_1 | 1.21 | 407 |
| 2985 | A11-M-B21 | HPLC_1 | 0.97 | 337 |
| 2986 | A6-M-B21 | HPLC_1 | 1.15 | 403 |
| 2987 | A10-M-B21 | HPLC_1 | 0.95 | 369 |
| 2988 | A1-M-B22 | HPLC_1 | 1.19 | 459 |
| 2989 | A2-M-B22 | HPLC_1 | 1.17 | 467 |
| 2990 | A6-M-B22 | HPLC_1 | 1.22 | 497 |
| 2991 | A10-M-B22 | HPLC_1 | 1.04 | 463 |
| 2992 | A1-M-B23 | HPLC_1 | 1.41 | 467 |
| 2993 | A2-M-B23 | HPLC_1 | 1.38 | 475 |
| 2994 | A7-M-B23 | HPLC_1 | 1.34 | 441 |

TABLE V-continued

| Entry | Compound | HPLC method | r.t. (min) | [M + H]+ |
|---|---|---|---|---|
| 2995 | A8-M-B23 | HPLC_1 | 1.24 | 425 |
| 2996 | A3-M-B23 | HPLC_1 | 1.41 | 511 |
| 2997 | A5-M-B23 | HPLC_1 | 1.39 | 519 |
| 2998 | A9-M-B23 | HPLC_1 | 1.16 | 510 |
| 2999 | A6-M-B23 | HPLC_1 | 1.41 | 505 |
| 3000 | A10-M-B23 | HPLC_1 | 1.26 | 471 |
| 3001 | A1-M-B24 | HPLC_1 | 1.23 | 417 |
| 3002 | A2-M-B24 | HPLC_1 | 1.2 | 425 |
| 3003 | A7-M-B24 | HPLC_1 | 1.16 | 391 |
| 3004 | A8-M-B24 | HPLC_1 | 1.04 | 375 |
| 3005 | A3-M-B24 | HPLC_1 | 1.24 | 461 |
| 3006 | A4-M-B24 | HPLC_1 | 1.3 | 459 |
| 3007 | A11-M-B24 | HPLC_1 | 1.09 | 389 |
| 3008 | A5-M-B24 | HPLC_1 | 1.23 | 469 |
| 3009 | A9-M-B24 | HPLC_1 | 0.97 | 460 |
| 3010 | A6-M-B24 | HPLC_1 | 1.24 | 455 |
| 3011 | A10-M-B24 | HPLC_1 | 1.06 | 421 |
| 3012 | A3-M-B11 | HPLC_1 | 1.17 | 409 |
| 3013 | A4-M-B11 | HPLC_1 | 1.23 | 407 |
| 3014 | A11-M-B11 | HPLC_1 | 1.01 | 337 |
| 3015 | A6-M-B11 | HPLC_1 | 1.17 | 403 |
| 3016 | A10-M-B11 | HPLC_1 | 0.98 | 369 |
| 3017 | A1-M-B12 | HPLC_1 | 1.42 | 441 |
| 3018 | A2-M-B12 | HPLC_1 | 1.39 | 449 |
| 3019 | A7-M-B12 | HPLC_1 | 1.36 | 415 |
| 3020 | A8-M-B12 | HPLC_1 | 1.26 | 399 |
| 3021 | A7-M-B22 | HPLC_1 | 1.13 | 433 |
| 3022 | A8-M-B22 | HPLC_1 | 1.01 | 417 |
| 3023 | A3-M-B22 | HPLC_1 | 1.21 | 503 |
| 3024 | A11-M-B22 | HPLC_1 | 1.07 | 431 |
| 3025 | A5-M-B22 | HPLC_1 | 1.2 | 511 |
| 3026 | A9-M-B22 | HPLC_1 | 0.96 | 502 |
| 3027 | A12-M-B1 | HPLC_1 | 1.07 | 363 |
| 3028 | A12-M-B4 | HPLC_1 | 1.12 | 377 |
| 3029 | A12-M-B5 | HPLC_1 | 1.27 | 485 |
| 3030 | A12-M-B8 | HPLC_1 | 1.29 | 459 |
| 3031 | A12-M-B9 | HPLC_1 | 1.29 | 461 |
| 3032 | A12-M-B10 | HPLC_1 | 1.37 | 493 |
| 3033 | A12-M-B11 | HPLC_1 | 1.18 | 391 |
| 3034 | A13-M-B1 | HPLC_1 | 0.84 | 297 |
| 3035 | A13-M-B4 | HPLC_1 | 0.9 | 311 |
| 3036 | A13-M-B5 | HPLC_1 | 1.1 | 419 |
| 3037 | A13-M-B9 | HPLC_1 | 1.13 | 395 |
| 3038 | A13-M-B10 | HPLC_1 | 1.24 | 427 |
| 3039 | A13-M-B11 | HPLC_1 | 0.99 | 325 |
| 3040 | A13-M-B12 | HPLC_1 | 1.31 | 401 |
| 3041 | A14-M-B2 | HPLC_1 | 1.06 | 389 |
| 3042 | A14-M-B4 | HPLC_1 | 0.81 | 327 |
| 3043 | A14-M-B5 | HPLC_1 | 1.02 | 435 |
| 3044 | A14-M-B6 | HPLC_1 | 1.02 | 405 |
| 3045 | A14-M-B7 | HPLC_1 | 1.25 | 431 |
| 3046 | A14-M-B8 | HPLC_1 | 1.04 | 409 |
| 3047 | A14-M-B9 | HPLC_1 | 1.04 | 411 |
| 3048 | A14-M-B10 | HPLC_1 | 1.14 | 443 |
| 3049 | A14-M-B11 | HPLC_1 | 0.89 | 341 |
| 3050 | A14-M-B12 | HPLC_1 | 1.22 | 417 |
| 3051 | A15-M-B2 | HPLC_1 | 1.09 | 371 |
| 3052 | A15-M-B4 | HPLC_1 | 0.84 | 309 |
| 3053 | A15-M-B5 | HPLC_1 | 1.04 | 417 |
| 3054 | A15-M-B6 | HPLC_1 | 1.04 | 387 |
| 3055 | A15-M-B8 | HPLC_1 | 1.07 | 391 |
| 3056 | A15-M-B9 | HPLC_1 | 1.07 | 393 |
| 3057 | A15-M-B10 | HPLC_1 | 1.17 | 425 |
| 3058 | A15-M-B11 | HPLC_1 | 0.92 | 323 |
| 3059 | A15-M-B12 | HPLC_1 | 1.25 | 399 |
| 3060 | A17-M-B1 | HPLC_1 | 1.12 | 359 |
| 3061 | A17-M-B4 | HPLC_1 | 1.17 | 373 |
| 3062 | A17-M-B5 | HPLC_1 | 1.3 | 481 |
| 3063 | A17-M-B8 | HPLC_1 | 1.33 | 455 |
| 3064 | A17-M-B9 | HPLC_1 | 1.33 | 457 |
| 3065 | A17-M-B10 | HPLC_1 | 1.42 | 489 |
| 3066 | A17-M-B11 | HPLC_1 | 1.23 | 387 |
| 3067 | A17-M-B12 | HPLC_1 | 1.47 | 463 |
| 3068 | A12-M-B13 | HPLC_1 | 1.35 | 493 |
| 3069 | A12-M-B14 | HPLC_1 | 1.26 | 405 |
| 3070 | A12-M-B15 | HPLC_1 | 1.26 | 425 |
| 3071 | A12-M-B21 | HPLC_1 | 1.17 | 391 |
| 3072 | A12-M-B24 | HPLC_1 | 1.26 | 443 |
| 3073 | A13-M-B13 | HPLC_1 | 1.22 | 427 |
| 3074 | A13-M-B14 | HPLC_1 | 1.09 | 339 |
| 3075 | A13-M-B15 | HPLC_1 | 1.09 | 359 |
| 3076 | A13-M-B16 | HPLC_1 | 1.14 | 377 |
| 3077 | A13-M-B17 | HPLC_1 | 1.22 | 443 |
| 3078 | A13-M-B18 | HPLC_1 | 1.23 | 409 |
| 3079 | A13-M-B19 | HPLC_1 | 1.24 | 409 |
| 3080 | A13-M-B20 | HPLC_1 | 1.3 | 427 |
| 3081 | A13-M-B21 | HPLC_1 | 0.98 | 325 |
| 3082 | A13-M-B22 | HPLC_1 | 1.07 | 419 |
| 3083 | A13-M-B23 | HPLC_1 | 1.29 | 427 |
| 3084 | A13-M-B24 | HPLC_1 | 1.1 | 377 |
| 3085 | A14-M-B13 | HPLC_1 | 1.13 | 443 |
| 3086 | A14-M-B14 | HPLC_1 | 1 | 355 |
| 3087 | A14-M-B15 | HPLC_1 | 1.01 | 375 |
| 3088 | A14-M-B16 | HPLC_1 | 1.04 | 393 |
| 3089 | A14-M-B17 | HPLC_1 | 1.13 | 459 |
| 3090 | A14-M-B18 | HPLC_1 | 1.14 | 425 |
| 3091 | A14-M-B19 | HPLC_1 | 1.16 | 425 |
| 3092 | A14-M-B20 | HPLC_1 | 1.23 | 443 |
| 3093 | A14-M-B21 | HPLC_1 | 0.88 | 341 |
| 3094 | A14-M-B22 | HPLC_1 | 0.99 | 435 |
| 3095 | A14-M-B23 | HPLC_1 | 1.21 | 443 |
| 3096 | A14-M-B24 | HPLC_1 | 1.01 | 393 |
| 3097 | A15-M-B13 | HPLC_1 | 1.15 | 425 |
| 3098 | A15-M-B14 | HPLC_1 | 1.03 | 337 |
| 3099 | A15-M-B15 | HPLC_1 | 1.03 | 357 |
| 3100 | A15-M-B16 | HPLC_1 | 1.08 | 375 |
| 3101 | A15-M-B17 | HPLC_1 | 1.16 | 441 |
| 3102 | A15-M-B18 | HPLC_1 | 1.17 | 407 |
| 3103 | A15-M-B19 | HPLC_1 | 1.19 | 407 |
| 3104 | A15-M-B20 | HPLC_1 | 1.25 | 425 |
| 3105 | A15-M-B21 | HPLC_1 | 0.91 | 323 |
| 3106 | A15-M-B22 | HPLC_1 | 1.01 | 417 |
| 3107 | A15-M-B23 | HPLC_1 | 1.24 | 425 |
| 3108 | A15-M-B24 | HPLC_1 | 1.04 | 375 |
| 3109 | A16-M-B15 | HPLC_1 | 1.25 | 437 |
| 3110 | A16-M-B16 | HPLC_1 | 1.29 | 455 |
| 3111 | A16-M-B23 | HPLC_1 | 1.42 | 505 |
| 3112 | A17-M-B13 | HPLC_1 | 1.39 | 489 |
| 3113 | A17-M-B14 | HPLC_1 | 1.3 | 401 |
| 3114 | A17-M-B15 | HPLC_1 | 1.29 | 421 |
| 3115 | A17-M-B17 | HPLC_1 | 1.38 | 505 |
| 3116 | A17-M-B20 | HPLC_1 | 1.44 | 489 |
| 3117 | A17-M-B21 | HPLC_1 | 1.21 | 387 |
| 3118 | A17-M-B24 | HPLC_1 | 1.29 | 439 |
| 3119 | A22-M-B2 | HPLC_1 | 0.98 | 416 |
| 3120 | A22-M-B3 | HPLC_1 | 1.02 | 436 |
| 3121 | A22-M-B4 | HPLC_1 | 0.74 | 354 |
| 3122 | A22-M-B5 | HPLC_1 | 0.94 | 462 |
| 3123 | A22-M-B6 | HPLC_1 | 0.94 | 432 |
| 3124 | A22-M-B7 | HPLC_1 | 1.17 | 458 |
| 3125 | A22-M-B8 | HPLC_1 | 0.96 | 436 |
| 3126 | A22-M-B9 | HPLC_1 | 0.96 | 438 |
| 3127 | A22-M-B10 | HPLC_1 | 1.06 | 470 |
| 3128 | A22-M-B11 | HPLC_1 | 0.82 | 368 |
| 3129 | A22-M-B12 | HPLC_1 | 1.13 | 444 |
| 3130 | A23-M-B2 | HPLC_1 | 0.98 | 444 |
| 3131 | A23-M-B3 | HPLC_1 | 1.03 | 464 |
| 3132 | A23-M-B4 | HPLC_1 | 0.74 | 382 |
| 3133 | A23-M-B5 | HPLC_1 | 0.95 | 490 |
| 3134 | A23-M-B6 | HPLC_1 | 0.95 | 460 |
| 3135 | A23-M-B8 | HPLC_1 | 0.96 | 464 |
| 3136 | A23-M-B9 | HPLC_1 | 0.96 | 466 |
| 3137 | A23-M-B10 | HPLC_1 | 1.06 | 498 |
| 3138 | A23-M-B11 | HPLC_1 | 0.82 | 396 |
| 3139 | A24-M-B3 | HPLC_1 | 1.02 | 478 |
| 3140 | A24-M-B9 | HPLC_1 | 0.96 | 480 |
| 3141 | A25-M-B1 | HPLC_1 | 0.86 | 297 |
| 3142 | A25-M-B2 | HPLC_1 | 1.15 | 373 |
| 3143 | A25-M-B3 | HPLC_1 | 1.21 | 393 |
| 3144 | A25-M-B4 | HPLC_1 | 0.91 | 311 |
| 3145 | A25-M-B5 | HPLC_1 | 1.11 | 419 |
| 3146 | A25-M-B6 | HPLC_1 | 1.11 | 389 |
| 3147 | A25-M-B7 | HPLC_1 | 1.35 | 415 |
| 3148 | A25-M-B8 | HPLC_1 | 1.14 | 393 |

TABLE V-continued

| Entry | Compound | HPLC method | r.t. (min) | [M + H]+ |
|---|---|---|---|---|
| 3149 | A25-M-B9 | HPLC_1 | 1.14 | 395 |
| 3150 | A25-M-B10 | HPLC_1 | 1.24 | 427 |
| 3151 | A25-M-B11 | HPLC_1 | 0.99 | 325 |
| 3152 | A25-M-B12 | HPLC_1 | 1.31 | 401 |
| 3153 | A21-M-B1 | HPLC_1 | 1.08 | 359 |
| 3154 | A21-M-B2 | HPLC_1 | 1.32 | 435 |
| 3155 | A21-M-B3 | HPLC_1 | 1.36 | 455 |
| 3156 | A21-M-B4 | HPLC_1 | 1.12 | 373 |
| 3157 | A21-M-B5 | HPLC_1 | 1.27 | 481 |
| 3158 | A21-M-B6 | HPLC_1 | 1.28 | 451 |
| 3159 | A21-M-B7 | HPLC_1 | 1.47 | 477 |
| 3160 | A21-M-B8 | HPLC_1 | 1.3 | 455 |
| 3161 | A21-M-B9 | HPLC_1 | 1.31 | 457 |
| 3162 | A21-M-B10 | HPLC_1 | 1.39 | 489 |
| 3163 | A21-M-B11 | HPLC_1 | 1.19 | 387 |
| 3164 | A21-M-B12 | HPLC_1 | 1.44 | 463 |
| 3165 | A19-M-B1 | HPLC_1 | 1.12 | 359 |
| 3166 | A19-M-B2 | HPLC_1 | 1.34 | 435 |
| 3167 | A19-M-B4 | HPLC_1 | 1.17 | 373 |
| 3168 | A19-M-B5 | HPLC_1 | 1.3 | 481 |
| 3169 | A19-M-B7 | HPLC_1 | 1.5 | 477 |
| 3170 | A19-M-B8 | HPLC_1 | 1.33 | 455 |
| 3171 | A19-M-B9 | HPLC_1 | 1.34 | 457 |
| 3172 | A19-M-B10 | HPLC_1 | 1.42 | 489 |
| 3173 | A19-M-B11 | HPLC_1 | 1.23 | 387 |
| 3174 | A20-M-B1 | HPLC_1 | 0.8 | 327 |
| 3175 | A20-M-B2 | HPLC_1 | 1.09 | 403 |
| 3176 | A20-M-B3 | HPLC_1 | 1.14 | 423 |
| 3177 | A20-M-B4 | HPLC_1 | 0.85 | 341 |
| 3178 | A20-M-B5 | HPLC_1 | 1.04 | 449 |
| 3179 | A20-M-B6 | HPLC_1 | 1.05 | 419 |
| 3180 | A20-M-B7 | HPLC_1 | 1.28 | 445 |
| 3181 | A20-M-B8 | HPLC_1 | 1.07 | 423 |
| 3182 | A20-M-B9 | HPLC_1 | 1.07 | 425 |
| 3183 | A20-M-B10 | HPLC_1 | 1.17 | 457 |
| 3184 | A20-M-B11 | HPLC_1 | 0.93 | 355 |
| 3185 | A20-M-B12 | HPLC_1 | 1.24 | 431 |
| 3186 | A22-M-B13 | HPLC_1 | 1.01 | 470 |
| 3187 | A22-M-B14 | HPLC_1 | 0.9 | 382 |
| 3188 | A22-M-B15 | HPLC_1 | 0.89 | 402 |
| 3189 | A22-M-B16 | HPLC_1 | 0.93 | 420 |
| 3190 | A22-M-B17 | HPLC_1 | 1.01 | 486 |
| 3191 | A22-M-B18 | HPLC_1 | 1.03 | 452 |
| 3192 | A22-M-B19 | HPLC_1 | 1.04 | 452 |
| 3193 | A22-M-B20 | HPLC_1 | 1.09 | 470 |
| 3194 | A22-M-B21 | HPLC_1 | 0.77 | 368 |
| 3195 | A22-M-B22 | HPLC_1 | 0.88 | 462 |
| 3196 | A22-M-B23 | HPLC_1 | 1.08 | 470 |
| 3197 | A22-M-B24 | HPLC_1 | 0.9 | 420 |
| 3198 | A23-M-B13 | HPLC_1 | 1.01 | 498 |
| 3199 | A23-M-B14 | HPLC_1 | 0.9 | 410 |
| 3200 | A23-M-B15 | HPLC_1 | 0.89 | 430 |
| 3201 | A23-M-B16 | HPLC_1 | 0.93 | 448 |
| 3202 | A23-M-B17 | HPLC_1 | 1 | 514 |
| 3203 | A23-M-B18 | HPLC_1 | 1.02 | 480 |
| 3204 | A23-M-B19 | HPLC_1 | 1.03 | 480 |
| 3205 | A23-M-B21 | HPLC_1 | 0.77 | 396 |
| 3206 | A23-M-B22 | HPLC_1 | 0.89 | 490 |
| 3207 | A21-M-B18 | HPLC_1 | 1.33 | 471 |
| 3208 | A21-M-B19 | HPLC_1 | 1.33 | 471 |
| 3209 | A21-M-B20 | HPLC_1 | 1.4 | 489 |
| 3210 | A21-M-B21 | HPLC_1 | 1.14 | 387 |
| 3211 | A21-M-B22 | HPLC_1 | 1.2 | 481 |
| 3212 | A21-M-B23 | HPLC_1 | 1.39 | 489 |
| 3213 | A21-M-B24 | HPLC_1 | 1.23 | 439 |
| 3214 | A19-M-B13 | HPLC_1 | 1.34 | 489 |
| 3215 | A19-M-B14 | HPLC_1 | 1.25 | 401 |
| 3216 | A19-M-B15 | HPLC_1 | 1.25 | 421 |
| 3217 | A19-M-B16 | HPLC_1 | 1.28 | 439 |
| 3218 | A19-M-B17 | HPLC_1 | 1.34 | 505 |
| 3219 | A19-M-B18 | HPLC_1 | 1.35 | 471 |
| 3220 | A19-M-B20 | HPLC_1 | 1.42 | 489 |
| 3221 | A19-M-B21 | HPLC_1 | 1.17 | 387 |
| 3222 | A19-M-B22 | HPLC_1 | 1.23 | 481 |
| 3223 | A19-M-B23 | HPLC_1 | 1.41 | 489 |
| 3224 | A19-M-B24 | HPLC_1 | 1.26 | 439 |
| 3225 | A20-M-B13 | HPLC_1 | 1.12 | 457 |
| 3226 | A20-M-B14 | HPLC_1 | 1 | 369 |
| 3227 | A20-M-B15 | HPLC_1 | 1 | 389 |
| 3228 | A20-M-B16 | HPLC_1 | 1.04 | 407 |
| 3229 | A20-M-B17 | HPLC_1 | 1.11 | 473 |
| 3230 | A20-M-B18 | HPLC_1 | 1.12 | 439 |
| 3231 | A20-M-B19 | HPLC_1 | 1.14 | 439 |
| 3232 | A20-M-B20 | HPLC_1 | 1.2 | 457 |
| 3233 | A20-M-B21 | HPLC_1 | 0.89 | 355 |
| 3234 | A20-M-B22 | HPLC_1 | 0.98 | 449 |
| 3235 | A20-M-B23 | HPLC_1 | 1.19 | 457 |
| 3236 | A20-M-B24 | HPLC_1 | 1.01 | 407 |
| 3237 | A24-M-B16 | HPLC_1 | 0.94 | 462 |
| 3238 | A24-M-B17 | HPLC_1 | 1 | 528 |
| 3239 | A24-M-B18 | HPLC_1 | 1.03 | 494 |
| 3240 | A25-M-B13 | HPLC_1 | 1.18 | 427 |
| 3241 | A25-M-B14 | HPLC_1 | 1.06 | 339 |
| 3242 | A25-M-B15 | HPLC_1 | 1.06 | 359 |
| 3243 | A25-M-B16 | HPLC_1 | 1.1 | 377 |
| 3244 | A25-M-B17 | HPLC_1 | 1.18 | 443 |
| 3245 | A25-M-B18 | HPLC_1 | 1.18 | 409 |
| 3246 | A25-M-B19 | HPLC_1 | 1.2 | 409 |
| 3247 | A25-M-B20 | HPLC_1 | 1.27 | 427 |
| 3248 | A25-M-B21 | HPLC_1 | 0.95 | 325 |
| 3249 | A25-M-B22 | HPLC_1 | 1.04 | 419 |
| 3250 | A25-M-B23 | HPLC_1 | 1.26 | 427 |
| 3251 | A25-M-B24 | HPLC_1 | 1.06 | 377 |
| 3252 | A21-M-B13 | HPLC_1 | 1.32 | 489 |
| 3253 | A21-M-B14 | HPLC_1 | 1.22 | 401 |
| 3254 | A21-M-B15 | HPLC_1 | 1.22 | 421 |
| 3255 | A21-M-B16 | HPLC_1 | 1.26 | 439 |
| 3256 | A21-M-B17 | HPLC_1 | 1.32 | 505 |
| 3257 | A26-M-B2 | HPLC_1 | 1.18 | 387 |
| 3258 | A26-M-B4 | HPLC_1 | 0.98 | 325 |
| 3259 | A26-M-B5 | HPLC_1 | 1.14 | 433 |
| 3260 | A26-M-B6 | HPLC_1 | 1.14 | 403 |
| 3261 | A26-M-B7 | HPLC_1 | 1.36 | 429 |
| 3262 | A26-M-B8 | HPLC_1 | 1.16 | 407 |
| 3263 | A26-M-B9 | HPLC_1 | 1.18 | 409 |
| 3264 | A26-M-B10 | HPLC_1 | 1.26 | 441 |
| 3265 | A26-M-B11 | HPLC_1 | 1.05 | 339 |
| 3266 | A26-M-B12 | HPLC_1 | 1.32 | 415 |
| 3267 | A27-M-B1 | HPLC_1 | 1.12 | 379 |
| 3268 | A27-M-B4 | HPLC_1 | 1.15 | 393 |
| 3269 | A27-M-B5 | HPLC_1 | 1.28 | 501 |
| 3270 | A27-M-B6 | HPLC_1 | 1.28 | 471 |
| 3271 | A27-M-B8 | HPLC_1 | 1.3 | 475 |
| 3272 | A27-M-B9 | HPLC_1 | 1.3 | 477 |
| 3273 | A27-M-B10 | HPLC_1 | 1.38 | 509 |
| 3274 | A27-M-B11 | HPLC_1 | 1.21 | 407 |
| 3275 | A28-M-B1 | HPLC_1 | 1.04 | 363 |
| 3276 | A28-M-B2 | HPLC_1 | 1.25 | 439 |
| 3277 | A28-M-B4 | HPLC_1 | 1.07 | 377 |
| 3278 | A28-M-B5 | HPLC_1 | 1.21 | 485 |
| 3279 | A28-M-B6 | HPLC_1 | 1.22 | 455 |
| 3280 | A28-M-B8 | HPLC_1 | 1.24 | 459 |
| 3281 | A28-M-B9 | HPLC_1 | 1.24 | 461 |
| 3282 | A28-M-B10 | HPLC_1 | 1.32 | 493 |
| 3283 | A28-M-B11 | HPLC_1 | 1.13 | 391 |
| 3284 | A29-M-B1 | HPLC_1 | 1.03 | 375 |
| 3285 | A29-M-B4 | HPLC_1 | 1.06 | 389 |
| 3286 | A29-M-B5 | HPLC_1 | 1.2 | 497 |
| 3287 | A29-M-B8 | HPLC_1 | 1.22 | 471 |
| 3288 | A29-M-B9 | HPLC_1 | 1.23 | 473 |
| 3289 | A29-M-B10 | HPLC_1 | 1.31 | 505 |
| 3290 | A29-M-B11 | HPLC_1 | 1.13 | 403 |
| 3291 | A30-M-B1 | HPLC_1 | 1.15 | 339 |
| 3292 | A30-M-B2 | HPLC_1 | 1.34 | 415 |
| 3293 | A30-M-B4 | HPLC_1 | 1.18 | 353 |
| 3294 | A30-M-B5 | HPLC_1 | 1.31 | 461 |
| 3295 | A30-M-B6 | HPLC_1 | 1.31 | 431 |
| 3296 | A30-M-B8 | HPLC_1 | 1.33 | 435 |
| 3297 | A30-M-B9 | HPLC_1 | 1.34 | 437 |
| 3298 | A30-M-B11 | HPLC_1 | 1.24 | 367 |
| 3299 | A33-M-B1 | HPLC_1 | 1.12 | 351 |
| 3300 | A33-M-B2 | HPLC_1 | 1.33 | 427 |
| 3301 | A33-M-B4 | HPLC_1 | 1.16 | 365 |
| 3302 | A33-M-B5 | HPLC_1 | 1.29 | 473 |

TABLE V-continued

| Entry | Compound | HPLC method | r.t. (min) | [M + H]+ |
|---|---|---|---|---|
| 3303 | A33-M-B6 | HPLC_1 | 1.29 | 443 |
| 3304 | A33-M-B7 | HPLC_1 | 1.48 | 469 |
| 3305 | A33-M-B8 | HPLC_1 | 1.32 | 447 |
| 3306 | A32-M-B11 | HPLC_1 | 1.15 | 353 |
| 3307 | A26-M-B13 | HPLC_1 | 1.23 | 441 |
| 3308 | A26-M-B14 | HPLC_1 | 1.13 | 353 |
| 3309 | A26-M-B17 | HPLC_1 | 1.24 | 457 |
| 3310 | A26-M-B18 | HPLC_1 | 1.24 | 423 |
| 3311 | A26-M-B20 | HPLC_1 | 1.32 | 441 |
| 3312 | A26-M-B21 | HPLC_1 | 1.03 | 339 |
| 3313 | A26-M-B22 | HPLC_1 | 1.11 | 433 |
| 3314 | A26-M-B24 | HPLC_1 | 1.13 | 391 |
| 3315 | A27-M-B13 | HPLC_1 | 1.36 | 509 |
| 3316 | A27-M-B14 | HPLC_1 | 1.27 | 421 |
| 3317 | A27-M-B17 | HPLC_1 | 1.36 | 525 |
| 3318 | A27-M-B20 | HPLC_1 | 1.44 | 509 |
| 3319 | A27-M-B21 | HPLC_1 | 1.19 | 407 |
| 3320 | A27-M-B22 | HPLC_1 | 1.24 | 501 |
| 3321 | A27-M-B23 | HPLC_1 | 1.42 | 509 |
| 3322 | A27-M-B24 | HPLC_1 | 1.27 | 459 |
| 3323 | A28-M-B13 | HPLC_1 | 1.3 | 493 |
| 3324 | A28-M-B14 | HPLC_1 | 1.21 | 405 |
| 3325 | A28-M-B16 | HPLC_1 | 1.23 | 443 |
| 3326 | A28-M-B17 | HPLC_1 | 1.3 | 509 |
| 3327 | A28-M-B18 | HPLC_1 | 1.3 | 475 |
| 3328 | A28-M-B24 | HPLC_1 | 1.24 | 443 |
| 3329 | A29-M-B13 | HPLC_1 | 1.33 | 505 |
| 3330 | A29-M-B14 | HPLC_1 | 1.22 | 417 |
| 3331 | A29-M-B17 | HPLC_1 | 1.33 | 521 |
| 3332 | A29-M-B21 | HPLC_1 | 1.13 | 403 |
| 3333 | A29-M-B24 | HPLC_1 | 1.23 | 455 |
| 3334 | A30-M-B13 | HPLC_1 | 1.44 | 469 |
| 3335 | A30-M-B14 | HPLC_1 | 1.35 | 381 |
| 3336 | A30-M-B16 | HPLC_1 | 1.38 | 419 |
| 3337 | A30-M-B17 | HPLC_1 | 1.45 | 485 |
| 3338 | A30-M-B18 | HPLC_1 | 1.45 | 451 |
| 3339 | A30-M-B20 | HPLC_1 | 1.54 | 469 |
| 3340 | A30-M-B22 | HPLC_1 | 1.32 | 461 |
| 3341 | A30-M-B23 | HPLC_1 | 1.52 | 469 |
| 3342 | A30-M-B24 | HPLC_1 | 1.35 | 419 |
| 3343 | A33-M-B13 | HPLC_1 | 1.42 | 481 |
| 3344 | A33-M-B14 | HPLC_1 | 1.33 | 393 |
| 3345 | A33-M-B15 | HPLC_1 | 1.33 | 413 |
| 3346 | A33-M-B16 | HPLC_1 | 1.36 | 431 |
| 3347 | A33-M-B17 | HPLC_1 | 1.43 | 497 |
| 3348 | A33-M-B19 | HPLC_1 | 1.44 | 463 |
| 3349 | A33-M-B20 | HPLC_1 | 1.52 | 481 |
| 3350 | A33-M-B21 | HPLC_1 | 1.23 | 379 |
| 3351 | A33-M-B22 | HPLC_1 | 1.3 | 473 |
| 3352 | A33-M-B23 | HPLC_1 | 1.51 | 481 |
| 3353 | A33-M-B24 | HPLC_1 | 1.33 | 431 |
| 3354 | A31-M-B13 | HPLC_1 | 1.34 | 455 |
| 3355 | A31-M-B14 | HPLC_1 | 1.24 | 367 |
| 3356 | A31-M-B15 | HPLC_1 | 1.24 | 387 |
| 3357 | A31-M-B16 | HPLC_1 | 1.28 | 405 |
| 3358 | A31-M-B17 | HPLC_1 | 1.36 | 471 |
| 3359 | A31-M-B18 | HPLC_1 | 1.36 | 437 |
| 3360 | A31-M-B20 | HPLC_1 | 1.44 | 455 |
| 3361 | A31-M-B21 | HPLC_1 | 1.14 | 353 |
| 3362 | A31-M-B22 | HPLC_1 | 1.21 | 447 |
| 3363 | A31-M-B24 | HPLC_1 | 1.24 | 405 |
| 3364 | A32-M-B13 | HPLC_1 | 1.36 | 455 |
| 3365 | A32-M-B14 | HPLC_1 | 1.25 | 367 |
| 3366 | A32-M-B15 | HPLC_1 | 1.25 | 387 |
| 3367 | A32-M-B16 | HPLC_1 | 1.29 | 405 |
| 3368 | A32-M-B17 | HPLC_1 | 1.36 | 471 |
| 3369 | A32-M-B18 | HPLC_1 | 1.36 | 437 |
| 3370 | A32-M-B19 | HPLC_1 | 1.38 | 437 |
| 3371 | A32-M-B20 | HPLC_1 | 1.45 | 455 |
| 3372 | A32-M-B21 | HPLC_1 | 1.15 | 353 |
| 3373 | A32-M-B22 | HPLC_1 | 1.22 | 447 |
| 3374 | A32-M-B23 | HPLC_1 | 1.44 | 455 |
| 3375 | A32-M-B24 | HPLC_1 | 1.25 | 405 |
| 3376 | A33-M-B9 | HPLC_1 | 1.33 | 449 |
| 3377 | A33-M-B10 | HPLC_1 | 1.4 | 481 |
| 3378 | A33-M-B11 | HPLC_1 | 1.22 | 379 |
| 3379 | A31-M-B1 | HPLC_1 | 1.03 | 325 |
| 3380 | A31-M-B2 | HPLC_1 | 1.25 | 401 |
| 3381 | A31-M-B4 | HPLC_1 | 1.07 | 339 |
| 3382 | A31-M-B5 | HPLC_1 | 1.21 | 447 |
| 3383 | A31-M-B6 | HPLC_1 | 1.22 | 417 |
| 3384 | A31-M-B8 | HPLC_1 | 1.24 | 421 |
| 3385 | A31-M-B9 | HPLC_1 | 1.24 | 423 |
| 3386 | A31-M-B10 | HPLC_1 | 1.33 | 455 |
| 3387 | A31-M-B11 | HPLC_1 | 1.14 | 353 |
| 3388 | A32-M-B1 | HPLC_1 | 1.05 | 325 |
| 3389 | A32-M-B2 | HPLC_1 | 1.26 | 401 |
| 3390 | A32-M-B4 | HPLC_1 | 1.08 | 339 |
| 3391 | A32-M-B5 | HPLC_1 | 1.22 | 447 |
| 3392 | A32-M-B6 | HPLC_1 | 1.23 | 417 |
| 3393 | A32-M-B9 | HPLC_1 | 1.25 | 423 |
| 3394 | A32-M-B10 | HPLC_1 | 1.34 | 455 |
| 3395 | A34-M-B4 | HPLC_1 | 1.21 | 387 |
| 3396 | A34-M-B5 | HPLC_1 | 1.33 | 495 |
| 3397 | A34-M-B8 | HPLC_1 | 1.35 | 469 |
| 3398 | A34-M-B9 | HPLC_1 | 1.36 | 471 |
| 3399 | A34-M-B10 | HPLC_1 | 1.42 | 503 |
| 3400 | A34-M-B11 | HPLC_1 | 1.27 | 401 |
| 3401 | A35-M-B4 | HPLC_1 | 1.09 | 403 |
| 3402 | A35-M-B5 | HPLC_1 | 1.22 | 511 |
| 3403 | A35-M-B8 | HPLC_1 | 1.24 | 485 |
| 3404 | A35-M-B9 | HPLC_1 | 1.26 | 487 |
| 3405 | A35-M-B10 | HPLC_1 | 1.33 | 519 |
| 3406 | A35-M-B11 | HPLC_1 | 1.15 | 417 |
| 3407 | A37-M-B6 | HPLC_1 | 0.95 | 438 |
| 3408 | A37-M-B11 | HPLC_1 | 0.83 | 374 |
| 3409 | A38-M-B2 | HPLC_1 | 0.99 | 422 |
| 3410 | A38-M-B3 | HPLC_1 | 1.02 | 442 |
| 3411 | A38-M-B4 | HPLC_1 | 0.75 | 360 |
| 3412 | A38-M-B5 | HPLC_1 | 0.95 | 468 |
| 3413 | A38-M-B6 | HPLC_1 | 0.95 | 438 |
| 3414 | A38-M-B8 | HPLC_1 | 0.97 | 442 |
| 3415 | A38-M-B9 | HPLC_1 | 0.97 | 444 |
| 3416 | A38-M-B10 | HPLC_1 | 1.05 | 476 |
| 3417 | A38-M-B11 | HPLC_1 | 0.82 | 374 |
| 3418 | A34-M-B13 | HPLC_1 | 1.42 | 503 |
| 3419 | A34-M-B14 | HPLC_1 | 1.33 | 415 |
| 3420 | A34-M-B16 | HPLC_1 | 1.36 | 453 |
| 3421 | A34-M-B17 | HPLC_1 | 1.42 | 519 |
| 3422 | A34-M-B18 | HPLC_1 | 1.42 | 485 |
| 3423 | A34-M-B20 | HPLC_1 | 1.49 | 503 |
| 3424 | A34-M-B21 | HPLC_1 | 1.24 | 401 |
| 3425 | A34-M-B22 | HPLC_1 | 1.29 | 495 |
| 3426 | A34-M-B24 | HPLC_1 | 1.33 | 453 |
| 3427 | A35-M-B13 | HPLC_1 | 1.32 | 519 |
| 3428 | A35-M-B14 | HPLC_1 | 1.2 | 431 |
| 3429 | A35-M-B17 | HPLC_1 | 1.31 | 535 |
| 3430 | A35-M-B21 | HPLC_1 | 1.11 | 417 |
| 3431 | A40-M-B13 | HPLC_1 | 1.13 | 413 |
| 3432 | A36-M-B21 | HPLC_1 | 0.87 | 394 |
| 3433 | A37-M-B14 | HPLC_1 | 0.9 | 388 |
| 3434 | A37-M-B16 | HPLC_1 | 0.94 | 426 |
| 3435 | A37-M-B17 | HPLC_1 | 1.02 | 492 |
| 3436 | A37-M-B21 | HPLC_1 | 0.8 | 374 |
| 3437 | A37-M-B24 | HPLC_1 | 0.92 | 426 |
| 3438 | A38-M-B13 | HPLC_1 | 1.02 | 476 |
| 3439 | A38-M-B14 | HPLC_1 | 0.9 | 388 |
| 3440 | A38-M-B16 | HPLC_1 | 0.95 | 426 |
| 3441 | A38-M-B17 | HPLC_1 | 1.02 | 492 |
| 3442 | A38-M-B18 | HPLC_1 | 1.04 | 458 |
| 3443 | A38-M-B20 | HPLC_1 | 1.08 | 476 |
| 3444 | A38-M-B21 | HPLC_1 | 0.8 | 374 |
| 3445 | A38-M-B23 | HPLC_1 | 1.08 | 476 |
| 3446 | A38-M-B24 | HPLC_1 | 0.92 | 426 |
| 3447 | A42-M-B1 | HPLC_1 | 1.1 | 381 |
| 3448 | A42-M-B4 | HPLC_1 | 1.14 | 395 |
| 3449 | A42-M-B5 | HPLC_1 | 1.29 | 503 |
| 3450 | A42-M-B6 | HPLC_1 | 1.29 | 473 |
| 3451 | A42-M-B7 | HPLC_1 | 1.48 | 499 |
| 3452 | A42-M-B8 | HPLC_1 | 1.32 | 477 |
| 3453 | A42-M-B9 | HPLC_1 | 1.32 | 479 |
| 3454 | A42-M-B10 | HPLC_1 | 1.4 | 511 |
| 3455 | A42-M-B11 | HPLC_1 | 1.21 | 409 |
| 3456 | A43-M-B1 | HPLC_1 | 0.82 | 339 |

TABLE V-continued

| Entry | Compound | HPLC method | r.t. (min) | [M + H]+ |
|---|---|---|---|---|
| 3457 | A43-M-B2 | HPLC_1 | 1.11 | 415 |
| 3458 | A43-M-B4 | HPLC_1 | 0.87 | 353 |
| 3459 | A43-M-B5 | HPLC_1 | 1.07 | 461 |
| 3460 | A43-M-B6 | HPLC_1 | 1.07 | 431 |
| 3461 | A43-M-B7 | HPLC_1 | 1.3 | 457 |
| 3462 | A43-M-B8 | HPLC_1 | 1.09 | 435 |
| 3463 | A43-M-B9 | HPLC_1 | 1.09 | 437 |
| 3464 | A43-M-B10 | HPLC_1 | 1.19 | 469 |
| 3465 | A43-M-B11 | HPLC_1 | 0.95 | 367 |
| 3466 | A43-M-B12 | HPLC_1 | 1.26 | 443 |
| 3467 | A44-M-B5 | HPLC_1 | 1.25 | 487 |
| 3468 | A44-M-B6 | HPLC_1 | 1.25 | 457 |
| 3469 | A44-M-B9 | HPLC_1 | 1.28 | 463 |
| 3470 | A45-M-B1 | HPLC_1 | 0.83 | 327 |
| 3471 | A45-M-B2 | HPLC_1 | 1.12 | 403 |
| 3472 | A45-M-B3 | HPLC_1 | 1.17 | 423 |
| 3473 | A45-M-B4 | HPLC_1 | 0.88 | 341 |
| 3474 | A45-M-B5 | HPLC_1 | 1.07 | 449 |
| 3475 | A45-M-B6 | HPLC_1 | 1.08 | 419 |
| 3476 | A45-M-B7 | HPLC_1 | 1.32 | 445 |
| 3477 | A45-M-B8 | HPLC_1 | 1.09 | 423 |
| 3478 | A45-M-B9 | HPLC_1 | 1.1 | 425 |
| 3479 | A45-M-B10 | HPLC_1 | 1.2 | 457 |
| 3480 | A45-M-B11 | HPLC_1 | 0.97 | 355 |
| 3481 | A45-M-B12 | HPLC_1 | 1.27 | 431 |
| 3482 | A46-M-B9 | HPLC_1 | 1.23 | 461 |
| 3483 | A46-M-B11 | HPLC_1 | 1.13 | 391 |
| 3484 | A46-M-B12 | HPLC_1 | 1.37 | 467 |
| 3485 | A42-M-B13 | HPLC_1 | 1.33 | 511 |
| 3486 | A42-M-B14 | HPLC_1 | 1.24 | 423 |
| 3487 | A42-M-B15 | HPLC_1 | 1.23 | 443 |
| 3488 | A42-M-B16 | HPLC_1 | 1.27 | 461 |
| 3489 | A42-M-B17 | HPLC_1 | 1.33 | 527 |
| 3490 | A42-M-B18 | HPLC_1 | 1.34 | 493 |
| 3491 | A42-M-B20 | HPLC_1 | 1.41 | 511 |
| 3492 | A42-M-B21 | HPLC_1 | 1.15 | 409 |
| 3493 | A42-M-B22 | HPLC_1 | 1.21 | 503 |
| 3494 | A42-M-B24 | HPLC_1 | 1.24 | 461 |
| 3495 | A43-M-B13 | HPLC_1 | 1.13 | 469 |
| 3496 | A43-M-B14 | HPLC_1 | 1.01 | 381 |
| 3497 | A43-M-B15 | HPLC_1 | 1.01 | 401 |
| 3498 | A43-M-B16 | HPLC_1 | 1.05 | 419 |
| 3499 | A43-M-B17 | HPLC_1 | 1.13 | 485 |
| 3500 | A43-M-B18 | HPLC_1 | 1.14 | 451 |
| 3501 | A43-M-B19 | HPLC_1 | 1.15 | 451 |
| 3502 | A43-M-B20 | HPLC_1 | 1.21 | 469 |
| 3503 | A43-M-B21 | HPLC_1 | 0.91 | 367 |
| 3504 | A43-M-B22 | HPLC_1 | 1 | 461 |
| 3505 | A43-M-B24 | HPLC_1 | 1.02 | 419 |
| 3506 | A44-M-B13 | HPLC_1 | 1.29 | 495 |
| 3507 | A44-M-B20 | HPLC_1 | 1.37 | 495 |
| 3508 | A44-M-B22 | HPLC_1 | 1.17 | 487 |
| 3509 | A44-M-B24 | HPLC_1 | 1.2 | 445 |
| 3510 | A45-M-B13 | HPLC_1 | 1.14 | 457 |
| 3511 | A45-M-B14 | HPLC_1 | 1.02 | 369 |
| 3512 | A45-M-B15 | HPLC_1 | 1.02 | 389 |
| 3513 | A45-M-B16 | HPLC_1 | 1.06 | 407 |
| 3514 | A45-M-B17 | HPLC_1 | 1.14 | 473 |
| 3515 | A45-M-B18 | HPLC_1 | 1.15 | 439 |
| 3516 | A45-M-B19 | HPLC_1 | 1.17 | 439 |
| 3517 | A45-M-B20 | HPLC_1 | 1.22 | 457 |
| 3518 | A45-M-B21 | HPLC_1 | 0.91 | 355 |
| 3519 | A45-M-B22 | HPLC_1 | 1.01 | 449 |
| 3520 | A45-M-B23 | HPLC_1 | 1.22 | 457 |
| 3521 | A45-M-B24 | HPLC_1 | 1.03 | 407 |
| 3522 | A6-M-B3 | HPLC_1 | 1.33 | 471 |
| 3523 | A6-M-B6 | HPLC_1 | 1.24 | 467 |
| 3524 | A9-M-B8 | HPLC_1 | 1.01 | 476 |
| 3525 | A9-M-B10 | HPLC_1 | 1.1 | 510 |
| 3526 | A7-M-B11 | HPLC_1 | 1.07 | 339 |
| 3527 | A9-M-B11 | HPLC_1 | 0.89 | 408 |
| 3528 | A4-M-B12 | HPLC_1 | 1.46 | 483 |
| 3529 | A3-M-B14 | HPLC_1 | 1.24 | 423 |
| 3530 | A4-M-B14 | HPLC_1 | 1.29 | 421 |
| 3531 | A7-M-B16 | HPLC_1 | 1.19 | 391 |
| 3532 | A9-M-B17 | HPLC_1 | 1.08 | 526 |
| 3533 | A2-M-B19 | HPLC_1 | 1.32 | 457 |
| 3534 | A4-M-B22 | HPLC_1 | 1.27 | 501 |
| 3535 | A16-M-B2 | HPLC_1 | 1.3 | 451 |
| 3536 | A16-M-B9 | HPLC_1 | 1.29 | 473 |
| 3537 | A16-M-B11 | HPLC_1 | 1.18 | 403 |
| 3538 | A12-M-B22 | HPLC_1 | 1.23 | 485 |
| 3539 | A48-M-B16 | HPLC_1 | 1.26 | 455 |
| 3540 | A16-M-B17 | HPLC_1 | 1.35 | 521 |
| 3541 | A16-M-B18 | HPLC_1 | 1.36 | 487 |
| 3542 | A17-M-B18 | HPLC_1 | 1.38 | 471 |
| 3543 | A17-M-B22 | HPLC_1 | 1.27 | 481 |
| 3544 | A17-M-B23 | HPLC_1 | 1.44 | 489 |
| 3545 | A30-M-B10 | HPLC_1 | 1.42 | 469 |
| 3546 | A28-M-B20 | HPLC_1 | 1.38 | 493 |
| 3547 | A28-M-B22 | HPLC_1 | 1.21 | 485 |
| 3548 | A33-M-B18 | HPLC_1 | 1.43 | 463 |
| 3549 | A34-M-B7 | HPLC_1 | 1.49 | 491 |
| 3550 | A40-M-B5 | HPLC_1 | 1.05 | 405 |
| 3551 | A40-M-B6 | HPLC_1 | 1.06 | 375 |
| 3552 | A40-M-B7 | HPLC_1 | 1.27 | 401 |
| 3553 | A40-M-B8 | HPLC_1 | 1.07 | 379 |
| 3554 | A40-M-B9 | HPLC_1 | 1.08 | 381 |
| 3555 | A40-M-B10 | HPLC_1 | 1.17 | 413 |
| 3556 | A35-M-B24 | HPLC_1 | 1.21 | 469 |
| 3557 | A40-M-B17 | HPLC_1 | 1.13 | 429 |
| 3558 | A40-M-B18 | HPLC_1 | 1.15 | 395 |
| 3559 | A40-M-B20 | HPLC_1 | 1.23 | 413 |
| 3560 | A40-M-B24 | HPLC_1 | 1.01 | 363 |
| 3561 | A36-M-B17 | HPLC_1 | 1.08 | 512 |
| 3562 | A37-M-B13 | HPLC_1 | 1.02 | 476 |
| 3563 | A39-M-B17 | HPLC_1 | 1.06 | 500 |
| 3564 | A44-M-B2 | HPLC_1 | 1.29 | 441 |
| 3565 | A44-M-B4 | HPLC_1 | 1.09 | 379 |
| 3566 | A44-M-B7 | HPLC_1 | 1.45 | 483 |
| 3567 | A44-M-B8 | HPLC_1 | 1.27 | 461 |
| 3568 | A44-M-B10 | HPLC_1 | 1.37 | 495 |
| 3569 | A44-M-B11 | HPLC_1 | 1.16 | 393 |
| 3570 | A46-M-B1 | HPLC_1 | 1.04 | 363 |
| 3571 | A46-M-B2 | HPLC_1 | 1.25 | 439 |
| 3572 | A46-M-B4 | HPLC_1 | 1.07 | 377 |
| 3573 | A46-M-B5 | HPLC_1 | 1.22 | 485 |
| 3574 | A46-M-B6 | HPLC_1 | 1.22 | 455 |
| 3575 | A46-M-B8 | HPLC_1 | 1.24 | 459 |
| 3576 | A46-M-B10 | HPLC_1 | 1.32 | 493 |
| 3577 | A43-M-B23 | HPLC_1 | 1.2 | 469 |
| 3578 | A44-M-B14 | HPLC_1 | 1.19 | 407 |
| 3579 | A44-M-B16 | HPLC_1 | 1.23 | 445 |
| 3580 | A44-M-B17 | HPLC_1 | 1.29 | 511 |
| 3581 | A44-M-B18 | HPLC_1 | 1.3 | 477 |
| 3582 | A44-M-B21 | HPLC_1 | 1.1 | 393 |
| 3583 | A46-M-B13 | HPLC_1 | 1.24 | 493 |
| 3584 | A46-M-B14 | HPLC_1 | 1.17 | 405 |
| 3585 | A46-M-B15 | HPLC_1 | 1.16 | 425 |
| 3586 | A46-M-B16 | HPLC_1 | 1.19 | 443 |
| 3587 | A46-M-B19 | HPLC_1 | 1.27 | 475 |
| 3588 | A5-M-B5 | HPLC_1 | 1.24 | 511 |
| 3589 | A5-M-B8 | HPLC_1 | 1.26 | 485 |
| 3590 | A1-M-B10 | HPLC_1 | 1.36 | 467 |
| 3591 | A6-M-B12 | HPLC_1 | 1.42 | 479 |
| 3592 | A5-M-B13 | HPLC_1 | 1.32 | 519 |
| 3593 | A4-M-B18 | HPLC_1 | 1.4 | 491 |
| 3594 | A5-M-B18 | HPLC_1 | 1.33 | 501 |
| 3595 | A9-M-B18 | HPLC_1 | 1.09 | 492 |
| 3596 | A12-M-B16 | HPLC_1 | 1.29 | 443 |
| 3597 | A12-M-B17 | HPLC_1 | 1.35 | 509 |
| 3598 | A12-M-B18 | HPLC_1 | 1.35 | 475 |
| 3599 | A12-M-B20 | HPLC_1 | 1.41 | 493 |
| 3600 | A27-M-B18 | HPLC_1 | 1.36 | 491 |
| 3601 | A29-M-B18 | HPLC_1 | 1.34 | 487 |
| 3602 | A35-M-B18 | HPLC_1 | 1.32 | 501 |
| 3603 | A40-M-B14 | HPLC_1 | 1 | 325 |
| 3604 | A46-M-B3 | HPLC_1 | 1.29 | 459 |
| 3605 | A46-M-B7 | HPLC_1 | 1.4 | 481 |
| 3606 | A46-M-B17 | HPLC_1 | 1.26 | 509 |
| 3607 | A46-M-B20 | HPLC_1 | 1.33 | 493 |

TABLE V-continued

| Entry | Compound | HPLC method | r.t. (min) | [M + H]+ |
|---|---|---|---|---|
| 3608 | A46-M-B21 | HPLC_1 | 1.09 | 391 |
| 3609 | A46-M-B22 | HPLC_1 | 1.13 | 485 |
| 3610 | A46-M-B23 | HPLC_1 | 1.31 | 493 |

Example 7

Loading of 4-fluorobenzylamine (Corresponding to Fragment A12 of Table I) onto Acid Sensitive Methoxy Benzaldehyde Polystyrene Resin (AMEBA II Resin)

The reaction was carried out by working as reported in example 4, in the presence of 4-fluorobenzylamine instead of isoamylamine.

Example 8

Preparation of A12-M-B139

Step a: Loading of the 7-azaindole Scaffold (Title Compound of Example 3) onto the Resin of Example 7

To the resin of example 7 (7.5 g, 0.77 mmol/g, 5.7 mmol) in anhydrous DMF (75 ml), 3-carboxy-5-nitro-7-azaindole (1.794 g, 8.67 mmol), TBTU (2.78 g, 8.67 mmol) and DIPEA (2.24 g, 17.34 mmol) were added. The reaction mixture was shaken at room temperature for 20 hours and then the resin was isolated by filtration. The resin was washed sequentially with DMF (75 ml), DCM (75 ml), DMF (75 ml), DCM (75 ml), MeOH (75 ml), DCM (75 ml), MeOH (75 ml), DCM (75 ml), MeOH (75 ml), TBME (75 ml×2) and dried in vacuo to give the resin bound 7-azaindole (8.50 g).

Resin Loading Check

Resin loading check was carried out to demonstrate the complete loading of the building block onto the resin and that no oligomerization has occurred whilst coupling with TBTU.

To the resin (0.035 g, 0.027 mmol) in DCM (1 ml) DIPEA (0.035 g, 0.265 mmol) and benzoyl chloride (0.038 g, 0.265 mmol) were added. The reaction mixture was shaken for 4 hours and the resin isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (1 ml of 60% TFA/DCM for 20 minutes) to give an off white solid (0.007 g, 64%).

LCMS (HPLC_1) (N-benzoylated indole): m/z 419 [M+H]+ at r.t. 1.56 min (97% by ELS detection).

Step b: N-BOC Protection of 7-azaindole on Solid Phase

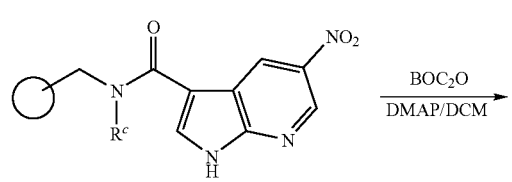

BOC₂O / DMAP/DCM →

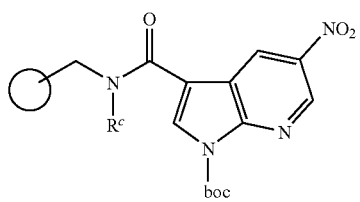

To the resin of step (a) (8.4 g, 5.7 mmol) in anhydrous DCM (75 ml), DMAP (0.07 g, 0.58 mmol) and di-tert-butyl-carbonate (12.60 g, 57.8 mmol) were added. The reaction mixture was shaken at room temperature for 20 hours and then the resin was isolated by filtration. The resin was washed sequentially with DMF (75 ml), DCM (75 ml), DMF (75 ml), DCM (75 ml), MeOH (75 ml), DCM (75 ml), MeOH (75 ml), DCM (75 ml), MeOH (75 ml), TBME (75 ml×2) and dried in vacuo to give the resin bound protected 7-azaindole (9.0 g).

1-N-azaindole Protection Check

1-N-azaindole protection check was carried out to demonstrate the complete protection with tertbutoxycarbonyl (boc) at the indazole nitrogen atom in position 1, and that no free NH groups were present.

To the resin (0.035 g, 0.027 mmol) in DCM (1 ml), DIPEA (0.035 g, 0.265 mmol) and benzoyl chloride (0.038 g, 0.265 mmol) were added. The reaction mixture was shaken for 4 hours and the resin isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml) MeOH (1 ml), DCM (1 ml), MeOH (1 ml), TBME (1 ml×2) and then air dried. The product was cleaved from the resin (1 ml of 60% TFA/DCM for 20 minutes) to give an off white solid (0.008 g, 80%). LCMS (HPLC_1): m/z 315 [M+H]+ at r.t. 1.26 min (91% by ELS detection).

Step c: Reduction of the Nitro Group

To the resin of step (b) (9 g, 5.7 mmol) in NMP (100 ml) it was added tin (II) chloride dihydrate (13.03 g, 57.75 mmol). The reaction mixture was shaken at room temperature for 20 hours and then the resin was isolated by filtration. The resin was washed sequentially with DMF (100 ml), DCM (100 ml), DMF (100 ml), DCM (100 ml), MeOH (100 ml), water (100 ml), MeOH (100 ml), DCM (100 ml), MeOH (100 ml), DCM (100 ml), MeOH (100 ml), TBME (100 ml×2) and dried in vacuo to give the resin bound azaindole (8.8 g). 0.01 g of resin were cleaved (1 ml of 60% TFA/DCM for 20 minutes) to give an off-white solid (0.0015 g, 69%).

LCMS (HPLC_1): m/z 285 [M+H]+ at r.t. 0.91 min (100% by ELS detection).

Step d: Phenyl Carbamate Formation (and Bis-Phenyl Carbamate)

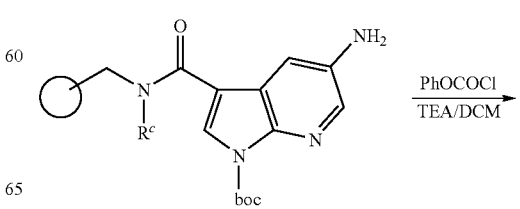

PhOCOCl / TEA/DCM →

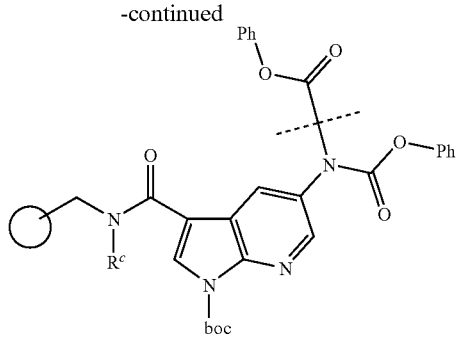

To the resin of step (c) (8.8 g, 5.78 mmol) in DCM (70 ml), triethylamine (11.66 g, 115.5 mmol) and phenyl chloroformate (18.01 g, 115.5 mmol) were added. The reaction mixture was shaken at room temperature for 20 hours and then the resin was isolated by filtration. The resin was washed sequentially with DMF (100 ml), DCM (100 ml), DMF (100 ml), DCM (100 ml), MeOH (100 ml), DCM (100 ml), MeOH (100 ml), DCM (100 ml), MeOH (100 ml), TBME (100 ml×2) and dried in vacuo to give the resin bound azaindole (9.5 g). 0.01 g of resin were cleaved (1 ml of 60% TFA/DCM for 20 minutes) to give an off-white solid (0.0025 g, 62%).

LCMS (HPLC_1) (only bis-carbamate observed): m/z 525 [M+H]$^+$ at r.t. 1.47 min (97% by ELS detection).

Step e: Urea Formation

To the resin of step (d) (0.11 g, 0.077 mmol) in DCM (1 ml), was added 2,6 dimethylpiperazine (corresponding to fragment B139 of Table II, 0.176 g, 1.54 mmol). The reaction mixture was shaken at room temperature for 72 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (60% TFA/DCM, 3×(3×0.5 ml)) to give an off white solid (0.031 g, 95%) corresponding to the compound A12-M-B139 (see entry 3769 of Table VI below).

$^1$H NMR-method 1 (MeOH d-4): 8.65 (1H, d, 2.3 Hz), 8.46 (1H, d, 2.3 Hz), 8.13 (1H, s), 7.44-7.37 (2H, m), 7.10-7.03 (2H, m), 4.57 (2H, s), 4.42 (1H, dd, 14.4 Hz, 2.0 Hz), 3.49-3.38 (1H, m), 3.34-3.31 (2H, m), 2.98-2.89 (2H, m), 1.39 (6H, d, 6.6 Hz), indole and amide NHs were not observed;

LCMS (HPLC_1): m/z 425 [M+H]$^+$ at r.t. 0.95 min (98% by ELS detection).

By working in analogy to what above described and by using any suitable starting material and reactant thereof, the following compounds of Table VI (i.e. library) were prepared:

TABLE VI

| Entry | Compound | HPLC method | r.t. (min) | [M + H]$^+$ |
|---|---|---|---|---|
| 3611 | A12-M-B98 | HPLC_1 | 1.17 | 418 |
| 3612 | A12-M-B100 | HPLC_1 | 0.89 | 436 |
| 3613 | A12-M-B101 | HPLC_1 | 1.19 | 436 |
| 3614 | A29-M-B98 | HPLC_1 | 1.14 | 430 |
| 3615 | A29-M-B100 | HPLC_1 | 0.87 | 448 |
| 3616 | A29-M-B102 | HPLC_1 | 1.15 | 410 |
| 3617 | A25-M-B98 | HPLC_1 | 1.01 | 352 |
| 3618 | A2-M-B98 | HPLC_1 | 1.14 | 400 |
| 3619 | A2-M-B103 | HPLC_1 | 1.1 | 366 |
| 3620 | A2-M-B100 | HPLC_1 | 0.86 | 418 |
| 3621 | A2-M-B102 | HPLC_1 | 1.14 | 380 |
| 3622 | A19-M-B96 | HPLC_1 | 1.16 | 392 |
| 3623 | A19-M-B98 | HPLC_1 | 1.21 | 414 |
| 3624 | A19-M-B103 | HPLC_1 | 1.17 | 380 |
| 3625 | A19-M-B100 | HPLC_1 | 0.93 | 432 |
| 3626 | A19-M-B99 | HPLC_1 | 0.9 | 393 |
| 3627 | A19-M-B102 | HPLC_1 | 1.21 | 394 |
| 3628 | A19-M-B101 | HPLC_1 | 1.23 | 432 |
| 3629 | A8-M-B98 | HPLC_1 | 0.98 | 350 |
| 3630 | A12-M-B104 | HPLC_1 | 1.24 | 432 |
| 3631 | A12-M-B105 | HPLC_1 | 1.29 | 486 |
| 3632 | A12-M-B106 | HPLC_1 | 1.19 | 436 |
| 3633 | A12-M-B107 | HPLC_1 | 1.22 | 432 |
| 3634 | A12-M-B108 | HPLC_1 | 0.96 | 469 |
| 3635 | A29-M-B108 | HPLC_1 | 0.95 | 481 |
| 3636 | A25-M-B105 | HPLC_1 | 1.17 | 420 |
| 3637 | A2-M-B104 | HPLC_1 | 1.22 | 414 |
| 3638 | A2-M-B106 | HPLC_1 | 1.17 | 418 |
| 3639 | A2-M-B108 | HPLC_1 | 0.94 | 451 |
| 3640 | A19-M-B104 | HPLC_1 | 1.28 | 428 |
| 3641 | A19-M-B105 | HPLC_1 | 1.33 | 482 |
| 3642 | A19-M-B106 | HPLC_1 | 1.23 | 432 |
| 3643 | A19-M-B107 | HPLC_1 | 1.27 | 428 |
| 3644 | A19-M-B108 | HPLC_1 | 1.02 | 465 |
| 3645 | A45-M-B97 | HPLC_1 | 0.85 | 334 |
| 3646 | A12-M-B109 | HPLC_1 | 0.95 | 439 |
| 3647 | A12-M-B110 | HPLC_1 | 1.02 | 453 |
| 3648 | A12-M-B111 | HPLC_1 | 0.92 | 385 |
| 3649 | A12-M-B112 | HPLC_1 | 0.92 | 371 |
| 3650 | A12-M-B113 | HPLC_1 | 1.19 | 436 |
| 3651 | A12-M-B114 | HPLC_1 | 0.97 | 412 |
| 3652 | A12-M-B115 | HPLC_1 | 0.96 | 386 |
| 3653 | A12-M-B116 | HPLC_1 | 1.06 | 366 |
| 3654 | A12-M-B117 | HPLC_1 | 0.95 | 433 |
| 3655 | A12-M-B118 | HPLC_1 | 0.99 | 439 |
| 3656 | A29-M-B109 | HPLC_1 | 0.94 | 451 |
| 3657 | A29-M-B111 | HPLC_1 | 0.9 | 397 |
| 3658 | A29-M-B112 | HPLC_1 | 0.89 | 383 |
| 3659 | A29-M-B115 | HPLC_1 | 0.94 | 398 |
| 3660 | A29-M-B116 | HPLC_1 | 1.04 | 378 |
| 3661 | A29-M-B117 | HPLC_1 | 0.94 | 445 |
| 3662 | A29-M-B118 | HPLC_1 | 0.97 | 451 |
| 3663 | A25-M-B109 | HPLC_1 | 0.78 | 373 |
| 3664 | A25-M-B112 | HPLC_1 | 0.73 | 305 |
| 3665 | A25-M-B115 | HPLC_1 | 0.78 | 320 |
| 3666 | A25-M-B116 | HPLC_1 | 0.87 | 300 |
| 3667 | A25-M-B117 | HPLC_1 | 0.78 | 367 |
| 3668 | A25-M-B118 | HPLC_1 | 0.82 | 373 |
| 3669 | A2-M-B109 | HPLC_1 | 0.92 | 421 |
| 3670 | A2-M-B111 | HPLC_1 | 0.88 | 367 |
| 3671 | A2-M-B112 | HPLC_1 | 0.87 | 353 |
| 3672 | A2-M-B113 | HPLC_1 | 1.16 | 418 |
| 3673 | A2-M-B114 | HPLC_1 | 0.93 | 394 |
| 3674 | A2-M-B115 | HPLC_1 | 0.92 | 368 |
| 3675 | A2-M-B117 | HPLC_1 | 0.92 | 415 |
| 3676 | A2-M-B118 | HPLC_1 | 0.95 | 421 |
| 3677 | A19-M-B109 | HPLC_1 | 1 | 435 |
| 3678 | A19-M-B110 | HPLC_1 | 1.06 | 449 |
| 3679 | A19-M-B111 | HPLC_1 | 0.97 | 381 |
| 3680 | A19-M-B112 | HPLC_1 | 0.96 | 367 |
| 3681 | A19-M-B114 | HPLC_1 | 1.02 | 408 |
| 3682 | A19-M-B115 | HPLC_1 | 1 | 382 |
| 3683 | A19-M-B117 | HPLC_1 | 1 | 429 |
| 3684 | A19-M-B118 | HPLC_1 | 1.03 | 435 |
| 3685 | A8-M-B109 | HPLC_1 | 0.75 | 371 |
| 3686 | A8-M-B115 | HPLC_1 | 0.75 | 318 |
| 3687 | A8-M-B117 | HPLC_1 | 0.74 | 365 |
| 3688 | A8-M-B118 | HPLC_1 | 0.79 | 371 |
| 3689 | A12-M-B119 | HPLC_1 | 1.09 | 382 |
| 3690 | A12-M-B120 | HPLC_1 | 0.98 | 439 |
| 3691 | A12-M-B121 | HPLC_1 | 1.23 | 398 |
| 3692 | A12-M-B122 | HPLC_1 | 1.24 | 398 |
| 3693 | A12-M-B123 | HPLC_1 | 0.98 | 474 |
| 3694 | A13-M-B123 | HPLC_1 | 0.81 | 408 |
| 3695 | A29-M-B119 | HPLC_1 | 1.07 | 394 |
| 3696 | A29-M-B120 | HPLC_1 | 0.96 | 451 |
| 3697 | A29-M-B121 | HPLC_1 | 1.22 | 410 |
| 3698 | A29-M-B122 | HPLC_1 | 1.23 | 410 |
| 3699 | A29-M-B123 | HPLC_1 | 0.96 | 486 |
| 3700 | A25-M-B120 | HPLC_1 | 0.81 | 373 |

TABLE VI-continued

| Entry | Compound | HPLC method | r.t. (min) | [M + H]+ |
|---|---|---|---|---|
| 3701 | A25-M-B121 | HPLC_1 | 1.07 | 332 |
| 3702 | A25-M-B122 | HPLC_1 | 1.09 | 332 |
| 3703 | A25-M-B124 | HPLC_1 | 1.1 | 332 |
| 3704 | A25-M-B123 | HPLC_1 | 0.81 | 408 |
| 3705 | A2-M-B120 | HPLC_1 | 0.94 | 421 |
| 3706 | A2-M-B121 | HPLC_1 | 1.21 | 380 |
| 3707 | A2-M-B122 | HPLC_1 | 1.22 | 380 |
| 3708 | A2-M-B124 | HPLC_1 | 1.22 | 380 |
| 3709 | A2-M-B123 | HPLC_1 | 0.94 | 456 |
| 3710 | A19-M-B120 | HPLC_1 | 1.02 | 435 |
| 3711 | A19-M-B125 | HPLC_1 | 1.29 | 406 |
| 3712 | A19-M-B121 | HPLC_1 | 1.27 | 394 |
| 3713 | A19-M-B122 | HPLC_1 | 1.28 | 394 |
| 3714 | A19-M-B123 | HPLC_1 | 1.02 | 470 |
| 3715 | A45-M-B119 | HPLC_1 | 0.89 | 346 |
| 3716 | A45-M-B120 | HPLC_1 | 0.79 | 403 |
| 3717 | A8-M-B122 | HPLC_1 | 1.07 | 330 |
| 3718 | A8-M-B123 | HPLC_1 | 0.78 | 406 |
| 3719 | A12-M-B126 | HPLC_1 | 0.94 | 419 |
| 3720 | A12-M-B127 | HPLC_1 | 1.34 | 424 |
| 3721 | A12-M-B128 | HPLC_1 | 0.99 | 439 |
| 3722 | A12-M-B129 | HPLC_1 | 1.09 | 491 |
| 3723 | A12-M-B130 | HPLC_1 | 0.97 | 440 |
| 3724 | A12-M-B131 | HPLC_1 | 1.14 | 414 |
| 3725 | A12-M-B132 | HPLC_1 | 1.08 | 487 |
| 3726 | A13-M-B129 | HPLC_1 | 0.92 | 425 |
| 3727 | A13-M-B131 | HPLC_1 | 0.95 | 348 |
| 3728 | A13-M-B132 | HPLC_1 | 0.91 | 421 |
| 3729 | A29-M-B126 | HPLC_1 | 0.92 | 431 |
| 3730 | A29-M-B128 | HPLC_1 | 0.97 | 451 |
| 3731 | A29-M-B129 | HPLC_1 | 1.07 | 503 |
| 3732 | A29-M-B130 | HPLC_1 | 0.95 | 452 |
| 3733 | A29-M-B131 | HPLC_1 | 1.12 | 426 |
| 3734 | A29-M-B133 | HPLC_1 | 0.96 | 459 |
| 3735 | A29-M-B132 | HPLC_1 | 1.06 | 499 |
| 3736 | A25-M-B126 | HPLC_1 | 0.75 | 353 |
| 3737 | A25-M-B129 | HPLC_1 | 0.93 | 425 |
| 3738 | A25-M-B130 | HPLC_1 | 0.79 | 374 |
| 3739 | A25-M-B131 | HPLC_1 | 0.97 | 348 |
| 3740 | A25-M-B133 | HPLC_1 | 0.81 | 381 |
| 3741 | A25-M-B132 | HPLC_1 | 0.92 | 421 |
| 3742 | A2-M-B126 | HPLC_1 | 0.9 | 401 |
| 3743 | A2-M-B129 | HPLC_1 | 1.06 | 473 |
| 3744 | A2-M-B130 | HPLC_1 | 0.93 | 422 |
| 3745 | A2-M-B131 | HPLC_1 | 1.11 | 396 |
| 3746 | A2-M-B132 | HPLC_1 | 1.04 | 469 |
| 3747 | A19-M-B126 | HPLC_1 | 0.99 | 415 |
| 3748 | A19-M-B127 | HPLC_1 | 1.38 | 420 |
| 3749 | A19-M-B128 | HPLC_1 | 1.03 | 435 |
| 3750 | A19-M-B129 | HPLC_1 | 1.13 | 487 |
| 3751 | A19-M-B130 | HPLC_1 | 1.01 | 436 |
| 3752 | A19-M-B131 | HPLC_1 | 1.19 | 410 |
| 3753 | A19-M-B134 | HPLC_1 | 1.03 | 475 |
| 3754 | A19-M-B133 | HPLC_1 | 1.02 | 443 |
| 3755 | A19-M-B132 | HPLC_1 | 1.12 | 483 |
| 3756 | A45-M-B129 | HPLC_1 | 0.9 | 455 |
| 3757 | A45-M-B131 | HPLC_1 | 0.93 | 378 |
| 3758 | A45-M-B132 | HPLC_1 | 0.89 | 451 |
| 3759 | A8-M-B126 | HPLC_1 | 0.72 | 351 |
| 3760 | A8-M-B129 | HPLC_1 | 0.9 | 423 |
| 3761 | A8-M-B131 | HPLC_1 | 0.93 | 346 |
| 3762 | A8-M-B134 | HPLC_1 | 0.79 | 411 |
| 3763 | A8-M-B133 | HPLC_1 | 0.78 | 379 |
| 3764 | A8-M-B132 | HPLC_1 | 0.89 | 419 |
| 3765 | A12-M-B135 | HPLC_1 | 1.11 | 414 |
| 3766 | A12-M-B136 | HPLC_1 | 1.32 | 424 |
| 3767 | A12-M-B137 | HPLC_1 | 1 | 412 |
| 3768 | A12-M-B138 | HPLC_1 | 0.98 | 441 |
| 3769 | A12-M-B139 | HPLC_1 | 0.95 | 425 |
| 3770 | A12-M-B140 | HPLC_1 | 1.17 | 428 |
| 3771 | A12-M-B141 | HPLC_1 | 1.04 | 455 |
| 3772 | A13-M-B135 | HPLC_1 | 0.92 | 348 |
| 3773 | A13-M-B142 | HPLC_1 | 0.72 | 375 |
| 3774 | A13-M-B138 | HPLC_1 | 0.79 | 375 |
| 3775 | A13-M-B139 | HPLC_1 | 0.76 | 359 |
| 3776 | A13-M-B141 | HPLC_1 | 0.86 | 389 |
| 3777 | A29-M-B142 | HPLC_1 | 0.9 | 453 |
| 3778 | A29-M-B136 | HPLC_1 | 1.29 | 436 |
| 3779 | A29-M-B143 | HPLC_1 | 0.93 | 425 |
| 3780 | A29-M-B138 | HPLC_1 | 0.96 | 453 |
| 3781 | A29-M-B139 | HPLC_1 | 0.93 | 437 |
| 3782 | A29-M-B141 | HPLC_1 | 1.01 | 467 |
| 3783 | A25-M-B142 | HPLC_1 | 0.73 | 375 |
| 3784 | A25-M-B143 | HPLC_1 | 0.77 | 347 |
| 3785 | A25-M-B138 | HPLC_1 | 0.81 | 375 |
| 3786 | A25-M-B139 | HPLC_1 | 0.77 | 359 |
| 3787 | A25-M-B141 | HPLC_1 | 0.87 | 389 |
| 3788 | A2-M-B142 | HPLC_1 | 0.88 | 423 |
| 3789 | A2-M-B136 | HPLC_1 | 1.29 | 406 |
| 3790 | A2-M-B143 | HPLC_1 | 0.91 | 395 |
| 3791 | A2-M-B138 | HPLC_1 | 0.94 | 423 |
| 3792 | A2-M-B139 | HPLC_1 | 0.92 | 407 |
| 3793 | A2-M-B140 | HPLC_1 | 1.14 | 410 |
| 3794 | A2-M-B141 | HPLC_1 | 1 | 437 |
| 3795 | A19-M-B144 | HPLC_1 | 1.3 | 394 |
| 3796 | A19-M-B142 | HPLC_1 | 0.96 | 437 |
| 3797 | A19-M-B136 | HPLC_1 | 1.34 | 420 |
| 3798 | A19-M-B143 | HPLC_1 | 0.99 | 409 |
| 3799 | A19-M-B138 | HPLC_1 | 1.02 | 437 |
| 3800 | A19-M-B139 | HPLC_1 | 0.99 | 421 |
| 3801 | A19-M-B141 | HPLC_1 | 1.07 | 451 |
| 3802 | A45-M-B135 | HPLC_1 | 0.91 | 378 |
| 3803 | A8-M-B141 | HPLC_1 | 0.84 | 387 |
| 3804 | A45-M-B141 | HPLC_1 | 0.84 | 419 |
| 3805 | A8-M-B142 | HPLC_1 | 0.7 | 373 |
| 3806 | A8-M-B138 | HPLC_1 | 0.77 | 373 |
| 3807 | A8-M-B139 | HPLC_1 | 0.73 | 357 |

Example 9

Loading of Piperazine (Corresponding to Fragment A50 of Table I) onto PNP Wang Resin.

To a shaken suspension of PNP Wang resin (p-nitrophenyl-carbonate Wang resin, 4.7 g, 0.52 mmol/g, 2.5 mmol) in anhydrous DMF (50 ml) at room temperature it was added piperazine (0.637 g, 7.41 mmol) and Hunig's base (0.956 g, 7.41 mmol). The reaction mixture was shaken for 20 hours and isolated by filtration. The resin was washed sequentially with DMF (50 ml), DCM (50 DMF (50 ml), DCM (50 ml), MeOH (50 ml), DCM (50 ml), MeOH (50 ml), DCM (50 ml), MeOH (50 ml), TBME (50 ml×2) and dried in vacuo to give the resin bound diamine (4.6 g).

The resin bound carbamate was taken onto the next step without further analysis.

Example 10

Preparation of A50-M-B25

Step a: Loading of the 7-azaindole Scaffold (Title Compound of Example 3) onto the Resin of Example 9

To the resin (4.6 g, 0.52 mmol/g, 2.4 mmol) in anhydrous DMF (50 ml), 3-carboxy-5-nitro-7-azaindole (0.743 g, 3.588 mmol), TBTU (1.152 g, 3.588 mmol) and DIPEA (0.927 g, 7.176 mmol) were added. The reaction mixture was shaken at room temperature for 20 hours and then the resin was isolated by filtration. The resin was washed sequentially with DMF (50 ml), DCM (50 ml), DMF (50 ml), DCM (50 ml), MeOH (50 ml), DCM (50 ml), MeOH (50 ml), DCM (50 ml), MeOH (50 ml), TBME (50 ml×2) and dried in vacuo to give the resin bound 7-azaindole (5.2 g).

Resin Loading Check

To the resin (0.035 g, 0.0182 mmol) in DCM (1 ml) DIPEA (0.024 g, 0.182 mmol) and benzoyl chloride (0.025 g, 0.182 mmol) were added. The reaction mixture was shaken for 4 hours and the resin isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (1 ml of 40% TFA/DCM) to give an off white solid (0.008 g, 80%).

LCMS: m/z 380 [M+H]$^+$, m/z 421 [M+MeCN+H]$^+$ at r.t. 1.44 min (84% purity at 215 nm).

Step b: Reduction of Nitro Group

To the resin (5. g, 2.3 mmol) in NMP (50 ml) was added tin (II) chloride dihydrate (5.4 g, 23.92 mmol). The reaction mixture was shaken at room temperature for 20 hours and then the resin was isolated by filtration. The resin was washed sequentially with DMF (50 ml), DCM (50 ml), DMF (50 ml), DCM (50 ml), MeOH (50 ml), water (50 ml), MeOH (50 ml), DCM (50 ml), MeOH (50 ml), DCM (50 ml), MeOH (50 ml), TBME (50 ml×2) and dried in vacuo to give the resin bound azaindole (5.0 g). 0.01 g of resin were cleaved (1 ml of 40% TFA/DCM) to give an off-white solid (0.0009 g, 75%).

LCMS: m/z 246 [M+H]$^+$ at r.t. 0.22 min (94% purity at 215 nm).

Step c: Capping with Acid Chlorides

To the resin (0.11 g, 0.05 mmol) in DCM (1 ml) was added Hunig's base (0.034 g, 0.26 mmol) and benzoyl chloride (corresponding to fragment B25 of table II, 0.036 g, 0.26 mmol). The reaction mixture was shaken at room temperature for 20 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The resin was shaken in acetonitrile/ammonia solution (1 ml, 4:1) for 4 hours and then isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (40% TFA/DCM, 3×0.5 ml) to give an off white solid (0.012 g, 63%) corresponding to compound A50-M-B25 (see entry 3808 of table VII below).

LCMS (HPLC_1): m/z 350 [M+H] at r.t. 0.83 min (95% by ELS detection).

By working as described in example 10 and by using any suitable resin supported amino derivative and any acyl chloride reactant, the following compounds (e.g. library) were prepared:

TABLE VII

| Entry | Compound | HPLC method | r.t. (min) | [M + H]$^+$ |
|---|---|---|---|---|
| 3808 | A50-M-B25 | HPLC_1 | 0.83 | 350 |
| 3809 | A51-M-B25 | HPLC_1 | 0.9 | 380 |
| 3810 | A52-M-B25 | HPLC_1 | 0.89 | 378 |
| 3811 | A50-M-B26 | HPLC_1 | 0.79 | 330 |
| 3812 | A51-M-B26 | HPLC_1 | 0.87 | 360 |
| 3813 | A53-M-B26 | HPLC_1 | 0.78 | 344 |
| 3814 | A50-M-B28 | HPLC_1 | 0.89 | 356 |
| 3815 | A54-M-B28 | HPLC_1 | 0.96 | 372 |
| 3816 | A51-M-B28 | HPLC_1 | 0.96 | 386 |
| 3817 | A55-M-B28 | HPLC_1 | 0.91 | 358 |
| 3818 | A53-M-B28 | HPLC_1 | 0.9 | 370 |
| 3819 | A52-M-B28 | HPLC_1 | 0.95 | 384 |
| 3820 | A51-M-B29 | HPLC_1 | 0.67 | 318 |
| 3821 | A50-M-B30 | HPLC_1 | 1 | 370 |
| 3822 | A54-M-B30 | HPLC_1 | 1.06 | 386 |
| 3823 | A51-M-B30 | HPLC_1 | 1.06 | 400 |
| 3824 | A52-M-B30 | HPLC_1 | 1.05 | 398 |
| 3825 | A54-M-B31 | HPLC_1 | 1.01 | 400 |
| 3826 | A51-M-B31 | HPLC_1 | 1.01 | 414 |
| 3827 | A52-M-B31 | HPLC_1 | 1 | 412 |
| 3828 | A50-M-B33 | HPLC_1 | 0.7 | 316 |
| 3829 | A51-M-B33 | HPLC_1 | 0.79 | 346 |
| 3830 | A54-M-B39 | HPLC_1 | 0.97 | 396 |
| 3831 | A51-M-B39 | HPLC_1 | 0.98 | 410 |
| 3832 | A51-M-B40 | HPLC_1 | 0.97 | 394 |
| 3833 | A50-M-B48 | HPLC_1 | 0.91 | 386 |
| 3834 | A51-M-B48 | HPLC_1 | 0.99 | 416 |
| 3835 | A50-M-B49 | HPLC_1 | 0.88 | 380 |
| 3836 | A51-M-B49 | HPLC_1 | 0.95 | 410 |
| 3837 | A53-M-B49 | HPLC_1 | 0.89 | 394 |
| 3838 | A51-M-B51 | HPLC_1 | 0.8 | 346 |
| 3839 | A50-M-B52 | HPLC_1 | 0.8 | 330 |
| 3840 | A51-M-B52 | HPLC_1 | 0.86 | 360 |
| 3841 | A50-M-B34 | HPLC_1 | 1.02 | 418 |
| 3842 | A51-M-B34 | HPLC_1 | 1.08 | 448 |
| 3843 | A50-M-B57 | HPLC_1 | 0.83 | 342 |
| 3844 | A51-M-B57 | HPLC_1 | 0.9 | 372 |
| 3845 | A50-M-B54 | HPLC_1 | 0.82 | 368 |
| 3846 | A51-M-B54 | HPLC_1 | 0.9 | 398 |
| 3847 | A50-M-B69 | HPLC_1 | 0.86 | 386 |
| 3848 | A51-M-B69 | HPLC_1 | 0.94 | 416 |
| 3849 | A50-M-B70 | HPLC_1 | 0.82 | 330 |
| 3850 | A51-M-B70 | HPLC_1 | 0.88 | 360 |
| 3851 | A50-M-B73 | HPLC_1 | 1.01 | 372 |
| 3852 | A51-M-B73 | HPLC_1 | 1.07 | 402 |
| 3853 | A53-M-B73 | HPLC_1 | 1.02 | 386 |
| 3854 | A50-M-B75 | HPLC_1 | 0.84 | 370 |
| 3855 | A51-M-B75 | HPLC_1 | 0.9 | 400 |
| 3856 | A51-M-B85 | HPLC_1 | 0.82 | 370 |
| 3857 | A50-M-B86 | HPLC_1 | 0.88 | 418 |

Example 11

Preparation of A50-M-B1

The title compound was prepared by working as described in steps (a) and (b) of example 10 and by carrying out the capping reaction of step (c) with sulfonyl chloride, as follows:

Step (c): Capping with Sulfonyl Clorides

To the resin (0.11 g, 0.052 mmol) being obtained in step (b) of example 10, in DCM (1 ml), pyridine (0.021 g, 0.26 mmol), DMAP (0.001 g, 0.0052 mmol) and methane sulfonyl chloride (corresponding to fragment B1 of table II, 0.030 g, 0.26 mmol) were added. The reaction mixture was shaken at room temperature for 20 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (40% TFA/DCM 3×0.5 ml) to give an off white solid (0.018 g, 100%) corresponding to the title compound A50-M-B1 (see entry 3858 of table VIII).

LCMS (HPLC_1): m/z 324 [M+H]$^+$ at r.t. 0.22 min (92% by ELS detection).

By working as described in example 11 and by using any suitably resin supported amino derivative and any sulfonyl chloride reactant, the following compounds were prepared:

TABLE VIII

| Entry | Compound | HPLC method | r.t. (min) | [M + H]$^+$ |
|---|---|---|---|---|
| 3858 | A50-M-B1 | HPLC_1 | 0.22 | 324 |
| 3859 | A50-M-B2 | HPLC_1 | 0.89 | 400 |

TABLE VIII-continued

| Entry | Compound | HPLC method | r.t. (min) | [M + H]+ |
|---|---|---|---|---|
| 3860 | A51-M-B2 | HPLC_1 | 0.97 | 430 |
| 3861 | A51-M-B4 | HPLC_1 | 0.75 | 368 |
| 3862 | A50-M-B8 | HPLC_1 | 0.89 | 420 |
| 3863 | A51-M-B8 | HPLC_1 | 0.95 | 450 |
| 3864 | A50-M-B11 | HPLC_1 | 0.72 | 352 |
| 3865 | A51-M-B11 | HPLC_1 | 0.84 | 382 |
| 3866 | A50-M-B12 | HPLC_1 | 1.05 | 428 |
| 3867 | A51-M-B12 | HPLC_1 | 1.12 | 458 |
| 3868 | A50-M-B15 | HPLC_1 | 0.84 | 386 |
| 3869 | A51-M-B15 | HPLC_1 | 0.91 | 416 |
| 3870 | A50-M-B22 | HPLC_1 | 0.84 | 446 |
| 3871 | A51-M-B22 | HPLC_1 | 0.9 | 476 |
| 3872 | A56-M-B22 | HPLC_1 | 0.87 | 474 |

The invention claimed is:

1. A method for inhibiting protein kinase activity of a kinase selected from the group consisting of cdk2/cyclin A, E, B1, D1, MAPK, EGFR, PKA, Cdk5/p25, IGF1-R, Aurora-2 or Cdc7/dbf4, ACK1, BRK, JAK2, MELK MPS1, NEK6, PDGFR, PDK1, PLK1, RET, ABL, AKT1, AKT2, AKT3, AUR2, IGFR1, IR, LCK, and combinations thereof, which comprises administering to a mammal in need thereof an effective amount of a compound of formula (I)

(I)

wherein R is selected from the group consisting of —$R^a$, —$COR^a$, —$CONR^aR^b$, —$SO_2R^a$ or —$COOR^a$;
$R_1$ is a group —$NR^cR^d$ or —$OR^c$;
wherein $R^a$, $R^b$, $R^c$ and $R^d$, are the same or different, and are each independently hydrogen or a group optionally further substituted, selected from straight or branched $C_1$-$C_6$ alkyl, $C_2$-$C_6$ straight or branched alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl or, taken together with the nitrogen atom to which they are bonded, either $R^a$ and $R^b$ as well as $R^c$ and $R^d$ can form an optionally substituted 4 to 7 membered heterocycle, optionally containing one additional ring heteroatom or heteroatomic group selected from S, O, N or NH;
or isomers, tautomers or a pharmaceutically acceptable salt thereof.

2. The method according to claim 1 further comprising subjecting the mammal in need thereof to a radiation therapy or chemotherapy regimen in combination with at least one cytostatic or cytotoxic agent.

3. The method according to claim 1 wherein the mammal in need thereof is a human.

4. A method for inhibiting protein kinase activity of a kinase selected from the group consisting of cdk2/cyclin A, E, B1, D1, MAPK, EGFR, PKA, Cdk5/p25, IGF1-R, Aurora-2 or Cdc7/dbf4, ACK1, BRK, JAK2, MELK, MPS1, NEK6, PDGFR, PDK1, PLK1, RET, ABL, AKT1, AKT2, AKT3, AUR2, IGFR1, IR, LCK, and combinations thereof, which comprises administering to a mammal in need thereof an effective amount of a composition comprising two or more compounds of formula (I)

(I)

wherein R is selected from the group consisting of —$R^a$, —$COR^a$, —$CONR^aR^b$, —$SO_2R^a$ or —$COOR^a$;
$R_1$ is a group —$NR^cR^d$ or —$OR^c$;
wherein $R^a$, $R^b$, $R^c$ and $R^d$, are the same or different, and are each independently hydrogen or a group optionally further substituted, selected from straight or branched $C_1$-$C_6$ alkyl, $C_2$-$C_6$ straight or branched alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl or, taken together with the nitrogen atom to which they are bonded, either $R^a$ and $R^b$ as well as $R^c$ and $R^d$ can form an optionally substituted 4 to 7 membered heterocycle, optionally containing one additional ring heteroatom or heteroatomic group selected from S, O, N or NH;
or isomers, tautomers or a pharmaceutically acceptable salt thereof.

\* \* \* \* \*